United States Patent
Francois et al.

(10) Patent No.: US 11,291,407 B2
(45) Date of Patent: Apr. 5, 2022

(54) DETECTION OF HIGH RISK DRUSEN

(71) Applicant: Apellis Pharmaceuticals, Inc., Waltham, MA (US)

(72) Inventors: Cedric Francois, Prospect, KY (US); Pascal Deschatelets, Lexington, MA (US)

(73) Assignee: Apellis Pharmaceuticals, Inc., Waltham, MA (US)

( * ) Notice: Subject to any disclaimer, the term of this patent is extended or adjusted under 35 U.S.C. 154(b) by 0 days.

(21) Appl. No.: 16/839,854

(22) Filed: Apr. 3, 2020

(65) Prior Publication Data

US 2020/0384126 A1 Dec. 10, 2020

Related U.S. Application Data

(62) Division of application No. 14/421,771, filed as application No. PCT/US2013/055394 on Aug. 16, 2013, now abandoned.

(60) Provisional application No. 61/684,682, filed on Aug. 17, 2012.

(51) Int. Cl.
| | |
|---|---|
| *A61P 27/02* | (2006.01) |
| *A61B 5/00* | (2006.01) |
| *C12Q 1/37* | (2006.01) |
| *A61K 49/00* | (2006.01) |

(52) U.S. Cl.
CPC .......... *A61B 5/4842* (2013.01); *A61B 5/4848* (2013.01); *A61K 49/0017* (2013.01); *A61P 27/02* (2018.01); *C12Q 1/37* (2013.01); *G01N 2333/4716* (2013.01); *G01N 2333/96433* (2013.01); *G01N 2800/164* (2013.01); *G01N 2800/50* (2013.01)

(58) Field of Classification Search
None
See application file for complete search history.

(56) References Cited

U.S. PATENT DOCUMENTS

| | | | |
|---|---|---|---|
| 6,087,120 | A | 7/2000 | Van Oeveren et al. |
| 7,351,524 | B2 | 4/2008 | Hageman et al. |
| 2008/0305046 | A1 | 12/2008 | Hafezi-Moghadam |
| 2008/0305504 | A1 | 12/2008 | Yu et al. |
| 2016/0067357 | A1 | 3/2016 | Francois et al. |

FOREIGN PATENT DOCUMENTS

| | | |
|---|---|---|
| WO | WO-2005/007663 A2 | 1/2005 |
| WO | WO-2007/062249 A2 | 5/2007 |
| WO | WO-2009/046198 A2 | 4/2009 |

OTHER PUBLICATIONS

Chung et al. Changes in the expression of proteome in the aqueous humor of patients with neovascular age-related macular degeneration. Assoc. Res. Vis. and Ophthalmol (ARVO) National Meeting, May 3, 2011, program 6685 poster D1172, 2 pages. (Year: 2011).*
Chi, Z-L. et al., Suppression of drusen formation by compstatin, a peptide inhibitor of complement C3 activation, on cynomolgus monkey with early-onset macular degeneration, Adv Exp Med Biol., 703: 127-135 (2010).
Chuang, C-H. et al., In Vivo Positron Emission Tomograpgy Imaging of Protease Activity by Generation of a Hydrophobic Product from a Noninhibitory Protease Substrate, Clin Cancer Res., 18(1): 238-247 (2012).
International Search Report for PCT/US2013/055394, 3 pages (dated Dec. 19, 2013).
Johnson, L.V. et al. Complement Activation and Inflammatory Processes in Drusen Formation and Age Related Macular Degeneration, Exp Eye Res., 73(6): 887-896 (2001).
Leung Kam. Polyethylene glycol-Cys-Arg-Ser-Gly-Pro-Leu-Gly-Val-Tyr-[ 18F] fluorobenzoyl-Lys-Lys-tetramethylrhodamine, Molecular Imaging and Contrast Agent Database (MICAD), I-4 (2012).
Liu, B. et al., Complement component C5a Promotes Expression of IL-22 and IL-17 from Human T cells and its Implication in Age-related Macular Degeneration, Journal of Translational Medicine, 9(111): 1-12 (2011).
Ricklin, D. and Lambris, J., Compstatin: A Complement Inhibitor on its Way to Clinical Application, Adv Exp Med Biol., 632:273-292 (2008).
Schlanitz, F.G. et al., Performance of Automated Drusen Detection by Polarization-Sensitive Optical Coherence Tomagraphy, Investigative Ophthalmology, 52(7): 4571-45-79 (2011).
Written Opinion for PCT/US2013/055394, 6 pages (dated Dec. 19, 2013).
Zipfel, P. F. et al. The Role of Complement in AMD, Adv. Exp. Med. Biol., 703: 9-24 (2010).

* cited by examiner

*Primary Examiner* — Jennifer Lamberski
(74) *Attorney, Agent, or Firm* — Choate, Hall & Stewart LLP; Rolando Medina; Melissa M. Adams

(57) ABSTRACT

In some aspects, methods of detecting complement activation in vivo, e.g., in an eye, are provided. In some embodiments, methods comprise detecting drusen containing or in close proximity to complement activation. In some embodiments methods comprise detecting one or more drusen having inflamed endothelium underlying or in close proximity thereto. In some embodiments methods comprise detecting eye-derived extracellular microvesicles, e.g., exosomes, in a body fluid. In some embodiments any of the methods further comprises treating a subject at risk of developing AMD, GA, or advanced AMD or at increased likelihood of rapid progression of AMD with a complement inhibitor. In some aspects, agents useful for performing one or more of the methods are described.

7 Claims, No Drawings

Specification includes a Sequence Listing.

DETECTION OF HIGH RISK DRUSEN

CROSS REFERENCE TO RELATED APPLICATIONS

The present invention is a divisional of Ser. No. 14/421,771, filed on Feb. 13, 2015, which is the National Stage of International Application No. PCT/US13/55394, filed Aug. 16, 2013, which claims priority to U.S. provisional patent application No. 61/684,682, filed Aug. 17, 2012, the entire contents of each of which are hereby incorporated by reference.

SEQUENCE LISTING

The instant application contains a sequence listing which has been submitted electronically in ASCII format and is hereby incorporated by reference in its entirety. Said ASCII copy, created on Nov. 14, 2013, is named 2008575-0049_SL.txt and is 47,234 bytes in size.

BACKGROUND

Age-related macular degeneration (AMD) is a leading cause of functional blindness in persons over 50 years of age worldwide. AMD results in a loss of vision in the center of the visual field because of damage to the macula, the central area of the retina. AMD is commonly classified into "dry" (non-exudative) and "wet" (exudative, or neovascular) forms. Dry AMD is typically characterized by atrophy of cells in the retinal pigment epithelium (RPE) layer. Overlying photoreceptor cells, and frequently also the underlying cells in the choroidal capillary layer, may also be affected. Confluent areas of RPE cell death sometimes accompanied by choriocapillaris atrophy) are referred to as geographic atrophy (GA). Patients with dry AMD experience a slow and progressive deterioration in central vision. Individuals with dry AMD can develop wet AMD, which is characterized by bleeding and/or leakage of fluid from abnormal vessels that have grown from the choroidal vessels beneath the RPE and the macula. Much of the vision loss that patients with wet AMD experience is frequently due to choroidal neovascularization (CNV) and its complications, which can be responsible for sudden and disabling loss of vision. Dry AMD is much more common than wet AMD, accounting for about 80%-90% of AMD patients. Dry AMD can also continue to progress in patients who have developed wet AMD. The clinical course of AMD is variable. For example, there is significant variability in the rate of progression among patients with dry AMD, and only a relatively small proportion of such patients develop wet AMD.

SUMMARY

In some embodiments, the invention provides methods of detecting complement activation in vivo. In some aspects, the invention provides methods of detecting high risk drusen in an eye. In some embodiments, the invention provides methods that apply the detection of complement activation in vivo for detection of high risk drusen. In some aspects, the invention provides compositions useful in practicing the methods.

In some aspects, the invention provides a method of detecting complement activation in a subject comprising: (a) providing a subject to whom a substrate for a complement activation pathway protease has been administered; and (b) detecting cleavage of the substrate, thereby detecting complement activation in the subject. In some embodiments the substrate produces a detectable signal upon cleavage; and step (b) detecting the signal. In some embodiments step (a) comprises administering the substrate to the subject. In some embodiments the substrate comprises a peptide substrate for a C3 convertase. In some embodiments the substrate produces a detectable signal upon cleavage; and step (b) comprises detecting the signal In some embodiments cleavage of the substrate produces a fluorescent, visible, magnetic, or infrared signal. In some embodiments the substrate is a fluorogenic substrate. In some embodiments the substrate comprises a peptide substrate for a C3 convertase linked to a first moiety and a second moiety, wherein cleavage of the substrate alters the distance between the first and second moieties, thereby resulting in a detectable signal. In some embodiments the substrate comprises a peptide substrate for a C3 convertase linked to a first moiety and a second moiety, wherein the first and second moiety are a FRET pair. In some embodiments the substrate comprises a peptide substrate for a C3 convertase linked to a first fluorophore and a second fluorophore at a characteristic distance wherein the fluorescences of the first and second fluorophores are mutually substantially quenched. In some embodiments the substrate comprises a peptide substrate for a C3 convertase linked to fluorophore and a quencher at a characteristic distance wherein the fluorescence of the fluorophore is quenched by the quencher. In some embodiments the subject is at risk of or suffering from a complement-mediated disorder of the eye. In some embodiments the subject is at risk of or suffering from age-related macular degeneration (AMD), glaucoma, or uveitis.

In some embodiments the subject is at risk of or suffering from age-related macular degeneration (AMD). In some embodiments the substrate is administered intravascularly, e.g., intravenously. In some embodiments the substrate is administered intravitreally. In some embodiments detecting is performed using a medical imaging device. In some embodiments detecting is performed using an ophthalmoscope. In some embodiments the method comprises detecting one or more drusen in an eye of the subject and detecting complement activation in or in close proximity to one or more of said drusen. In some embodiments the subject has early AMD in one or both eyes. In some embodiments the method comprises detecting one or more drusen in an eye of the subject suffering from early AMD and detecting complement activation in or in close proximity to one or more of said drusen.

In some embodiments the method comprises comparing the level of cleavage detected in step (b) with a reference level. In some embodiments the method comprises comprising classifying the subject into a prognostic, diagnostic, or treatment-relevant category based at least in part on the result of step (b). In some embodiments the method comprises classifying the subject into a prognostic category based at least in part on the result of step (b), wherein an increased level of complement activation indicates that the subject is at increased risk of progression or worsening of the disorder. In some embodiments the method comprises detecting one or more drusen in an eye of the subject, detecting complement activation in or in close proximity to one or more of said drusen, and classifying the subject or eye into a prognostic category based at least in part on detecting complement activation in or in close proximity to one or more of said drusen, wherein an increased level of complement activation in or in close proximity to at least one of said drusen indicates that the subject is at increased risk of development or progression of AMD. In some embodiments the method comprises detecting one or more drusen in an eye of the subject with early AMD, detecting complement activation in or in close proximity to one or more of said drusen, and classifying the eye or subject as being at increased risk of progression to advanced AMD if the subject has an increased level of complement activation in or in close proximity to at least one of said drusen. In some embodiments the method comprises detecting one or more drusen in an eye of the subject, detecting complement activation in or in close proximity to one or more of said drusen, and estimating the likelihood that the eye or subject will develop advanced AMD within a given time period based at least in part on the level of complement activation. In some embodiments the time period is between 6 months and 5 years. In some embodiments the time period is 6 months or 1, 2, 3, 4, or 5 years. In some embodiments the subject has early AMD. In some embodiments the method comprises classifying the subject into a treatment-relevant category based at least in part on the result of step (b), wherein an increased level of complement activation indicates that the subject is a suitable candidate for treatment with a complement inhibitor.

In some embodiments the method comprises administering a complement inhibitor to the subject. In some embodiments the method comprises administering a complement inhibitor to the subject based at least in part on the result of step (b).

In some aspects, the invention provides a method of monitoring a change in complement activation in a subject over time, the method comprising (a) performing a method of detecting complement activation in vivo at first and second time points; and (b) comparing the result obtained at the first and second time points. In some embodiments the first and second time points are at least 24 hours apart. In some embodiments the method comprises administering a therapeutic agent to the subject between the first and second time points. In some embodiments the therapeutic agent is a complement inhibitor. In some embodiments the subject suffers from AMD.

In some aspects, the invention provides a method of detecting a high risk druse in an eye of a subject, the method comprising detecting complement activation in or in close proximity to the druse or detecting inflamed endothelium underlying or in close proximity to the druse. In some embodiments the method comprises detecting complement activation in or in close proximity to the druse. In some embodiments the method comprises detecting cleavage of a substrate for a complement activation pathway protease in or in close proximity to the druse. In some embodiments the method comprises detecting a marker expressed by inflamed endothelium. In some embodiments the marker is a selectin. In some embodiments the method comprises detecting an imaging agent bound to a marker expressed by inflamed endothelium. In some embodiments the imaging agent comprises a detectable label and a targeting moiety, wherein the targeting moiety binds to a marker expressed by inflamed endothelium. In some embodiments the targeting moiety comprises sLeX or a mimetic thereof. In some embodiments the method comprises the subject has early AMD. In some embodiments the method comprises comprising classifying the eye or subject into a prognostic, diagnostic, or treatment-relevant category based at least in part on the detection of complement activation in one or more drusen in the eye and/or detection of inflamed endothelium underlying or in close proximity to one or more drusen in the eye.

In some embodiments the method comprises classifying the eye or subject into a prognostic category based at least in part on the detection of complement activation in or in close proximity to one or more drusen in the eye, wherein an increased level of complement activation indicates that the subject is at increased risk of progression or worsening of AMD. In some embodiments the method comprises classifying the eye or subject into a prognostic, diagnostic, or treatment-relevant category based at least in part on the detection of inflamed endothelium underlying or in close proximity to one or more drusen in the eye. In some embodiments the method comprises classifying the subject into a prognostic category based at least in part on the detection of inflamed endothelium underlying or in or in close proximity to one or more drusen in the eye, wherein an increased level of inflamed endothelium indicates that the subject is at increased risk of progression or worsening of AMD. In some embodiments the method comprises detecting complement activation in or in close proximity to one or more drusen in vivo and detecting inflamed endothelium underlying or in close proximity to one or more drusen in vivo. In some embodiments the method comprises detecting both complement activation and inflamed endothelium associated with a druse.

In some embodiments the method comprises detecting one or more drusen in an eye of the subject, detecting complement activation in or in close proximity to at least one of said drusen or detecting inflamed endothelium underlying or in close proximity to at least one of said drusen, and estimating the likelihood that the subject will develop advanced AMD within a given time period, such as a time period between 6 months and 5 years, based at least in part on the level of complement activation, inflamed endothelium, or both. In some embodiments the time period is 6 months or 1, 2, 3, 4, or 5 years.

In some embodiments the method comprises administering a complement inhibitor to the subject. In some embodiments the method comprises administering an anti-Th17 agent to the subject.

In some aspects, the invention provides a method of identifying an eye at increased risk of developing advanced AMD, the method comprising detecting complement activation in or in close proximity to one or more drusen in an eye of a subject in vivo or detecting inflamed endothelium underlying or in close proximity to one or more drusen in an eye of a subject in vivo. In some embodiments the method comprises classifying the eye or subject into a prognostic, diagnostic, or treatment-relevant category based at least in part on the detection of complement activation. In some embodiments the eye has early or intermediate AMD.

In some embodiments the method comprises classifying the subject into a prognostic category based at least in part on the detection of complement activation, wherein an increased level of complement activation indicates that the subject is at increased risk of progression or worsening of AMD. In some embodiments the method comprises detecting complement activation in or in close proximity to one or more drusen, and classifying the subject as being at increased risk of progression to advanced AMD if the subject has an increased level of complement activation in or in close proximity to at least one of said drusen. In some embodiments the method comprises detecting complement activation in or in close proximity to at least one drusen, and providing an estimate of the likelihood that the subject will develop advanced AMD within a given time period, such as a time period between 6 months and 5 years based at least in part on the level of complement activation. In some embodiments the time period is 6 months or 1, 2, 3, 4, or 5 years. In some embodiments the method comprises classifying the eye or subject into a prognostic, diagnostic, or treatment-relevant category based at least in part on the detection of inflamed endothelium underlying or in or in close proximity to one or more drusen in the eye. In some embodiments the method comprises classifying the subject into a prognostic category based at least in part on the detection of inflamed endothelium underlying or in or in close proximity to one or more drusen in the eye, wherein an increased level of inflamed endothelium indicates that the subject is at increased risk of progression or worsening of AMD. In some embodiments the method comprises detecting inflamed endothelium underlying or in or in close proximity to at least one drusen, and classifying the subject as being at increased risk of progression to advanced AMD if the subject has an increased level of inflamed endothelium underlying or in or in close proximity to at least one of said drusen. In some embodiments the method comprises detecting inflamed endothelium underlying or in close proximity to at least one drusen, and estimating the likelihood that the subject will develop advanced AMD within a given time period based at least in part on the level of inflamed endothelium. In some embodiments the time period is between 6 months and 5 years. In some embodiments the time period is 6 months or 1, 2, 3, 4, or 5 years.

In some embodiments the subject has early AMD or intermediate AMD. In some embodiments the method comprises classifying the subject into a treatment-relevant category based at least in part on the detection of complement activation, inflamed endothelium, or both, wherein an increased level of complement activation, inflamed endothelium, or both, indicates that the subject is a suitable candidate for treatment with a complement inhibitor.

In some aspects, the invention provides a method of identifying a subject at increased risk of development or progression of AMD, the method comprising detecting inflamed endothelium underlying or in close proximity to one or more drusen in an eye of the subject. In some embodiments inflamed endothelium is detected using an imaging agent targeted to inflamed endothelium. In some embodiments the imaging agent comprises a targeting moiety that binds to a marker exposed at the surface of inflamed endothelium. In some embodiments the targeting moiety comprises an antibody, aptamer, peptide, or carbohydrate. In some embodiments the targeting moiety comprises a selectin ligand. In some embodiments the marker comprises a cell adhesion molecule or selectin. In some embodiments the imaging agent comprises particles having a targeting moiety at their surface. In some embodiments the imaging agent is detectable by ultrasound, magnetic resonance imaging, nuclear imaging, or fluorescence detection.

In some embodiments the imaging agent comprises microbubbles, microparticles, nanoparticles, quantum dots, or fluorescently labeled particles. In some embodiments the imaging agent is administered intravascularly, e.g., intravenously. In some embodiments the imaging agent is administered locally, at or near a site in the body at which it is of interest to assess complement activation. In some embodiments the imaging agent is administered to or near the eye. In some embodiments the imaging agent is administered by periocular administration. In some embodiments the imaging agent is administered by intraocular administration. In some embodiments the imaging agent is administered to or near the posterior segment of the eye, e.g., to the vitreous, e.g., by intravitreal injection. In some embodiments the imaging agent is administered to the eye using iontophoresis. In some embodiments the imaging agent is administered to the eye using eyedrops.

In some aspects, a pharmaceutically acceptable composition comprising any of the diagnostic agents is provided. In some embodiments the pharmaceutically acceptable composition is suitable for administration to the eye. In some embodiments the pharmaceutically acceptable composition comprises a gel, ointment, emulsion, suspension, liquid composition, or gel-forming composition. In some embodiments a pharmaceutically acceptable composition is in the form of eyedrops. In some embodiments the detecting is performed using a medical imaging device. In some embodiments the detecting is performed using an ophthalmoscope. In some embodiments the subject has early AMD.

In some embodiments the method comprises detecting inflamed endothelium underlying or in close proximity to one or more drusen in an eye of the subject, and estimating the likelihood that the subject will develop advanced AMD within a given time period, such as a time period between 6 months and 5 years, based at least in part on the detection of inflamed endothelium. In some embodiments the time period is between 6 months and 5 years. In some embodiments the time period is 6 months or 1, 2, 3, 4, or 5 years. In some embodiments the subject has early AMD.

In some aspects, the invention provides a method of assessing an eye in a subject, the method comprising determining, based at least in part on an in vivo complement activation assay, whether or not the eye exhibits evidence of complement activation. In some embodiments the method comprising determining whether or not the eye exhibits evidence of complement activation in or in close proximity to a drusen.

In some aspects, the invention provides a method of assessing an eye in a subject, the method comprising determining whether or not the eye contains one or more high risk drusen. In some embodiments the method comprises determining the number, size, and/or volume of high risk drusen in the eye. In some embodiments determining whether or not the eye contains at least one high risk drusen comprises determining whether there is complement activation in or in close proximity to a druse. In some embodiments determining whether or not the eye contains one or more high risk drusen comprises determining whether there is inflamed endothelium underlying or in close proximity to one or more drusen.

In some aspects, the invention provides a method of determining risk of developing geographic atrophy (GA) or neovascular age-related macular degeneration (AMD) in a human subject, the method comprising detecting the presence of one or more high risk drusen in an eye of the subject, wherein the presence of one or more high risk drusen indicates increased risk of developing GA or neovascular AMD and the absence of high risk drusen indicates decreased risk of developing GA or neovascular AMD.

In some embodiments the subject has early AMD or intermediate AMD and the presence of one or more high risk drusen indicates increased risk of developing GA or neovascular AMD and the absence of high risk drusen indicates decreased risk of developing GA or neovascular AMD. In some embodiments the presence of one or more high risk drusen indicates increased risk of developing GA involving the fovea.

In some embodiments, any of the methods may comprise determining the number, size, and/or volume of drusen in at least one eye of the subject.

In some embodiments, any of the methods may comprise determining the number, size, and/or volume of high risk drusen in at least one eye of the subject.

In some aspects, the invention provides a method of identifying a subject at increased risk of development or progression of AMD, the method comprising: detecting an increased level of eye-derived extracellular vesicles (EVs) in a body fluid of the subject, wherein an increased level of said exosomes is indicative that the subject is at increased risk of development or progression of AMD. In some embodiments the EVs comprise exosomes. In some embodiments the eye-derived EVs, e.g., exosomes, are identified at least in part based on an eye-specific cellular marker. In some embodiments the eye-specific cellular marker comprises an opsin.

In some aspects, the invention provides a method of identifying a subject at increased risk of development or progression of AMD, the method comprising: detecting an increased level of a Th17 biomarker or Th17 cells in a subject or in a body fluid of the subject, wherein an increased level of said Th17 biomarker or Th17 cells is indicative that the subject is at increased risk of development or progression of AMD. In some embodiments the Th17 biomarker is a Th17-associated cytokine.

In some embodiments, a subject has at least one genetic risk factor for AMD, wherein the genetic risk factor optionally comprises at least one allele of a gene that encodes a complement component or complement regulatory protein, wherein the allele is associated with an increased risk of AMD.

In some embodiments any of the methods may comprise obtaining a genotype of the subject with respect to one or more alleles associated with an increased or decreased risk of AMD. In some embodiments any of the methods may comprise assessing the subject for presence or absence of one or more alleles associated with increased or decreased risk of developing a complement-mediated disorder.

In some embodiments any of the methods may comprise assessing the subject for presence of one or more alleles associated with increased or decreased risk of developing AMD, wherein the one or more alleles optionally comprises an allelic variation in a gene encoding CFH, CFB, C3, HTRA1, LOC387715, LIPC, CETP, ABCA1, TIMP3, or COL8A1.

In some embodiments any of the methods may comprise classifying a druse, multiple drusen, a group or pattern of drusen, eye, or subject into a risk category or estimating a likelihood, wherein the classifying or estimating is based at least in part on a demographic, environmental, or genetic risk factor for AMD.

In some embodiments any of the methods may comprise administering a therapeutic agent to the subject.

In some embodiments any of the methods may comprise comprises administering a complement inhibitor to the subject, e.g., by intravitreal injection.

In some embodiments the complement inhibitor is a compstatin analog, e.g., any compstatin analog described herein.

In some embodiments a medical imaging system comprising a device capable of detecting complement activation or inflamed endothelium in the eye of a subject is provided. In some embodiments the device comprises a scanning laser ophthalmoscope or camera. In some embodiments the imaging system is capable of capturing a fluorescence image, capturing an image of drusen, and identifying high risk drusen based on proximity of the drusen to regions of complement activation or inflamed endothelium. In some embodiments the medical imaging system is used in any of the methods.

In some aspects, any of the compositions or agents useful in performing the methods may be provided as kits.

DETAILED DESCRIPTION OF CERTAIN EMBODIMENTS

I. Glossary

Descriptions and information relating to certain terms used in the present disclosure are collected here for convenience.

"Analyte" means any entity, particularly a chemical, biochemical or biological entity to be assessed, e.g., whose presence, amount (e.g., concentration or mass), activity, composition, or other property(ies) is/are to be detected, measured, quantified, evaluated, analyzed, etc. An "analyte" can be a single molecular species or can be composed of multiple distinct molecular species.

The term "antibody" refers to an immunoglobulin or a portion thereof containing at least a portion of an immunoglobulin domain capable of binding to an antigen. An antibody may be derived from natural sources, or partly or wholly synthetically produced (e.g., using recombinant DNA techniques, chemical synthesis, etc.). An antibody can be of any species, e.g., human, rodent, rabbit, goat, chicken, camelid, etc. An antibody may be a member of any immunoglobulin class, including any of the human classes: IgG, IgM, IgA, IgD, and IgE. As used herein, the term "antibody" encompasses antibody fragments such as an Fab, F(ab')$_2$, scFv (single-chain variable), or other fragment that retains an antigen binding site, including recombinantly produced or chemically synthesized fragments, e.g., scFv molecules produced recombinantly and/or using chemical synthesis. scFv refers to a protein comprising the variable regions of the heavy chain (VH) and the light chain (VL) of an antibody, which may be joined by a linker. See, e.g., Allen, T., Nature Reviews Cancer, Vol. 2, 750-765, 2002, and references therein. Single domain antibodies, e.g., nanobodies, and diabodies, are encompassed by the term antibody. An antibody may be polyclonal or monoclonal, though for purposes of the present invention monoclonal antibodies are generally preferred. In certain embodiments a F(ab)$_2$ or Fab fragment, scFv, or single domain antibody is used while in other embodiments antibodies comprising an Fc domain are used. Monovalent, bivalent or multivalent antibodies can be used. In some embodiments an antibody is bispecific. An antibody may be a chimeric antibody in which, for example, a variable domain of rodent origin is fused to a constant domain of human origin, thus retaining the specificity of the rodent antibody. If parts of the variable domains are also replaced by human portions, the antibody may be referred to as "humanized". Methods for producing antibodies that specifically bind to virtually any molecule of interest are known in the art. For example, monoclonal or polyclonal antibodies can be purified from natural sources, e.g., from blood or ascites fluid of an animal that produces the antibody (e.g., following immunization with the molecule or an antigenic fragment thereof) or can be produced recombinantly, in cell culture. Methods of generating antibody fragments, e.g., by digestion, disulfide reduction, or synthesis are known in the art. Antibodies, e.g., fully human monoclonal antibodies, may be identified using phage display (or other display methods such as yeast display, ribosome display, bacterial display). Display libraries, e.g., phage display libraries, are available (and/or can be generated by one of ordinary skill in the art) that can be screened to identify an antibody that binds to an antigen of interest, e.g., using panning. See, e.g., Sidhu, S. (ed.) *Phage Display in Biotechnology and Drug Discovery* (Drug Discovery Series; CRC Press; 1$^{st}$ ed., 2005; Aitken, R. (ed.) *Antibody Phage Display: Methods and Protocols* (Methods in Molecular Biology) Humana Press; 2nd ed., 2009. In some embodiments, a human antibody or portion thereof is generated, for example, in rodents whose genome incorporates human immunoglobulin genes, or using a display technology such as phage display, etc. The heavy and light chain of IgG immunoglobulins (e.g., rodent or human IgGs) contain four framework regions (FR1 through FR4) separated respectively by three complementarity determining regions (CDR1 through CDR3). The CDRs, particularly the CDR3 regions, especially the heavy chain CDR3, are largely responsible for antibody specificity. In some embodiments, a humanized antibody is generated by "grafting" one or more CDR sequences or portions thereof from a non-human species (e.g., mouse) into a human antibody sequence. It will be appreciated that the alterations to antibody sequence that are involved in the humanization process are effected through techniques at the nucleic acid level, e.g., standard recombinant nucleic acid techniques. In some embodiments only the specificity determining residues (SDRs), the CDR residues that are most crucial in the antibody-ligand interaction, are grafted. The SDRs may be identified, e.g., through use of a database of the three-dimensional structures of the antigen-antibody complexes of known structures or by mutational analysis of the antibody-combining site. In some embodiments an approach is used that involves retention of more CDR residues, namely grafting of so-called "abbreviated" CDRs, the stretches of CDR residues that include all the SDRs. In some embodiments, humanization retains those murine framework residues deemed essential for the integrity of the antigen-combining site. See, e.g., Kashmiri, S V, Methods. 36(1):25-34 (2005), for further discussion of SDR grafting. See, e.g., Almagro J C, Fransson J. Humanization of antibodies. *Front Biosci.* 13:1619-33 (2008) for review of various methods of obtaining humanized antibodies. In some embodiments, a monoclonal antibody is produced using recombinant methods in suitable host cells, e.g., prokaryotic or eukaryotic host cells. Methods for production and purification of recombinant proteins are well known to those of ordinary skill in the art.

The terms "approximately" or "about" in reference to a number generally include numbers that fall within ±10%, in some embodiments ±5%, in some embodiments ±1%, in some embodiments ±0.5% of the number unless otherwise stated or otherwise evident from the context (except where such number would impermissibly exceed 100% of a possible value). In any embodiment in which a numerical value is prefaced by "about", an embodiment in which the exact value is recited is provided. Where an embodiment in which a numerical value is not prefaced by "about" is provided, an embodiment in which the value is prefaced by "about" is also provided. Where a range is preceded by "about", embodiments are provided in which "about" applies to the lower limit and to the upper limit of the range or to either the lower or the upper limit, unless the context clearly dictates otherwise.

"Cellular marker" refers to a molecule (e.g., a protein, RNA (e.g., mRNA or microRNA), DNA, lipid, carbohydrate, or small molecule), complex, or portion thereof, the presence and/or level of which in or on a cell (e.g., at least partly exposed at the cell surface) characterizes, indicates, or identifies one or more cell type(s), cell lineage(s), or tissue type(s) or characterizes, indicates, or identifies a particular state (e.g., a diseased or physiological state such as activated or not activated, apoptotic or non-apoptotic, etc.). It will be understood that cellular marker(s) may also characterize, indicate, or identify cell-derived material, such as extracellular vesicles (e.g., exosomes), membrane preparations, lysates, or other cell-derived material. A level may be described in a variety of different ways, e.g., high/low; +/−; numerically, etc. The presence, absence, or level of certain cellular marker(s) may indicate a particular physiological or diseased state of a patient, organ, tissue, or cell. It will be understood that multiple cellular markers may be assessed or used to, e.g., identify or isolate or target a cell type of interest, diagnose a disease, etc. In some embodiments between 1 and 10 cellular markers may be assessed, e.g., 1, 2, 3, 4, or 5. A cellular marker present on or at the surface of cells or cell-derived material, e.g., extracellular vesicles (e.g., exosomes), may be referred to as a "cell surface marker" (CSM). It will be understood that a CSM may be only partially exposed at the cell surface. In some embodiments a CSM or portion thereof is accessible to a specific binding agent present in the environment in which such cell or cell-derived material is located, so that the binding agent may be used to, e.g., identify, label, isolate, or target the cell or cell-derived material. In some embodiments a CSM is a protein at least part of which is located outside the plasma membrane of a cell. In some embodiments the protein is an integral membrane protein or peripheral membrane protein. In some embodiments the protein is a transmembrane protein. Examples of CSMs include CD molecules, receptors with an extracellular domain, channels, and cell adhesion molecules. A cellular marker may be cell type specific. A cell type specific marker is generally expressed or present at a higher level in or on (at the surface of) a particular cell type or cell types than in or on many or most other cell types (e.g., other cell types in the body or in an artificial environment) and/or is generally expressed or present at a higher level in or on (at the surface of) cell-derived material (e.g., extracellular vesicles, e.g., exosomes) derived from a particular cell type or cell types than in or on cell-derived material (e.g., cell-derived material of the same sort, e.g., extracellular vesicles, e.g., exosomes) derived from cells of many or most other cell types. In some cases a cell type specific marker is present at detectable levels only in or on a particular cell type of interest and/or in or on cell-derived material from cells of such cell type. However, as will be appreciated by those of ordinary skill in the art, useful cell type specific markers may not be and often are not absolutely specific for the cell type or cell-derived material of interest. A cellular marker, e.g., a cell type specific marker, may be present at levels at least 1.5-fold, at least 2-fold or at least 3-fold greater in or on the surface of a particular cell type than in a reference population of cells. In some embodiments a cellular marker, e.g., a cell type specific marker, may be present at levels at least 4-5 fold, between 5-10 fold, between 10-fold and 20-fold, between 20-fold and 50-fold, between 50-fold and 100-fold, or more than 100-fold greater than its average expression in a reference population. In some embodiments a reference population of cells is a mixture containing cells from multiple (e.g., 5-10; 10-20, or more) of different tissues or organs in approximately equal amounts. It will be understood that the afore-mentioned levels and ranges apply likewise to cellular markers, e.g., cell type specific markers, present on or in cell-derived materials, such as extracellular vesicles, e.g., exosomes. In general, the presence and/or level of a cellular marker may be determined using standard techniques such as hybridization-based methods (e.g., Northern blotting, hybridization to probes in solution or on a solid support such as oligonucleotide or cDNA microarrays, reverse transcription PCR (e.g., quantitative reverse transcription PCR), sequencing (e.g., RNA-Seq), immunological methods such as immunoblotting, immunohistochemistry, fluorescence detection following staining with fluorescently labeled antibodies (e.g., flow cytometry, spectroscopy, fluorescence microscopy), ELISA assays, similar methods using non-antibody ligands that specifically bind to the marker, protein microarray analysis, bead array assays (such as the Luminex xMAP technology or Cytometric Bead Array (CBA) system from BD Biosciences), liquid chromatography, mass spectrometry, etc. It will be appreciated that a probe or primer suitable for detecting a nucleic acid typically comprises a nucleic acid that is at least partly complementary to the nucleic acid to be detected. The probe or primer may be, e.g., between 8 and about 25, 30, 35, 40, 45, 50, or 60 nucleotides long, in various embodiments. Longer nucleic acids may be used in certain embodiments. The length and degree of complementarity may be selected as appropriate to provide sufficient specificity to distinguish a nucleic acid of interest from others that may be present in a sample. In some embodiments a probe or primer comprises a sequence that is perfectly complementary to at least 8, 10, 12, 15, 18, or 20 nucleotides of a nucleic acid to be detected or amplified.

A CSM, e.g., a cell type specific CSM, may be used to detect or isolate cells or cell-derived material or as a target in order to deliver an agent to cells. For example, the agent may be linked to a moiety that binds to a CSM. Suitable binding moieties include, e.g., antibodies or ligands, e.g., small molecules, aptamers, or polypeptides. Methods known in the art can be used to separate cells that express a cellular marker, e.g., a CSM, from cells that do not, if desired. In some embodiments a specific binding agent can be used to physically separate cells that express a CSM from cells that do not. In some embodiments, flow cytometry is used to quantify cells that express a cellular marker, e.g., a CSM, or to separate cells that express a cellular marker, e.g., a CSM, from cells that do not. For example, in some embodiments cells are contacted with a fluorescently labeled antibody that binds to the CSM. Fluorescence activated cell sorting (FACS) is then used to separate cells based on fluorescence. Such methods, among others, may be used to identify, detect, or isolate cell-derived materials.

A "complement component" or "complement protein" is a protein that is involved in activation of the complement system or participates in one or more complement-mediated activities. Components of the classical complement pathway include, e.g., C1q, C1r, C1s, C2, C3, C4, C5, C6, C7, C8, C9, and the C5b-9 complex, also referred to as the membrane attack complex (MAC) and active fragments or enzymatic cleavage products of any of the foregoing (e.g., C3a, C3b, C4a, C4b, C5a, etc.). Components of the alternative pathway include, e.g., factors B, D, and properdin. Components of the lectin pathway include, e.g., MBL2, MASP-1, and MASP-2. Complement components also include cell-bound receptors for soluble complement components, wherein such receptor mediates one or more biological activities of such soluble complement component following binding of the soluble complement component. Such receptors include, e.g., C5a receptor (C5aR), C3a receptor (C3aR), Complement Receptor 1 (CR1), Complement Receptor 2 (CR2), Complement Receptor 3 (CR3, also known as CD45), etc. It will be appreciated that the term "complement component" is not intended to include those molecules and molecular structures that serve as "triggers" for complement activation, e.g., antigen-antibody complexes, foreign structures found on microbial or artificial surfaces, etc.

A "complement-mediated disorder" is any disorder in which complement activation is known or suspected of being a contributing and/or at least partially causative factor in at least some subjects suffering from the disorder. "Disorder" is used interchangeably herein with "disease", "condition", and similar words to refer to any impairment of health or state of abnormal functioning of an organism, e.g., any state in which medical and/or surgical management is indicated or for which a subject appropriately seeks medical and/or surgical attention. Non-limiting examples of complement-mediated disorders include, but are not limited to, (i) various disorders characterized by hemolysis or hemolytic anemia such as atypical hemolytic uremic syndrome, cold agglutinin disease, paroxysmal nocturnal hemoglobinuria, transfusion reactions; (ii) transplant rejection (e.g., hyperacute or acute transplant rejection) or transplant dysfunction; (iii) disorders involving ischemia/reperfusion injury such as trauma, surgery (e.g., aneurysm repair), myocardial infarction, ischemic stroke; (iv) disorders affecting the respiratory system, such as asthma, chronic obstructive pulmonary disease (COPD), chronic rhinosinusitis, nasal polyposis; (v) disorders affecting the musculoskeletal system, such as arthritis, e.g., rheumatoid arthritis; (vi) ocular disorders such as age-related macular degeneration (AMD), diabetic retinopathy, glaucoma, uveitis; (vii) disorders affecting the skin, such as psoriasis; (viii) disorders affecting the nervous system, such as multiple scleroris, neuropathic pain; (ix) disorders affecting one or more glands, such as thyroiditis, type I diabetes. In some embodiments a complement-mediated disorder is an autoimmune disorder. In some embodiments an autoimmune disorder is characterized by production of autoantibodies against, e.g., modified self proteins. The listing of a particular disorder within a particular category is for convenience and is not intended to limit the invention. It will be understood that certain disorders could appropriately be listed in multiple categories and/or affect multiple body systems.

The term "complement activation pathway protease" (CAPP) refers to a complement component or convertase that catalyzes proteolytic cleavage ("cleaves") at least one complement component in one or more complement activation pathways. Examples of complement activation pathway proteases are C1s in its activated form, factor D, C3 convertase of the classical and lectin pathways (C4b2a), C3 convertase of the alternative pathway (C3bBb; C3bBbP), C5 convertase of the classical and lectin pathways (C4b2a3b), and C5 convertase of the alternative pathway (C3bBbC3b; C3bBbC3bP).

A "complement regulatory protein" is a protein involved in regulating complement activity. A complement regulatory protein may down-regulate complement activity by, e.g., inhibiting complement activation or by inactivating or accelerating decay of one or more activated complement proteins. Examples of complement regulatory proteins include C1 inhibitor, C4 binding protein, clusterin, vitronectin, CFH, factor I, and the cell-bound proteins CD46, CD55, CD59, CR1, CR2, and CR3.

The term "label" (also referred to as "detectable label") refers to any moiety that facilitates detection and, optionally, quantification, of an entity that comprises it or to which it is physically associated, e.g., attached. In general, a label may be detectable by, e.g., spectroscopic, photochemical, biochemical, immunochemical, electrical, optical, chemical, or other means. In some embodiments a detectable label produces an optically detectable signal (e.g., emission and/or absorption of light), which can be detected e.g., visually or using suitable instrumentation such as a light microscope, a spectrophotometer, a fluorescent microscope, a fluorescent sample reader, or a fluorescence activated cell sorter, a camera, or any device containing a photodetector. Labels that may be used in various embodiments include, e.g., organic materials (including organic small molecule fluorophores (sometimes termed "dyes"), quenchers (e.g., dark quenchers), polymers, fluorescent proteins); enzymes; inorganic materials such as metal chelates, colloidal metal, metal and semiconductor nanocrystals (e.g., quantum dots); compounds that exhibit luminescence upon enzyme-catalyzed oxidation such as naturally occurring or synthetic luciferins (e.g., firefly luciferin or coelenterazine and structurally related compounds); haptens (e.g., biotin, dinitrophenyl, digoxigenin); radioactive atoms (e.g., radioisotopes such as $^3$H, $^{14}$C, $^{32}$P, $^{33}$P, $^{35}$S, $^{125}$I), stable isotopes (e.g., $^{13}$C, $^2$H); magnetic or paramagnetic molecules or particles, etc. Fluorescent dyes include, e.g., acridine dyes; BODIPY, coumarins, cyanine dyes, napthalenes (e.g., dansyl chloride, dansyl amide), xanthene dyes (e.g., fluorescein, rhodamines), and derivatives of any of the foregoing. Examples of fluorescent dyes include Cy3, Cy3.5, Cy5, Cy5.5, Cy7, Alexa® Fluor dyes, DyLight® Fluor dyes, FITC, TAMRA, Oregon Green dyes, Texas Red, to name but a few. Fluorescent proteins include green fluorescent protein (GFP), blue, sapphire, yellow, red, orange, and cyan fluorescent proteins and fluorescent variants such as enhanced GFP (eGFP), mFruits such as mCherry, mTomato, mStrawberry; R-Phycoerythrin, etc. Enzymes useful as labels include, e.g., enzymes that act on a substrate to produce a detectable substance, e.g., a colored, fluorescent, or luminescent substance. The enzyme may be, e.g., a dehydrogenase; an oxidoreductase such as a reductase or oxidase; a transferase that catalyzes the transfer of functional groups, such as an amino; carboxyl, methyl, acyl, or phosphate group; a hydrolase that may hydrolyzes a bond such as ester, glycoside, ether, or peptide bond; a lyase; an isomerase; or a ligase. Examples include luciferases, horseradish peroxidase, acid or alkaline phosphatase, beta-galactosidase, etc. Useful substrates of such enzymes are known in the art. For example, para-Nitrophenylphosphate (pNPP) is a chromogenic substrate for acid and alkaline phosphatase. When the detectable label is an alkaline phosphatase, a suitable substrate may be an umbelliferone derivative, e.g., 4-methyl-umbellipheryl phosphate. Tetramethyl benzidine (TMB) is a substrate for horseradish peroxidase. In some embodiments a label may be a hapten, such as adamantine, biotin, DNP, or carbazole. The hapten may allow the formation of an aggregate when contacted with a multi-valent antibody or (strep)avidin containing moiety. The hapten may also allow easy attachment of a molecule to which it is attached to a solid substrate. Luciferases include those from various insects (e.g., fireflies, beetles) and marine organisms (e.g., cnidaria such as *Renilla* (e.g., *Renilla reniformis*, copepods such as *Gaussia* (e.g., *Gaussia princeps*) or *Metridia* (e.g., *Metridia longa, Metridia pacifica*), and modified versions of the naturally occurring proteins. A wide variety of systems for labeling and/or detecting labels or labeled entities are known in the art. Numerous detectable labels and methods for their use, detection, modification, and/or incorporation into or conjugation to biomolecules such as nucleic acids or proteins, etc., are described in Iain Johnson, I., and Spence, M. T. Z. (Eds.), *The Molecular Probes® Handbook—A Guide to Fluorescent Probes and Labeling Technologies*. 11th edition (Life Technologies/Invitrogen Corp.) available online on the Life Technologies website and/or in Hermanson, G T., *Bioconjugate Techniques*, $2^{nd}$ ed., Academic Press (2008). Many labels are available as derivatives that are attached to or incorporate a reactive functional group so that the label can be conveniently conjugated to a biomolecule or other entity of interest that comprises an appropriate second functional group (which second functional group may either occur naturally in the biomolecule or may be introduced during or after synthesis). For example, an active ester (e.g., a succinimidyl ester), carboxylate, isothiocyanate, or hydrazine group can be reacted with an amino group; a carbodiimide can be reacted with a carboxyl group; a maleimide, iodoacetamide, or alkyl bromide (e.g., methyl bromide) can be reacted with a thiol (sulfhydryl); an alkyne can be reacted with an azide (via a click chemistry reaction such as a copper-catalyzed or copper-free azide-alkyne cycloaddition). Thus, for example, an N-hydroxysuccinide (NHS)-functionalized derivative of a fluorophore or hapten (such as biotin) can be reacted with a primary amine such as that present in a lysine side chain in a protein or in an aminoallyl-modified nucleotide incorporated into a nucleic acid during synthesis. A label may be directly attached to an entity or may be attached to an entity via a spacer or linking group, e.g., an alkyl, alkylene, aminoallyl, aminoalkynyl, or oligoethylene glycol spacer or linking group, which may have a length of, e.g., between 1 and 4, 4-8, 8-12, 12-20 atoms, or more in various embodiments. A label or labeled entity may be directly detectable or indirectly detectable in various embodiments. A label or labeling moiety may be directly detectable (i.e., it does not require any further reaction or reagent to be detectable, e.g., a fluorophore is directly detectable) or it may be indirectly detectable (e.g., it is rendered detectable through reaction or binding with another entity that is detectable, e.g., a hapten is detectable by immunostaining after reaction with an appropriate antibody comprising a reporter such as a fluorophore or enzyme; an enzyme acts on a substrate to generate a directly detectable signal). A label may be used for a variety of purposes in addition to or instead of detecting a label or labeled entity. For example, a label can be used to isolate or purify a substance comprising the label or having the label attached thereto. The term "labeled" is used herein to indicate that an entity (e.g., a molecule, probe, cell, tissue, etc.) comprises or is physically associated with (e.g., via a covalent bond or noncovalent association) a label, such that the entity can be detected. In some embodiments a detectable label is selected such that it generates a signal that can be measured and whose intensity is related to (e.g., proportional to) the amount of the label. In some embodiments two or more different labels or labeled entities are used or present in a composition. In some embodiments the labels may be selected to be distinguishable from each other. For example, they may absorb or emit light of different wavelengths. In some embodiments the labels may be selected to interact with each other. For example, a first label may be a donor molecule that transfers energy to a second label, which serves as an acceptor molecule through nonradiative dipole-dipole coupling as in resonance energy transfer (RET), e.g., Förster resonance energy transfer (FRET, also commonly known as fluorescence resonance energy transfer).

The term "characteristic distance", as used herein, refers to the distance of separation over which a donor can transfer its excitation energy to an acceptor through intramolecular coupling (e.g., the "Forster distance"). A typical range for a characteristic distance is between about 1 nm to about 10 nm.

The term "Forster Resonance Energy Transfer" or "FRET" (sometimes referred to as "fluorescence resonance energy transfer") refers to an energy transfer mechanism occurring between two molecules: a donor and an acceptor (i.e., a FRET pair) positioned within a range of about 1 to about 10 nanometers of each other wherein one member of the FRET pair (the donor) is excited within its excitation wavelength range and transfers energy to a second molecule (the acceptor) and the donor returns to the electronic ground state. The donor is a fluorophore. The acceptor may be a fluorophore or a non-emitting chromophore (dark quencher). A dark quencher is a substance that absorbs excitation energy from a fluorophore and dissipates the energy as heat; while a typical (fluorescent) quencher re-emits much of this energy as light.

The term "fluorophore", as used herein, refers to a compound, e.g., a small molecule, that, when excited by exposure to light of a particular wavelength, emits light at a different wavelength. Fluorophores may be described in terms of their emission spectrum, or "color." Green fluorophores (for example Cy3™, FITC, and Oregon Green™) may be characterized by their emission at wavelengths generally in the range of 515-540 nanometers. Red fluorophores (for example Texas Red™, Cy5™, and tetramethylrhodamine) may be characterized by their emission at wavelengths generally in the range of 590-690 nanometers. Near infrared (NIR) fluorophores (for example Cy5.5™ Cy7™ or Dylight™750 (Thermo-Fisher-Scientific, Waltham, Mass.)) may be characterized by their emission at wavelengths generally in the range of 690-900 nanometers. Emission spectrum, absorption maximum, and/or emission maximum are also of use for purposes of description. The term "fluorogenic composition" refers to a composition that comprises at least one fluorophore. A "composition" as used herein may be composed of a single constituent or may contain two or more constituents. Fluorophores and quenchers (whether fluorophores or dark quenchers) are sometimes referred to herein as "dyes". Examples of dyes include any of a variety of rhodamines, coumarins, porphyrins, anthraquinones, anthrapyrazoles, perylenequinones, xanthenes, cyanines, acridines, phenoxazines, phenothiazines, and derivatives thereof.

The term "quenching" refers to any process that decreases the fluorescence intensity of a given substance. Quenching may entail the partial or full absorption of energy emitted by a fluorescent donor. The energy may be emitted by the donor in the form of light (by photon emission) or transferred between the donor and the acceptor nonradiatively (without absorption or emission of photons).

The term "spectral overlap", as used herein, generally refers to the range of values where the emission spectrum (i.e., the amount of electromagnetic radiation of each frequency that a donor molecule or substance emits when it is excited) of a donor overlaps the absorption spectrum of an acceptor (i.e., fraction of incident electromagnetic radiation absorbed by the acceptor at each frequency over a range of frequencies).

"Dequenching", as used herein, refers to the increase in fluorescence emission due to the decrease or absence of a FRET partner or change in characteristic distance. Thus, dequenching may occur, for example, when there is increase in distance between a donor-acceptor pair resulting in increased fluorescence emission.

"Linked", as used herein with respect to two or more moieties, means that the moeities are physically associated or connected with one another to form a molecular structure that is sufficiently stable so that the moieties remain associated under the conditions in which the linkage is formed and, preferably, under the conditions in which the new molecular structure is used, e.g., physiological conditions. In certain preferred embodiments of the invention the linkage is a covalent linkage. In other embodiments the linkage is noncovalent. Moieties may be linked either directly or indirectly. When two moieties are directly linked, they are either covalently bonded to one another or are in sufficiently close proximity such that intermolecular forces between the two moieties maintain their association. When two moieties are indirectly linked, they are each linked either covalently or noncovalently to a third moiety, which maintains the association between the two moieties. In general, when two moieties are referred to as being linked by a "linking moiety" or "linking portion" (which terms are used interchangeably herein), the linkage between the two linked moieties is indirect, and typically each of the linked moieties is covalently bonded to the linking moiety. Two moieties may be linked using a "linker". A linker can be any suitable moiety that reacts with the entities to be linked within a reasonable period of time, under conditions consistent with stability of the entities (portions of which may be protected as appropriate, depending upon the conditions), and in sufficient amount, to produce a reasonable yield. Typically the linker will contain at least two functional groups, one of which reacts with a first entity and the other of which reacts with a second entity. It will be appreciated that after the linker has reacted with the entities to be linked, the term "linker" may refer to the part of the resulting structure that originated from the linker, or at least the portion that does not include the reacted functional groups. A linking moiety may comprise a portion that does not participate in a bond with the entities being linked, and whose main purpose may be to spatially separate the entities from each other. Such portion may be referred to as a "spacer".

"Nucleic acid" is used interchangeably with "polynucleotide" and encompasses polymers of nucleotides. "Oligonucleotide" refers to a relatively short nucleic acid, e.g., typically between about 4 and about 100 nucleotides (nt) long, e.g., between 8-60 nt or between 10-40 nt long. Nucleotides include, e.g., ribonucleotides or deoxyribonucleotides. In some embodiments a nucleic acid comprises or consists of DNA or RNA. In some embodiments a nucleic acid comprises or includes only standard nucleobases (often referred to as "bases"). The standard bases are cytosine, guanine, adenine (which are found in DNA and RNA), thymine (which is found in DNA) and uracil (which is found in RNA), abbreviated as C, G, A, T, and U, respectively. In some embodiments a nucleic acid may comprise one or more non-standard nucleobases, which may be naturally occurring or non-naturally occurring (i.e., artificial; not found in nature) in various embodiments. In some embodiments a nucleic acid may comprise one or more chemically or biologically modified bases (e.g., alkylated (e.g., methylated) bases), modified sugars (e.g., 2'-O-alkyribose (e.g., 2'-O methylribose), 2'-fluororibose, arabinose, or hexose), modified phosphate groups or modified internucleoside linkages (i.e., a linkage other than a phosphodiester linkage between consecutive nucleosides, e.g., between the 3' carbon atom of one sugar molecule and the 5' carbon atom of another), such as phosphorothioates, 5'-N-phosphoramidites, alkylphosphonates, phosphorodithioates, phosphate esters, alkylphosphonothioates, phosphoramidates, carbamates, carbonates, phosphate triesters, acetamidates, carboxymethyl esters and peptide bonds). In some embodiments a modified base has a label (e.g., a small organic molecule such as a fluorophore dye or hapten) covalently attached thereto. In some embodiments the label or a functional group to which a label can be attached is incorporated or attached at a position that is not involved in Watson-Crick base pairing such that a modification at that position will not significantly interfere with hybridization. For example the C-5 position of UTP and dUTP is not involved in Watson-Crick base-pairing and is a useful site for modification or attachment of a label. In some embodiments a "modified nucleic acid" is a nucleic acid characterized in that (1) at least two of its nucleosides are covalently linked via a non-standard internucleoside linkage (i.e., a linkage other than a phosphodiester linkage between the 5' end of one nucleotide and the 3' end of another nucleotide); (2) it incorporates one or more modified nucleotides (which may comprise a modified base, sugar, or phosphate); and/or (3) a chemical group not normally associated with nucleic acids in nature has been covalently attached to the nucleic acid. Modified nucleic acids include, e.g., locked nucleic acids (in which one or more nucleotides is modified with an extra bridge connecting the 2' oxygen and 4' carbon i.e., at least one 2'-O,4'-C-methylene-β-D-ribofuranosyl nucleotide), morpholinos (nucleic acids in which at least some of the nucleobases are bound to morpholine rings instead of deoxyribose or ribose rings and linked through phosphorodiamidate groups instead of phosphates), and peptide nucleic acids (in which the backbone is composed of repeating N-(2-aminoethyl)-glycine units linked by peptide bonds and the nucleobases are linked to the backbone by methylene carbonyl bonds). Modifications may occur anywhere in a nucleic acid. A modified nucleic acid may be modified throughout part or all of its length, may contain alternating modified and unmodified nucleotides or internucleoside linkages, or may contain one or more segments of unmodified nucleic acid and one or more segments of modified nucleic acid. A modified nucleic acid may contain multiple different modifications, which may be of different types. A modified nucleic acid may have increased stability (e.g., decreased susceptibility to spontaneous or nuclease-catalyzed hydrolysis) or altered hybridization properties (e.g., increased affinity or specificity for a target, e.g., a complementary nucleic acid), relative to an unmodified counterpart having the same nucleobase sequence. In some embodiments a modified nucleic acid comprises a modified nucleobase having a label covalently attached thereto. Non-standard nucleotides and other nucleic acid modifications known in the art as being useful in the context of nucleic acid detection reagents, RNA interference (RNAi), aptamer, or antisense-based molecules for research or therapeutic purposes are contemplated for use in various embodiments of the instant invention. See, e.g., *The Molecular Probes® Handbook—A Guide to Fluorescent Probes and Labeling Technologies* (cited above), *Bioconjugate Techniques* (cited above), Crooke, S T (ed.) Antisense drug technology: principles, strategies, and applications, Boca Raton: CRC Press, 2008; Kurrcek. J. (ed.) *Therapeutic oligonucleotides*, RSC biomolecular sciences. Cambridge: Royal Society of Chemistry, 2008. A nucleic acid can be single-stranded, double-stranded, or partially double-stranded. An at least partially double-stranded nucleic acid can have one or more overhangs, e.g., 5' and/or 3' overhang(s). Where a nucleic acid sequence is disclosed herein, it should be understood that its complement and double-stranded form is also disclosed.

"Polypeptide", as used herein, refers to a polymer of amino acids, optionally including one or more amino acid analogs. A protein is a molecule composed of one or more polypeptides. A peptide is a relatively short polypeptide, typically between about 2 and 60 amino acids in length, e.g., between 8 and 40 amino acids in length. The terms "protein", "polypeptide", and "peptide" may be used interchangeably. Polypeptides used herein may contain amino acids such as those that are naturally found in proteins, amino acids that are not naturally found in proteins, and/or amino acid analogs that are not amino acids. As used herein, an "analog" of an amino acid may be a different amino acid that structurally resembles the amino acid or a compound other than an amino acid that structurally resembles the amino acid. A large number of art-recognized analogs of the 20 amino acids commonly found in proteins (the "standard" amino acids) are known. One or more of the amino acids in a polypeptide may be modified, for example, by the addition of a chemical entity such as a carbohydrate group, a phosphate group, a farnesyl group, an isofarnesyl group, a fatty acid group, a linker for conjugation, functionalization, or other modification, etc. Certain non-limiting suitable analogs and modifications are described in WO2004026328 and/or below. The polypeptide may be acetylated, e.g., at the N-terminus and/or amidated, e.g., at the C-terminus.

"Posterior segment of the eye" refers to the portion of the eye behind the lens, including the vitreous, choroid, and retina (including the macula).

As used herein, the term "purified" refers to agents that have been separated from most of the components with which they are associated in nature or when originally generated or with which they were associated prior to purification. In general, such purification involves action of the hand of man. Purified agents may be partially purified, substantially purified, or pure. Such agents may be, for example, at least 50%, 60%, 70%, 75%, 80%, 85%, 90%, 95%, 96%, 97%, 98%, 99%, or more than 99% pure. In some embodiments, a nucleic acid, polypeptide, or small molecule is purified such that it constitutes at least 75%, 80%, 85%, 90%, 95%, 96%, 97%, 98%, 99%, or more, of the total nucleic acid, polypeptide, or small molecule material, respectively, present in a preparation. In some embodiments, an organic substance, e.g., a nucleic acid, polypeptide, or small molecule, is purified such that it constitutes at least 75%, 80%, 85%, 90%, 95%, 96%, 97%, 98%, 99%, or more, of the total organic material present in a preparation. Purity may be based on, e.g., dry weight, size of peaks on a chromatography tracing (GC, HPLC, etc.), molecular abundance, electrophoretic methods, intensity of bands on a gel, spectroscopic data (e.g., NMR), elemental analysis, high throughput sequencing, mass spectrometry, or any art-accepted quantification method. In some embodiments, water, buffer substances, ions, and/or small molecules (e.g., synthetic precursors such as nucleotides or amino acids), can optionally be present in a purified preparation. A purified agent may be prepared by separating it from other substances (e.g., other cellular materials), or by producing it in such a manner to achieve a desired degree of purity. In some embodiments "partially purified" with respect to a molecule produced by a cell means that a molecule produced by a cell is no longer present within the cell, e.g., the cell has been lysed and, optionally, at least some of the cellular material (e.g., cell wall, cell membrane(s), cell organelle(s)) has been removed and/or the molecule has been separated or segregated from at least some molecules of the same type (protein, RNA, DNA, etc.) that were present in the lysate.

A "sample" may be any biological specimen. In some embodiments a sample comprises a body fluid such as blood, saliva, or urine. In some embodiments a sample comprises cells, tissue, or cellular material (e.g., material derived from cells, such as a cell lysate or fraction thereof or extracellular vesicles). A sample may be obtained from (i.e., originates from, was initially removed from) a subject. Methods of obtaining samples are known in the art and include, e.g., collecting body fluids such as blood (e.g., via a peripheral blood draw), saliva, or urine. In some embodiments a sample contains at least some intact cells at the time it is removed from a subject. A sample may be subjected to one or more processing steps after having been obtained from a subject and/or may be split into one or more portions. For example, in some embodiments a sample comprises plasma or serum or a fraction thereof obtained from a blood sample that has been processed to obtain such plasma or serum or fraction. Processing may include isolating or purifying one or more components, amplifying one or more components, lysing cells, etc. The term "sample" encompasses processed samples, portions of samples, etc., and such samples are considered to have been obtained from the subject from whom the initial sample was removed. In some embodiments a sample may be obtained from an individual who has been diagnosed with or is suspected of having AMD. A sample, e.g., a sample used in a method or composition disclosed herein, may have been procured directly from a subject, or indirectly, e.g., by receiving the sample from one or more persons or entities that procured the sample directly from the subject, e.g., by performing a blood draw, biopsy, surgery, or other procedure on the subject, or from a person or entity that subsequently processed the sample so procured.

The term "small molecule" refers to an organic molecule that is less than about 2 kilodaltons (kDa) in mass. In some embodiments, the small molecule is less than about 1.5 kDa, or less than about 1 kDa. In some embodiments, the small molecule is less than about 800 daltons (Da), 600 Da, 500 Da, 400 Da, 300 Da, 200 Da, or 100 Da. Often, a small molecule has a mass of at least 50 Da. In some embodiments, a small molecule contains multiple carbon-carbon bonds and can comprise one or more heteroatoms and/or one or more functional groups important for structural interaction with proteins (e.g., hydrogen bonding), e.g., an amine, carbonyl, hydroxyl, or carboxyl group, and in some embodiments at least two functional groups. Small molecules often comprise one or more cyclic carbon or heterocyclic structures and/or aromatic or polyaromatic structures, optionally substituted with one or more of the above functional groups.

"Reactive functional groups" as used herein refers to groups including, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds, N-hydroxysuccinimide esters, maleimides, sulfhydryls, and the like. Methods to prepare each of these functional groups are well known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989, and Hermanson, G., Bioconjugate Techniques, $2^{nd}$ ed., Academic Press, San Diego, 2008).

"Protease cleavage site" refers to the site in a polypeptide that is cleaved by a protease. It will be understood that the protease typically catalyzes hydrolysis of a peptide bond between two amino acid residues.

"Specific binding" generally refers to a physical association between a target polypeptide (or, more generally, a target molecule) and a binding molecule such as an antibody or ligand. The association is typically dependent upon the presence of a particular structural feature of the target such as an antigenic determinant, epitope, binding pocket or cleft, recognized by the binding molecule. For example, if an antibody is specific for epitope A, the presence of a polypeptide containing epitope A or the presence of free unlabeled A in a reaction containing both free labeled A and the binding molecule that binds thereto, will reduce the amount of labeled A that binds to the binding molecule. It is to be understood that specificity need not be absolute but generally refers to the context in which the binding occurs. For example, it is well known in the art that numerous antibodies cross-react with other epitopes in addition to those present in the target molecule. Such cross-reactivity may be acceptable depending upon the application for which the antibody is to be used. In some instances such cross-reactivity may be useful, such as if it is desired to detect, isolate, or target any of multiple molecules that have similar or at least in part identical sequence or structure. One of ordinary skill in the art will be able to select antibodies or ligands having a sufficient degree of specificity to perform appropriately in any given application (e.g., for detection of a target molecule, for therapeutic purposes, etc). It is also to be understood that specificity may be evaluated in the context of additional factors such as the affinity of the binding molecule for the target versus the affinity of the binding molecule for other targets, e.g., competitors. If a binding molecule exhibits a high affinity for a target molecule that it is desired to detect and low affinity for nontarget molecules, the antibody will likely be an acceptable reagent. Once the specificity of a binding molecule is established in one or more contexts, it may be employed in other, preferably similar, contexts without necessarily re-evaluating its specificity. In some embodiments, the affinity (as measured by the equilibrium dissociation constant, Kd) of two molecules that exhibit specific binding is $10^{-3}$ M or less, e.g., $10^{-4}$ M or less, e.g., $10^{-5}$ M or less, e.g., $10^{-6}$ M or less, $10^{-7}$ M or less, $10^{-8}$ M or less, or $10^{-9}$ M or less under the conditions tested, e.g., under physiological conditions. Testing may be performed using, e.g., surface plason resonance (e.g., Biacore technology), isothermal titration calorimetry, differential scanning calorimetry, or other art-accepted methods.

A "subject" according to the instant invention is typically a human, a non-human primate, or a lower animal (e.g., a mouse or rat). In some embodiments the subject expresses or contains at least some primate (e.g., human) complement component C3 and, optionally, one or more additional primate complement component(s). In some embodiments the subject is male. In some embodiments the subject is female. In some embodiments the subject is an adult, e.g., a human at least 18 years of age, e.g., between 18 and 100 years of age.

"Diagnose" as used herein refers to determining that a disease or feature of a disease is present or determining the severity or classifying a disease or feature of a disease. Diagnosing encompasses determining that a subject has or does not have an increased likelihood of developing a disease or of experiencing progression or rapid progression of a disease. In certain embodiments diagnosing comprises prognosis, i.e., predicting the likely course or outcome of a disease or a feature of a disease, which may take into consideration any treatment or approach used to alter or attempt to alter the course or outcome. Diagnose in some embodiments encompasses monitoring a subject in whom a disease or feature of disease has been detected. A "diagnostic agent" is any agent that may be administered to a subject to facilitate diagnosis or used ex vivo as a component of an assay to facilitate diagnosis. In some embodiments a diagnostic agent comprises a polypeptide, peptide, small molecule, nucleic acid, carbohydrate, polymer, lipid, nanoparticle, microparticle, nanbubble, or microbubble. In some embodiments a diagnostic agent comprises a label. In some embodiments a diagnostic agent is detectable from outside the body, e.g., non-invasively. In some embodiments a diagnostic agent is an imaging agent. The term "imaging agent" encompasses agents that may be administered to a subject to facilitate the acquisition of an image therefrom. An imaging agent may absorb and/or emit energy (e.g., after appropriate excitation) and/or may have intrinsic properties (e.g., density, magnetism) that allow it to be detected by a suitable detector. It will be understood that in some embodiments a diagnostic agent may be usable or used for one or more purposes in addition to or instead of diagnosis. It will also be understood that in some embodiments an imaging agent may be usable or used for one or more purposes in addition to or instead of imaging.

"Treating", as used herein in regard to treating a subject, refers to providing treatment, i.e, providing any type of medical or surgical management of a subject. The treatment can be provided in order to reverse, alleviate, inhibit the progression of, prevent or reduce the likelihood of a disease, or in order to reverse, alleviate, inhibit or prevent the progression of, prevent or reduce the likelihood of one or more symptoms or manifestations of a disease. "Prevent" refers to causing a disease or symptom or manifestation of a disease not to occur for at least a period of time in at least some individuals. Treating can include administering a compound or composition to the subject following the development of one or more symptoms or manifestations indicative of a disease, e.g., in order to reverse, alleviate, reduce the severity of, and/or inhibit or prevent the progression of the disease and/or to reverse, alleviate, reduce the severity of, and/or inhibit or one or more symptoms or manifestations of the disease. A compound or composition can be administered to a subject who has developed a disease, or is at increased risk of developing the disease relative to a member of the general population. A compound or composition can be administered to a subject who has developed a disease and is at increased risk of developing one or more particular symptoms or manifestations of the disease relative to other individuals diagnosed with the disease, or relative to the subject's typical or average risk for such symptom or manifestation. For example, the subject may have been exposed to a "trigger" that places the subject at increased risk or may have a genotype or other risk factor associated with increased risk. A compound or composition can be administered prophylactically, i.e., before development of any symptom or manifestation of the disease or before the subject would be diagnosed as meeting art-accepted criteria for having the disease. Typically in this case the subject will be at risk of developing the disease, e.g., relative to a member of the general population, optionally matched in terms of age, sex, and/or other demographic variable(s).

An "effective amount" or "effective dose" of an agent (or composition containing such agent) refers to the amount sufficient to achieve a desired biological and/or pharmacological effect and/or to allow detection of a particular analyte, disease, etc., e.g., when delivered to a cell or organism according to a selected administration form, route, and/or schedule. As will be appreciated by those of ordinary skill in this art, the absolute amount of a particular agent or composition that is effective may vary depending on such factors as the desired biological or pharmacological endpoint, the agent to be delivered, the target tissue, etc. Those of ordinary skill in the art will further understand that an "effective amount" may be contacted with cells or administered to a subject in a single dose, or through use of multiple doses, in various embodiments.

As used herein, "alkyl" refers to a saturated straight, branched, or cyclic hydrocarbon having from about 1 to about 22 carbon atoms (and all combinations and subcombinations of ranges and specific numbers of carbon atoms therein), with from about 1 to about 12, or about 1 to about 7 carbon atoms being preferred in certain embodiments of the invention. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, cyclohexyl, cyclooctyl, adamantyl, 3-methylpentyl, 2,2-dimethylbutyl, and 2,3-dimethylbutyl.

As used herein, "halo" refers to F, Cl, Br or I.

As used herein, "alkanoyl" refers to an optionally substituted straight or branched aliphatic acyclic residue having about 1 to 10 carbon atoms (and all combinations and subcombinations of ranges and specific number of carbon atoms) therein, e.g., from about 1 to 7 carbon atoms which, as will be appreciated, is attached to a terminal C=O group with a single bond (and may also be referred to as an "acyl group"). Alkanoyl groups include, but are not limited to, formyl, acetyl, propionyl, butyryl, isobutyryl, pentanoyl, isopentanoyl, 2-methyl-butyryl, 2,2-dimethoxypropionyl, hexanoyl, heptanoyl, octanoyl, and the like, and for purposes of the present invention a formyl group is considered an alkanoyl group. "Lower alkanoyl" refers to an optionally substituted straight or branched aliphatic acyclic residue having about 1 to about 5 carbon atoms (and all combinations and subcombinations of ranges and specific number of carbon atoms). Such groups include, but are not limited to, formyl, acetyl, propionyl, butyryl, isobutyryl, pentanoyl, isopentanoyl, etc.

As used herein, "aryl" refers to an optionally substituted, mono- or bicyclic aromatic ring system having from about 5 to about 14 carbon atoms (and all combinations and subcombinations of ranges and specific numbers of carbon atoms therein), with from about 6 to about 10 carbons being preferred. Non-limiting examples include, for example, phenyl and naphthyl.

As used herein, "aralkyl" refers to alkyl radicals bearing an aryl substituent and having from about 6 to about 22 carbon atoms (and all combinations and subcombinations of ranges and specific numbers of carbon atoms therein), with from about 6 to about 12 carbon atoms being preferred in certain embodiments. Aralkyl groups can be optionally substituted. Non-limiting examples include, for example, benzyl, naphthylmethyl, diphenylmethyl, triphenylmethyl, phenylethyl, and diphenylethyl.

As used herein, the terms "alkoxy" and "alkoxyl" refer to an optionally substituted alkyl-O— group wherein alkyl is as previously defined. Exemplary alkoxy and alkoxyl groups include methoxy, ethoxy, n-propoxy, i-propoxy, n-butoxy, and heptoxy.

As used herein, "carboxy" refers to a —C(=O)OH group.

As used herein, "alkoxycarbonyl" refers to a —C(=O) O-alkyl group, where alkyl is as previously defined.

As used herein, "aroyl" refers to a —C(=O)-aryl group, wherein aryl is as previously defined. Exemplary aroyl groups include benzoyl and naphthoyl.

The term "cyclic ring system" refers to an aromatic or non-aromatic, partially unsaturated or fully saturated, 3- to 10-membered ring system, which includes single rings of 3 to 8 atoms in size and bi- and tri-cyclic ring systems which may include aromatic 5- or 6-membered aryl or aromatic heterocyclic groups fused to a non-aromatic ring. These heterocyclic rings include those having from 1 to 3 heteroatoms independently selected from the group consisting of oxygen, sulfur, and nitrogen. In certain embodiments, the term heterocyclic refers to a non-aromatic 5-, 6-, or 7-membered ring or a polycyclic group wherein at least one ring atom is a heteroatom selected from the group consisting of 0, S, and N, including, but not limited to, a bi- or tri-cyclic group, comprising fused six-membered rings having between one and three heteroatoms independently selected from the group consisting of the oxygen, sulfur, and nitrogen. In some embodiments, "cyclic ring system" refers to a cycloalkyl group which, as used herein, refers to groups having 3 to 10, e.g., 4 to 7 carbon atoms. Cycloalkyls include, but are not limited to cyclopropyl, cyclobutyl, cyclopentyl, cyclohexyl, cycloheptyl and the like, which, is optionally substituted. In some embodiments, "cyclic ring system" refers to a cycloalkenyl or cycloalkynyl moiety, which is optionally substituted.

Typically, substituted chemical moieties include one or more substituents that replace hydrogen. Exemplary substituents include, for example, halo, alkyl, cycloalkyl, aralkyl, aryl, sulfhydryl, hydroxyl (—OH), alkoxyl, cyano (—CN), carboxyl (—COOH), —C(=O)O-alkyl, aminocarbonyl (—C(=O)NH$_2$), —N-substituted aminocarbonyl (—C(=O)NHR"), CF$_3$, CF$_2$CF$_3$, and the like. In relation to the aforementioned substituents, each moiety R" can be, independently, any of H, alkyl, cycloalkyl, aryl, or aralkyl, for example.

As used herein, "L-amino acid" refers to any of the naturally occurring levorotatory alpha-amino acids normally present in proteins or the alkyl esters of those alpha-amino acids. The term "D-amino acid" refers to dextrorotatory alpha-amino acids. Unless specified otherwise, all amino acids referred to herein are L-amino acids.

As used herein, an "aromatic amino acid" is an amino acid that comprises at least one aromatic ring, e.g., it comprises an aryl group.

As used herein, an "aromatic amino acid analog" is an amino acid analog that comprises at least one aromatic ring, e.g., it comprises an aryl group.

All articles, books, patent applications, patents, other publications, websites, and databases mentioned in this application are incorporated herein by reference. In the event of a conflict between the specification and any of the incorporated references the specification (including any amendments thereto) shall control. Unless otherwise specifically indicated, art-accepted abbreviations are used herein.

II. Methods of Identifying Eyes or Subjects at Increased Risk of AMD Development or Progression In some aspects, the invention provides methods of identifying an eye or subject having an increased risk of developing AMD or at increased risk of progression of AMD. In some embodiments, methods of identifying an eye or subjects having an increased risk of developing geographic atrophy (GA) or neovascular AMD are provided. In some embodiments, methods of identifying an eye or subject having increased risk of developing advanced AMD are provided. In some embodiments, methods of identifying an eye or subject having an increased risk of rapid progression of AMD are provided. In various embodiments progression is (i) progression from early AMD to intermediate AMD or from early AMD to advanced AMD; (ii) progression from early AMD or intermediate AMD to wet AMD or GA; (iii) progression from intermediate AMD to advanced AMD; (iv) progression from non-central GA (GA not involving the fovea) to central GA (GA involving the fovea); (v) development of GA; or (vi) development of wet AMD. In some embodiments rapid progression refers to progression within 6 months. In some embodiments rapid progression refers to progression within 1 year.

In some embodiments, the methods are based at least in part on analyzing drusen in an eye of a subject, e.g., a subject at risk of or suffering from AMD. Drusen are localized extracellular deposits of lipoproteinaceous material that accumulate between the retinal pigment epithelium (RPE) and the capillary network in the choroid (choriocapillaris), typically between the RPE and Bruch's membrane (a multilayered extracellular matrix complex that separates the RPE from the choriocapillaris). It will be appreciated that the term "druse" is sometimes used in the art to refer to a single such deposit (i.e., as a singular referent) while "drusen" is sometimes used in the art to refer to multiple such deposits (i.e., as a plural referent). As used herein, the term "drusen" should be understood to encompass a single "druse" or multiple "drusen" in various embodiments unless indicated to the contrary or clearly evident from the context. Also, reference to "a druse" should be understood to encompass reference to a single "druse" or multiple "drusen" in various embodiments unless indicated to the contrary or clearly evident from the context. Drusen are a clinical hallmark of AMD and are typically the earliest clinical finding in AMD. The presence, location, size, and number of drusen are factors used in the art for classifying AMD into stages and monitoring its progression. However, a few small drusen are commonly observed in the eyes of people over 40 years of age, most of whom do not go on to develop AMD.

Among other things, the present disclosure provides the recognition that the presence of one or more drusen in association with complement activation or in association with inflamed endothelium is correlated with an increased likelihood of development or progression of AMD. Complement is an arm of the immune system that plays an important role in defending the body against infectious agents. The complement system comprises more than 30 serum and cellular proteins that are involved in three major pathways, known as the classical, alternative, and lectin pathways. These pathways involve conversion of one or more complement components from an inactive state to a functionally active form in which, by themselves or as part of a complex, they activate downstream components of the pathway or serve as effectors. Conversion to an active form (activation) often occurs as a result of proteolytic cleavage. Complement activation pathways and components thereof are described in further detail below.

As used herein, a druse characterized by presence of complement activation in or in close proximity thereto is considered to be "associated with" complement activation, and a druse characterized by presence of inflamed endothelium underlying or in close proximity thereto is is considered to be "associated with" inflamed endothelium. A druse that is associated with complement activation, inflamed endothelium, or both is sometimes referred to herein as a "high risk druse". Thus in some embodiments a high risk druse is a druse in which complement activation is occurring or that is located in close proximity to a region where complement activation is occurring. In some embodiments a high risk druse is a druse that has inflamed endothelium underlying or in close proximity to it. In some embodiments a method comprises identifying one or more high risk drusen in a subject's eye. In some embodiments identifying a high risk druse comprises detecting complement activation in or in close proximity to a druse, wherein the presence of complement activation in or in close proximity to the druse indicates that the druse is a high risk druse. Methods useful for detecting complement activation in the eye are described below. In some embodiments identifying a high risk druse comprises detecting inflamed endothelium underlying or in close proximity to the druse, wherein the presence of inflamed endothelium underlying or in close proximity to the druse indicates that the druse is a high risk druse. Methods useful for detecting inflamed endothelium in the eye are described below. In some embodiments identifying a high risk druse comprises detecting complement activation in or in close proximity to a druse and detecting inflamed endothelium underlying a druse or in close proximity to the druse, wherein the presence of both complement activation in or in close proximity to the druse and inflamed endothelium underlying or in close proximity to the druse indicates that the druse is a high risk druse. As used herein, the phrase "in close proximity to a druse" refers to locations within a distance of 1 mm from the edge (outer limit) of a druse. In some embodiments a location "in close proximity to a druse" is within a distance of 10 microns, 25 microns, 50 microns, 100 microns, 250 microns, 500 microns, or 750 microns from the edge of a druse.

In some embodiments a region of complement activation in close proximity to a druse is located at least partly in Bruch's membrane or at least partly in the RPE layer. A region of inflamed endothelium underlying or in close proximity to a druse may be located in any layer of the choroidal vasculature or, in certain embodiments, in the retinal vasculature. In some embodiments a region of inflamed endothelium is in the choriocapillaris (the capillary layer adjacent to Bruch's membrane). In some embodiments a region of inflamed endothelium is in Sattler's layer (the layer of medium diameter blood vessels in the choroid). In some embodiments a region of inflamed endothelium is in Haller's layer (the outermost layer of the choroid containing larger diameter blood vessels). For purposes of determining whether a region of complement activation or a region of inflamed endothelium in the choroidal vasculature is in close proximity to a druse, the anterior-posterior dimension may be disregarded. For example, the anterior-posterior thickness of Bruch's membrane or any portion of the choroid or vessel wall between the inflamed endothelium and the druse may be disregarded. In other words, the distance between the edge of a druse and a region of complement activation or inflamed endothelium may be measured assuming that the region of complement activation or inflamed endothelium is located at the same anterior-posterior "depth" as the druse with respect to the retinal surface, i.e., disregarding the distance between the region of complement activation or inflamed endothelium and the druse along the anterior-posterior axis.

As used herein, the phrase "identifying a druse" encompasses determining that a druse is present in an eye of a subject. The phrase "identifying a high risk druse" encompasses determining that a high druse is present in an eye of a subject. The phrase "analyzing a druse" encompasses (i) locating the edge or measuring the size of a druse; (ii) determining the location of a druse with respect to one or more landmarks or structures in or deep to the retina (e.g., the fovea, macula, optic nerve head, optic disc, etc.); (iii) classifying a druse morphology as "hard" or "soft" (indistinct); (iv) determining whether complement activation is present in or in close proximity to a druse; and/or (v) determining whether inflamed endothelium is present underlying or in close proximity to a druse. In some embodiments a druse, e.g., a high risk druse, is analyzed to (i) locate its edge or determine its size or location; (ii) classify it as "hard" or as "soft" based on whether its edges are relatively well-delineated (hard) or relatively poorly delineated (soft, indistinct); (iii) determine the level of complement activation or the level of inflammation of endothelium in, underlying, or in close proximity to the druse. As used herein, the term "size" in reference to a druse, a region of complement activation, or a region of inflamed endothelium may refer, in various embodiments, to the diameter, the area, the volume, or any other dimension or set of dimensions that provide(s) an indication of the physical magnitude of the druse or region, in other words, any dimension or set of dimensions that provide(s) an indication of how large the druse or region is. Appropriate dimension(s) may be selected by one of ordinary skill in the art and may depend at least in part on the type of imaging modality used. Size may be used to compare drusen with other drusen or monitored over time. "Level" of complement activation or inflamed endothelium refers to a semi-quantitative or quantitative assessment of the degree, intensity, or strength of complement activation or inflammation. A level may be expressed using terms such as "high", "medium", "low", symbols (e.g., −, +, ++, +++), numbers, or any other suitable means.

In some embodiments a high risk druse may be classified or assigned a score based at least in part on the level of complement activation or the size of a region of complement activation in or in close proximity to the druse and/or based at least in part on the level of inflammation or the size of a region of inflamed endothelium underlying or in close proximity to the druse, wherein the classification or score is correlated with development or progression of AMD. For example, a druse that exhibits a high level of complement activation may be assigned a higher score (indicative of a greater likelihood of development or progression of AMD) than a druse that exhibits a low level of complement activation. A druse associated with a region of endothelium that exhibits intense inflammation may be assigned a higher score than a druse associated with a region of less intensely inflamed endothelium. In some embodiments a classification or score may be assigned to a high risk druse based at least in part on its size, morphology, location, or a combination of such features, wherein the classification or score is correlated with development or progression of AMD. In some embodiments drusen size, morphology, location, or a combination of such features is used. For example, in some embodiments a large high risk druse is assigned a higher score than a small high risk druse having about the same level of complement activation. In some embodiments a high risk druse located close to the fovea is assigned a higher score than an otherwise comparable high risk druse located further away from the fovea. In some embodiments drusen pattern (e.g., interdrusen spacing) is considered, e.g., whether drusen are clustered together or more widely scattered.

In some embodiments methods are provided for assessing an eye, e.g., for identifying or imaging high risk drusen in an eye. In some embodiments methods described herein make use of one or more image(s) of at least a portion of the fundus of an eye. Any of a variety of imaging modalities and/or imaging devices used in ophthalmology may be employed. In some embodiments one or more analog (film-based) images is obtained. In some embodiments one or more digital images is obtained. As used herein, "image" encompasses physical visual representations (e.g., photographs, images on display screens such as cathode ray tubes, light-emitting diode (LED) display, etc.) and numeric representations (e.g., binary representations), which may be stored on paper, on a computer-readable medium, any tangible or non-transitory medium, etc. An image may be a still image, series of images, or moving image (video) in various embodiments. In some embodiments a fundus camera is used. The fundus camera maybe an analog or digital camera. In some embodiments one or more en face images is obtained. For example, in some embodiments a druse is identified or analyzed based at least in part on color fundus photographs, e.g., stereoscopic color fundus photographs. The photographs may be taken using standard methods, such as those used in the Age-Related Eye Disease Study (AREDS) study (Age-Related Eye Disease Study Research Group. The Age-Related Eye Disease Study system for classifying age-related macular degeneration from stereoscopic color fundus photographs: AREDS report No. 6. Am J Ophthalmol 2001; 132: 668-681). In some embodiments a druse is identified or analyzed at least in part using scanning laser ophthalmoscopy. In some embodiments a druse is identified or analyzed at least in part using optical coherence tomography (OCT), e.g., spectral domain optical coherence tomography (SD-OCT) (see, e.g., Yehoshua Z, et al. Ophthalmic Surg Lasers Imaging. 2010; 41 Suppl:S6-S14, for a review of SD-OCT in imaging of AMD). Examples of OCT devices suitable for imaging drusen include the Stratus OCT and/or Cirrus HD-OCT (Carl Zeiss Meditec Inc, Dublin, Calif.) and the Spectralis OCT (Heidelberg Engineering, Heidelberg, Germany). In some embodiments an OCT fundus image (OFI) that represents an en face summary view of B-scans from an OCT dataset is generated. The OFIs can be used to register the SD-OCT datasets to fundus photos and to calibrate color fundus images so that correlation can be achieved between the retinal cross-sectional geometry seen on the OCT B-scans and retinal landmark(s) seen on en-face imaging. An example of methodology that can be used to automatically determine drusen area and volume using SD-OCT is described in Gregori, G., et al., Ophthalmology, 2011; 118(7): 1373-1379. In some embodiments SD-OCT and confocal scanning laser ophthalmoscopy (cSLO) are performed using a combined imaging instrument. For example, the Spectralis HRA+OCT (Heidelberg Engineering) offers SD-OCT as well as five different confocal scanning laser ophthalmoscope (cSLO) fundus imaging modalities: fluorescein angiography, ICG angiography, red-free imaging, infrared imaging, and blue laser autofluorescence. In some embodiments simultaneous SD-OCT and cSLO imaging are performed. In some embodiments drusen volume is determined using image-stabilized scanning laser ophthalmoscope or SD-OCT. In some embodiments choroid is imaged using enhanced depth imaging optical coherence tomography (EDI-OCT) (Spaide R F, et al., Am J Ophthalmol. 2008; 146(4):496-50, reviewed in Spaide, R F., Applications for OCT Enhanced Depth Imaging, Retina Today, September 2011, pp. 57-60). In some embodiments a scanning laser ophthalmoscope utilizes adaptive optics (AO-SLO).

In various embodiments a druse or the edge, size, morphology, or location of a druse or the boundary of a region in close proximity to a druse is identified or determined by a person, by a computer, or in part by a person and in part by a computer. In some embodiments a region of complement activation or a region of inflamed endothelium or the edge, size, morphology or the boundary of a region in close proximity to a druse or the location of a region of complement activation or a region of inflamed endothelium is identified or determined by a human, by a computer, or in part by a human and in part by a computer. A person involved in acquiring, examining, and/or interpreting images of the fundus may be, e.g., an ophthalmologist or other person of ordinary skill in the art of reading images of the fundus such as fundus photographs, fluorescein angiography images, OCT images, and/or other imaging modalities used in ophthalmology. In some embodiments an imaging device used to obtain an image of at least a portion of a fundus comprises or interfaces with software appropriate to identify a druse or to determine the edge, size, morphology, or location of a druse or the boundary of a region in close proximity to a druse and/or appropriate to identify a region of complement activation or a region of inflamed endothelium or to determine the edge, size, or location of a region of complement activation or a region of inflamed endothelium. In some embodiments the number, size, morphology, location, area, or volume of high risk drusen characterized by complement activation in or in close proximity thereto or characterized by inflamed endothelium underlying or in close proximity thereto is determined. In some embodiments at least two images are obtained, wherein a first image shows drusen and a second image shows regions of complement activation or inflamed endothelium. The first and second images may be overlaid or displayed simultaneously to facilitate identification or quantification of areas of overlap or close proximity.

In some embodiments the location of one or more landmarks or structures in the eye (e.g., the fovea, foveal center, macula, optic nerve head, optic disc, a blood vessel, etc.) is determined manually (i.e., by a human) or automatically (e.g., using appropriate computer software). In some embodiments the location of a druse, e.g., a high risk druse, is determined with respect to one or more landmarks or structures in the eye. In some embodiments a landmark may be used for purposes of image registration. Image registration refers to the process of aligning two or more images of the same scene (e.g., a region of the eye) so that common features overlap. Image registration facilitates examination of the same feature(s) of interest (e.g., drusen, regions of complement activation, regions of inflamed endothelium) across different images, which may have been obtained using different imaging modalities or different imaging conditions or at different time points.

In some embodiments the number of high risk drusen or the area or volume occupied by high risk drusen in an eye or a region of an eye is determined. In some embodiments the number of high risk drusen having at least a certain size or falling within a certain size range in an eye or a region of an eye is determined. For example, in some embodiments the number of small, intermediate sized, or large high risk drusen in an eye or a region of an eye is determined. In some embodiments a region of an eye is a circle centered on the center of the fovea. In some embodiments the circle has a diameter of 3 mm, 4 mm, 5 mm, 6 mm, 7 mm, 8 mm, 9 mm, 10 mm, or more. In some embodiments a region of an eye is within one third disc diameter (DD) of the center of the macula, within 1 DD of the center, or within 2 DD of the center. In some embodiments a larger number or area of high risk drusen in an eye or a region of an eye is indicative of an increased likelihood of development or progression of AMD. In some embodiments at least 2, 3, 4, 5, 6, 7, 8, 9, 10, 12, 15, 20, 25, or more drusen are identified, detected, analyzed, or classified.

In some embodiments, at least two images are captured with different imaging modalities, e.g., stereoscopic fundus photograph and SLO; SLO and OCT, etc. In some embodiments a first image depicts drusen and a second image depicts region(s) where complement activation is present, regions where inflamed endothelium is present, or both. In some embodiments the two or more images are overlaid so that drusen and region(s) where complement activation or inflamed endothelium is present can be viewed on the same image. It will be understood that the images may be overlaid digitally by manipulating the corresponding datasets. The data may be displayed as a false color image in which different colors may be assigned to regions having different levels of complement activation or different intensity of inflammation. For example, red may be used to depict areas of intense complement activation or intense inflammation while blue may be used to depict areas where complement activation or endothelial inflammation is low. In some embodiments at least two fluorescence images are captured following excitation at different wavelengths and/or by detecting emission at different wavelengths. In some embodiments a first wavelength may be used to excite or detect an imaging agent that reports on complement activation, and a second wavelength may be used to excite or detect an imaging agent that reports on endothelial inflammation. In some embodiments the total area of overlap between drusen and regions of complement activation or between drusen and regions of inflamed endothelium is determined.

In some embodiments, a method of providing prognostic, diagnostic, or treatment-relevant information comprises detecting one or more high risk drusen in an eye; and generating a prediction of the likelihood that the eye will develop AMD based at least in part on detecting the one or more high risk drusen. In some embodiments, a method of providing prognostic, diagnostic, or treatment-relevant information comprises detecting one or more high risk drusen in an eye; and generating a diagnosis or prediction of the likelihood that the eye will develop advanced AMD based at least in part on detecting the one or more high risk drusen. In some embodiments an eye does not meet criteria for AMD. The eye may be diagnosed as having "pre-AMD" if one or more high risk drusen or regions of complement activation or inflamed endothelium is present. In some embodiments, an eye has early AMD, and the method identifies the eye as being at increased risk of developing intermediate or advanced AMD. In some embodiments, an eye has early or intermediate AMD, and the method identifies the eye as being at increased risk of developing geographic atrophy. In some embodiments, an eye has early or intermediate AMD, and the method identifies the eye as being at increased risk of developing wet AMD. In some embodiments, the eye has early or intermediate AMD, and the method identifies the eye as being at increased risk of developing advanced AMD. In some embodiments a method comprises detecting one or more high risk drusen in an eye of the subject, and predicting the likelihood that the subject will develop advanced AMD within a given time period based at least in part on detecting the one or more high risk drusen. In some embodiments the time period is between 6 months and 5 years. In some embodiments the time period is 6 months or 1, 2, 3, 4, or 5 years. In some embodiments, for example, an eye or subject may be diagnosed as having at least a certain likelihood of developing AMD, GA, central GA, or wet AMD within a given time period. For example, an eye or subject may be predicted to develop AMD, GA, central GA, or wet AMD with a likelihood of at least 30%, at least 50%, at least 75%, within a given time period. One of ordinary skill in the art will appreciate that "predicting", "predicting the likelihood", and like terms typically refer to forecast of an increased or a decreased probability that a result, outcome, event, etc., of interest exists or will occur, e.g., when particular criteria or conditions are met, as compared with the probability that such result, outcome, or event, etc., exists or will occur when such criteria or conditions are not met. "Predicting", "predicting the likelihood", and like terms do not imply or require the ability to predict with 100% accuracy and do not imply or require the ability to provide a numerical value for a likelihood (although such value may be provided in some embodiments).

In some embodiments a method comprises detecting complement activation in an eye of a subject and predicting the likelihood that the eye will develop AMD based at least in part on detecting subretinal complement activation in the eye, wherein increased subretinal complement activation is indicative of an increased likelihood of development or progression of AMD. In some embodiments the method comprises comparing the level of complement activation with a suitable reference level, wherein if the level measured in the eye is increased as compared with the reference level, the eye has increased likelihood of development or progression of AMD. In some embodiments a reference level is the average level of complement activation found in healthy, age-matched control subjects. In some embodiments a reference level is a level that was previously determined for that particular eye. In some embodiments the complement activation is located between the RPE and the choriocapillaris. In some embodiments the complement activation is at least partly associated with one or more drusen. In some embodiments the complement activation is at least partly concentrated in relatively discrete regions. In some embodiments at least some of the discrete regions may be associated with one or more drusen. In some embodiments the complement activation is diffuse. In some embodiments the method comprises determining the size of one or more regions of complement activation and/or determining the intensity of one or more regions of complement activation.

In some embodiments a method comprises detecting inflamed endothelium in an eye of a subject and predicting the likelihood that the eye will develop AMD based at least in part on detecting inflamed endothelium in the eye, wherein presence of inflamed endothelium is indicative of an increased likelihood of development or progression of AMD. In some embodiments the inflamed endothelium is located in the choriocapillaris. In some embodiments the inflamed endothelium is at least partly associated with one or more drusen. In some embodiments the inflamed endothelium is at least partly concentrated in relatively discrete regions. In some embodiments at least some of the discrete regions may be associated with one or more drusen. In some embodiments the inflamed endothelium is diffuse. In some embodiments the method comprises determining the size of one or more regions of inflamed endothelium and/or determining the intensity of one or more regions of inflamed endothelium.

In certain aspects, as described further below, a method of assessing a subject having or suspected of having or being at risk of AMD comprises testing a body fluid of the subject for the presence of eye-derived extracellular vesicles, e.g., exosomes. In certain aspects, as described further below, a method of assessing a subject having or suspected of having or being at risk of AMD comprises testing a subject's eye or body fluid, e.g., blood, for presence of one or more Th17 biomarkers. In certain aspects, as described further below, a method of assessing a subject having or suspected of having or being at risk of AMD comprises testing a subject's eye or body fluid, e.g., blood, for presence of one or more macrophage activity markers or VEGF. In certain aspects, as described further below, a method of assessing a subject having or suspected of having or being at risk of AMD comprises testing eye-derived exosomes obtained from the subject for presence of VEGF, one or more Th17 biomarkers, or one or more activity markers.

In some embodiments of any aspect herein, an increased level (e.g., of complement activation, inflamed endothelium, eye-derived extracellular vesicles, Th17 biomarker) indicative of increased risk of developing AMD or progression of AMD or rapid progression of AMD is increased by at least 10%, 20%, 30%, 40%, 50%, 60%, 70%, 80%, 90%, 100%, 2-fold, 5-fold, 10-fold, 20-fold, 30-fold, 40-fold, 50-fold, or more, relative to a reference level, e.g., a level found in normal (apparently healthy) individuals not suffering from AMD. Optionally normal individuals are matched for one or more demographic variables such as age, ethnicity, etc. It will be appreciated that an appropriate reference level may be determined for a given test using particular reagents, protocols, equipment, etc. It will be appreciated that a range of levels may be present in normal individuals not suffering from AMD. In some embodiments a reference level is an upper limit of a normal range, where a "normal range" may be considered to be a range that would include 95% of values obtained from normal individuals not suffering from AMD or that would include 95% of the general population, in either case optionally matched for one or more demographic variables.

In various aspects, the invention provides a variety of AMD risk markers and methods of identification thereof. The term "AMD risk marker" refers to any molecule, complex, or structure, the presence or level or particular characteristics of which correlate with and/or are indicative of an increased risk that a subject will develop or will experience progression, e.g., rapid progression, of AMD. In certain embodiments a diagnostic workup for a subject having or suspected of having or being at risk of AMD comprises one, more than one, or all of the following: (a) assessing one or both of the subject's eye(s) for complement activation, inflamed endothelium, and/or high risk drusen; (b) assessing a subject's body fluid, e.g., blood, for presence of eye-derived EVs; (c) assessing a subject's eye or body fluid, e.g., blood, for one or more Th17 biomarkers; (d) assessing a subject's eye or body fluid, e.g., blood, for VEGF or one or more macrophage activity markers. Any of these approaches may be used individually or in combination in various embodiments, optionally together with other information such as genotypic information. In some embodiments a first test that comprises detecting an analyte (e.g., an eye-derived exosome, eye-derived cellular marker, Th17 biomarker) in a body fluid, e.g., blood (or in or on EVs isolated from a body fluid), is performed. If the test is "positive", i.e., the analyte is detected, e.g., at or above a certain level, a second test may be performed, such as a test that comprises detecting complement activation in vivo in the eye, detecting inflamed endothelium in the eye, and/or detecting high risk drusen. In some embodiments a first test that comprises detecting a Th17 biomarker in a body fluid, e.g., blood (or in or on EVs isolated from a body fluid), is performed. If the test is "positive", i.e., the analyte is detected, e.g., at or above a certain level, a second test may be performed, such as a test that comprises detecting eye-derived exosomes in a body fluid, detecting complement activation in vivo in the eye, detecting inflamed endothelium in the eye, and/or detecting high risk drusen. The various methods described herein may be performed in any sequence or combination. Such sequences and combinations are within the scope of the invention. The methods may be combined to yield an overall diagnostic method having a desired degree of specificity and/or sensitivity. In certain embodiments of any aspect herein, "detecting" may comprise quantifying.

In some embodiments a result, prediction, or other information obtained or derived by assessing an eye for high risk drusen, complement activation, or inflamed endothelium, or assessing a body fluid for eye-derived extracellular vesicles, or Th17 biomarkers, is provided to the subject or provided to or obtained by the subject's health care provider. The result, prediction, or other information may assist the subject in deciding whether to receive treatment or in selecting a particular treatment and/or may assist the health care provider in advising the subject, e.g., recommending or selecting a treatment or dose. For example, if a subject is determined to be at increased risk of developing AMD, GA, or advanced AMD in an eye, or to have at least a specified risk of developing AMD, GA, or advanced AMD in an eye within a given time period, the subject may elect to be treated with a complement inhibitor or a health care provider may advise or select or administer a complement inhibitor as a treatment. In some embodiments, detecting high risk drusen before the onset of AMD allows timely therapeutic intervention before damage has occurred. In some embodiments, detecting high risk drusen in a subject with early AMD or intermediate AMD indicates that initiation of therapy with a complement inhibitor is warranted, whereas a subject with early AMD or intermediate AMD but not having high risk drusen may continue to be monitored, e.g., at regular intervals, such as about every 3-6 months, about every 6-12 months.

In some embodiments the ability to detect complement activation in vivo may facilitate identification of triggers (e.g., infection, exposure) that result in complement activation. Identifying such triggers may allow them to be avoided or allow rapid therapeutic intervention following the trigger. The ability to detect complement activation in vivo may also facilitate determining beneficial or deleterious responses of the complement system to insults such as infection or diseases such as cancer, etc., which may allow better treatment.

In some embodiments the ability to detect complement activation in vivo provides new methods of assessing complement inhibitor efficacy and/or selecting appropriate doses or dosing intervals. For example, a complement inhibitor which is a candidate therapeutic agent may be administered to a subject in whom complement activation in vivo has been detected. The effect of the complement inhibitor on the complement activation is determined. In some embodiments, if the complement inhibitor effectively reduces or eliminates the complement activation at doses that are well tolerated by a subject, the complement inhibitor is likely to be beneficial in treating a complement-mediated disorder.

In some embodiments any of the methods described herein in relation to drusen may be applied to pseudodrusen in addition to or instead of drusen. As used herein "pseudodrusen" refers to subretinal drusen-like deposits located anterior to the retinal pigment epithelium (RPE), e.g., lying at least in part between the RPE and the interface of the inner and outer segments of the photoreceptors, or located deep to Bruch's membrane in the choroid. Pseudodrusen include those deposits referred to in the art as "reticular pseudodrusen" or "drusenoid deposits" in the art. As used herein, the term "high risk pseudodrusen" refers to a pseudodruse associated with complement activation or associated with inflamed endothelium. Thus in some embodiments an eye is assessed to determine whether complement activation is present in or in close proximity to a pseudodruse and/or to determine whether inflamed endothelium is present underlying or in close proximity to a pseudodruse. In some embodiments, a method of assessing the likelihood of development or progression of AMD in the eye of a subject comprises assessing the eye for the presence of one or more high risk pseudodrusen, wherein the presence of one or more high risk pseudodrusen is correlated with an increased likelihood of development or progression of AMD.

In some embodiments a method comprises predicting the likelihood of progression of an eye from early AMD to intermediate AMD. In some embodiments a method comprises predicting the likelihood of progression of an eye from intermediate AMD to advanced AMD. An eye may be classified as having no AMD, early AMD, intermediate AMD, or advanced AMD. A subject may be classified or diagnosed as having no AMD, early AMD, intermediate AMD, or advanced AMD in one or both eyes. If a subject is classified or diagnosed as having AMD of a particular stage without specifying whether one or both eyes are affected, it will be assumed that the classification or diagnosis reflects the condition of the more severely affected eye. For example, a subject with "advanced AMD" is assumed to have advanced AMD in at least one eye.

Methods of the invention may include providing a subject at risk of or suffering from an eye disorder characterized by age-related macular degeneration, choroidal neovascularization, retinal neovascularization, or any combination of these. Methods for diagnosis of eye disorders, e.g., AMD, are known in the art. Any suitable tests and criteria can be used to identify a subject at risk of or suffering from AMD. Visual acuity can be measured using, for example, a Snellen chart, a Bailey-Lovie chart, a decimal progression chart, a Freiburg visual acuity test, a measurement of minimum angle of resolution (MAR) etc. Metamorphopsia (visual distortion) may be measured using an Amsler chart. Contrast sensitivity may be measured using a Pelli-Robson chart. Diagnostic studies include, but are not limited to, standard opthalmologic examination of the fudus, stereo biomicroscopic examination of the macula, intravenous fundus fluorescein angiography, fundus photography, indocyanine green videoangiography, and OCT. Certain terms used in ophthalmology and/or clinical details relating to ophthalmology may be found in American Academy of *Ophthalmology* (American Academy of *Ophthalmology* Retina Panel. Preferred Practice Pattern® Guidelines. Age-Related Macular Degeneration. San Francisco, Calif.: American Academy of *Ophthalmology*, 2008 and/or in Gass J D M. Stereoscopic Atlas of Macular Diseases: Diagnosis and Treatment, 4th ed. St. Louis, Mo.: CV Mosby, 1997 or Ryan S J, Hinton D R, Schachat A P, Wilkinson C P, eds. Retina, 4th ed. St. Louis, Mo.: CV Mosby, 2005.

A subject may be considered at risk of developing AMD if he or she has one or more close relatives (e.g., parent, grandparent, sibling, cousin, uncle, aunt), who has received a diagnosis of AMD. Individuals who smoke and/or consume a high fat diet are also at increased risk. The incidence of AMD increases with age. Therefore, an individual over approximately 50 years of age, generally at least 60 or at least 70 years of age may be considered at increased risk in certain embodiments, e.g., in combination with one or more additional risk factors such as a genetic risk factor or smoking history. In certain embodiments a subject has one or more genetic polymorphisms associated with increased likelihood of developing AMD, some of which are noted above. In certain embodiments a method comprises determining that a subject has a genetic polymorphism that increases the risk of AMD. "Determining" as used here refers to establishing that a subject has a genetic polymorphism that increases the risk of AMD, either by performing or ordering a suitable test, or by receiving results of a test performed or ordered by another, wherein the test ascertains whether the subject has the polymorphism. Genetic polymorphisms associated with increased risk of AMD are known in the art. In some embodiments a genetic polymorphism is in the gene encoding CFH, CFB, C2, C3, HTRA1, LOC387715, CFHR1, CFHR3, APOE, LIPC, CETP, ABCA1, TIMP3, or COL8A1. In some embodiments the polymorphism alters the coding sequence of the complement-related protein. In some embodiments the polymorphism results in altered expression level of the complement-related protein. In some embodiments the polymorphism results in altered activity or localization of the complement-related protein. In some embodiments the polymorphism alters the electrophoretic mobility of the complement-related protein. "Polymorphism" as used herein encompasses any type of genetic variation. In some embodiments the polymorphism is a single nucleotide polymorphism (SNP). In some embodiments the polymorphism is selected from: polymorphisms (Tyr402His, rs1061170), rs2274700, rs1061147, and rs7535263 in the CFH gene. In some embodiments the polymorphism is selected from any polymorphism described in Li, M, et al., Nat Genet, 38:1049-54, 2006 (see, Tables 1 and 2); Gold, B., et al., Nat. Genet, 38: 458-62, 2006; Dinu, V., et al., Genetic Epidemiology, 31: 224-237, 2007 (see, e.g., Tables 3 and 5), Yates, J. R. W., N. Engl. J. Med., 357: 19-27, 2007 (see, e.g., Tables 2 and 3), Francis, P., et al., PLoS ONE. November 28; 2(11):e1197, 2007 (see, e.g., Tables 1 and 2 therein), wherein the polymorphism is associated with an increased or decreased susceptibility to AMD. In some embodiments the polymorphism is a deletion, e.g., CFHR1 deletion is associated with decreased risk of AMD. In general, a genetic test may comprise isolating DNA or RNA and determining the identity of one or more nucleotides, e.g., at a specified position. Determining may comprise sequencing, hybridizing to an allele-specific probe or primer, etc. Analysis of proteins, wherein the protein is altered as a result of a genetic polymorphism, may also be used.

In some embodiments early, intermediate, or advanced AMD are defined in accordance with the classification scheme used in the Age-Related Eye Diseases Study (AREDS) (The Age-Related Eye Disease Study Research Group. A randomized, placebo-controlled, clinical trial of high-dose supplementation with vitamins C and E, beta carotene, and zinc for age-related macular degeneration and vision loss: AREDS report number 8. Arch Ophthalmol 2001; 119:1417-36). The classification of AMD from the AREDS is summarized as follows:

No AMD (AREDS category 1) is characterized by no or few small drusen (<63 microns in diameter).

Early AMD (AREDS category 2) is characterized by presence of a combination of multiple small drusen, few intermediate drusen (63 to 124 microns in diameter), or RPE abnormalities.

Intermediate AMD (AREDS category 3) is characterized by presence of extensive intermediate drusen, at least one large druse (at least 125 microns in diameter), or geographic atrophy not involving the center of the macula (fovea).

Advanced AMD (AREDS category 4) is characterized by geographic atrophy involving the center of the macula (fovea) and/or neovascular macular degeneration. Neovascular macular degeneration is typically associated with manifestations of CNV and/or retinal or RPE detachment associated with subretinal serous fluid, exudates, and/or blood. Other manifestations of neovascular AMD may include retinal hard exudates, subretinal and sub-RPE fibrovascular proliferation, and/or disciform scar.

Other classification schemes, or modified forms of the AREDS scheme, may be used. For example, in some embodiments an eye exhibiting geographic atrophy is considered to have advanced AMD whether or not the fovea is involved.

In some embodiments, a medical imaging system is provided, the medical imaging system capable of being used to identify high risk drusen. In some embodiments the imaging system comprises a device capable of delivering light of appropriate wavelength to excite a fluorophore (e.g., to the eye) and/or capable of capturing an image resulting from light emitted by a fluorophore or other detectable label. In some embodiments computer-readable instructions on a computer-readable medium are provided, the computer-readable instructions to perform at least a portion of a method of identifying high risk drusen, e.g., to gather data or images and/or to analyze data or an image acquired by an imaging device so as to identify high risk drusen.

As will be appreciated by one of ordinary skill in the art, certain aspects of the present invention may make use of, or be embodied, for example, as a system, apparatus, method or computer program product. Accordingly, certain aspects may take the form of hardware, software, or embodiments combining software and hardware aspects that may all generally be referred to herein as a "system", e.g., a medical imaging system. In some embodiments a medical imaging system comprises image analysis functionality. Certain aspects may take the form of a computer program product embodied in any tangible medium (e.g., a non-transitory storage medium) having computer usable program instructions embodied in the medium. Any combination of one or more computer usable or computer readable medium(s) may be utilized in various embodiments. The computer-usable or computer-readable medium may be, for example but not limited to, an electronic, magnetic, optical, electromagnetic, infrared, or semiconductor system, apparatus, device. Examples of a computer-readable medium include the following: a hard disk, a random access memory (RAM), a read-only memory (ROM), an erasable programmable read-only memory (e.g., EPROM or Flash memory), a portable compact disc read-only memory (CDROM), a floppy disk, an optical storage device, or a magnetic storage device. A computer-usable or computer-readable medium may in some embodiments be paper or another suitable medium on which the program is printed or embodied, as the program can be electronically captured, for instance, via optical scanning of the paper or other medium (optionally employing optical character recognition), then compiled, interpreted, or otherwise processed in a suitable manner, if necessary, and then stored in a computer memory and/or executed by a computer processor. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therein. The computer usable program code may be transmitted using any appropriate medium, including but not limited to wireless, physical wires, wireline, optical fiber cable, etc.

It will be understood that a system may include various standard components such as one or more peripheral devices, e.g., one or more input devices (e.g., keyboard, mouse, etc.), one or more output devices (e.g., a display), data storage/memory component(s) (e.g., random access memory, read only memory), communications circuitry, etc. It will be understood that different users may employ computer systems having any of a wide variety of different components or configurations.

One or more components of a system may be distributed across one or more computer systems, one or more of which may be coupled to a communications network. For example, various embodiments may be distributed among one or more computer systems configured to provide a service (e.g., servers) to one or more client computers, or to perform a task as part of a distributed system. For example, various embodiments may be performed on a client-server system that includes components distributed among one or more server systems that perform various functions. These components may communicate over one or more communication networks using a communication protocol. For example, images may be acquired in a first location (e.g., a physician's office) and transmitted to a second location, where they may be processed, analyzed, evaluated, compared, stored, etc. References to a "network" or "communication network", unless otherwise indicated or specified, can include one or more intranets or the Internet.

In some embodiments any of the assessment, diagnostic, and/or treatment decision methods may be performed at least in part by one or more computers or other apparatus, which apparatus may comprise one or more computers or processors. In some embodiments any of the assessment, diagnostic, and/or treatment decision methods may be embodied or stored at least in part on a computer-readable medium having computer-executable instructions thereon.

In some embodiments one or more images or datasets or analysis thereof is stored in a database or electronic medical record.

Certain embodiments disclosed herein encompass the physical transformation of a substrate into at least two fragments when cleaved by a protease. Certain embodiments disclosed herein encompass the introducing of specific diagnostic agents into a subject, and, in some embodiments, the cleavage of, binding to, or physical interaction of such diagnostic agents to a molecule or structure in the subject and, in some embodiments, detection of such cleavage, binding, or physical interaction, such detection having a number of practical applications.

Any of the various methods, e.g., diagnostic methods, herein may include any one or more of the following steps: (a) administering a diagnostic agent to a subject; (b) detecting a diagnostic agent in a subject; (c) obtaining a sample from a subject; (d) processing a sample (e.g., by at least in part removing one or more components, separating one or more components from one or more other components, isolating or purifying one or more components, adding one or more substances thereto, transferring a sample from a first vessel or apparatus to a second vessel or apparatus; (e) contacting a sample with a reagent (e.g., by adding a reagent to a sample or adding a sample to a vessel or apparatus containing a reagent useful for detecting an analyte ("detection reagent")); (f) detecting a signal from or in a sample; (g) comparing a measurement with a reference value, and/or such other active steps as may be appropriate as will be apparent from the description herein. Any one or more steps may, where appropriate be performed at least in part by or using an appropriate apparatus or system. Samples may be obtained from a subject using conventional methods, such as those commonly used to obtain peripheral blood samples, urine samples, etc., for diagnostic purposes. In some embodiments a method may comprise directing another entity or individual to perform one or more steps of a method. In some embodiments such directing may comprise electronically ordering a diagnostic test. In some embodiments a method may comprise receiving a result of a step or method performed by another entity or individual. In some embodiments directing or receiving is performed electronically, e.g., using a computer.

In some embodiments a reference laboratory or reading center may receive a sample or dataset (the dataset may comprise image data and may, in some embodiments, be transmitted electronically). The reference laboratory or reading center may receive, optionally electronically, a request to perform an assay or evaluate an image for presence of complement activation, inflamed endothelium, or high risk drusen. The reference laboratory or reading center may perform the assay or evaluate the image and may report the result(s) to the requestor or as directed by the requestor. The requestor may be, e.g., a subject's health care provider or a person operating under direction of the subject's health care provider. In some embodiments at least a portion of a method may be performed as a service, e.g., for a fee, by, e.g., such a reference laboratory or reading center, which may optionally be accredited by a professional organization or government agency.

In some aspects, a method of preparing a subject for performance of a diagnostic procedure, e.g., an imaging procedure, is provided, the method comprising administering a diagnostic agent to the subject, wherein the diagnostic agent facilitates detection of complement activation in vivo. In some aspects, a method of preparing a subject for performance of a diagnostic procedure, e.g., an imaging procedure, is provided, the method comprising administering a diagnostic agent to the subject, wherein the diagnostic agent facilitates detection of inflamed endothelium, e.g., in the eye. In some aspects, a method of preparing a subject for performance of a diagnostic procedure, e.g., an imaging procedure, is provided, the method comprising administering a diagnostic agent to the subject, wherein the diagnostic agent facilitates detection of high risk drusen. The method may further comprise obtaining an image at least in part by detecting the diagnostic agent or a portion thereof in vivo. Suitable diagnostic agents are described herein.

In certain aspects, the invention provides methods of making the various diagnostic agents and compositions described herein.

III. Detecting Complement Activation In Vivo

In some aspects, the present invention provides compositions and methods useful for detecting complement activation in vivo (in a living subject). As noted above, complement activation can occur via three major pathways. The classical pathway is usually triggered by binding of a complex of antigen and IgM or IgG antibody to C1. C1 is a complex is composed of one molecule of C1q, two molecules of C1r, and two molecules of C1s, or $C1qr_2s_2$. The binding of C1q to IgM or IgG complexed with antigen leads to conformational changes in C1q, which leads to activation of C1r. C1r is a serine protease that cleaves C1s (another serine protease). Activated C1 (the $C1r_2s_2$ portion) cleaves C4 and C2 to produce C4a and C4b, in addition to C2a and C2b. C4b and C2a combine to form classical pathway C3 convertase (C4b2a), which cleaves C3 to form C3a and C3b. Binding of C3b to C3 convertase produces a C5 convertase (C4b2a3b).

The lectin pathway is initiated by binding of mannose-binding lectin (MBL) and MBL-associated serine protease (MASP) to carbohydrates. The MBL-1 gene (known as LMAN-1 in humans) encodes a type I integral membrane protein localized in the intermediate region between the endoplasmic reticulum and the Golgi. The MBL-2 gene encodes the soluble mannose-binding protein found in serum. In the human lectin pathway, MASP-1 and MASP-2 are involved in the proteolysis of C4 and C2, leading to a C3 convertase as described above for the classical pathway. For example, activated MASP-2 cleaves C4 and C2.

The alternative pathway is initiated by and amplified at, e.g., microbial surfaces and various complex polysaccharides. In this pathway, hydrolysis of C3 to $C3(H_2O)$, which occurs spontaneously at a low level (sometimes referred to as C3 tickover), leads to binding of factor B, which is cleaved by factor D, generating a fluid phase C3 convertase that activates complement by cleaving C3 into C3a and C3b. C3b binds to targets such as cell surfaces and forms a complex with factor B, which is then cleaved by factor D, resulting in alternative pathway C3 convertase (C3bBb). The C3bBb complex is stabilized by binding of factor P. Surface-bound C3 convertases (C3bBbP) cleave and activate additional C3 molecules, resulting in rapid C3b deposition in close proximity to the site of activation. C3b recruits additional molecules of factors B, D and P, leading to formation of additional C3 convertase, which in turn generates additional C3b. This process results in a cycle of C3 cleavage and C3 convertase formation that signicantly amplifies the response. Cleavage of C3 and binding of another molecule of C3b to the C3 convertase gives rise to a C5 convertase (C3bBbC3bP).

The C5 convertases cleave C5 to produce C5a and C5b. C5b then binds to C6, C7, and C8 to form C5b-8, which catalyzes polymerization of C9 to form the C5b-9 membrane attack complex (MAC). The MAC inserts itself into target cell membranes and causes cell lysis. Sub-lytic amounts of MAC on the membrane of cells may have a variety of deleterious consequences. C3a, C4a, and C5a are anaphylotoxins and, among other things, mediate multiple reactions in the acute inflammatory response. C3a and C5a are also chemotactic factors that attract immune system cells such as neutrophils and mast cells.

Complement activity is normally regulated in vivo by various mammalian proteins referred to as complement control proteins (CCPs) or regulators of complement activation (RCA) proteins (U.S. Pat. No. 6,897,290). These complement regulatory proteins normally serve to limit complement activation that might otherwise occur on cells and tissues of the mammalian, e.g., human host. Thus, "self" cells are normally protected from the deleterious effects that would otherwise ensue were complement activation to proceed unchecked on these cells. Complement regulatory proteins vary in ligand specificity and mechanism(s) of complement inhibition. They may accelerate the normal decay of convertases and/or function as cofactors for factor I, to enzymatically cleave C3b and/or C4b into smaller fragments. CCPs are characterized by the presence of multiple (typically 4-56) homologous motifs known as short consensus repeats (SCR), complement control protein (CCP) modules, or SUSHI domains, about 50-70 amino acids in length that contain a conserved motif including four disulfide-bonded cysteines (two disulfide bonds), proline, tryptophan, and many hydrophobic residues. The CCP family includes complement receptor type 1 (CR1; C3b:C4b receptor), complement receptor type 2 (CR2), membrane cofactor protein (MCP; CD46), decay-accelerating factor (DAF), complement factor H (fH), and C4b-binding protein (C4 bp). CD59 is a membrane-bound complement regulatory protein unrelated structurally to the CCPs. Further details regarding the complement system are found, e.g., in Kuby Immunology, 6th ed., 2006; Paul, W. E., *Fundamental Immunology*, Lippincott Williams & Wilkins; 6th ed., 2008; and/or Walport M J., Complement. First of two parts. *N Engl J Med.,* 344(14):1058-66, 2001.

Complement activation is a contributing or underlying pathological factor in a wide range of disorders, referred to herein as "complement-mediated disorders". Immunological methods such as ELISA assays can be used to detect various complement proteins or cleavage products resulting from complement activation in samples of body fluids such as blood. Such methods can be useful for purposes such as diagnosing complement protein deficiency states or determining that significant systemic complement activation has occurred in a subject. Immunological methods, e.g., immunohistochemistry, can be used to detect various complement proteins and cleavage products in tissue biopsy samples. The present disclosure encompasses the recognition that such assays have a number of shortcomings. For example, they offer limited ability to specifically assess complement activation occurring locally in a variety of tissues and organs such as the eye in living subjects.

In some aspects, the invention provides methods of detecting complement activation in the body of a living subject ("in vivo"). In some embodiments, the methods comprise detecting complement activation that occurs at a particular location in the body. In some embodiments complement activation is detected in the eye of a subject. In some embodiments complement activation is detected in or in close proximity to one or more drusen in the eye of a subject. In some embodiments, a druse is classified into a risk category based at least in part on detecting complement activation in or in close proximity to the druse. In some embodiments, a drusen pattern or group comprising multiple drusen is classified into a risk category based at least in part on detecting complement activation in or in close proximity to at least some of the drusen in the drusen pattern or group of drusen. In some embodiments the risk category is used to determine the likelihood that the subject will develop AMD or experience progression of AMD in the eye within a given time period. In certain embodiments compositions of use in performing the methods are described herein.

Complement activation can be considered to be occurring during a given time period at a particular location if at least one complement activation pathway protease (CAPP) is present and active during such time period at such location and/or if at least one complement effector is being produced during such time period at such location at levels greater than would result from spontaneous hydrolysis (e.g., normal C3 tickover). In some embodiments, methods of detecting complement activation comprise detecting an active complement activation pathway protease. An active complement activation pathway protease is a complement component or convertase present in a form in which it is capable of cleaving (catalyzing cleavage of) a substrate. In some embodiments activated C1s is detected. In some embodiments factor D is detected. In some embodiments C3 convertase of the classical and lectin pathways (C4b2a) and/or C3 convertase of the alternative pathway (C3bBb; C3bBbP) is detected. In some embodiments C5 convertase of the classical and lectin pathways (C4b2a3b) and/or C5 convertase of the alternative pathway (C3bBbC3b; C3bBbC3bP) is detected.

In some embodiments an active complement activation pathway protease is detected by detecting activity of the protease. In some embodiments, activity of a CAPP is detected by detecting cleavage of a CAPP substrate that takes place in vivo. In some embodiments a CAPP substrate is administered to a subject. Cleavage of the substrate is detected and serves as an indicator of the presence of an active CAPP and, therefore, of complement activation. In some embodiments the substrate is appropriately labeled so that its cleavage results in a detectable signal. The signal serves as an indicator of the presence of an active CAPP and, therefore, of complement activation. In some embodiments the magnitude of the signal serves as an indicator of the level of complement activation, e.g., the magnitude of the signal correlates with the number of substrate molecules cleaved, which correlates with the level of complement activation. In some aspects, the present invention provides CAPP substrates that are appropriately labeled to be useful to detect complement activation in vivo.

In some aspects, a substrate for a CAPP is any compound, e.g., any polypeptide, that may be acted upon by the CAPP, i.e., the CAPP may catalyze cleavage of the substrate. In some embodiments a substrate for a CAPP comprises a peptide that comprises a cleavage site for the CAPP. In some embodiments a substrate for a CAPP comprises a peptide that comprises a protease recognition sequence for the CAPP. "Protease recognition sequence" refers to an amino acid sequence that is recognized by a protease and specifies a site at which cleavage by the protease occurs. For example, the protease may require or prefer, in order for cleavage to occur, that specific positions with respect to a cleavage site are occupied by certain amino acids and/or that certain positions with respect to a cleavage site amino acids are not occupied by certain amino acids.

According to standard nomenclature, amino acid residues in a polypeptide that is a substrate of a protease are designated P1, P2, P3, P4, P5, etc., in the N-terminal direction from the bond that is cleaved by the protease while the residues in C-terminal direction from the cleaved bond are designated P1', P2', P3', P4', P5', etc., as shown below, where the cleavage site is indicated by a dagger (†).

Cleavage Site

P5-P4-P3-P2-P1†P1'-P2'-P3'-P4'-P5'

A protease recognition sequence may be defined by specifying the particular amino acids that are typically present and/or are typically absent at at least some of positions P5, P4, P3, P2, P1, P1', P2', P3', P4', and P5' in proteins that are substrates of the protease, e.g., physiological substrates or non-physiological substrates of the protease. A "physiological substrate" of a particular protease refers to a naturally occurring substrate of the protease that is cleaved by the protease in vivo under at least some conditions in the absence of intervention by man. A "physiological cleavage site" for a particular protease refers to a site that is normally cleaved by the protease in vivo under at least some conditions in the absence of intervention by man. A "non-physiological substrate" of a particular protease refers to a substrate that is not a physiological substrate of the protease. A non-physiological substrate may comprise the sequence of a naturally occurring protein or a non-naturally protein, e.g., a protein having a sequence invented by man. A "non-physiological cleavage site" for a particular protease refers to a site that is cleaved by the protease but that is not a physiological cleavage site. As will be appreciated by those of ordinary skill in the art, it is often the case the respective CAPP in each substrate. The amino acid immediately N-terminal to the cleavage site (i.e., P1) and the amino acid immediately C-terminal to the cleavage site (i.e., P1') are shown in bold font and underlined. It will be understood that C3 convertases of each pathway cleave at the same position in C3; C5 convertases of each pathway cleave at the same position in C5; and activated C1s and MASP2 cleave at the same position in C2 and at the same position in C4.

TABLE 1

Complement Activation Pathway Proteases and Examples of Substrates

| Complement Activation Pathway Protease | Substrate/Gene ID | Peptide Spanning Cleavage Site | SEQ ID NO: |
|---|---|---|---|
| Activated C1s (in C1r$^2$s$^2$) | C2 (Gene ID: 717) | GATNPTQKTKESLGRKIQIQRSGHL NLYLL | 70 |
| | C4A (Gene ID: 720) C4B (Gene ID: 721) | LRKKSRDKGQAGLQRALEILQEED LIDEDD | 71 |
| MASP2 | C2 (Gene ID: 717) | GATNPTQKTKESLGRKIQIQRSGHL NLYLL | 70 |
| | C4A (Gene ID: 720) C4B (Gene ID: 721) | LRKKSRDKGQAGLQRALEILQEED LIDEDD | 71 |
| | MASP2 (Gene ID: 10747) | CEPVCGLSARTTGGRIYGGQKAKP GDFPWQ | 72 |
| | C1 inhibitor (Gene ID: 710) | TGVEAAAASAISVARTLLVFEVQQ PFLFVLWDQQ | 73 |
| | Thrombin precursor (also called coagulation factor 2 or prothrombin; Gene ID: 2147) | GRTATSEYQTFFNPRTFGSGEADCG LRPLF | 74 |
| Factor D | Factor B (Gene ID: 629) | VDAEDGHGPGEQQKRKIVLDPSGS MNIYLV | 75 |
| C4b2a (classical pathway C3 convertase) | C3 (Gene ID: 718) | LRRQHARASHLGLARSNLDEDIIAE ENIVS | 76 |
| C3bBb (alternate pathway C3 convertase) | C3 (Gene ID: 718) | LRRQHARASHLGLARSNLDEDIIAE ENIVSR | 76 |
| C4b2a3b (classical pathway C5 convertase) | C5 (Gene ID: 727) | QLRANISHKDMQLGRLHMKTLLPV SKPEIR | 77 |
| C3bBbC3b (alternate pathway C5 convertase) | C5 (Gene ID: 727) | QLRANISHKDMQLGRLHMKTLLPV SKPEIR | 77 | that particular positions in a protease recognition sequence can be occupied by any of a number of different amino acids, which may share one or more properties such as similar size, charge, aromaticity, etc.

Methods of detecting complement activation in vivo encompass detecting any active complement activation pathway protease. Certain complement activation pathway proteases are listed in Table 1. Certain physiological substrates of each protease are listed in the second column from the left, along with Gene IDs of the human genes encoding these substrates from the "Gene" database of the National Center for Biotechnology (NCBI), available through Entrez at the NCBI website. The second column from the right in Table 1 shows the sequence of the 30 amino acid peptide that spans and is centered on the physiological cleavage site for One of ordinary skill in the art will, if desired, readily be able to obtain sequences of the respective human CAPP proteins and mRNA and those of numerous other species, e.g., rodents such as mouse, rat, rabbit; non-human primate such as rhesus monkey, etc., from public databases such as UniProt, RefSeq, Genbank, etc. For example, the Gene IDs of C3 for mouse, rat, and rhesus monkey are 12266 (*Mus musculus*), 24232 (*Rattus norvegicus*), and 703613 (*Macaca mulatta*) respectively. If desired the protein or mRNA sequences in the RefSeq database may be taken as reference sequences. For example, NM 000064.2 and NP 000055.2 may be used as reference sequences for human C5 mRNA and protein; NM 001735.2 and NP 001726.2 may be used as reference sequences for human C5 mRNA and protein. It will be understood that these sequences represent the precursor forms of the respective proteins, prior to removal of the signal sequence that directs secretion. It will also be understood that multiple isoforms and/or polymorphic variants of certain of these proteins exist and, in general, any isoform or variant comprising a protease recognition sequence for a CAPP of interest may be used in various embodiments. For example, C4A and C4B are C4B are isoforms of C4 encoded by two highly homologous genes. It will be understood that the sequences of the substrates from non-human species may differ slightly from those of the human sequences.

In some embodiments a substrate of a CAPP of use to detect complement activation comprises a peptide whose sequence comprises a portion of the sequence of a physiological substrate of the CAPP, wherein the portion of the sequence encompasses a physiological cleavage site for the CAPP. For example, in some embodiments the sequence comprises at least the 1, 2, 3, 4, 5, 6, 7, 8, 9, 10, 11, 12, 13, 14, 15, 16, 17, 18, 19 or 20 amino acids that are located immediately N-terminal to a physiological cleavage site for the CAPP in a physiological substrate of the CAPP. In some embodiments the sequence further comprises at least the 1, 2, 3, 4, 5, 6, 7, 8, 9, 11, 12, 13, 14, 15, 16, 17, 18, 19, or 20 amino acids that are located immediately C-terminal to a physiological cleavage site for the CAPP in a physiological substrate of the CAPP. In some embodiments the sequence spans the cleavage site, i.e., it comprises at least P1-P1'. In some embodiments the sequence comprises at least P2-P1, at least P2-P1-P1', at least P1-P1'-P2', at least P3-P2-P1, at least P2-P1-P P2', at least P3-P2-P1-P1', at least P1-P1'-P2'-P3', at least P4-P3-P2-P1, at least P4-P3-P2-P1-P1', at least P3-P2-P1-P1'-P2', at least P2-P1-P1'-P2'-P3', at least P1-P1'-P2'-P3'-P4', at least P4-P3-P2-P1-P1'-P2', at least P3-P2-P1-P1'-P2'-P3', at least P2-P1-P1'-P2'-P3'-P4', at least P4-P3-P2-P1-P1'-P2'-P3', at least P3-P2-P1-P1'-P2'-P3'-P4', or at least P4-P3-P2-P1-P1'-P2'-P3'-P4'.

In some embodiments a substrate of a CAPP of use to detect complement activation is between 5 and 600 amino acids long. In some embodiments a substrate is at least 8, 10, 12, or 15 amino acids long. In some embodiments a substrate is no more than 15, 20, 25, 30, 35, 40, 45, or 50 amino acids long. For example, in some embodiments the length of a substrate is between 10 and 20 amino acids, between 20 and 30 amino acids, or between 30 and 40 amino acids. In some embodiments a substrate is at least 80%, 85%, 90%, 95%, 96%, 97%, 98%, 99%, or more identical to a sequence at least 5, 10, 20, 30, 40, 50, 60, 70, 80, 90, 100, 125, 150, 175, 200, 250, 300, 350, 400, 450, 500, 500, or 600 amino acids long that spans a physiological cleavage site for a CAPP in a physiological substrate of the CAPP.

In some embodiments complement activation is measured by a method that comprises detecting activated C1s. Activated C1s cleaves C4 and C2 in the classical pathway. In some embodiments activated C1s is detected by detecting cleavage of a substrate for activated factor C1s. In some embodiments the substrate is a peptide substrate. In some embodiments a peptide substrate for C1s comprises a sequence of 2, 3, 4, 5, 6, 7, 8, 9, 12, 11, 12, 13, 14, 15, 16, 17, 18, 19, 20, 21, 22, 23, 24, 25, 26, 27, 28, 29, or 30 continuous amino acids of SEQ ID NO: 70 or SEQ ID NO: 71, wherein the sequence comprises the P1 residue of SEQ ID NO: 70 or SEQ ID NO: 71, respectively.

In some embodiments complement activation is measured by a method that comprises detecting MASP2. In some embodiments activated C1s is detected by detecting cleavage of a substrate for MASP2. In some embodiments the substrate is a peptide substrate. In some embodiments a peptide substrate for MASP2 comprises a sequence of 2, 3, 4, 5, 6, 7, 8, 9, 12, 11, 12, 13, 14, 15, 16, 17, 18, 19, 20, 21, 22, 23, 24, 25, 26, 27, 28, 29, or 30 continuous amino acids of SEQ ID NO: 70, SEQ ID NO: 71, SEQ ID NO: 72, SEQ ID NO: 73, or SEQ ID NO: 74, wherein the sequence comprises the P1 residue of SEQ ID NO: 70, SEQ ID NO: 71, SEQ ID NO: 72, SEQ ID NO: 73, or SEQ ID NO: 74, respectively.

In some embodiments complement activation is measured by a method that comprises detecting factor D. Factor D is a serine protease that cleaves factor B in the alternative pathway, yielding the noncatalytic Ba and the catalytic Bb. In some embodiments factor D is detected by detecting cleavage of a substrate for factor D. In some embodiments the substrate is a peptide substrate. In some embodiments a peptide substrate for factor D comprises a sequence of 2, 3, 4, 5, 6, 7, 8, 9, 12, 11, 12, 13, 14, 15, 16, 17, 18, 19, or 20 continuous amino acids of SEQ ID NO: 75, wherein the sequence comprises the P1 residue of SEQ ID NO: 75.

In some embodiments complement activation is measured by a method that comprises detecting C3 convertase. In some embodiments the method comprises detecting C3 convertases of both the classical and lectin pathway and the alternative pathway. In some embodiments detecting C3 convertase comprises detecting cleavage of a substrate of C3 convertase. In some embodiments the substrate is a peptide substrate. In some embodiments a peptide substrate of C3 convertase comprises a sequence of 2, 3, 4, 5, 6, 7, 8, 9, 12, 11, 12, 13, 14, 15, 16, 17, 18, 19, 20, 21, 22, 23, 24, 25, 26, 27, 28, 29, or 30 continuous amino acids of SEQ ID NO: 76, wherein the sequence comprises the P1 residue of SEQ ID NO: 76. For example, in some embodiments the peptide substrate comprises LARSNL (SEQ ID NO: 78); LARSNLD (SEQ ID NO: 79), LARSNLDE (SEQ ID NO: 80), LARSNLDED (SEQ ID NO: 81), LARSNLDEDI (SEQ ID NO: 82), LARSNLDEDII (SEQ ID NO: 83); GLARSNLD (SEQ ID NO: 84), GLARSNLDE (SEQ ID NO: 85), GLARSNLDED (SEQ ID NO: 86), GLARSNLDEDI (SEQ ID NO: 87), or GLARSNLDEDII (SEQ ID NO: 88). In some embodiments the sequence of the peptide substrate comprises any of SEQ ID NOS: 78-88 and further comprises an additional 1, 2, 3, 4, or 5 amino acids at the N-terminus and/or an additional 1, 2, 3, 4, or 5 amino acids at the C-terminus, wherein at least some of the additional amino acids are those found N-terminal or C-terminal, respectively, to SEQ ID NO: 78-88, respectively, as it appears within SEQ ID NO: 76. US Pat. Pub. No. 20080305504 discloses certain substrates of C3 convertase and their use, solely in vitro, to measure complement activation. In some embodiments of the present invention, such substrate(s) may be used in a composition or method for detecting or measuring complement activation in vivo.

In some embodiments complement activation is measured by a method that comprises detecting C5 convertase. In some embodiments the method comprises detecting C5 convertases of both the classical and lectin pathway and the alternative pathway. In some embodiments detecting C5 convertase comprises detecting cleavage of a substrate of C5 convertase. In some embodiments the substrate is a peptide substrate. In some embodiments a peptide substrate of C5 convertase comprises a sequence of 2, 3, 4, 5, 6, 7, 8, 9, 12, 11, 12, 13, 14, 15, 16, 17, 18, 19, 20, 21, 22, 23, 24, 25, 26, 27, 28, 29, or 30 continuous amino acids of SEQ ID NO: 77, wherein the sequence comprises the P1 residue of SEQ ID NO: 77. In certain embodiments the peptide substrate comprises LGRLHM (SEQ ID NO: 89); LGRLHMK (SEQ ID NO: 90); QLGRLHM (SEQ ID NO: 91); QLGRLHMK (SEQ ID NO: 92); LGRLHMKT (SEQ ID NO: 93); MQLG RLHM (SEQ ID NO: 94); MQLGRLHMK (SEQ ID NO: 95); DMQLGRLHM (SEQ ID NO: 96); DMQLGRLHMK (SEQ ID NO: 97).

In some embodiments the sequence of the peptide substrate comprises any of SEQ ID NOS: 89-97 and further comprises an additional 1, 2, 3, 4, or 5 amino acids at the N-terminus and/or an additional 1, 2, 3, 4, or 5 amino acids at the C-terminus, wherein at least some of the additional amino acids are those found N-terminal or C-terminal, respectively, to SEQ ID NO: 89-97, respectively, as it appears within SEQ ID NO: 77.

In some embodiments a peptide substrate comprises a sequence from rat or mouse C3, wherein the sequence contains that portion of rat or mouse C3 that is homologous with any of the peptides from human C3 described herein. The NCBI RefSeq protein accession number for mouse (*Mus musculus*) C3 is NP_033908.2. The NCBI RefSeq accession number of the protein is NP_058690.2. The GenBank accession number for cynomolgus monkey (*Macaca faciculata*) C3 obtained via conceptual translation from genome sequencing is EHH59117.1. (It will be understood that the numeral following the decimal point in the accession numbers refers to the current version number.) A portion of the sequences of human C3, rat C3, mouse C3, and cynomolgus monkey C3 from the afore-mentioned reference sequences, spanning the cleavage site for C3 convertase, is reproduced below, showing the alignment. The P1 and P1' amino acids in each sequence are in bold and underlined. SEQ ID NO: 100 is from the human C3 sequence. SEQ ID NO: 101 is from the rat C3 sequence. SEQ ID NO: 102 is from the mouse C3 sequence. SEQ ID NO: 103 is from the cynomolgus sequence.

```
                                           (SEQ ID NO: 100)
KKVFLDCCNYITELRRQHARASHLGLARSNLDEDIIAEENIVSRSEFPESW

LWNVEDLKE (SEQ ID NO: 101)
LKAFMDCCNYITKLREQHRRDHVLGLARSDVDEDIIPEEDIISRSHFPESW

LWTIEELKE (SEQ ID NO: 102)
IKAFIDCCNHITKLREQHRRDHVLGLARSELEEDIIPEEDIISRSHFPQSW

LWTIEELKE (SEQ ID NO: 103)
KKAFLDCCNYITELRRQHARASHLGLARSNLDEDIIAEENIVSRSEFPESW

LWKIEELKE
```

Thus, for example, a rat sequence corresponding to the human sequence of SEQ ID NO: 83 is LARSDVDEDII (SEQ ID NO: 104). A mouse sequence corresponding to the human sequence of SEQ ID NO: 83 is LARSELEEDII (SEQ ID NO: 105). As will be evident from the above alignment, the cynomolgus monkey sequence corresponding to SEQ ID NO: 83 is the same as SEQ ID NO: 83. Similar embodiments are provided for other C3 sequences and for other CAPP substrates mentioned herein.

As noted above, in some embodiments a CAPP substrate is labeled so that cleavage of the substrate results in a detectable signal. In some embodiments a substrate comprises first and second labels. In some embodiments the first and second labels are linked to the substrate, e.g., via covalent bonds. In some embodiments the first and second labels comprise first and second dyes. In some embodiments the first and second dyes form a donor-acceptor pair, e.g., a FRET pair. In some embodiments the first and second labels that form a donor-acceptor pair, e.g., a FRET pair, are both fluorophores. In some embodiments one of the members of the donor-acceptor pair is a fluorophore and the other member is a dark quencher. In general, the first and second labels are linked to the substrate on opposite sides of the cleavage site, so that cleavage of the substrate results in altering the distance between the first and second labels. The donor and acceptor are typically positioned (e.g., linked to the substrate) such that the distance between them is within the characteristic distance for that donor-acceptor pair (generally between 1 nm and 10 nm) much or substantially or essentially all of the time when the substrate is intact, i.e., prior to cleavage of the substrate. Cleavage of the substrate separates the donor and acceptor such that the distance between them becomes greater than the characteristic distance for the donor-acceptor pair, thus dequenching at least one fluorophore, producing a detectable optical signal when light of appropriate wavelength to excite the fluorophore is delivered. The excitation light may be delivered by, e.g., a laser. In some embodiments the alteration in distance that occurs due to cleavage of the substrate results in dequenching of at least one of the labels, which dequenching is detected. In some embodiments, altered donor fluorescence lifetime is detected. The detectable optical signal may be observed using known techniques useful for fluorescence detection. In some embodiments any suitable fluorescence detector is used. In some embodiments a fluorescence detector comprises a photomultiplier (PMT) and a charge-coupled device (CCD), e.g., a CCD camera. In some embodiments a scanning laser ophthalmoscope is used to deliver the light and detect the signal. The dyes may be attached to a substrate at various positions. In some embodiments, the dyes are present at or near the termini of the substrate. In some embodiments, the first dye is linked to an amino acid residue that is on one terminus of the substrate and the second dye is linked to the amino acid residue that is not at the terminus of the substrate. In some embodiments, both dyes are linked to amino acid residues that are not at the termini of the substrate. The optimal distance between the donor and acceptor moieties will be that distance wherein the emissions of the donor moiety are maximally absorbed by the acceptor moiety. This optimal distance varies with the specific moieties used, and may be readily determined by one of ordinary skill in the art using well-known techniques. In some embodiments the donor and acceptor are positioned such that the number of amino acids located between amino acids bearing a donor and acceptor is between 1 and 20, e.g., between 2 and 15, e.g., between 3 and 12. In some embodiments the number of amino acids located between amino acids bearing a donor and acceptor is 4, 5, 6, 7, 8, 9, 10, 11, or 12.

In some embodiments a substrate substantially lacks fluorescence prior to cleavage and exhibits high fluorescence upon cleavage (with appropriate excitation). In some embodiments first and second fluorophores are selected and linked to the substrate such that the fluorescences of the first and second fluorophores are mutually substantially quenched. In some embodiments mutual fluorescence quenching is achieved using a dye pair that exhibits double energy transfer involving a direct (donor's emission and acceptor's absorption) and a reverse (acceptor's emission and donor's absorption) spectral overlap. Thus the emission spectrum of the donor significantly overlap with the absorption spectrum of the acceptor, but also part of the emission spectrum of the acceptor overlaps with the absorption spectrum of the donor. The donor may be considered to be the compound that initially emits in response to externally provided excitation. In some embodiments lack of fluorescence prior to cleavage is achieved using a dark quencher as the acceptor moiety.

Some exemplary fluorophores that may be used as donors or acceptors, e.g., in FRET pairs, include, without limitation: 4-acetamido-4'-isothiocyanatostilbene-2,2'disulfonic acid acridine and derivatives such as acridine isothiocyanate, 5-(2'-aminoethyl)aminonaphthalene-1-sulfonic acid (EDANS), 4-amino-N-[3-vinylsulfonyl)phenyl]naphthalimide-3,5disulfonate (LuciferYellow VS), N-(4-anilino-1-naphthyl)maleimide, Anthranilamide, Brilliant Yellow; coumarin and derivatives such as 7-amino-4-methylcoumarin (AMC, Coumarin 120), 7-amino-4-trifluoromethylcoumarin (Coumarin 151), cyanosine, 4'-6-diaminidino-2-phenylindole (DAPI), 5', 5''-dibromopyrogallol-sulfonephthalein (Bromopyrogallol Red), 7-diethylamino-3-(4'-isothiocyanatophenyl)-4-methylcoumarin, 4-(4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansyl chloride) or the similar compound dansyl amide; eosin and derivatives such as eosin isothiocyanate; erythrosin and derivatives such as erythrosin B, erythrosin isothiocyanate; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein isothiocyanate, fluorescamine (only fluorescent when it reacts with primary amines), IR144, IR1446, Malachite Green isothiocyanate, 4-methylumbelliferone, pararosaniline, Phenol Red, B-phycoerythrin, o-phthaldialdehyde (only fluorescent when it reacts with primary amines); pyrene and derivatives such as pyrene butyrate, succinimidyl 1-pyrene butyrate, Reactive Red 4 (Cibacron® Brilliant Red 3B-A); rhodamine and derivatives such as 6-carboxy-X-rhodamine (ROX), 6-carboxyrhodamine (R6G), lissamine rhodamine B sulfonyl chloride, rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, tetramethyl rhodamine isothiocyanate (TRITC), riboflavin, BODIPY dyes, AlexaFluor™ dyes, both of which are available from, e.g., Life Technologies (Invitrogen), CA, Cyanine dyes (Cy™3, Cy™3B, Cy™5, Cy™7) (available from, e.g., GE Health-Care Life-Sciences), HiLyte Fluor™ dyes (available from, e.g., AnaSpec), fluorescent IRDyes® (LI-COR Biosciences, Lincoln, Nebr.) e.g., IRDye® 680RD, IRDye® 750, IRDye® 700DX, or IRDye® 800CW.

In some embodiments an indocyanine green (ICG) derivative such as cypate or a mono-amino-functionalized ICG analog, NH$_2$-ICG, is used as a fluorophore. Such compounds retain the optical features of ICG while making it possible to attach biomolecules such as peptides at designated positions. Chemical structures of ICG, NH$_2$-ICG ICG-CO$_2$H, and cypate are shown below.

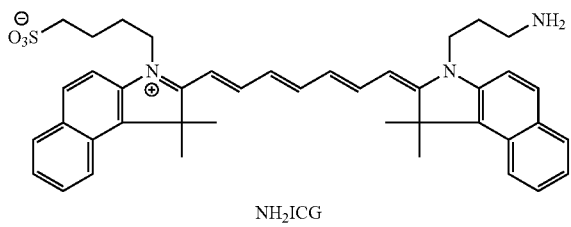

NH$_2$ICG

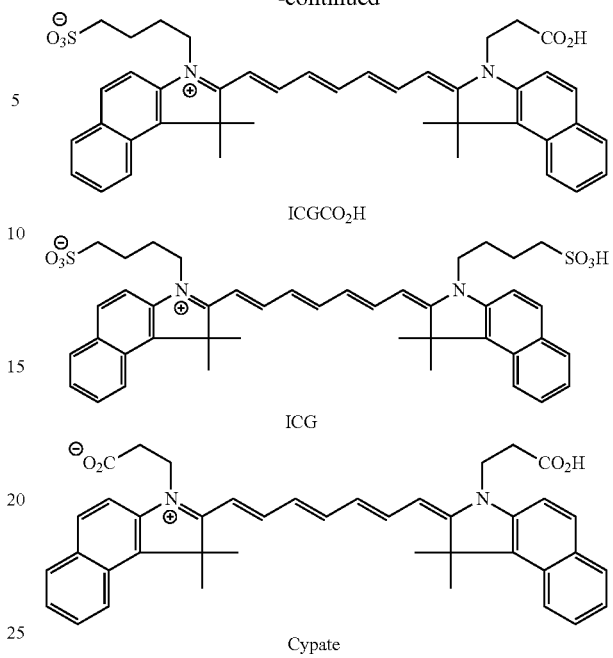

ICGCO$_2$H

ICG

Cypate

In some embodiments, NIR5.5-2 and NIR7.0-2 are used. These compounds are water-soluble NIR cyanine dyes that, when associated within a peptidic architecture, exhibit mutual fluorescence quenching both at 705 (NIR5.5-2) and 798 nm (NIR7.0-2) (Bouteiller C, et al., Bioconjug Chem. 2007; 18(4): 1303-17). These dyes may be generated using postsynthetic derivatization of a cyanine precursor in order to introduce functionalities useful for bioconjugation of these NIR fluorophores. For example, as described in Bouteiller, et al., for NIR5.5-2, a reactive amino group can be acylated with a trisulfonated linker for water solubility, and for NIR7.0-2, a vinylic chlorine atom can be derivatized through a SRN1 reaction for the introduction of a monoreactive carboxyl group for labeling purposes.

Some exemplary compounds that may be used as acceptors only, e.g., as dark quenchers, include, but are not limited to, 4-(4-dimethylaminophenyl) diazenylbenzoic acid; 4-(4-dimethylaminophenyl) diazenylbenzoic acid (DABCYL) and derivatives, Cy™ 5Q, and Cy™7Q. DABSYL may be used with, e.g., fluorescein, EDANS, or other fluorophores that emit in the green wavelength range. Other dark quenchers include, e.g., Black Hole Quenchers (Biosearch Technologies, Novato, Calif.), certain of which are disclosed in International Publication No. WO01/86001. Such quenchers comprise an aromatic moiety comprising a N,N-dialkylaniline and described as having characteristic long-wavelength (disclosed to be preferably from about 500 nm to about 700 nm) absorption maxima. For example, BHQ-3 has an approximately 673 nm wavelength absorption maximum; QXL™ quenchers (AnaSpec, Inc., Fremont, Calif.); BlackBerry™ quenchers (Berry & Associates, Inc., Dexter, Mich.) are disclosed in U.S. Ser. No. 11/346,688. Such quenchers comprise at least three radicals covalently linked via exocyclic diazo bonds, the at least three radicals including at least one comprising a julolidine and the remainder of the at least three radicals being selected from the group of substituted and unsubstituted aryls, substituted and unsubstituted heteroaryls, and combinations thereof; Iowa black FQ™ and Iowa black RQ™ (Integrated DNA Technologies, Coralville, Iowa); IRDye QC-1 (LI-COR Biosciences, Lincoln, Nebr.) is an amino-substituted cyanine dye with a conjugated cyclic heptamethine structure that quenches fluorophores from the visible to the near-infrared range (500-900 nm) (Peng, X., et al., Analytical Biochemistry, 2009; 388: 220-228). Many of these quenchers are available as amine-reactive, thiol-reactive, or carboxy-reactive derivatives. Details regarding fluorophores and quenchers may be found in the scientific and patent literature and information provided by manufacturers of the respective compounds.

Without wishing to be bound by any theory, substrates that utilize a dark quencher as an acceptor may have a number of advantages over substrates in which both donor and acceptor are fluorophores. For example, they may exhibit lower background fluorescence which can lead to a larger signal-to-noise ratio, and, therefore, greater dynamic range. In addition, absence of secondary fluorescence arising from a dark quencher facilitates simultaneous resolution of multiple fluorophores, making dark quencher probes amenable to multiplex assays, if desired. For example, in some embodiments a CAPP substrate comprises protease recognition sequences for two different CAPPs, e.g., C3 convertase and C5 convertase. The substrate may comprise two or more labels, e.g., two, three, or four labels. For example, the substrate may comprise two fluorophores having distinct emission maxima and one or more quenchers. In some embodiments the labels are selected and arranged so that a signal is generated upon cleavage by either CAPP, wherein in some embodiments the signals are distinguishable. In some embodiments the labels are selected and arranged so that a signal is generated upon cleavage by CAPPs.

One of ordinary skill in the art can easily determine, using art-known techniques of spectrophotometry, which fluorophores will make suitable donor-acceptor FRET pairs. Preferred FRET pairs demonstrate appreciable FRET efficiency. The FRET efficiency is affected by three parameters, i.e., (1) the distance between the donor and the acceptor; (2) the spectral overlap of the donor emission spectrum and the acceptor absorption spectrum; and (3) the relative orientation of the donor emission dipole moment and the acceptor absorption dipole moment. In some embodiments paired fluorophores that comprise the substrate may be selected to optimize one or more of these three parameters. For example, donor and acceptor molecules having emission and excitation maxima differing by no more than about 10 nm, 20 nm, 30 nm, 40 nm, or 50 nm may be selected in some embodiments. One of ordinary skill in the art may also take into consideration the quantum yield of fluorescence of the donor and/or the extinction coefficient of the acceptor and the spectral overlap between the emission of the donor and the absorbance of the acceptor. One of ordinary skill in the art will readily be able to select appropriate fluorophores or dark quenchers for use as FRET donors and acceptors. In some embodiments a quencher, e.g., a dark quencher, is capable of quenching a fluorophore with an efficiency of at least 80%, 85%, 90%, 92.5%, 95%, 96%, 97%, 98%, 99%, or more. In some embodiments a donor and acceptor pair that do not substantially bind to each other are selected. In some embodiments a donor that emits in the near-infrared (NIR) range and a quencher capable of effectively quenching the donor are used. In some embodiments a donor and acceptor pair that do not substantially experience interference from or overlap with autofluorescence when used in vivo are selected. In some embodiments a peptide substrate is characterized in that it shows a fluorescence increase of at least 5-fold, 7-fold, 10-fold, 15-fold, 20-fold, 30-fold, 40-fold, 50-fold, 60-fold, 70-fold, 80-fold, 90-fold, 100-fold, or more after proteolytic cleavage by a CAPP.

In some embodiments an imaging agent comprises a fluorophore and a metal nanoparticle (NP), e.g., a gold nanoparticle (GNP) or silver nanoparticle (SNP). When a fluorophore is placed at a relatively short distance, e.g., within 10 nm, from a metal particle possessing a strong plasmon field, the electrons of the fluorophore participating in the excitation/emission interact with the field. The interaction can result in a change in the fluorescence emission level, i.e., quenching or enhancement (Kang et al. Journal of Nanobiotechnology 2011, 9:16). In some embodiments this phenomenon is exploited in a peptide substrate for a CAPP, e.g., in order to enhance the fluorescence of a fluorophore or to quench the fluorophore. In some embodiments the NP is at least partly coated with a biocompatible polymer, and the fluorophore is placed on the outermost layer of the polymer coated NP. The fluorophore may be conjugated to the polymer or applied in combination with a polymer as part of a coating layer. In some embodiments the fluorophore is cypate or another ICG-based fluorophore. In some embodiments the effect of the NP on the fluorophore (e.g., amount of enhancement or quenching) is determined at least in part by the distance between the NP and the fluorophore and/or the composition of the coating layer. Such parameters can be selected to achieve a desired effect. For example, the distance between an NP and a fluorophore can be tailored using a biocompatible spacer to attach the fluorophore to the surface of the NP. In some embodiments the spacer comprises a peptide that is a substrate for a CAPP. In some embodiments the length of the spacer and/or composition of the coating layer is selected so that the fluorophore is substantially quenched prior to cleavage. Upon cleavage, the fluorophore is released and dequenching occurs. In some embodiments a small molecule quencher is provided. In some embodiments the fluorophore is quenched by a quencher attached to the peptide. The length of the spacer and/or composition of the coating layer is selected so that the fluorescence of the fluorophore is enhanced; however, the fluorophore is quenched by a quencher attached to the peptide prior to cleavage. Following cleavage the quencher is released, resulting in dequenching. The enhancement provided by the NP increases the signal, thereby facilitating detection.

In some embodiments nanoparticles, e.g., gold (Au) nanoclusters or quantum dots (QDs) are used as donors or acceptors. In some embodiments a rare earth compound, e.g., lanthanide complex or chelate or closely related metal such as yttrium or scandium, is used as a donor or acceptor. In some embodiments a lanthanide is terbium (III), europium(III), or ytterbium. In some embodiments QDs or other particles are coated or encapsulated in a biocompatible, hydrophilic material, e.g., a biocompatible organic polymer (s).

In some embodiments a peptide substrate is specific for a CAPP in that it resists cleavage in vitro by a wide range of proteases that may be found in blood or interstitial fluid or having a proteolytic domain exposed at the cell surface or released by dying cells. For example, in some embodiments a CAPP substrate resists cleavage by at least some matrix metalloproteases (MMPs), ADAM (a disintegrin and metalloprotease domain) family members, elastase, thrombin, plasmin, etc. In some embodiments a peptide substrate is specific for a CAPP of interest in that it is not significantly cleaved in vivo following administration to a subject who has a deficiency of the CAPP, e.g., a deficiency due to a naturally occurring mutation or, in the case of a non-human subject, a genetically engineered mutation, in a gene that encodes the CAPP, a subunit of the CAPP, or an activator of the CAPP.

In some embodiments the amount of signal due specifically to cleavage of a peptide substrate by a CAPP may be distinguished from background signal by comparing produced by the peptide substrate to the signal produced by a control peptide that is similar to the peptide substrate but is substantially less susceptible to cleavage or essentially not cleavable by the CAPP. In some embodiments a control peptide is identical to an actual CAPP substrate except that P1 is replaced by a different amino acid so as to render the peptide substantially less susceptible to cleavage or essentially not cleavable by the CAPP. In some embodiments a control peptide is identical to an actual CAPP substrate except that one or more L-amino acid(s) between P4 and P4' is replaced by the corresponding D amino acid(s) so as to render the peptide not cleavable by the CAPP. The specific amino acids and the number of amino acids to be replaced so as to render the peptide substantially less susceptible to cleavage or essentially not cleavable by the CAPP can be readily determined. A control peptide may be used to, e.g., optimize a substrate in vitro.

In some embodiments a method of detecting complement activation in a subject comprises: (a) providing a subject to whom a substrate (e.g., a labeled substrate) for a proteolytically active complement component or convertase has been administered; and (b) detecting cleavage of the substrate, thereby detecting complement activation in the subject. In some embodiments the substrate produces a detectable signal upon cleavage; and step (b) comprises detecting the signal. In some embodiments the method comprises administering the substrate to the subject. In some embodiments a method of preparing a subject for detection of complement activation in the subject comprises: (a) administering a substrate (e.g., a labeled substrate) for a proteolytically active complement component or convertase to the subject. In some embodiments the substrate produces a detectable signal upon cleavage; In some embodiments the method further comprises detecting cleavage of the substrate in the subject.

The substrate may be administered using any suitable method. In some embodiments the substrate is administered into the vascular system, e.g., intravenously, e.g., by intravenous injection. In some embodiments the substrate is administered locally to the eye. In general, the substrate may be administered using any method known in the art to be useful for delivery of ocular diagnostic or therapeutic agents. In some embodiments the substrate is administered into the posterior segment of the eye, e.g., into the vitreous, e.g., by intravitreal injection.

In some embodiments the method comprises delivering to the subject, e.g., to the eye, light of an appropriate wavelength to excite a fluorophore attached to the substrate. In some embodiments cleavage of the substrate is detected within no more than 10, 20, 30, 45, 60, or 120 minutes following administration of the substrate to the subject. In general, the substrate may be administered using any suitable method. Various methods of administration and delivery vehicles and formulations are discussed further below. In some embodiments the peptide substrate is administered, e.g., intravenously, in an amount between 0.1 mg/kg and 200 mg/kg, e.g., between 1 mg/kg and 50 mg/kg. In some embodiments a peptide substrate is administered intravitreally (e.g., by intravitreal injection) to a human subject in a volume of up to about 25 microliters-100 microliters, e.g., about 50 microliters. In some embodiments between 1 µg and 2000 µg of the agent (dry weight) is administered to the eye, e.g., intravitreally, e.g., between 1 µg and 10 µg, 10 µg and 100 µg, 100 µg and 500 µg, 500 µg and 1000 µg, 1000 µg and 2000 µg. In some embodiments about 10 µg, about 150 µg, about 450 µg, about 1050 µg, or about 1500 µg are administered to the eye. The concentration administered may be the maximal concentration that is soluble in the carrier and safe for administration. Optimal concentrations and amounts may be readily determined. It is noted that complement activation may in various embodiments be detected at any location in the body where excitation light can be delivered and signal detected. In some embodiments a fiber optic device is used. In some embodiments an endoscope, bronchoscope, catheter, or other device is used. In some embodiments complement activation is detected in the skin, in or under a mucus membrane, in a blood vessel, e.g., in an atherosclerotic plaque, in the respiratory tract, in the gastrointestinal tract, etc. In some embodiments the CAPP substrate is delivered via an endoscope, bronchoscope, or catheter, which device may also be used to deliver light or to detect a signal in certain embodiments.

Peptide substrates may generally be prepared by various synthetic methods of peptide synthesis known in the art via condensation of amino acid residues, e.g., in accordance with conventional peptide synthesis methods, or may be prepared by expression in vitro or in living cells from appropriate nucleic acid sequences encoding them using methods known in the art. For example, peptides may be synthesized using standard solid-phase methodologies. Potentially reactive moieties such as amino and carboxyl groups, reactive functional groups, etc., may be protected and subsequently deprotected using various protecting groups and methodologies known in the art. Peptides may be purified using standard approaches such as reversed-phase HPLC. Separation of diasteriomeric peptides, if desired, may be performed using known methods such as reversed-phase HPLC. Preparations may be lyophilized, if desired, and subsequently dissolved in a suitable solvent, e.g., water. The pH of the resulting solution may be adjusted, e.g. to physiological pH, using a base such as NaOH. Peptide preparations may be characterized by mass spectrometry if desired, e.g., to confirm mass. The incorporation of labels may be performed using standard methods. Such methods may involve the use of appropriate derivatives of the label, wherein the derivatives comprise suitable reactive functional groups to permit conjugation to peptide termini or side chain(s) of amino acids in the peptide. Methods and functional groups useful for conjugation are described in Hermanson, G., *Bioconjugate Techniques*, $2^{nd}$ ed., Academic Press, San Diego, 2008. Furthermore, protocols suitable for conjugating to or incorporating labels into biomolecules are widely available from manufacturers of the respective label.

In some embodiments a substrate of a CAPP further comprises at least one amino acid that is not found at a corresponding position when the substrate is aligned with a physiological substrate of the CAPP. For example, the substrate may comprise an amino acid having a side chain comprising a functional group that can be conveniently modified, e.g., so that a moiety comprising a label or targeting moiety can be readily attached. For example, in some embodiments a peptide sequence found in a physiological substrate and encompassing a CAPP cleavage site is extended by one or more amino acids at the N-terminus, C-terminus, or both, wherein at least one of the amino acids has a side chain that comprises a reactive functional group such as a primary or secondary amine, a sulfhydryl group, a carboxyl group (which may be present as a carboxylate group), a guanidino group, a phenol group, an indole ring, a thioether, or an imidazole ring, wherein the reactive functional group may be used, e.g., to attach a label or a moiety comprising a label. Examples of amino acids having side chains that comprise such reactive functional groups are described below. The amino acid(s) may be standard or non-standard. Non-standard amino acids may be naturally occurring or not found in nature. Lysine (abbreviated interchangeably as Lys or K), which comprises a side chain comprising a primary amine, is used as an example, but other amino acids could be used, and such embodiments are encompassed by the present disclosure. For example, in some embodiments C3 convertase substrate of SEQ ID NO: 88: GLARSNLDEDII (SEQ ID NO: 88) is extended to include a Lysine at the C-terminus, resulting in GLA RSNLDEDIIK (SEQ ID NO: 99), which may also be represented Gly-Leu-Ala-Arg-Ser-Asn-Leu-Asp-Glu-Asp-Ile-Ile-Lys (SEQ ID NO: 99) using the three letter abbreviations for amino acids. In some embodiments first and second dyes are attached to the $NH_2$ at the N-terminus and to the $NH_2$ of the lysine side chain. Any one or more of the amino acid(s) may be protected as appropriate during synthesis of substrate and/or, in some embodiments, during labeling. For example, in some embodiments a Lys side chain is protected while a label is added to the $NH_2$ group at a peptide's N-terminus. In some embodiments an amino acid that has already been modified to have a label attached thereto is used to synthesize a substrate. For example, Fmoc-Lys(DABCYL)-OH may be used to synthesize a peptide comprising a DABCYL-labeled Lys residue. Of course other dyes or amino acids may be used. In some embodiments an amino acid that comprises a reactive functional group is modified to incorporate a label after peptide synthesis. Various fluorophores and dark quenchers are available commercially as derivatives comprising reactive functional groups selected for their ability to react with one or more of the reactive functional groups that are typically found in or readily introduced into proteins. For example, fluorophores and dark quenchers may be available as N-hydroxysuccininde(NHS) esters, which react readily with primary amines, or as maleimides, which react with thiols. Typical functional groups that link the fluorophores or dark quenchers to the amino acid residues include, but are not limited to, amide linkages, ester linkages, ether linkages, imide linkages, and thioether linkages. In some embodiments a cross-linker is used to attach a fluorophore or dark quencher to a peptide substrate. Numerous homobifunctional and heterobifunctional crosslinkers are known in the art and may be used in such embodiments.

In some embodiments a peptide substrate comprises a blocking moiety at the N-terminus, C-terminus, or both. In certain embodiments a blocking moiety present at the N- or C-terminus of any of the substrates described herein is any moiety that stabilizes a peptide against nonspecific degradation that may otherwise occur in mammalian (e.g., rodent, human or non-human primate) blood, tissue, or interstitial fluid. For example, a blocking moiety $B^1$ at the N-terminus could be any moiety that alters the structure of the N-terminus of a peptide so as to inhibit cleavage of a peptide bond between the N-terminal amino acid of the peptide and the adjacent amino acid. A blocking moiety $B^2$ at the C-terminus could be any moiety that alters the structure of the C-terminus of a peptide so as to inhibit cleavage of a peptide bond between the C-terminal amino acid of the peptide and the adjacent amino acid. It will be understood that the blocking moiety should not significantly affect cleavage of the substrate by the protease whose detection is desired. Any suitable blocking moieties known in the art may be used. Exemplary blocking moieties are described below in the discussion of compstatin analogs. In some embodiments any such blocking moiet(ies) are used at the N-terminus and/or C-terminus of a peptide substrate of a CAPP. For example, in certain embodiments a peptide substrate is acetylated at the N-terminus, amidated at the C-terminus, or both. In some embodiments a blocking moiety comprises or consists of a non-standard amino acid. In some embodiments a non-standard amino acid of use in a blocking moiety is a n-amino acid, e.g., β-Alanine (β-Ala). For example, in some embodiments a β-amino acid, e.g., β-Ala, is at the N-terminus and/or at the C-terminus. In some embodiments a β-amino acid, e.g., β-Ala, is at the N-terminus, and the C-terminus is amidated. In some embodiments a β-amino acid, e.g., β-Ala, is at the C-terminus, and the N-terminus is acetylated.

In some embodiments, one or more amino acids in a peptide, e.g., an amino acid at the N- or C-terminus, may be linked to an adjacent amino acid via a non-peptide bond or linking portion. Any one or more of the linking portions described herein may be used in various embodiments.

In some embodiments a CAPP substrate may comprise or be attached to a moiety that enhances extravasation or tissue penetration of the substrate. In some embodiments the moiety is a lipophilic moiety. In some embodiments a CAPP substrate may comprise or be attached to a targeting moiety, e.g., any of the targeting moieties described below.

In some embodiments a CAPP substrate comprises one or more charged groups. In some embodiments one, two, or more amino acids are included, e.g., added at either or both ends, to provide such charged groups, e.g., in order to increase iontophoretic mobility or solubility of the agent. One of ordinary skill in the art will be aware of amino acids bearing charged side chains at various different pH ranges.

In some embodiments a diagnostic agent, e.g., a CAPP substrate, is tested in vitro. For example, the substrate is contacted in vitro with one or more CAPPs in the presence or absence of a complement activating agent. Cleavage of the CAPP is detected. An increase in cleavage in the presence of the complement activating agent indicates that the agent is useful for detecting complement activation. Such in vitro tests may be used e.g., to optimize the substrate, e.g., for selecting substrates with high cleavage efficiency and/or high signal or low background, for selecting dyes or for selecting the positions at which dyes are attached to the substrate. In some embodiments such a test is performed in the presence of a complement inhibitor capable of inhibiting the CAPP, in order, e.g., to assess specificity of the substrate for cleavage by a CAPP as compared with other proteases that may be present in the composition (e.g., proteases found in serum).

In some embodiments a diagnostic agent, e.g., a CAPP substrate, is tested in vivo. In some embodiments such testing comprises administering the agent to a non-human subject and delivering a complement-activating stimulus or substance to the subject. For example, an agent may be tested by IV or intravitreal administration and activating complement in the eye either using, e.g., blue light or by injecting lipopolysaccharide (LPS) or another substance capable of activating complement directly into the eye, followed by detection of the diagnostic agent. In some embodiments the non-human subject has drusen or drusenoid deposits or lesions resembling those existing in human subjects with AMD, e.g., as a result of a genetic manipulation, strain background, or administration of various substances.

Methods of detecting cleavage of a CAPP substrate by methods other than fluorescence-based detection are within the scope of the present disclosure. Methods of detecting complement activation in vivo other than by detecting cleavage of a substrate are within the scope of the present disclosure.

IV. Identification of High Risk Drusen by Detecting Inflamed Endothelium

In some embodiments, a high risk druse is identified at least in part by detecting inflamed endothelium underlying or in close proximity to the druse. In some embodiments, a drusen pattern or group comprising multiple drusen is classified into a risk category based at least in part on detecting inflamed endothelium underling or in close proximity to at least some of the drusen in the drusen pattern or group of drusen. Endothelial cells line the inner surface of blood vessels and play important roles in the inflammatory response. Inflammatory mediators and cytokines, such as IL-1 and TNFα, induce endothelial cells to secrete chemokines and increase their expression of various cell surface adhesion molecules, such as intracellular adhesion molecule-1 (ICAM-1), vascular cell adhesion molecule-1 (VCAM-1), integrins, and selectins. Chemokines are chemotactic to leukocytes, attracting them to sites of inflammation. Leukocyte emigration from the blood into tissue during inflammation involves rolling of leukocytes along endothelial cell surfaces, to which they subsequently adhere. Leukocyte rolling and adherence to endothelium and movement of leukocytes through endothelial junctions into the extravascular space is promoted by interactions with adhesion molecules on endothelial cell surfaces. P-selectin is found on the cell surface of endothelial cells and platelets. It binds to glycoprotein on the cell surface of leukocytes. E-selectin, also known as CD62 antigen-like family member E (CD62E), endothelial-leukocyte adhesion molecule 1 (ELAM-1), or leukocyte-endothelial cell adhesion molecule 2 (LECAM2), is a cell adhesion molecule expressed only on endothelial cells activated by cytokines. Like other selectins, it plays an important part in inflammation. In humans, E-selectin is encoded by the SELE geneP-selectin and other adhesion molecules are involved in rolling and arresting leukocytes on the endothelium prior to leukocyte migration into the extravascular space.

Bruch's membrane is the innermost layer of the choroid and separates the RPE from the underlying layer of capillaries (choriocapillaris). "Inflamed endothelium" is used herein interchangeably with "activated endothelium" and refers to endothelium that has been stimulated by one or more inflammation-associated cytokines such as IL-1 and TNFα and/or that exhibits features characteristic of endothelium located at sites of inflammation, such as increased expression of VCAM-1, ICAM-1, integrin(s) and/or selectin (s). For purposes hereof, inflamed endothelium in one or more blood vessels of the choroid, e.g., one or more capillaries of the choriocapillaris, is referred to as "inflamed choroidal endothelium".

Inflamed endothelium, e.g., inflamed choroidal endothelium, can be detected using a variety of approaches. In some embodiments inflamed endothelium is detected using an imaging agent comprising a detectable label. In some embodiments the imaging agent comprises a detectable label and a targeting moiety that binds to a marker of inflamed endothelium. In some embodiments the marker is present at the surface of inflamed endothelial cells. The imaging agent binds to the marker via the targeting moiety, thereby becoming concentrated at sites of inflamed endothelium and allowing detection of the inflamed endothelium by detecting the label.

In some embodiments the imaging agent is detectable by ultrasound, magnetic resonance imaging, nuclear imaging (e.g., positron emission tomography (PET), scintigraphy, or single photon emission computer tomography (SPECT), fluorescence detection, or multiphoton microscopy. In some embodiments an imaging agent comprises an MRI contrast agent, e.g., a gadolinium-based, iron-based, or manganese-based contrast agent. In some embodiments a contrast agent is superparamagnetic (e.g., iron oxide contrast agent such as superparamagnetic iron oxide particles or superparamagnetic iron platinum particles) or paramagnetic (e.g., manganese-based particles).

In some embodiments an imaging agent comprises a radiolabel. In some embodiments a radiolabel comprises a radioisotope. In some embodiments the radioisotope is detectable by a gamma camera using, e.g., SPECT or scintigraphy. For example, the radioisotope may be $^{99m}$Tc, $^{123}$I, $^{131}$I, $^{111}$In, $^{57}$Co, $^{153}$Sm, $^{51}$Cr, $^{201}$Tl, $^{67}$Ga, or $^{75}$Se. In some embodiments the radioisotope is detectable using PET scanning. For example, in some embodiments the radioisotope may be $^{18}$F, $^{11}$C, $^{13}$N, $^{15}$O, $^{68}$Ga, or $^{82}$Rb. In some embodiments a Lys residue in a peptide substrate is labeled with the 4-[$^{18}$F]fluorobenzoate for detection using PET scanning.

In some embodiments imaging and/or detection of an imaging agent is performed using Raman spectroscopy. In some embodiments imaging and/or detection of an imaging agent is performed using multiphoton microscopy (MPM), which includes two-photon autofluorescence (2PAF), second harmonic generation (SHG), third harmonic generation (THG), fluorescence lifetime (FLIM), and coherent anti-Stokes Raman Scattering (CARS). The In some embodiments an imaging agent may be represented as: T-L-D, where T represents a targeting moiety, L represents an optional linking portion, and D represents a moiety comprising a detectable label. In some aspects, a targeting moiety can comprise, e.g., an antibody, polypeptide, peptide, nucleic acid (e.g., an aptamer), carbohydrate, small molecule, or supramolecular complex, that specifically binds to the target molecule. In some embodiments, the affinity (as measured by the equilibrium dissociation constant, Kd) of targeting moiety for the target molecule (as measured by the equilibrium dissociation constant, Kd) is $10^{-3}$ M or less, e.g., $10^{-4}$ M or less, e.g., $10^{-5}$ M or less, e.g., $10^{-6}$ M or less, $10^{-7}$ M or less, $10^{-8}$ M or less, or $10^{-9}$ M or less under the conditions tested, e.g., under physiological conditions.

In some embodiments a target molecule is any molecule that is present at the surface of endothelial cells in inflamed endothelium or otherwise present in inflamed endothelium, wherein the molecule is present at a higher level in inflamed endothelium than in normal, non-inflamed endothelium. In some embodiments a target molecule is an integrin, selectin, or cell adhesion molecule, e.g., one whose expression or exposure is increased in inflammation. In some embodiments a targeting moiety comprises a selectin ligand, e.g., a ligand for a C-type lectin, e.g., P-selection and/or E-selectin. In some embodiments a selectin ligand is capable of binding to both one or more selectins and one or more integrins. P-selectin glycoprotein ligand-1 (PSGL-1), also termed SELPLG selectin P ligand (Gene ID: 6404 (human); 20345 (mouse)) is a glycoprotein found on certain cells, e.g., white blood cells, that binds to P-selectin, E-selectin, and L-selectin. Binding of PSGL-1 to selectins occurs in part via sLeX (α-Neup5Ac-(2→3)-β-Galp-(1→4)[α-Fucp-(1→3)]-GlcpNAc-R), a tetrasaccharide carbohydrate that can be found attached to 0-glycans of PSGL-1. sLeX interacts with selectins on endothelial cells and facilitates leukocyte recruitment into sites of inflammation. In some embodiments a selectin ligand comprises sialyl-Lewis X (sLeX), sialyl Lewis A (sLeA), or an sLeX or sLeA mimetic. In some embodiments sLeX, sLeA, or an sLeX or sLeA mimetic, is sulfated. In some embodiments PSGL-1, e.g., recombinant PSGL-1, or a portion thereof that retains ability to bind to one or more selectins, is used as a targeting moiety. Recombinant forms of PSGL-1 are known in the art. In some embodiments a conjugate of PSGL to an antibody or portion thereof (e.g., the agent sometimes referred to as rPSGL-Ig) is used. In some embodiments an sLex mimetic emulates the sLex/sulfated tyrosine motif that is involved in P-selectin binding by PSGL-1.

In some embodiments a selectin ligand, e.g., sLex, is obtained from naturally occurring sources or synthesized at least in part chemically or enzymatically (see, e.g., Cao, H., Carbohydr Res. 2008; 343(17):2863-9 for an exemplary description of sLeX synthesis). For purposes of description sLeX will be used as an example of a selectin ligand, but it will be understood that other selectin ligands are used in certain embodiments. The structure of sLeX is shown below.

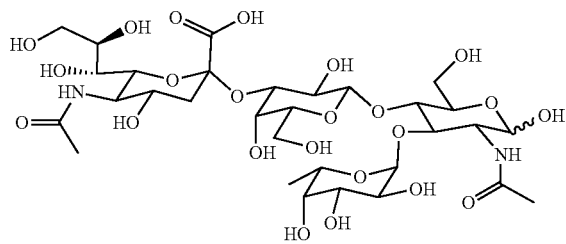 [SMILES: CC(=O)NC1C(O)OC(CO)C(OC2OC(CO)C(O)C(OC3(C(=O)O)CC(O)C(NC(C)=O)C([C@H](O)[C@H](O)CO)O3)C2O)C1OC1OC(C)C(O)C(O)C1O]

In some embodiments an sLeX mimetic is any molecule that structurally resembles sLeX and competes with sLeX for binding to P-selectin and/or E-selectin. In some embodiments one or more functional groups of sLeX is modified to facilitate conjugation of the oligosaccharide to a second moiety, e.g., a peptide, fluorophore, or other moiety, to a particular position. For example, in some embodiments a modified sLex tetrasaccharide comprising a functional group not present elsewhere in the molecule, such as a primary or secondary amine, is used. For example, in some embodiments an sLex tetrasaccharide with a propylamine aglycon modification, e.g., as depicted below and described in Cao, supra, is used.

The propylamine aglycon can be used as a chemical handle for further conjugation, e.g., for attachment to a peptide, fluorophore, or other moiety. For example, the primary amine may be reacted with an NHS ester.

In some embodiments a non-natural glycopeptide comprises sLex and a peptide, wherein the non-natural glycopeptide exhibits higher affinity for a selectin, e.g., P-selectin and/or E-selectin, than does sLeX. Exemplary non-natural glycopeptides exhibiting such increased affinity are known in the art (see, e.g., Matsuda M, et al., J Med Chem. 2001; 44(5):715-24). In some embodiments, a glycopeptide comprising Lys-Gly-Arg-Gly-Asp-Ser (SEQ ID NO: 106) is used. For example, in some embodiments the sequence is extended at the C-terminus to include an additional amino acid comprising a side chain comprising a primary or secondary amine or other functional group, which may be used to conjugate a label thereto or to conjugate the peptide to a polymer or particle.

In some embodiments a polyvalent polymer nanoparticle comprising multiple selectin ligands attached to its surface is used, such as that disclosed in John A E, et al., FASEB J. 2003; 17(15):2296-8. Epub 2003).

In some embodiments a small molecule is used as an sLeX mimetic. Suitable molecules are known in the art. In some embodiments a molecule developed as an sLeX-mimicking selectin antagonists can be used. For example, quinic acids or quinolone salicylic acids may be used (see, e.g., Kaila N, et al., (2005). J Med Chem 48: 4346-4357; Kaila N, et al. (2007) J Med Chem 50: 21-39). In certain embodiments PSI-697 (2-(4-Chlorobenzyl)-3-hydroxy-7,8, 9,10-tetrahydrobenzo[H]quinoline-4-carboxylic acid) is used (Kaila N, et al. (2007) J Med Chem 50: 40-64. In some embodiments a small molecule ligand, e.g., a quinic acid based ligand, is displayed multivalently (Shimay, Y, et al., J Med Chem. 2009; 52(19):5906-15). In some embodiments a small molecule selectin ligand is GMI-1070 (depicted below) or an analog thereof (Chang, J., et al., Blood, 2010; 116(10): 1779-1786).

1

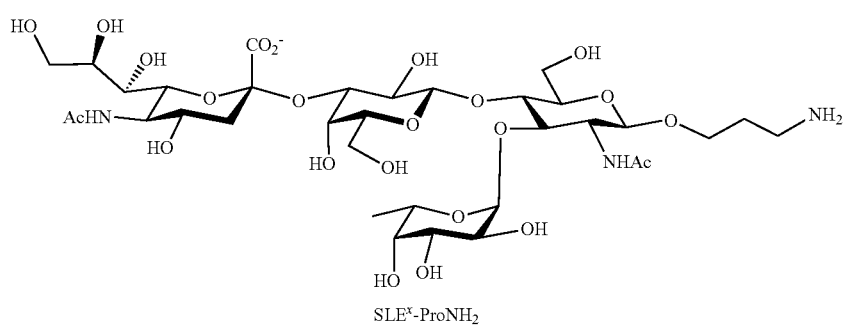

SLE$^x$-ProNH$_2$

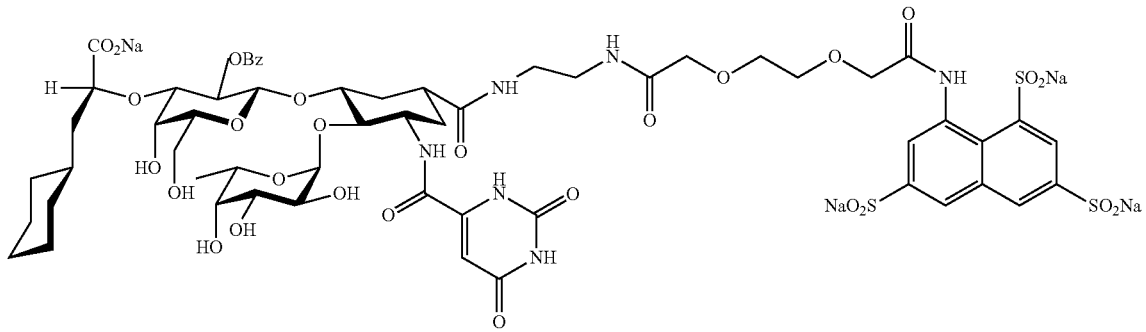

Examples of selectin ligands, e.g., sLeX mimetics, that may be used in certain embodiments as targeting moieties are found in, e.g., WO/2005/054264 (GLYCOMIMETIC ANTAGONISTS FOR BOTH E- AND P-SELECTINS), WO/2006/127906 (HETEROBIFUNCTIONAL COMPOUNDS FOR SELECTIN INHIBITION), WO2007028050 (HETEROBIFUNCTIONAL PAN-SELECTIN INHIBITORS) disclosing selectin modulators that comprise particular glycomimetics alone or linked to a member of a class of compounds termed BASAs (Benzyl Amino Sulfonic Acids) or a member of a class of compounds termed BACAs (Benzyl Amino Carboxylic Acids); WO/1999/010359 (LIPOSOMIC BASED SIALYL LEWIS X MIMETICS); WO/1998/014458 (ANTIINFLAMMATORY CELL ADHESION INHIBITORS) discloses mimetics of oligosaccharides, e.g., derivatives of sLeX and LexA; WO/2005/090284 (NON-GLYCOSYLATED/NON-GLYCOSIDIC/NON-PEPTIDIC SMALL MOLECULE PSGL-1 MIMETICS FOR THE TREATMENT OF INFLAMMATORY DISORDERS); WO/1995/003059 (BIVALENT SIALYL LEWIS X SACCHARIDES); WO/2002/089819 (GLYCOCONJUGATES AND USES THEREOF); WO/1997/012892 (SYNTHETIC MULTIVALENT sLEX CONTAINING POLYLACTOSAMINES AND METHODS FOR US; WO/1999/029705 (SIALYL LEWIS X AND SIALYL LEWIS A GLYCOMIMETICS); WO/1994/026760 (SIALYL Lex ANALOGUES AS INHIBITORS OF CELLULAR ADHESION); WO/2002/062810 (LINKABLE SIALYL LEWIS X ANALOGS); WO/1998/018805 (SUGAR DERIVATIVES AS SIALYL LEWIS X MIMETICS).

In some embodiments an aptamer, peptide, antibody, affibody, anticalin, adnectin, or synbody, that binds to one or more selectins, integrins, or cell adhesion molecules (e.g., VCAM) is used as a targeting moiety.

A targeting moiety and a detectable label may be conjugated directly to each other or may be attached via a linker or may be attached to a third moiety in various embodiments. Methods of preparing conjugates will be apparent to those of ordinary skill in the art. The particular method and reagents selected will depend on the particular moieties to be conjugated and available functional groups thereof. Conjugation methods described herein for preparing CAPP substrates or long-acting compstatin analogs may be applied or adapted to produce imaging agents comprising a targeting moiety and a label in certain embodiments. In some embodiments a targeting moiety and a detectable label are covalently attached. In some embodiments a noncovalent binding pair such as biotin-(strept)avidin, antibody-antigen, or other moieties exhibiting a strong and specific non-covalent interaction are used. In some embodiments an imaging agent is multivalent in that it comprises multiple targeting moieties and/or multiple detectable label moieties. The targeting moieties and/or detectable labels may be the same, or two or more different targeting moieties or detectable agents may be used.

In some embodiments an imaging agent comprises a plurality of particles. In some embodiments the particles are microparticles. Microparticles and nanoparticles can have a range of dimensions. In some embodiments a microparticle has a diameter between 100 nm and 100 microns (μm). In some embodiments a microparticle has a diameter between 100 nm and 1 μm, between 1 μm and 20 μm, or between 1 μm and 10 μm. In some embodiments a microparticle has a diameter between 100 nm and 250 nm, between 250 nm and 500 nm, between 500 nm and 750 nm, or between 750 nm and 1 μm. In some embodiments a nanoparticle has a diameter between 10 nm and 100 nm, e.g., between 10 nm and 20 nm, between 20 nm and 50 nm, or between 50 nm and 100 nm. In some embodiments particles are substantially uniform in size or shape. In some embodiments particles are substantially spherical. In some embodiments a particle population has an average diameter falling within any of the afore-mentioned size ranges. If desired, particle size can be determined using methods known in the art, such as dynamic light scattering or nanoparticle tracking analysis (Filipe V, Pharm Res. 2010; 27(5):796-810). In some embodiments particles may be sized or selected using a sieve, screen, or mesh. Apparatus known in the art (e.g., sifters, separators) may be used. In some embodiments a particle population consists of between about 20% and about 100% particles falling within any of the afore-mentioned size ranges or a subrange thereof, e.g. about 40%, 40%, 50%, 60%, 70%, 80%, 90%, 95%, etc. In the case of non-spherical particles, the longest straight dimension between two points on the surface of the particle rather than the diameter may be used as a measure of particle size, wherein such dimension may have any of the length ranges mentioned above.

In some embodiments a particle comprises a polymer. In some embodiments the polymer is biodegradable. In some embodiments the particle has a targeting moiety attached to its surface and comprises a detectable label. Various polymers, e.g., biocompatible polymers, can be used. A particle may be composed of a single polymer or multiple polymers. A particle may be homogeneous or non-homogeneous in composition. In some embodiments a particle comprises a core and at least one shell or coating layer, wherein, in some embodiments, the composition of the core differs from that of the shell or coating layer. In some embodiments a detectable label or targeting moiety is attached to the shell or coating layer. In some embodiments a particle is composed at least in part of a polymer that comprises a plurality of reactive functional groups to which a targeting moiety or detectable label can be attached. For example, the polymer may comprise hydroxyl groups, carboxyl groups, primary or secondary amine groups, etc.

A polymer may be a homopolymer, copolymer (including block copolymers), straight, branched-chain, or cross-linked. Natural or synthetic polymers can be used in various embodiments. Useful polymers include, but are not limited to, poly-lactic acid (PLA), poly-glycolic acid (PGA), poly-lactide-co-glycolide (PLGA), poly(phosphazine), poly (phosphate ester), polycaprolactones, polyanhydrides, ethylene vinyl acetate, polyorthoesters, polyethers, and poly (beta amino esters). In certain embodiments the formulation comprises poly-lactic-co-glycolic acid (PLGA) and can be prepared as described in Lewis, "Controlled Release of Bioactive Agents from Lactide/Glycolide polymer," in Biodegradable Polymers as Drug Delivery Systems, M. Chasin & R. Langer, Ed. (Marcel Dekker, New York), 1990. See also, Jones, D., Pharmaceutical Applications of Polymers for Drug Delivery, ISBN 1-85957-479-3, ChemTec Publishing, 2004. Formulations described in either of these references can be used. Other polymers useful in various embodiments include polyamides, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, poly(methyl methacrylate), poly(ethyl methacrylate), poly(butylmethacrylate), poly(isobutyl methacrylate), poly (hexylmethacrylate), poly(isodecyl methacrylate), poly (lauryl methacrylate), poly(phenyl methacrylate), poly (methyl acrylate), poly(isopropyl acrylate), poly(isobutyl acrylate), poly(octadecyl acrylate), polyethylene, polypropylene, poly(ethylene glycol), poly(ethylene oxide), poly (ethylene terephthalate), poly(vinyl alcohols), polyvinyl acetate, poly vinyl chloride, polystyrene, polyvinylpyrrolidone, poly(butyric acid), poly(valeric acid), and poly(lactide-cocaprolactone). Peptides, polypeptides, proteins such as collagen or albumin, polysaccharides such as sucrose, chitosan, dextran, alginate, hyaluronic acid (or derivatives of any of these) and dendrimers are of use in certain embodiments. Methods for preparation of such formulations will be apparent to those skilled in the art. Liposomes or other lipid-containing particles may be used in certain embodiments. Additional polymers include cellulose derivatives such as, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxymethylcellulose, carboxylethyl cellulose, cellulose triacetate, cellulose sulphate sodium salt, polycarbamates or polyureas, cross-linked poly(vinyl acetate) and the like, ethylene-vinyl ester copolymers such as ethylene-vinyl acetate (EVA) copolymer, ethylene-vinyl hexanoate copolymer, ethylene-vinyl propionate copolymer, ethylene-vinyl butyrate copolymer, ethylene-vinyl pentantoate copolymer, ethylene-vinyl trimethyl acetate copolymer, ethylene-vinyl diethyl acetate copolymer, ethylene-vinyl 3-methyl butanoate copolymer, ethylene-vinyl 3-3-dimethyl butanoate copolymer, and ethylene-vinyl benzoate copolymer, or mixtures thereof. Chemical derivatives of the afore-mentioned polymers, e.g., substitutions, additions of chemical groups, for example, alkyl, alkylene, hydroxylations, oxidations, and other modifications routinely made by those skilled in the art can be used. Particles comprising or composed at least in part of inorganic substances may be used. For example, particles may comprise metal, silica, or other inorganic substances. In some embodiments mesoporous silica particles are used.

In some embodiments a particle is impregnated with or encapsulates a detectable label. In some embodiments a detectable label is attached to the surface of a particle. In some embodiments a particle is at least in part composed of a detectable material, e.g., a metal, or has at least one property that renders the particle detectable using a non-invasive detection method. For example, in some embodiments gas-filled microbubbles or nanobubbles that can be detected by ultrasound are used. In some embodiments microparticles comprise iron oxide. In some embodiments microparticles comprising iron oxide are visualized and quantified using an OCT system, an approach that has been described in the context of atherosclerosis (Jefferson, A. Atherosclerosis. 2011; 219(2):579-87).

In some embodiments, inflamed endothelium is detected at least in part by detecting an active inflammation-associated protease. As used herein, the term "inflammation-associated protease" (IAP) refers to a protease that plays a role in inflammation. In some embodiments an IAP is a protease whose expression or activity is upregulated during inflammation. In some embodiments an IAP is a protease that activates (by cleaving) one or more inflammatory mediators or one or more receptors for an inflammatory mediator. The luminal surface of endothelial cells is coated with a carbohydrate-rich surface layer, collectively referred to as the endothelial glycocalyx, that contains adsorbed proteins and membrane bound proteoglycans (Reitsma S, et al. Pflugers Arch. 2007; 454:345-359). Alterations in the endothelial glycocalyx, such as proteolytic cleavage of one or more of its protein components, may increase exposure of underlying cell adhesion molecules, thereby enhancing leukocyte adhesion and/or extravasation. In some embodiments inflamed endothelium is detected at least in part by detecting an alteration in the endothelial glycocalyx or by detecting an IAP that is capable of cleaving a component of the endothelial glycocalyx.

In some embodiments an IAP is produced by endothelial cells. In some embodiments an IAP is a matrix metalloprotease (MMP). MMPs can be stored within and released by the endothelium. For example, it has been shown that both the active and pro-enzyme forms of MMP-2 and MMP-9 are stored in vesicles in endothelial cells, suggesting the existence of mechanisms by which MMP's can be rapidly released by endothelial cells. In some embodiments an IAP is produced by leukocytes. In some embodiments an IAP is an elastase, e.g., macrophage or neutrophil elastase.

In some embodiments an active IAP is detected by detecting cleavage of a substrate of the IAP, in a similar manner as described above for detection of active CAPPs, e.g., using a substrate comprising a fluorophore and a quencher, wherein cleavage of the substrate results in dequenching of the fluorophore. Subtrates and protease recognition sequences of proteases, e.g., various IAPB, are known to those of ordinary skill in the art and may be found in databases such as MEROPS (Rawlings, N. D., Barrett, A. J. & Bateman, A. (2012) MEROPS: the database of proteolytic enzymes, their substrates and inhibitors. Nucleic Acids Res 40, D343-D350), or databases that comprise part of the Proteolysis MAP (PMAP; Igarashi Y., Nucleic Acids Res. 2009; 37(Database issue):D611-8) such as ProteaseDB, SubstrateDB, CutDB (Igarashi Y., et al. Nucleic Acids Res. 2007), ProfileDB, etc., or may be experimentally determined. Peptide substrates of IAPB, the cleavage of which can be detected in vivo, can be generated as described above for CAPPs. In some embodiments a peptide substrate of an IAP comprising one or more labels is administered to a subject and its cleavage in the choroidal endothelium underlying or in close proximity to a druse is detected, thereby detecting a high risk druse.

In some embodiments a substrate comprises a protease recognition sequence for a CAPP and a protease recognition sequence for an IAP. The substrate may comprise two or more labels, e.g., two, three, or four labels. For example, the substrate may comprise two fluorophores having distinct emission maxima and one or more quenchers. In some embodiments the labels are selected and arranged so that a signal is generated upon cleavage by either a CAPP or an IAP. In some embodiments the labels are selected and arranged that a signal is generated upon cleavage by either a CAPP or an IAP, wherein the signals are distinguishable. In some embodiments the labels are selected and arranged so that a signal is generated upon cleavage by both a CAPP and an IAP.

In some embodiments a peptide substrate of an IAP further comprises or is physically associated with a targeting moiety that binds to inflamed endothelium or is attached to a particle. In some embodiments the particle comprises a targeting moiety at its surface that binds to inflamed endothelium. Particles and targeting moieties discussed above may be used. Attaching a substrate and/or targeting moiety to a particle allows delivery of multiple copies of the substrate and enhances binding to regions where the relevant target is exposed. Tens, hundreds, thousands, or more substrate moieties or targeting moieties may be present or attached to a multivalent polymer or particle in various embodiments.

The imaging agents for detecting inflamed endothelium may be administered intravenously or using any appropriate method. Appropriate doses may be readily determined. Detection is achieved using appropriate apparatus, which will depend on the particular label(s) used. In some embodiments a method of detecting inflamed endothlium in a subject comprises: (a) providing a subject to whom a substrate (e.g., a labeled substrate) for an IAP has been administered; and (b) detecting cleavage of the substrate, thereby detecting inflamed endothelium in the subject. In some embodiments the substrate produces a detectable signal upon cleavage; and step (b) comprises detecting the signal. In some embodiments the method comprises administering the substrate to the subject. In some embodiments a method of preparing a subject for detection of inflamed endothelium therein comprises: administering a substrate of an IAP to the subject. In some embodiments the method comprises detecting cleavage of the substrate, thereby detecting inflamed endothelium in the subject.

VI. Eye-Derived Extracellular Vesicles as AMD Risk Markers

In some aspects, the present disclosure provides methods of identifying or monitoring a subject at increased risk of development or progression of AMD, the method comprising detecting extracellular vesicles (EVs) in a body fluid of a subject, wherein the EVs originate from cells in the eye. EVs originating from cells in the eye may be referred to herein as "eye-derived extracellular vesicles". Extracellular vesicles (EVs) are membrane-bound vesicles originating from cells. They comprise a lipid bilayer that contains membrane-associated proteins and encloses components derived from the cytosol of the cell of origin. Several types of extracellular vesicles are known. EVs include (i) exosomes: typically about 30-about 100 nm diameter membranous vesicles of endocytic origin generated by exocytic fusion of multivesicular bodies with the plasma membrane; (ii) microvesicles (MV) (also sometimes referred to as shedding microvesicles or ectosomes): large membranous vesicles (typically about 100 nm-about 1000 nm diameter) that bud and are shed directly from the plasma membrane; and (iii) apoptotic blebs, also termed apoptotic bodies (often about 1000 nm-about 5000 nm diameter): released by dying cells. It will be understood that these size ranges are not absolute. For example, MV or apoptotic blebs that have smaller diameters than the typical values listed may exist; exosomes may have larger diameters than the typical values listed, e.g., up to about 150 nm.

Exosomes are formed by invagination and budding from the limiting membrane of late endosomes. They accumulate in multivesicular bodies (MVBs) from where they are released by fusion with the plasma membrane. As a result, these EVs contain cytosol and exposed extracellular domains of certain membrane-associated proteins (Stoorvogel et al.; (2002); Traffic 3:321-330; Thery C, et al., (2009); Nat Rev Immunol. 9:581-593; Mathivanan S, Ji H, Simpson R J (2010); J Proteomics 73: 1907-1920). Exosomes are distinct from apoptotic bodies as well as from larger microvesicles (MVs) that are generated by plasma membrane shedding. Many cell types have been shown to generate exosomes including dendritic cells, reticulocytes, T lymphocytes, B cells, macrophages, platelets, epithelial cells, neurons, retinal pigment epithelial cells, and tumor cells of various types. Depending at least in part on their cellular origin, exosomes may expose various cellular proteins at their surface, which in some instances may be different from proteins that are normally located in the plasma membrane of the cells of origin. Although exosomal protein composition varies with the cell and tissue of origin, many or most exosomes contain at least one of a common set of proteins, e.g., in addition to protein(s) that are more specific to the cell or tissue of origin. Proteins commonly exposed at the surface of exosomes, which may serve as markers of exosomes, include, e.g., tetraspannins, adhesion molecules, MHC molecules, and/or metalloproteinases. Exosome membranes may be characterized by presence of lipid rafts. Exosome constituents (internal contents and/or membrane-bound contents, which may be at least partly exposed at the exosome surface) reflect the origin and in some embodiments physiological state of the source cells. Exosomes contain, for example, proteins produced by the source cells. In addition to proteins, exosomes carry mRNA as well as microRNAs (miRNAs). Exosome production and content may be influenced by molecular signals received by the cell of origin, e.g., molecules and cells in the local environment of the cell of origin. Exosomes are believed to play various roles in, among other things, intracellular communication and immune system modulation.

In some aspects, the present invention provides the insight that EVs, e.g., exosomes, released from ocular cells undergoing early and/or late events in AMD pathogenesis may be detected in body fluids such as blood or urine. Detection of such EVs in a body fluid, e.g., in a sample comprising body fluid obtained from a subject, may be used to diagnose increased risk that a subject will develop AMD or will experience progression or rapid progression of AMD. In certain embodiments, for example, detection of eye-derived EVs, e.g., eye-derived exosomes, in a body fluid, e.g., blood, is indicative of an increased likelihood that a subject who does not have AMD will develop AMD, or that a subject with early AMD will develop GA or wet AMD, or that a subject with early or intermediate AMD will develop advanced AMD.

In some embodiments, a method comprises isolating EVs and detecting presence of one or more cellular markers in or on at least some of the EVs, wherein the cellular marker(s) are cell-type specific markers specific for cells in the eye. Such markers may be referred to as "eye-specific cellular markers". EVs, e.g., exosomes, can be isolated using any of a variety of methods known in the art. As they are small particles, EVs may be recovered from a blood sample by first removing the larger cellular elements from a blood sample, by, for example, low speed centrifugation, e.g., centrifugation at about 1500 g for 10 minutes. A population of EVs, e.g., exosomes is typically more extensively purified, e.g., by methods comprising one or more centrifugation steps. For example, exosomes may be separated from plasma or serum by three successive centrifugations at 1200 g for 5 minutes, 1,200 g for 20 minutes, and 10,000 g for 30 minutes, followed by centrifugation for one hour at 100,000 g, washing the resulting pellet with PBS, resuspending in PBS and then centrifuging again at 100,000 g for 1 hour, after which the resultant pellet may be resuspended in PBS. It will be understood that this isolation method is merely exemplary. In some embodiments a protocol for exosome isolation comprises ultracentrifugation and a subsequent sucrose density gradient ultracentrifugation or sucrose cushion centrifugation. An exemplary protocol for exosome isolation is described in Thery C, Amigorena S, Raposo G, Clayton A (2006) Isolation and characterization of exosomes from cell culture supernatants and biological fluids. Curr Protoc Cell Biol (Chapter 3:Unit 3) 22. In some embodiments EVs, e.g., exosomes, are isolated using chromatography, e.g., liquid chromatrography. In some embodiments EVs, e.g., exosomes, are isolated using a method that comprises a precipitation-based technique. ExoQuick™ and ExoQuick-TC™ (System Biosciences, Inc., Mountain View, Calif., USA) are kits that are useful for isolating exosomes using polymer-based precipitation. ExoQuick™ is optimized for collecting exosomes from serum or other biological fluid. If desired, the size of EVs can be determined using methods such as dynamic light scattering or nanoparticle tracking analysis. Other methods of determining EV size include, e.g., transmission electron microscopy and atomic force microscopy. Such methods may be applied to a portion of an EV preparation to obtain an indication of the average size or size distribution of the EVs in the preparation. EVs falling within a given size range or having particular EV marker(s) exposed at their surface may be selected or purified using methods such as flow cytometry (Orozco A F, Lewis D E Cytometry A. 2010 June; 77(6):502-14). Antibodies may be used in flow cytometry as labels or as immunoaffinity reagents to isolate EVs, e.g., exosomes. In some embodiments a filter is used to isolate EVs, optionally in combination with centrifugation, immunoisolation, flow cytometry, etc. A filter may have pore sizes appropriate to retain or allow passage of particles, e.g., EVs, within a particular size range. Two or more filters may be used. In some embodiments a filter has a pore size below about 30 nm in diameter. In some embodiments a filter has a pore size between about 30 nm and about 100 nm in diameter, between about 100 nm and about 200 nm in diameter, etc. Appropriate filters may, if desired, be used to remove proteins (e.g., soluble serum proteins), viruses, or other materials from an EV preparation. The afore-mentioned methods may be modified as appropriate to isolate or enrich for exosomes, MVs or apoptotic bodies, as desired. In some embodiments exosomes are purified at least in part based on presence of an exosome marker at their surface. In some embodiments an exosome marker is a tetraspannin, CD24, CD9, Annexin-1, Alix, CD63, Hsp70, phosphatidylserine (detectable by Annexin V binding), CD81, CD9, LAMP1, or TSG101. MV markers include phosphatidylserine (detectable by Annexin V binding) and tissue factor. In some embodiments EVs are isolated at least in part based on presence of an eye-specific marker at their surface. In some embodiments EVs in an exosome preparation has an average diameter between 30 nm and 100 nm, e.g., between 40 nm and 90 nm. In some embodiments at least 50%, 60%, 70%, 80%, 90%, or more of EVs in a preparation have a diameter between 30 nm and 100 nm, e.g., between 40 nm and 90 nm.

Once a population of EVs, e.g., exosomes, is obtained, it may be further analyzed for presence of one or more eye-specific markers and/or for presence of VEGF or one or more macrophage activity markers (discussed further below). In some aspect, presence of one or more eye-specific markers indicates that at least some of the EVs originated from ocular cells. In some embodiments, if the EVs, e.g., exosomes, were isolated based at least in part on presence of an eye-specific cellular marker at their surface, they may not be further analyzed since the isolation itself is of course sufficient to establish the presence of eye-derived EVs. In some aspects, the level of the one or more eye-specific markers is indicative of the amount of eye-derived exosomes released from cells in the eye. In some aspects, presence or an increased level of eye-derived exosomes as compared with a reference level indicates an increased risk of developing or progression of AMD or rapid progression of AMD, e.g., progression within a given time period, e.g., 6 months, 1year, 2 years, 5 years, etc. Ocular cells include, e.g., retinal cells and RPE cells. Retinal cells include photoreceptor cells (rod and cone cells), ganglion cells, amacrine cells, and retinal glial cells. In some embodiments EVs may not be purified from a blood sample; instead the blood sample (optionally serum or plasma) is tested for presence of one or more eye-specific cellular markers.

Numerous eye-specific markers are known and may be used in various embodiments. In some embodiments an eye-specific marker is a cell surface marker. In some embodiments an eye-specific marker is specific for one or more particular ocular cell types, e.g., RPE cells or photoreceptor cells. In some embodiments an eye-specific marker functions primarily or exclusively in phototransduction (i.e., the absorption of light by visual pigments (opsins with covalently attached retinal) in the retinal rod and cone photoreceptors and its conversion into an electrical signal (which signal propagates to higher-order retinal neurons (the bipolar and ganglion cells) and eventually to the brain via the optic nerve) or in phototransduction deactivation. In some embodiments an eye-specific cellular marker is an opsin. Opsins are G protein coupled receptors (GPCRs) that have seven-transmembrane structure similar to that of other GPCRs, but are distinguished by a lysine residue that is a site for binding of the chromophore retinal in the seventh helix. Most opsins activate particular G proteins in a light-dependent manner, whereas a few serve as retinal photoisomerases, generating the chromophore used by other opsins. In some embodiments an opsin is a visual opsin (which term refers to transducin-coupled opsins). In some embodiments an opsin is a cone opsin. In some embodiments a cone opsin is OPN1LW (opsin 1, long-wave-sensitive), OPN1MW (opsin 1, medium-wave-sensitive), OPN1SW (opsin 1, short-wave-sensitive); or OPN1MW2

(opsin 1, medium-wave-sensitive 2). In some embodiments an opsin is rhodopsin (RHO). In some embodiments an opsin is retinal pigment epithelium-derived rhodopsin homolog (RRH). In some embodiments an opsin is opsin 4 (OPN4), also known as melanopsin (MOP), also known as opsin 4. In some embodiments an opsin is opsin 5 (OPN5), also known as neuropsin. In some embodiments a binding agent, e.g., an antibody, capable of binding to any of multiple different opsins may be used. For example, an antibody that binds to a highly conserved region may be used. Further information regarding opsins may be found in Terakita, A., Genome Biology 2005, 6:213. In some embodiments an eye-specific marker is a transducin or a subunit thereof. Transducin is a heterotrimeric G protein with three polypeptide chains (subunits): α, β and γ. Transducin is naturally expressed in vertebrate retina rods and cones, with different α subunits in rod and cones. Heterotrimeric transducin is activated by metarhodopsin II, a conformational form of opsin resulting from the absorption of a photon by the chromophore retinal, which is covalently linked to the opsin. Further discussion regarding mammalian phototransduction and deactivation of the phototransduction cascade, is found in Luo D G, et al., Proc Natl Acad Sci USA. 2008; 105(29):9855-62 and references therein.

In some embodiments an eye-specific cellular marker is an arrestin. In some embodiments an eye-specific cellular marker is recoverin (RCVRN). In some embodiments an eye-specific marker is a crystallin, e.g., an alpha crystallin, e.g., alphaA-crystallin or alphaB-crystallin. In some embodiments anarrestin is, ARR3 (arrestin 3, retinal) or SAG (S-antigen; retina and pineal gland (arrestin). In some embodiments an eye-specific cellular marker is present in photoreceptor outer segments. In some embodiments an eye-specific cellular marker is ARL6, BBS1, BBS2, BBS4, BBS5, BBS7, BBS9, BBS10, BBS12, CEP290, MKKS, TRIM32, TTC8, RGR, AIPL1, CRX, GUCA1A, GUCY2D, PROM1, PRPH2, RIMS1, SEMA4A, UNC119, ABCA4, CACNA2D4, CERKL, CNGB3, KCNV2, RDH5, RPGRIP1, CACNA1F, RPGR, GNAT1, PDE6B, CABP4, GRK1, GRM6, SAG, CACNA1F, NYX, MYO7A, CDH23, MYO7A, PCDH15, USH1C, CRX, IMPDH1, AIPL1, CEP290, CRB1, CRX, GUCY2D, LRAT, RD3, RDH12, RPE65, TULP1, BEST1, C1QTNF5, EFEMP1, ELOVL4, FSCN2, GUCA1B, HMCN1, TIMP3, CA4, CRX, FSCN2, GUCA1B, IMPDH1, NR2E3, NRL, PRPF3, PRPF8, PRPF31, ROM1, RP1, RP9, SEMA4A, CERKL, CNGA1, CNGB1, CRB1, LRAT, MERTK, PDE6A, PDE6B, RLBP1, RP1, SEMA4A, TTC8, USH2A, RP2, LRP5, CDH23, CLRN1, GPR98, PCDH15, USH1G, CRB1, FZD4, CDH3, CNGB3, CYP4V2, OAT, RBP4, RLBP1, CACNA1F, CHM, NDP, or RS1.

The sequences of the genes and proteins represented by the afore-mentioned gene symbols are readily available to those of ordinary skill in the art and can be found, e.g., by searching in the NCBI or Uniprot databases mentioned above. In some embodiments an eye-specific marker is a miRNA. miRNA profiles for ocular cells are known in the art or can be readily determined. In some embodiments an eye-specific cellular marker is retinal or a precursor thereof or breakdown product thereof. In some aspects, EVs, e.g., exosomes are analyzed for presence or level of one or more molecules that may have been taken up by the cells of origin (e.g., ocular cells) from their local environment via endocytosis. In some aspects, EVs, e.g., exosomes are analyzed for presence or level of one or more molecules that may reflect a particular physiological state, e.g., a diseased or activated state, of the cells of origin (e.g., ocular cells). For example, ocular cells having a protein or miRNA profile indicative of exposure to Th17 activity (e.g., contact with Th17 cells and/or exposure to one or more Th17-associated cytokines, e.g., at higher than normal levels) may reflect such exposure in the contents of EVs derived from such ocular cells. In some embodiments one or more such proteins or miRNAs indicative of exposure to Th17 activity is detected.

Cellular markers, e.g., eye-specific cellular markers, or other cellular molecules, in or on at least some of the EVs may be detected using any suitable method for detecting such markers. Exemplary methods useful for detecting markers are discussed above. It will be understood that the EVs may be processed appropriately to facilitate detection. For example, EVs may be lysed or their membrane at least partially disrupted to at least partially release their contents. Reagents, e.g., antibodies, nucleic acid probes or primers, etc., useful for detecting various eye-specific cellular markers or Th17 biomarkers or other cellular markers of interest may be obtained from commercial suppliers such as Sigma-Aldrich (St. Louis, Mo., USA) or Abcam (Cambridge, Mass., USA) or generated using methods routinely used in the art for producing such reagents. In some embodiments a reagent capable of specifically binding to multiple eye-specific cellular markers may be used. For example, the reagent may bind to a sequence or structure, e.g., an epitope, that is identical or highly conserved in multiple different cellular markers.

In certain embodiments an eye-specific marker is detected using an ELISA assay. As used herein, the term "ELISA assay" refers to any of a number of techniques that may be used to detect the presence of an analyte of interest in a sample. In ELISA assays the analyte of interest is directly or indirectly immobilized on a support and is contacted with a first specific binding agent that binds to the analyte and a detection enzyme is used to detect the first specific binding agent. Suitable detection enzymes are known in the art, and a number are mentioned above. The detection enzyme is contacted with a substrate on which it acts to generate a detectable signal. For example, the substrate may be a chromogenic or fluorogenic substrate that generates a colored or fluorescent moiety, when acted on by the enzyme, e.g., when cleaved by the enzyme. The detection enzyme may be linked to the first specific binding agent. In many embodiments, however, the detection enzyme is linked, e.g., covalently linked, to a second specific binding agent that specifically binds to the first specific binding agent. In some embodiments, the detection enzyme is linked, e.g., covalently linked, to a third specific binding agent that binds to the second specific binding agent. For example, the second specific binding agent may be linked to biotin and the detection enzyme linked to avidin or streptavidin. A number of different ELISA assay types may be used. These general assay formats are well known in the art. In a sandwich ELISA, a first specific binding agent that binds to the analyte is immobilized on a support and used to "capture" analyte present in the sample. The first specific binding agent may be referred to as a "capture agent". Analyte present in the sample binds to the first specific binding agent and is thereby immobilized. Unbound material may be removed. One or more washing steps may be performed. A composition comprising a second specific binding agent specific for the analyte is then contacted with the support. The second specific binding agent serves as a "primary detection agent" and binds to analyte that had been immobilized via binding to the first specific binding agent. Unbound second specific binding agent is typically removed. The second specific binding agent is then detected. In some embodiments the second specific binding agent has an enzyme linked thereto. In some embodiments the second specific binding agent does not have an enzyme linked thereto but instead is detected using a third specific binding agent ("secondary detection agent") that binds to the second specific binding agent and has an enzyme linked thereto. In some embodiments the primary detection agent comprises an antibody and the secondary detection agent comprises an antibody that binds to the antibody of the primary detection agent (e.g., to the Fc domain). It will be appreciated that in such cases it may be desirable to avoid using capture agent and primary detection agent that comprise antibodies raised in the same species in order to avoid the secondary detection agent binding to the capture agent. In some embodiments the primary detection agent comprises an antibody linked to a first member of a specific binding pair, and the secondary detection agent comprises an antibody linked to the other member of the specific binding pair, thus enabling use of a secondary detection agent that does not bind to the antibody portion of the primary detection agent. For example, the primary detection agent may comprise an antibody to which biotin has been conjugated, and the secondary detection agent may comprise avidin or streptavidin conjugated to an enzyme or may comprise a preformed complex between avidin or streptavidin and a biotinylated enzyme. In another embodiment the primary detection agent comprises an antibody conjugated to biotin, and the secondary detection agent comprises avidin or streptavidin conjugated to an enzyme or comprises a complex between avidin or streptavidin and a biotinylated enzyme. Biotin/avidin and biotinistreptavidin are exemplary specific binding pairs and that others could be used in these embodiments. Often the capture agent and the primary detection agent are different. For example, it may be desirable to select capture and primary detection agents that bind to different portions of an analyte to avoid binding by the capture agent from interfering with binding by the primary detection agent. In some embodiments, the capture agent is a monoclonal antibody that binds to an analyte and the primary detection agent is a polyclonal antibody that binds to the analyte. In some embodiments, the capture agent may be a polyclonal antibody that binds to an analyte and the primary detection agent may be a monoclonal antibody that binds to the analyte. The polyclonal antibody will typically contain a plurality of antibody molecules that bind to different epitopes of an antigen. Thus capturing an analyte using a monoclonal antibody is not expected to interfere with detection using a polyclonal antibody, and capturing an analyte using a polyclonal antibody is not expected to interfere with detection using a monoclonal antibody as a primary detection agent. In some embodiments the capture agent and the primary detection agent are monoclonal antibodies that bind to different epitopes of an analyte. In an indirect ELISA, the analyte is attached directly to the support, e.g., by adsorption. Often other substances present in the sample (e.g., other proteins) are also adsorbed. A first specific binding agent that serves as a primary detection agent is contacted with the support and binds to the analyte. Unbound specific binding agent is removed and the support is washed. In some embodiments the primary detection agent comprises a detection enzyme, which is contacted with a substrate to detect the analyte. Alternately a second specific binding agent that specifically binds to the first specific binding agent is contacted with the support and binds to the first specific binding agent. Unbound second specific binding agent is removed. The second specific binding agent has a detection enzyme linked thereto, which is used to detect the analyte. In other embodiments, the second specific binding agent does not comprise a detection enzyme. Instead, after allowing the second specific binding agent to bind to the primary detection agent, unbound second specific binding agent is removed and the support is then contacted with a third specific binding agent that binds to the second specific binding agent and has a detection enzyme linked thereto, which is used to detect the analyte. In a competitive ELISA, a first specific binding agent that recognizes the analyte is contacted with a sample containing analyte. The resulting assay composition is maintained to allow formation of binding agent/analyte complexes. The assay composition is then contacted with a support that has analyte attached thereto. Specific binding agent that is not in a complex with the analyte in the assay composition binds to analyte attached to the support. Unbound specific binding agent is then removed. Binding agent that remains bound to the support is then detected using a second binding agent to which an enzyme is bound. A substrate is added, and the enzyme acts on the substrate to generate a detectable signal. In this type of ELISA assay, the higher the analyte concentration, the weaker the resulting signal. In some embodiments an assay is similar to a traditional ELISA assay in that it involves detecting an analyte that has been immobilized on a support, but use a detectable label that is not an enzyme. For example, a specific binding agent used for detection purposes may be labeled with a detectable label other than an enzyme, e.g., a fluorescent or chemiluminescent substance such as fluorescein, rhodamine, phycoerythrin, a quantum dot, etc. The term "ELISA assay", as used herein, should be understood to encompass embodiments in which such non-enzyme detectable labels are used. ELISA assays may be performed in a variety of ways depending at least in part on the nature of the support. For example, an analyte or capture agent may be immobilized on the surface of a receptacle such as a well of a multiwell plate, e.g., by adsorption or via a reactive functional group. After capture of an analyte and washing to remove unbound material, reagents for detecting an analyte may be added to the well in a sequence of steps separated by washing steps in which unbound reagents are removed. Alternately, reagents for detecting an analyte can be placed in different receptacles and an analyte or capture agent immobilized on a surface that can be transferred from one receptacle to another, with washing steps between transfers. For example, the analyte could be immobilized on a rod or pin, which is dipped sequentially into a receptacle containing a first specific binding agent, a receptacle containing a second specific binding agent that binds to the first specific binding agent, and then a receptacle containing an enzyme substrate (with wash steps in between). In some embodiments the capture agent is immobilized on a rod or pin which is dipped into a receptacle containing a sample and then sequentially into a receptacle containing a second specific binding agent, and a receptacle containing an enzyme substrate (with wash steps in between). In some embodiment a particle-based ELISA is used. Suitable particles for use in performing biological assays, e.g., immunoassays, are known in the art and are commercially available from, e.g., Promega, Inc. (Madison, Wis., USA), Sigma-Aldrich (St. Louis, Mo., USA), Magsphere, Inc. (Pasadena, Calif., USA), Dynal (now part of Life Technologies, Carlsbad, Calif., USA). In some embodiments, magnetic beads are retained in a receptacle using a magnetic force while reagents are sequentially added to the receptacle and removed. In one embodiment, a particle-based ELISA assay uses spectrally discrete polystyrene beads to immobilize the capture antibody (or other capture agent). For example, carboxy-coated microspheres internally labeled with two fluorescent dyes that produce up to 100 different spectral addresses available from Bio-Rad Laboratories, Inc. (Hercules, Calif., USA.) may be used. Similar to some traditional sandwich ELISA assays, each antibody-coupled bead captures analytes that are detected with a biotinylated antibody and phycoerythrin-conjugated streptavidin (SA-PE). For each capture antibody-coupled bead, the reader simultaneously measures the fluorescent signals of the bead's particular spectral address and of the SA-PE. Each mean fluorescence intensity reading corresponds to the average of the fluorescent signals from many (e.g., hundreds to thousands) of antibody-coupled beads having a particular spectral address. In the absence of cross-reactivity, each reading can assess the concentration of multiple analytes that are detected by spectrally distinct beads. The Bio-Plex Multiplex Suspension Array System (Bio-rad) and Luminex's (Luminex; Austin, Tex., USA.) flow cytometer with carboxylate xMap™ microspheres (also Luminex) are commercially available platforms that can be used to implement such assays. Specific binding agents might be selected that bind to any peptide, polypeptide, small molecule, or other analyte that is or may be present in a biological sample in which an analyte of interest is to be assessed. In certain embodiments a capture agent may be immobilized on a support by any suitable means, provided that it remains capable of retaining the analyte following immobilization. For example, a capture agent may be immobilized by adsorption, covalent interaction, chelation, molecular recognition, etc. In some embodiments a capture agent is immobilized via a physical interaction between the capture agent and the support, while in other embodiments the capture agent and support each interact with a third entity that links the capture agent to the support. For example, in some embodiments a first member of a specific binding pair is linked to the support and a second member of the specific binding pair is linked to the capture agent. Binding of the members of the specific binding pair to each other immobilizes the capture agent. In yet other embodiments a bifunctional specific binding agent is used to attach the capture agent to the support. The bifunctional specific binding agent contains a first domain that links it to the support (or to a moiety that is linked to the support) and a second domain that links it to the capture agent (or to a moiety that is linked to the capture agent). In some embodiments, capture agents are immobilized on discrete spots on a support, e.g., within individual wells of a microtiter plate. For example, a microtiter plate in which a binding agent, e.g., a monoclonal antibody, against an eye-specific marker is adsorbed to individual wells may be used to perform certain of the assays. One of ordinary skill in the art will appreciate that ELISA assays may include additional steps not necessarily described in detail above, such as blocking, washing, preparing standard curves, etc. Performing such steps is routine.

In some embodiments an article of manufacture comprising a solid support is provided, e.g., a microtiter plate or a collection of beads, comprising binding agents suitable for binding a plurality of different analytes of interest herein, e.g., a plurality of eye-specific markers. The different binding agents may be located at discrete positions, e.g., in distinct wells or at distinct locations or attached to distinct populations of beads, to allow detection and, optionally, quantitation, of a plurality of different eye-specific markers. In some embodiments at least 2, 3, 4, 5, 10, 15, 20, or more analytes, e.g., eye-specific markers are detectable using the article of manufacture. Control binding agents may be provided as well as those intended to capture an analyte of interest. In some embodiments the article of manufacture is provided as a kit. In some embodiments the kit comprises instructions for use and/or one or more additional items, such as a reaction buffer, detection agent, wash buffer, or control reagent.

VII. Th17 Cells or TH17 Biomarkers as AMD Risk Markers

In some aspects, the present disclosure provides methods of identifying or monitoring a subject at increased risk of development or progression of AMD, the method comprising detecting Th17 cells or a Th17 biomarker in a body fluid of the subject. In some embodiments a subject is tested for Th17 cells (e.g., Th17 cell number or relative number) and/or for one or more biomarkers associated with Th17 cells and/or Th17 activity ("Th17 biomarker"). "Th17 biomarker" encompasses any molecule or detectable indicator that correlates with Th17 cell presence (e.g., number or concentration of Th17 cells) and/or correlates with at least one Th17 cell activity. In some embodiments, a Th17 biomarker comprises a level of a Th17-associated cytokine. In some embodiments a Th17-associated cytokine is a cytokine that promotes formation and/or activation of Th17 cells, e.g., IL-6, IL-21, IL-23, and/or IL-1β. In some embodiments a Th17-associated cytokine is a cytokine produced by Th17 cells, e.g., IL-17 (e.g., IL-17A and/or IL-17F), IL-21, and/or IL-22. In some embodiments an increased amount or increased relative amount of a Th17-associated activity is indicative of increased Th17 cells and/or increased Th17-associated activity. In some embodiments a relative amount is an amount as compared with a different cytokine. In some embodiments the different cytokine is associated with Treg cells. In some embodiments the different cytokine is IL-10. In some embodiments levels of 2, 3, 4, 5, or more Th17-associated cytokines are measured. A collective index or score indicative of the level of Th17-associated activity may be obtained and used as a Th17 biomarker. In some embodiments the presence or level of Th17 cells themselves is assessed for any purpose for which a Th17 biomarker may be assessed. In some embodiments the presence or level of Tregs is assessed. In some embodiments Tregs are identified based on expression of FOXP3.

In some embodiments, a Th17 biomarker level is measured in a sample obtained from a subject. In some embodiments a sample comprises a body fluid, e.g., blood or urine. In some embodiments a level is compared with a reference value. In some embodiments a reference value may be a normal value (e.g., a value within a normal range, e.g., an upper limit of a normal range). In some embodiments a reference value may be a value established for the subject at a previous time, e.g., at least 3 months previously. In some embodiments, if a measured value deviates significantly from a reference value or shows a trend towards increased deviation from a reference value, the subject is identified as being at increased risk of developing AMD or at increased risk of progression, e.g., rapid progression of AMD. In some embodiments, if a measured value deviates significantly from a reference value or shows a trend towards increased deviation from a reference value, the subject is identified as being at increased risk of developing GA or wet AMD. In some embodiments the subject has early AMD. In some embodiments, if a measured value in a subject with early or intermediate AMD deviates significantly from a reference value or shows a trend towards increased deviation from a reference value, the subject is identified as being at increased risk of developing advanced AMD. A "normal range" may be a range that encompasses at least 95% of healthy individuals. In some embodiments a reference value may be a value associated with a disease, e.g., a value typically found in subjects suffering from a disease in an untreated state. In some embodiments a normal or disease-associated range may depend at least in part on demographic factors such as age, sex, etc., and can be adjusted accordingly. An appropriate reference value or range may be established empirically, e.g., for different age groups, AMD stages, and/or different Th17 biomarkers and/or, in some embodiments, for individual subjects. Methods useful for detecting Th17 biomarkers include any methods of detecting cellular markers, e.g., proteins (e.g., cytokines) or RNA or cells expressing such markers.

In some embodiments, in vivo assessment of Th17 cells and/or a Th17 biomarker is envisioned. For example, in some embodiments a detectably labeled agent that binds to Th17 cells (e.g., to a cell surface marker or combination thereof that is reasonably specific for Th17 cells) or that bind to a Th17-associated cytokine is administered to a subject. A suitable imaging method is used to visualize the agent in vivo. In some embodiments, for example, an image is obtained of the eye or a portion thereof, e.g., at least a portion of the fundus. In some embodiments in vivo detection allows assessment of the immunological microenvironment in the eye. In some embodiments a detectable label comprises a fluorescent, radioactive, ultrasound, or magnetically detectable moiety. In some embodiments an imaging method comprises magnetic resonance imaging, ultrasound imaging, optical imaging (e.g., fluorescence imaging or bioluminescence imaging), or nuclear imaging. In some embodiments a fluorescent moiety comprises a near-infrared or infrared fluorescent moiety (emitting in the near-infrared or infrared region of the spectrum). In some embodiments an imaging method comprises positron emission tomography (PET), and single photon emission computed tomography (SPECT). In some embodiments a detectable label is attached to an agent that binds directly to a target to be detected. In some embodiments a detectable label is associated with or incorporated into or comprises particles, which in some embodiments have at their surface an agent that binds directly to a target to be detected. It will be appreciated that if multiple AMD risk markers are assessed by methods that comprise administering diagnostic agents to a subject, the various diagnostic agents may be labeled using distinct labels and/or may be detectable using distinct detection modalities and/or may be administered at different times, so as to allow the various diagnostic agents to be distinguished from one another. For example, fluorophores that emit at distinct wavelengths may be used or a second diagnostic agent may be administered sufficiently long after administration of a first diagnostic agent so as to allow the first diagnostic agent to be substantially washed out or eliminated. In some embodiments, a signal from a first diagnostic agent may be extinguished by photobleaching prior to administration of a second diagnostic agent.

In some embodiments, information obtained from a Th17 biomarker assessment is used together with additional information, e.g., genotype information, environmental exposure information, and/or current or historical medical information regarding a subject, e.g., to develop a prognosis or prediction relating to AMD or to determine whether or when to administer a complement-inhibitor and/or anti-Th17 agent and/or to select a dose or dosing regimen for a subject. In some embodiments current medical or historical information of a subject includes, e.g., the presence or absence of any of various Th17-associated diseases. For example, if a subject is already known to have a Th17-mediated disease other than AMD, such information may be taken into consideration in generating a prognosis or prediction relating to AMD. In some embodiments detection of one or more high risk drusen and/or detection of eye-derived EVs and/or detection of elevated levels of an eye-derived cellular marker in a body fluid sample confirms that the subject is at risk of developing or progression of AMD.

In some embodiments an article of manufacture comprising a solid support is provided, e.g., a microtiter plate or a collection of beads, comprising binding agents suitable for binding a plurality of different analytes of interest herein, e.g., a plurality of Th17-associated cytokines. The different binding agents may be located at discrete positions, e.g., in distinct wells or at distinct locations or attached to distinct populations of beads, to allow detection and, optionally, quantitation, of a plurality of different Th17-associated cytokines. In some embodiments at least 2, 3, 4, 5, 10, 15, 20, or more analytes are detectable using the article of manufacture. Control binding agents may be provided as well as those intended to capture an analyte of interest. In some embodiments the article of manufacture comprises binding agents suitable for detecting one or more eye-specific cellular markers, e.g., as described above. In some embodiments the article of manufacture is provided as a kit, e.g., as described above.

VIII. Other Blood Biomarkers Indicative of AMD Development or Progression

In some aspects, the invention provides a method of identifying a subject at risk of AMD development or progression, the method comprising detecting vascular endothelial growth factor (VEGF) or a macrophage activity marker in a subject or in a sample obtained from the subject. In some embodiments an increased level of VEGF or a macrophage activity marker, as compared to a reference value, is detected in the subject or sample. VEGF, as used herein, refers to any one or more VEGF family member or isoforms of VEGF. VEGF family members include VEGF-A, VEGF-B, VEGF-C, and VEGF-D. In some embodiments VEGF is VEGF-A or a VEGF-A isoform. VEGF-A promotes endothelial cell proliferation and survival as well as vascular permeability. VEGF-A exists in several different isoforms containing 121, 145, 165, 189, and 208 amino acids (in humans). In some embodiments VEGF-A comprises VEGF-A165.

Under the influence of Th17 activity (e.g., contact with Th17 cells and/or exposure to one or more Th17-associated cytokines, e.g., at higher than normal levels) both M1 and M2 type macrophages can display increased activity. In some embodiments a macrophage activity marker is any molecule that is produced by macrophages at increased levels upon exposure of the macrophage(s) to Th17 cells and/or upon exposure to one or more cytokines produced by Th17 cells. In some embodiments a marker of macrophage activity is produced by M1 macrophage. In some embodiments a marker of macrophage activity is produced by M2 macrophage. In some embodiments a marker of macrophage activity is: IL12, IL-23, RNI, or CXCL10. Without limiting the invention in any way, such markers may be produced at least in part by M1 macrophages. In some embodiments a marker of macrophage activity is: IL-10, Arg1, Fizz1, Ym1, SR, MR, GR, CD163, stabilin-1, LYVE-1, FR, IL-1decoyR, IL-IRA, CCL17, CCL22, CCL24, VEGF, EGF, a cathepsin, an MMP, or MSF. Without limiting the invention in any way, such markers may be produced at least in part by M2 macrophages.

In some embodiments, VEGF or a marker of macrophage activity is detected in a body fluid, e.g., in the blood, and/or in isolated EVs, e.g., exosomes, e.g., eye-specific EVs, e.g., eye-specific exosomes. In some embodiments, VEGF or a marker of macrophage activity is detected in combination with detecting increased eye-specific cellular markers in a body fluid, e.g., blood. In some embodiments a method comprises detecting both increased levels of VEGF and increased levels of one or more macrophage activity markers other than VEGF. In some embodiments a method comprises detecting both (a) increased levels of VEGF or increased levels of one or more macrophage activity markers other than VEGF; and (b) an eye-derived cellular marker or eye-derived EVs, e.g., eye-derived exosomes in a body fluid, e.g., blood. In some embodiments a method comprises detecting VEGF or a macrophage activity marker in eye-derived EVs, e.g., eye-derived exosomes. VEGF or macrophage activity markers may be detected and, optionally, quantified, using methods generally described herein with regard to cellular markers and/or Th17 biomarkers.

Detecting VEGF or a macrophage activity marker may be used in combination with or as part of any of the methods described herein.

IX. Complement Inhibitors, Anti Th17 Agents, and Treatment Therewith

In some embodiments a complement inhibitor and/or an anti-Th17 agent is administered to a subject, e.g., a subject in whom complement activation, inflamed endothelium, eye-derived extracellular vesicles, and/or at least one increased Th17 biomarker or other AMD risk marker has been detected as described herein. In some embodiments the subject has at least one eye containing one or more high risk drusen. In some embodiments the complement inhibitor and/or anti-Th17 agent is administered locally to an eye containing one or more high risk drusen. In some embodiments a complement inhibitor and/or anti-Th17 agent is administered locally to both eyes, i.e., to an eye in which complement activation, inflamed endothelium, or one or more high risk drusen were detected and to the fellow eye. The fellow eye may or may not have one or more high risk drusen in various embodiments. In some embodiments a complement inhibitor and/or anti-Th17 agent is administered via an administration route that achieves systemic delivery, e.g., so that both eyes are exposed to therapeutically useful levels of the agent. In some embodiments the systemic administration route is intravenous or subcutaneous administration. In some embodiment the subject has early AMD or intermediate AMD. In some embodiments the subject is identified as at increased risk of developing GA or advanced AMD. In some aspects, treating the subject disrupts a DC-Th17-B-Ab-C-DC cycle (see PCT/US12/43845 (METHODS OF TREATING CHRONIC DISORDERS WITH COMPLEMENT INHIBITORS) for further discussion of this cycle. DC is an abbreviation for dendritic cell; B for B cell; Ab, for antibody and C for complement.)

Certain methods of treating complement-mediated disorders using complement inhibitors, e.g., compstatin analogs, and various complement inhibitors and compositions useful therefor are described in U.S. Ser. No. 11/544,389 (COMPSTATIN AND ANALOGS THEREOF FOR EYE DISORDERS); Ser. No. 12/161,410 (INJECTABLE COMBINATION THERAPY FOR EYE DISORDERS); U.S. Ser. No. 12/681,392 (SUSTAINED DELIVERY OF COMPSTATIN ANALOGS FROM GELS); and/or U.S. Ser. No. 12/525,799 (LOCAL COMPLEMENT INHIBITION FOR TREATMENT OF COMPLEMENT-MEDIATED DISORDERS); PCT/US12/37648 (CELL-REACTIVE, LONG-ACTING, OR TARGETED COMPSTATIN ANALOGS AND USES THEREOF); or PCT/US12/43845 (METHODS OF TREATING CHRONIC DISORDERS WITH COMPLEMENT INHIBITORS). In certain embodiments complement activation is detected in vivo in a subject, e.g., as described herein, and/or inflamed endothelium is detected, and/or eye-derived EVs are detected, and/or a Th17 biomarker is detected, and the subject is treated, e.g., using a complement inhibitor, composition, or method described in any of the foregoing. In some embodiments a subject is treated with a complement inhibitor and subsequently monitored for complement activation in vivo or for inflamed endothelium or eye-derived EVs or a Th17 biomarker. The monitoring may be used, e.g., to determine when to retreat the subject. For example, in some embodiments the presence of complement activation, e.g., at an above normal level, or an increase in complement activation as compared with a previous examination, indicates a need for retreatment.

In some embodiments an anti-Th17 agent comprises any agent that inhibits formation or activity of Th17 cells. In some embodiments an anti-Th17 agent comprises an agent that inhibits the production or activity of a cytokine produced by Th17 cells or that promotes formation or activity of Th17 cells. In some embodiments an anti-Th17 agent comprises an agent that inhibits the production or activity of IL-1β, IL-6, IL-21, IL-22, IL-17, or IL-23. In some embodiments an anti-Th17 agent comprises an antibody, small molecule, aptamer, polypeptide, or RNAi agent. In some embodiments an anti-Th17 agent comprises an antibody, small molecule, aptamer, or polypeptide that binds to IL-1β, IL-6, IL-21, IL-22, IL-17, or IL-23 or that binds to receptor for any of the foregoing. An agent that binds to the receptor should block binding of the endogenous ligand but not substantially activate the receptor. Certain methods of treating complement-mediated disorders using anti-Th17 agents and various and various anti-Th17 agents and compositions useful therefor are described in PCT/US12/43845 (METHODS OF TREATING CHRONIC DISORDERS WITH COMPLEMENT INHIBITORS). In certain embodiments complement activation is detected in vivo in a subject, e.g., as described herein, and/or inflamed endothelium is detected, and/or eye-derived EVs are detected, and/or a Th17 biomarker is detected, and the subject is treated, e.g., using an anti-Th17 agent, composition, or method described in PCT/US12/43845.

In some embodiments an anti-Th17 agent is an anti-IL-23 agent. An IL-23 agent is an agent (e.g., a molecule or complex) that partially or fully bocks, inhibits, neutralizes, prevents or interferes with a biological activity of IL-23. In some embodiments a biological activity of IL-23 is the ability to induce IL-17 production by activated T cells. IL-23 is a heterodimeric cytokine composed of two subunits. The IL-23 beta subunit, also called p40, is shared with another cytokine, interleukin-12 (IL-12). The IL-23 alpha subunit is also called p19. The IL-23 subunits are joined by a disulfide bond. IL-23 signals via binding to a heterodimeric receptor, composed of IL-12Rbetal (IL12RB1), which is shared by the IL-12 receptor, and IL-23R (Parham C, et al. (2002) J. Immunol. 168 (11): 5699-708). IL-23R associates constitutively with Janus kinase 2 (JAK2), and also binds to transcription activator STAT3 in a ligand-dependent manner. The IL-23 signal transduction cascade parallels those of various other cytokines, in that ligand binding leads to activation of JAKs. The JAKs then phosphorylate the IL-23R at key sites, forming docking sites for the STATs.

Subsequently, the JAKs phosphorylate the STATs, which dimerize and translocate to the nucleus where they activate target genes. In some embodiments an anti-IL-23 agent comprises an antibody that binds to the p19 or p40 subunit of IL-23. In some embodiments an anti-IL-23 agent, e.g., an anti-IL-23 antibody, binds to the p40 subunit and inhibits both IL-23 and IL-12.

Certain anti-IL-23 agents and methods of identifying and/or making such agents are disclosed in U.S. Ser. No. 10/697,599. For example, screening methods and assays that may be readily employed by the ordinary skilled artisan to identify and/or produce a variety of anti-IL-23 agents (referred to sometimes as "IL-23 antagonists" in U.S. Ser. No. 10/697,599) are disclosed.

In certain embodiments an anti-IL-23 antibody that binds to the p40 subunit of IL-23 is ustekinumab or a fragment thereof. Ustekinumab (experimental name CNTO 1275, proprietary commercial name Stelara®, Centocor; CAS Number: 815610-63-0) is a human monoclonal antibody of the IgG1 subclass. Exemplary anti-IL-23 antibodies that bind to the p19 subunit of human IL-23, and isolated nucleic acids that encode at least one anti-IL-23p19 antibody, vectors, host cells, and methods of making, are described in U.S. Ser. No. 11/617,503. Additional anti-IL-23 antibodies that bind to the p19 subunit are described in U.S. Ser. No. 11/762,738.

In some embodiments an anti-IL-23 agent comprises an IL-23p40 specific immunoglobulin derived proteis (see, e.g., U.S. Ser. No. 11/768,582).

In some embodiments an IL-23 inhibitor comprises a polypeptide comprising a soluble IL-23R or a variant or fragment thereof capable of binding to IL-23 in solution. In some embodiments a soluble IL-23R lacks the portion of IL-23R encoded by exon 9 of the IL-23R alpha gene. See, e.g., Yu, R Y, J Immunol. (2010) 15; 185(12):7302-8. In some embodiments a soluble IL-23R lacks the portion of IL-23 encoded by exon 9 and at least a portion of exon 8 of the IL-23R alpha gene.

In some embodiments, IL-23 activity is inhibited by interfering with IL-23 signal transduction, e.g., by inhibiting one or more processes or proteins involved in the IL-23 signal transduction pathway. For example, in some embodiments IL-23 signaling is inhibited using a JAK inhibitor or a STAT inhibitor. In some embodiments a JAK inhibitor inhibits JAK expression. Methods of use to inhibit JAK expression in some embodiments include the use of RNAi agents (e.g., siRNA) or antisense oligonucleotides. In some embodiments a JAK inhibitor inhibits JAK binding to IL-23 receptor. In some embodiments a JAK inhibitor inhibits JAK dimerization. In some embodiments a JAK inhibitor inhibits JAK kinase activity. For example, in some embodiments a JAK inhibitor binds to the JAK kinase domain, e.g., to the ATP binding site. Numerous JAK inhibitors are known in the art. For example, INCB028050 is an orally bioavailable JAK1/JAK2 inhibitor with reported nanomolar potency against JAK1 (5.9 nM) and JAK2 (5.7 nM) (Fridman, J S, et al., J Immunol. 2010; 184(9):5298-307). INCB028050 is reported to inhibit intracellular signaling of multiple proinflammatory cytokines including IL-6 and IL-23 at concentrations <50 nM. Small molecule JAK2 inhibitors include, e.g., AZD1480 and AZ960.

In some embodiments a STAT inhibitor inhibits STAT expression. Methods of use to inhibit STAT expression in some embodiments include the use of RNAi agents (e.g., siRNA) or antisense oligonucleotides. In some embodiments a STAT inhibitor inhibits STAT binding to JAK. In some embodiments a STAT inhibitor inhibits STAT dimerization or nuclear translocation. In some embodiments a STAT inhibitor comprises a phosphopeptide which, e.g., competes with STAT for binding to phosphorylated JAK. WO/2008/151037 discloses certain peptide-based STAT inhibitors of use in certain embodiments. In some embodiments a STAT inhibitor inhibits STAT binding to DNA. For example, a decoy oligonucleotide comprising a sequence substantially identical to an endogenous DNA sequence to which STAT naturally binds in human cells may bind to STAT and prevent it from binding to its endogenous binding site(s). Small molecule STAT3 inhibitors include, e.g., STA-21, IS3 295, and S3I-M2001. See Huang, S., Clin Cancer Res 2007; 13:1362-1366 and references therein, which are incorporated herein by reference, for further information regarding certain STAT inhibitors.

In some embodiments an anti-Th17 agent is an anti-IL-17 agent. An IL-17 agent is an agent (e.g., a molecule or complex) that partially or fully bocks, inhibits, neutralizes, prevents or interferes with a biological activity of IL-17. Exemplary anti-IL-17 polypeptides, e.g., anti-IL-17 antibodies, are described in, e.g., U.S. Ser. No. 11/658,344. Additional anti-IL-17 antibodies are described in U.S. Ser. No. 11/762,738. In some embodiments an anti-IL-17 agent comprises at least a portion of an IL-17 receptor, wherein the portion binds to IL-17. Exemplary IL-17 receptor polypeptides are disclosed in, e.g., U.S. Ser. No. 09/022,260.

It will be understood that a polypeptide comprising a binding domain of any of the various anti-Th17 antibodies or other polypeptides described herein can be transferred into other polypeptide backbones or used as isolated agents in certain embodiments. It will further be understood that variants may be used. For example, a variant may be at least 90%, 91%, 92%, 93%, 94%, 95%, 96%, 97%, 98%, 99%, or more identical to a binding domain of a receptor. In some embodiments an antibody that competes with a particular antibody known in the art for binding to a cytokine of interest may be used. In some embodiments an antibody of the IgG class is modified so that it lacks an Fc domain that may activate complement. For example, a variable domain of an IgG1 antibody may be grafted to a constant region of an IgG4 antibody.

A variety of different complement inhibitors may be used in various embodiments. In general, a complement inhibitor may belong to any of a number of compound classes, such as peptides, polypeptides, antibodies, small molecules, and nucleic acids (e.g., aptamers or RNAi agents such as short interfering RNAs). In certain embodiments a complement inhibitor inhibits an enzymatic activity of a complement protein. An enzymatic activity may be proteolytic activity, such as ability to cleave another complement protein. In some embodiments, a complement inhibitor inhibits cleavage of C3, C5, or factor B. In some embodiments, a complement inhibitor acts on C3. In some embodiments, a complement inhibitor acts on a complement component that lies upstream of C3 in the complement activation cascade. In some embodiments, a complement inhibitor inhibits activation or activity of at least one soluble complement protein produced in the eye.

In some embodiments, a complement inhibitor comprises an antibody that substantially lacks the capacity to activate complement. For example, the antibody may have less than 10%, less than 5%, or less than 1% complement stimulating activity as compared with full length human IgG1. In some embodiments, the antibody comprises a CH2 domain that has reduced ability to bind C1q as compared with human IgG1 CH2 domain. In some embodiments, the antibody contains CH1, CH2, and/or CH3 domains from human IgG4 and/or does not contain CH1, CH2, and/or CH3 domains from human IgG1.

In some embodiments, a complement inhibitor used in an inventive dosing regimen has a molecular weight of 1 kD or less. In some embodiments, a complement inhibitor has a molecular weight between 1 kD and 2 kD, between 2 kD and 5 kD, between 5 kD and 10 kD, between 10 kD and 20 kD, between 20 kD and 30 kD, between 30 kD and 50 kD, between 50 kD and 100 kD, or between 100 kD and 200 kD.

A complement inhibitor may be at least in part identical to a naturally occurring complement inhibiting agent or a variant or fragment thereof. A variety of different complement inhibiting polypeptides are produced by viruses (e.g., Poxviruses, Herpesviruses), bacteria (e.g., *Staphylococcus*), and other microorganisms. Complement inhibiting proteins are produced by various parasites, e.g., ectoparasites, such as ticks. A complement inhibitor can comprise at least a portion of a mammalian complement control or complement regulatory protein or receptor. In some embodiments a complement inhibitor is or has been in preclinical or clinical development for at least one disorder. See Ricklin, D., et al. "Complement-targeted Therapeutics", Nature Biotechnology, 25(11): 1265-75, 2007, for discussion of certain complement inhibitors that are or have been in preclinical or clinical development.

In some embodiments between 1 µg and 2000 µg of a complement inhibitor, e.g., a compstatin analog, or other agent (dry weight) is administered to the eye, e.g., intravitreally, e.g., between 1 µg and 10 µg, 10 µg and 100 µg, 100 µg and 500 µg, 500 µg and 1000 µg, 1000 µg and 2000 µg. In some embodiments about 10 µg, about 150 µg, about 350 µg, about 450 µg, about 500 µg, about 650 µg, about 750 µg, about 850 µg, about 950 µg, about 1050 µg, about 1150 µg, about 1250 µg, about 1350 µg, about 1450 µg, or about 1550 µg are administered to the eye, e.g., by intravitreal injection.

The following sections discuss non-limiting exemplary complement inhibitors of use in various embodiments described herein. Complement inhibitors have been classified in various groups for purposes of convenience. It will be understood that certain complement inhibitors fall into multiple categories.

Compstatin Analogs and Mimetics

Compstatin is a cyclic peptide that binds to C3 and inhibits complement activation by, e.g., inhibiting cleavage of C3 to C3a and C3b by convertase. U.S. Pat. No. 6,319,897 describes a peptide having the sequence Ile-[Cys-Val-Val-Gln-Asp-Trp-Gly-His-His-Arg-Cys]-Thr (SEQ ID NO: 1), with the disulfide bond between the two cysteines denoted by brackets. It will be understood that the name "compstatin" was not used in U.S. Pat. No. 6,319,897 but was subsequently adopted in the scientific and patent literature (see, e.g., Morikis, et al., *Protein Sci.,* 7(3):619-27, 1998) to refer to a peptide having the same sequence as SEQ ID NO: 2 disclosed in U.S. Pat. No. 6,319,897, but amidated at the C terminus as shown in Table 2 (SEQ ID NO: 8). The term "compstatin" is used herein consistently with such usage (i.e., to refer to SEQ ID NO: 8). Compstatin analogs that have higher complement inhibiting activity than compstatin have been developed. See, e.g., WO2004/026328 (PCT/US2003/029653), Morikis, D., et al., *Biochem Soc Trans.* 32(Pt 1):28-32, 2004, Mallik, B., et al., *J. Med. Chem.,* 274-286, 2005; Katragadda, M., et al. *J. Med. Chem.,* 49: 4616-4622, 2006; WO2007062249 (PCT/US2006/045539); WO2007044668 (PCT/US2006/039397), WO/2009/046198 (PCT/US2008/078593); WO/2010/127336 (PCT/US2010/033345) and discussion below.

Compstatin analogs may be acetylated or amidated, e.g., at the N-terminus and/or C-terminus. For example, compstatin analogs may be acetylated at the N-terminus and amidated at the C-terminus. Consistent with usage in the art, "compstatin" as used herein, and the activities of compstatin analogs described herein relative to that of compstatin, refer to compstatin amidated at the C-terminus (Mallik, 2005, supra).

Concatamers or multimers of compstatin or a complement inhibiting analog thereof are also of use in the present invention.

As used herein, the term "compstatin analog" includes compstatin and any complement inhibiting analog thereof. The term "compstatin analog" encompasses compstatin and other compounds designed or identified based on compstatin and whose complement inhibiting activity is at least 50% as great as that of compstatin as measured, e.g., using any complement activation assay accepted in the art or substantially similar or equivalent assays. Certain suitable assays are described in U.S. Pat. No. 6,319,897, WO2004/026328, Morikis, supra, Mallik, supra, Katragadda 2006, supra, WO2007062249 (PCT/US2006/045539); WO2007044668 (PCT/US2006/039397), WO/2009/046198 (PCT/US2008/078593); and/or WO/2010/127336 (PCT/US2010/033345). The assay may, for example, measure alternative or classical pathway-mediated erythrocyte lysis or be an ELISA assay. In some embodiments, an assay described in WO/2010/135717 (PCT/US2010/035871) is used.

The activity of a compstatin analog may be expressed in terms of its $IC_{50}$ (the concentration of the compound that inhibits complement activation by 50%), with a lower $IC_{50}$ indicating a higher activity as recognized in the art. The activity of a preferred compstatin analog for use in the present invention is at least as great as that of compstatin. It is noted that certain modifications known to reduce or eliminate complement inhibiting activity and may be explicitly excluded from any embodiment of the invention. The $IC_{50}$ of compstatin has been measured as 12 µM using an alternative pathway-mediated erythrocyte lysis assay (WO2004/026328). It will be appreciated that the precise $IC_{50}$ value measured for a given compstatin analog will vary with experimental conditions (e.g., the serum concentration used in the assay). Comparative values, e.g., obtained from experiments in which $IC_{50}$ is determined for multiple different compounds under substantially identical conditions, are of use. In one embodiment, the $IC_{50}$ of the compstatin analog is no more than the $IC_{50}$ of compstatin. In certain embodiments of the invention the activity of the compstatin analog is between 2 and 99 times that of compstatin (i.e., the analog has an $IC_{50}$ that is less than the $IC_{50}$ of compstatin by a factor of between 2 and 99). For example, the activity may be between 10 and 50 times as great as that of compstatin, or between 50 and 99 times as great as that of compstatin. In certain embodiments of the invention the activity of the compstatin analog is between 99 and 264 times that of compstatin. For example, the activity may be 100, 110, 120, 130, 140, 150, 160, 170, 180, 190, 200, 210, 220, 230, 240, 250, 260, or 264 times as great as that of compstatin. In certain embodiments the activity is between 250 and 300, 300 and 350, 350 and 400, or 400 and 500 times as great as that of compstatin. The invention further contemplates compstatin analogs having activities between 500 and 1000 times that of compstatin, or more, e.g., between 1000 and 2000 times that of compstatin, or more. In certain embodiments the $IC_{50}$ of the compstatin analog is between about 0.2 µM and about 0.5 µM. In certain embodiments the $IC_{50}$ of the compstatin analog is between about 0.1 µM and about 0.2 μM. In certain embodiments the $IC_{50}$ of the compstatin analog is between about 0.05 μM and about 0.1 μM. In certain embodiments the $IC_{50}$ of the compstatin analog is between about 0.001 μM and about 0.05 μM.

The $K_d$ of compstatin binding to C3 can be measured using isothermal titration calorimetry (Katragadda, et al., *J. Biol. Chem.*, 279(53), 54987-54995, 2004). Binding affinity of a variety of compstatin analogs for C3 has been correlated with their activity, with a lower $K_d$ indicating a higher binding affinity, as recognized in the art. A linear correlation between binding affinity and activity was shown for certain analogs tested (Katragadda, 2004, supra; Katragadda 2006, supra). In certain embodiments of the invention the compstatin analog binds to C3 with a $K_d$ of between 0.1 μM and 1.0 μM, between 0.05 μM and 0.1 μM, between 0.025 μM and 0.05 μM, between 0.015 μM and 0.025 μM, between 0.01 μM and 0.015 μM, or between 0.001 μM and 0.0104.

Compounds "designed or identified based on compstatin" include, but are not limited to, compounds that comprise an amino acid chain whose sequence is obtained by (i) modifying the sequence of compstatin (e.g., replacing one or more amino acids of the sequence of compstatin with a different amino acid or amino acid analog, inserting one or more amino acids or amino acid analogs into the sequence of compstatin, or deleting one or more amino acids from the sequence of compstatin); (ii) selection from a phage display peptide library in which one or more amino acids of compstatin is randomized, and optionally further modified according to method (i); or (iii) identified by screening for compounds that compete with compstatin or any analog thereof obtained by methods (i) or (ii) for binding to C3 or a fragment thereof. Many useful compstatin analogs comprise a hydrophobic cluster, a β-turn, and a disulfide bridge.

In certain embodiments of the invention the sequence of the compstatin analog comprises or consists essentially of a sequence that is obtained by making 1, 2, 3, or 4 substitutions in the sequence of compstatin, i.e., 1, 2, 3, or 4 amino acids in the sequence of compstatin is replaced by a different standard amino acid or by a non-standard amino acid. In certain embodiments of the invention the amino acid at position 4 is altered. In certain embodiments of the invention the amino acid at position 9 is altered. In certain embodiments of the invention the amino acids at positions 4 and 9 are altered. In certain embodiments of the invention only the amino acids at positions 4 and 9 are altered. In certain embodiments of the invention the amino acid at position 4 or 9 is altered, or in certain embodiments both amino acids 4 and 9 are altered, and in addition up to 2 amino acids located at positions selected from 1, 7, 10, 11, and 13 are altered. In certain embodiments of the invention the amino acids at positions 4, 7, and 9 are altered. In certain embodiments of the invention amino acids at position 2, 12, or both are altered, provided that the alteration preserves the ability of the compound to be cyclized. Such alteration(s) at positions 2 and/or 12 may be in addition to the alteration(s) at position 1, 4, 7, 9, 10, 11, and/or 13. Optionally the sequence of any of the compstatin analogs whose sequence is obtained by replacing one or more amino acids of compstatin sequence further includes up to 1, 2, or 3 additional amino acids at the C-terminus. In one embodiment, the additional amino acid is Gly. Optionally the sequence of any of the compstatin analogs whose sequence is obtained by replacing one or more amino acids of compstatin sequence further includes up to 5, or up to 10 additional amino acids at the C-terminus. It should be understood that compstatin analogs may have any one or more of the characteristics or features of the various embodiments described herein, and characteristics or features of any embodiment may additionally characterize any other embodiment described herein, unless otherwise stated or evident from the context. In certain embodiments of the invention the sequence of the compstatin analog comprises or consists essentially of a sequence identical to that of compstatin except at positions corresponding to positions 4 and 9 in the sequence of compstatin.

Compstatin and certain compstatin analogs having somewhat greater activity than compstatin contain only standard amino acids ("standard amino acids" are glycine, leucine, isoleucine, valine, alanine, phenylalanine, tyrosine, tryptophan, aspartic acid, asparagine, glutamic acid, glutamine, cysteine, methionine, arginine, lysine, proline, serine, threonine and histidine). Certain compstatin analogs having improved activity incorporate one or more non-standard amino acids. Useful non-standard amino acids include singly and multiply halogenated (e.g., fluorinated) amino acids, D-amino acids, homo-amino acids, N-alkyl amino acids, dehydroamino acids, aromatic amino acids (other than phenylalanine, tyrosine and tryptophan), ortho-, meta- or para-aminobenzoic acid, phospho-amino acids, methoxylated amino acids, and α,α-disubstituted amino acids. In certain embodiments of the invention, a compstatin analog is designed by replacing one or more L-amino acids in a compstatin analog described elsewhere herein with the corresponding D-amino acid. Such compounds and methods of use thereof are an aspect of the invention. Exemplary non-standard amino acids of use include 2-naphthylalanine (2-Nal), 1-naphthylalanine (1-Nal), 2-indanylglycine carboxylic acid (2Ig1), dihydrotrpytophan (Dht), 4-benzoyl-L-phenylalanine (Bpa), 2-α-aminobutyric acid (2-Abu), 3-α-aminobutyric acid (3-Abu), 4-α-aminobutyric acid (4-Abu), cyclohexylalanine (Cha), homocyclohexylalanine (hCha), 4-fluoro-L-tryptophan (4fW), 5-fluoro-L-tryptophan (5fW), 6-fluoro-L-tryptophan (6fW), 4-hydroxy-L-tryptophan (4OH-W), 5-hydroxy-L-tryptophan (5OH-W), 6-hydroxy-L-tryptophan (6OH-W), 1-methyl-L-tryptophan (1MeW), 4-methyl-L-tryptophan (4MeW), 5-methyl-L-tryptophan (5MeW), 7-aza-L-tryptophan (7aW), α-methyl-L-tryptophan (αMeW), β-methyl-L-tryptophan (βMeW), N-methyl-L-tryptophan (NMeW), ornithine (orn), citrulline, norleucine, γ-glutamic acid, etc.

In certain embodiments of the invention the compstatin analog comprises one or more Trp analogs (e.g., at position 4 and/or 7 relative to the sequence of compstatin). Exemplary Trp analogs are mentioned above. See also Beene, et. al. *Biochemistry* 41: 10262-10269, 2002 (describing, inter alia, singly- and multiply-halogenated Trp analogs); Babitzke & Yanofsky, I *Biol. Chem.* 270: 12452-12456, 1995 (describing, inter alia, methylated and halogenated Trp and other Trp and indole analogs); and U.S. Pat. Nos. 6,214,790, 6,169,057, 5,776,970, 4,870,097, 4,576,750 and 4,299,838. Other Trp analogs include variants that are substituted (e.g., by a methyl group) at the α or β carbon and, optionally, also at one or more positions of the indole ring. Amino acids comprising two or more aromatic rings, including substituted, unsubstituted, or alternatively substituted variants thereof, are of interest as Trp analogs. In certain embodiments of the invention the Trp analog, e.g., at position 4, is 5-methoxy, 5-methyl-, 1-methyl-, or 1-formyl-tryptophan. In certain embodiments of the invention a Trp analog (e.g., at position 4) comprising a 1-alkyl substituent, e.g., a lower alkyl (e.g., $C_1$-$C_5$) substituent is used. In certain embodiments, N(α) methyl tryptophan or 5-methyltryptophan is used. In some embodiments, an analog comprising a 1-alkanyol substituent, e.g., a lower alkanoyl (e.g., $C_1$-$C_5$) is used. Examples include 1-acetyl-L-tryptophan and L-β-tryptophan.

In certain embodiments the Trp analog has increased hydrophobic character relative to Trp. For example, the indole ring may be substituted by one or more alkyl (e.g., methyl) groups. In certain embodiments the Trp analog participates in a hydrophobic interaction with C3. Such a Trp analog may be located, e.g., at position 4 relative to the sequence of compstatin. In certain embodiments the Trp analog comprises a substituted or unsubstituted bicyclic aromatic ring component or two or more substituted or unsubstituted monocyclic aromatic ring components.

In certain embodiments the Trp analog has increased propensity to form hydrogen bonds with C3 relative to Trp but does not have increased hydrophobic character relative to Trp. The Trp analog may have increased polarity relative to Trp and/or an increased ability to participate in an electrostatic interaction with a hydrogen bond donor on C3. Certain exemplary Trp analogs with an increased hydrogen bond forming character comprise an electronegative substituent on the indole ring. Such a Trp analog may be located, e.g., at position 7 relative to the sequence of compstatin.

In certain embodiments of the invention the compstatin analog comprises one or more Ala analogs (e.g., at position 9 relative to the sequence of compstatin), e.g., Ala analogs that are identical to Ala except that they include one or more CH2 groups in the side chain. In certain embodiments the Ala analog is an unbranched single methyl amino acid such as 2-Abu. In certain embodiments of the invention the compstatin analog comprises one or more Trp analogs (e.g., at position 4 and/or 7 relative to the sequence of compstatin) and an Ala analog (e.g., at position 9 relative to the sequence of compstatin).

In certain embodiments of the invention the compstatin analog is a compound that comprises a peptide that has a sequence of (X'aa)$_n$-Gln-Asp-Xaa-Gly-(X"aa)$_m$, (SEQ ID NO: 2) wherein each X'aa and each X"aa is an independently selected amino acid or amino acid analog, wherein Xaa is Trp or an analog of Trp, and wherein n>1 and m>1 and n+m is between 5 and 21. The peptide has a core sequence of Gln-Asp-Xaa-Gly (SEQ ID NO: 107), where Xaa is Trp or an analog of Trp, e.g., an analog of Trp having increased propensity to form hydrogen bonds with an H-bond donor relative to Trp but, in certain embodiments, not having increased hydrophobic character relative to Trp. For example, the analog may be one in which the indole ring of Trp is substituted with an electronegative moiety, e.g., a halogen such as fluorine. In one embodiment Xaa is 5-fluorotryptophan. Absent evidence to the contrary, one of skill in the art would recognize that any non-naturally occurring peptide whose sequence comprises this core sequence and that inhibits complement activation and/or binds to C3 will have been designed based on the sequence of compstatin. In an alternative embodiment Xaa is an amino acid or amino acid analog other than a Trp analog that allows the Gln-Asp-Xaa-Gly (SEQ ID NO: 107) peptide to form a β-turn.

In certain embodiments of the invention the peptide has a core sequence of X'aa-Gln-Asp-Xaa-Gly (SEQ ID NO: 3), where X'aa and Xaa are selected from Trp and analogs of Trp. In certain embodiments of the invention the peptide has a core sequence of X'aa-Gln-Asp-Xaa-Gly (SEQ ID NO: 3), where X'aa and Xaa are selected from Trp, analogs of Trp, and other amino acids or amino acid analogs comprising at least one aromatic ring. In certain embodiments of the invention the core sequence forms a β-turn in the context of the peptide. The β-turn may be flexible, allowing the peptide to assume two or more conformations as assessed for example, using nuclear magnetic resonance (NMR). In certain embodiments X'aa is an analog of Trp that comprises a substituted or unsubstituted bicyclic aromatic ring component or two or more substituted or unsubstituted monocyclic aromatic ring components. In certain embodiments of the invention X'aa is selected from the group consisting of 2-napthylalanine, 1-napthylalanine, 2-indanylglycine carboxylic acid, dihydrotryptophan, and benzoylphenylalanine. In certain embodiments of the invention X'aa is an analog of Trp that has increased hydrophobic character relative to Trp. For example, X'aa may be 1-methyltryptophan. In certain embodiments of the invention Xaa is an analog of Trp that has increased propensity to form hydrogen bonds relative to Trp but, in certain embodiments, not having increased hydrophobic character relative to Trp. In certain embodiments of the invention the analog of Trp that has increased propensity to form hydrogen bonds relative to Trp comprises a modification on the indole ring of Trp, e.g., at position 5, such as a substitution of a halogen atom for an H atom at position 5. For example, Xaa may be 5-fluorotryptophan.

In certain embodiments of the invention the peptide has a core sequence of X'aa-Gln-Asp-Xaa-Gly-X"aa (SEQ ID NO: 4), where X'aa and Xaa are each independently selected from Trp and analogs of Trp and X"aa is selected from His, Ala, analogs of Ala, Phe, and Trp. In certain embodiments of the invention X'aa is an analog of Trp that has increased hydrophobic character relative to Trp, such as 1-methyltryptophan or another Trp analog having an alkyl substituent on the indole ring (e.g., at position 1, 4, 5, or 6). In certain embodiments X'aa is an analog of Trp that comprises a substituted or unsubstituted bicyclic aromatic ring component or two or more substituted or unsubstituted monocyclic aromatic ring components. In certain embodiments of the invention X'aa is selected from the group consisting of 2-napthylalanine, 1-napthylalanine, 2-indanylglycine carboxylic acid, dihydrotryptophan, and benzoylphenylalanine. In certain embodiments of the invention Xaa is an analog of Trp that has increased propensity to form hydrogen bonds with C3 relative to Trp but, in certain embodiments, not having increased hydrophobic character relative to Trp. In certain embodiments of the invention the analog of Trp that has increased propensity to form hydrogen bonds relative to Trp comprises a modification on the indole ring of Trp, e.g., at position 5, such as a substitution of a halogen atom for an H atom at position 5. For example, Xaa may be 5-fluorotryptophan. In certain embodiments X"aa is Ala or an analog of Ala such as Abu or another unbranched single methyl amino acid. In certain embodiments of the invention the peptide has a core sequence of X'aa-Gln-Asp-Xaa-Gly-X"aa (SEQ ID NO: 4), where X'aa and Xaa are each independently selected from Trp, analogs of Trp, and amino acids or amino acid analogs comprising at least one aromatic side chain, and X"aa is selected from His, Ala, analogs of Ala, Phe, and Trp. In certain embodiments X"aa is selected from analogs of Trp, aromatic amino acids, and aromatic amino acid analogs.

In certain preferred embodiments of the invention the peptide is cyclic. The peptide may be cyclized via a bond between any two amino acids, one of which is (X'aa)$_n$ and the other of which is located within (X"aa)$_m$. In certain embodiments the cyclic portion of the peptide is between 9 and 15 amino acids in length, e.g., 10-12 amino acids in length. In certain embodiments the cyclic portion of the peptide is 11 amino acids in length, with a bond (e.g., a disulfide bond) between amino acids at positions 2 and 12.

For example, the peptide may be 13 amino acids long, with a bond between amino acids at positions 2 and 12 resulting in a cyclic portion 11 amino acids in length.

In certain embodiments the peptide comprises or consists of the sequence X'aa1-X'aa2-X'aa3-X'aa4-Gln-Asp-Xaa-Gly-X"aa1-X"aa2-X"aa3-X"aa4-X"aa5 (SEQ ID NO: 5). In certain embodiments X'aa4 and Xaa are selected from Trp and analogs of Trp, and X'aa1, X'aa2, X'aa3, X"aa1, X"aa2, X"aa3, X"aa4, and X"aa5 are independently selected from among amino acids and amino acid analogs. In certain embodiments X'aa4 and Xaa are selected from aromatic amino acids and aromatic amino acid analogs. Any one or more of X'aa1, X'aa2, X'aa3, X"aa1, X"aa2, X"aa3, X"aa4, and X"aa5 may be identical to the amino acid at the corresponding position in compstatin. In one embodiment, X"aa1 is Ala or a single methyl unbranched amino acid. The peptide may be cyclized via a covalent bond between (i) X'aa1, X'aa2, or X'aa3; and (ii) X"aa2, X"aa3, X"aa4 or X"aa5. In one embodiment the peptide is cyclized via a covalent bond between X'aa2 and X"aa4. In one embodiment the covalently bound amino acid are each Cys and the covalent bond is a disulfide (S—S) bond. In other embodiments the covalent bond is a C—C, C—O, C—S, or C—N bond. In certain embodiments one of the covalently bound residues is an amino acid or amino acid analog having a side chain that comprises a primary or secondary amine, the other covalently bound residue is an amino acid or amino acid analog having a side chain that comprises a carboxylic acid group, and the covalent bond is an amide bond. Amino acids or amino acid analogs having a side chain that comprises a primary or secondary amine include lysine and diaminocarboxylic acids of general structure $NH_2(CH_2)_nCH(NH_2)COOH$ such as 2,3-diaminopropionic acid (dapa), 2,4-diaminobutyric acid (daba), and ornithine (orn), wherein n=1 (dapa), 2 (daba), and 3 (orn), respectively. Examples of amino acids having a side chain that comprises a carboxylic acid group include dicarboxylic amino acids such as glutamic acid and aspartic acid. Analogs such as beta-hydroxy-L-glutamic acid may also be used. In some embodiments a peptide is cyclized with a thioether bond, e.g., as described in PCT/US2011/052442 (WO/2012/040259). For example, in some embodiments a disulfide bond in any of the peptides is replaced with a thioether bond. In some embodiments, a cystathionine is formed. In some embodiments the cystathionine is a delta-cystathionine or a gamma-cystathionine. In some embodiments a modification comprises replacement of a Cys-Cys disulfide bond between cysteines at X'aa2 and X"aa4 in SEQ ID NO: 5 (or corresponding positions in other sequences) with addition of a $CH_2$, to form a homocysteine at X'aa2 or X"aa4, and introduction of a thioether bond, to form a cystathionine. In one embodiment, the cystathionine is a gamma-cystathionine. In another embodiment, the cystathionine is a delta-cystathionine. Another modification of use in certain embodiments comprises replacement of the disulfide bond with a thioether bond without the addition of a $CH_2$, thereby forming a lantithionine. In some embodiments a compstatin analog having a thioether in place of a disulfide bond has increased stability, at least under some conditions, as compared with the compstatin analog having the disulfide bond.

In certain embodiments, the compstatin analog is a compound that comprises a peptide having a sequence:

Xaa1-Cys-Val-Xaa2-Gln-Asp-Xaa2*-Gly-Xaa3-His-Arg-Cys-Xaa4 (SEQ ID NO: 6); wherein:

Xaa1 is Ile, Val, Leu, $B^1$-Ile, $B^1$-Val, $B^1$-Leu or a dipeptide comprising Gly-Ile or $B^1$-Gly-Ile, and $B^1$ represents a first blocking moiety;

Xaa2 and Xaa2* are independently selected from Trp and analogs of Trp;

Xaa3 is His, Ala or an analog of Ala, Phe, Trp, or an analog of Trp;

Xaa4 is L-Thr, D-Thr, Ile, Val, Gly, a dipeptide selected from Thr-Ala and Thr-Asn, or a tripeptide comprising Thr-Ala-Asn, wherein a carboxy terminal —OH of any of the L-Thr, D-Thr, Ile, Val, Gly, Ala, or Asn optionally is replaced by a second blocking moiety $B^2$; and the two Cys residues are joined by a disulfide bond. In some embodiments, Xaa4 is Leu, Nle, His, or Phe or a depeptide selected from Xaa5-Ala and Xaa5-Asn, or a tripeptide Xaa5-Ala-Asn, wherein Xaa5 is selected from Leu, Nle, His or Phe, and wherein a carboxy terminal —OH of any of the L-Thr, D-Thr, Ile, Val, Gly, Leu, Nle, His, Phe, Ala, or Asn optionally is replaced by a second blocking moiety $B^2$; and the two Cys residues are joined by a disulfide bond.

In other embodiments Xaa1 is absent or is any amino acid or amino acid analog, and Xaa2, Xaa2*, Xaa3, and Xaa4 are as defined above. If Xaa1 is absent, the N-terminal Cys residue may have a blocking moiety $B^1$ attached thereto.

In another embodiment, Xaa4 is any amino acid or amino acid analog and Xaa1, Xaa2, Xaa2*, and Xaa3 are as defined above. In another embodiment Xaa4 is a dipeptide selected from the group consisting of: Thr-Ala and Thr-Asn, wherein the carboxy terminal —OH or the Ala or Asn is optionally replaced by a second blocking moiety $B^2$.

In any of the embodiments of the compstatin analog of SEQ ID NO: 6, Xaa2 may be Trp.

In any of the embodiments of the compstatin analog of SEQ ID NO: 6, Xaa2 may be an analog of Trp comprising a substituted or unsubstituted bicyclic aromatic ring component or two or more substituted or unsubstituted monocyclic aromatic ring components. For example, the analog of Trp may be selected from 2-naphthylalanine (2-NaI), 1-naphthylalanine (1-NaI), 2-indanylglycine carboxylic acid (Ig1), dihydrotrpytophan (Dht), and 4-benzoyl-L-phenylalanine.

In any of the embodiments of the compstatin analog of SEQ ID NO: 6, Xaa2 may be an analog of Trp having increased hydrophobic character relative to Trp. For example, the analog of Trp may be selected from 1-methyltryptophan, 4-methyltryptophan, 5-methyltryptophan, and 6-methyltryptophan. In one embodiment, the analog of Trp is 1-methyltryptophan. In one embodiment, Xaa2 is 1-methyltryptophan, Xaa2* is Trp, Xaa3 is Ala, and the other amino acids are identical to those of compstatin.

In any of the embodiments of the compstatin analog of SEQ ID NO: 6, Xaa2* may be an analog of Trp such as an analog of Trp having increased hydrogen bond forming propensity with C3 relative to Trp, which, in certain embodiments, does not have increased hydrophobic character relative to Trp. In certain embodiments the analog of Trp comprises an electronegative substituent on the indole ring. For example, the analog of Trp may be selected from 5-fluorotryptophan and 6-fluorotryptophan.

In certain embodiments of the invention Xaa2 is Trp and Xaa2* is an analog of Trp having increased hydrogen bond forming propensity with C3 relative to Trp which, in certain embodiments, does not have increased hydrophobic character relative to Trp. In certain embodiments of the compstatin analog of SEQ ID NO: 6, Xaa2 is analog of Trp having increased hydrophobic character relative to Trp such as an analog of Trp selected from 1-methyltryptophan, 4-methyltryptophan, 5-methyltryptophan, and 6-methyltryptophan, and and Xaa2* is an analog of Trp having increased hydrogen bond forming propensity with C3 relative to Trp which, in certain embodiments, does not have increased hydrophobic character relative to Trp. For example, in one embodiment Xaa2 is methyltryptophan and Xaa2* is 5-fluorotryptophan.

In certain of the afore-mentioned embodiments, Xaa3 is Ala. In certain of the afore-mentioned embodiments Xaa3 is a single methyl unbranched amino acid, e.g., Abu.

The invention further provides compstatin analogs of SEQ ID NO: 6, as described above, wherein Xaa2 and Xaa2* are independently selected from Trp, analogs of Trp, and other amino acids or amino acid analogs that comprise at least one aromatic ring, and Xaa3 is His, Ala or an analog of Ala, Phe, Trp, an analog of Trp, or another aromatic amino acid or aromatic amino acid analog.

In certain embodiments of the invention the blocking moiety present at the N- or C-terminus of any of the compstatin analogs described herein is any moiety that stabilizes a peptide against degradation that would otherwise occur in mammalian (e.g., human or non-human primate) blood or interstitial fluid. For example, blocking moiety $B^1$ could be any moiety that alters the structure of the N-terminus of a peptide so as to inhibit cleavage of a peptide bond between the N-terminal amino acid of the peptide and the adjacent amino acid. Blocking moiety $B^2$ could be any moiety that alters the structure of the C-terminus of a peptide so as to inhibit cleavage of a peptide bond between the C-terminal amino acid of the peptide and the adjacent amino acid. Any suitable blocking moieties known in the art could be used. In certain embodiments of the invention blocking moiety $B^1$ comprises an acyl group (i.e., the portion of a carboxylic acid that remains following removal of the —OH group). The acyl group typically comprises between 1 and 12 carbons, e.g., between 1 and 6 carbons. For example, in certain embodiments of the invention blocking moiety $B^1$ is selected from the group consisting of: formyl, acetyl, proprionyl, butyryl, isobutyryl, valeryl, isovaleryl, etc. In one embodiment, the blocking moiety $B^1$ is an acetyl group, i.e., Xaa1 is Ac-Ile, Ac-Val, Ac-Leu, or Ac-Gly-Ile.

In certain embodiments of the invention blocking moiety $B^2$ is a primary or secondary amine (—NH$_2$ or —NHR$^1$, wherein R is an organic moiety such as an alkyl group).

In certain embodiments of the invention blocking moiety $B^1$ is any moiety that neutralizes or reduces the positive charge that may otherwise be present at the N-terminus at physiological pH. In certain embodiments of the invention blocking moiety $B^2$ is any moiety that neutralizes or reduces the negative charge that may otherwise be present at the C-terminus at physiological pH.

In certain embodiments a blocking moiety comprises or consists of a non-standard amino acid. In some embodiments a non-standard amino acid of use in a blocking moiety is a n-amino acid. In some embodiments the beta-amino acid is β-Alanine (β-Ala), though other β-amino acids may be used.

In certain embodiments of the invention, the compstatin analog is acetylated or amidated at the N-terminus and/or C-terminus, respectively. A compstatin analog may be acetylated at the N-terminus, amidated at the C-terminus, and or both acetylated at the N-terminus and amidated at the C-terminus. In certain embodiments of the invention a compstatin analog comprises an alkyl or aryl group at the N-terminus rather than an acetyl group.

In certain embodiments, the compstatin analog is a compound that comprises a peptide having a sequence:

Xaa1-Cys-Val-Xaa2-Gln-Asp-Xaa2*-Gly-Xaa3-His-Arg-Cys-Xaa4 (SEQ ID NO: 7); wherein:

Xaa1 is Ile, Val, Leu, Ac-Ile, Ac-Val, Ac-Leu or a dipeptide comprising Gly-Ile or Ac-Gly-Ile;

Xaa2 and Xaa2* are independently selected from Trp and analogs of Trp;

Xaa3 is His, Ala or an analog of Ala, Phe, Trp, or an analog of Trp;

Xaa4 is L-Thr, D-Thr, Ile, Val, Gly, a dipeptide selected from Thr-Ala and Thr-Asn, or a tripeptide comprising Thr-Ala-Asn, wherein a carboxy terminal —OH of any of L-Thr, D-Thr, Ile, Val, Gly, Ala, or Asn optionally is replaced by —NH$_2$; and the two Cys residues are joined by a disulfide bond. In some embodiments, Xaa4 is Leu, Nle, His, or Phe or a depeptide selected from Xaa5-Ala and Xaa5-Asn, or a tripeptide Xaa5-Ala-Asn, wherein Xaa5 is selected from Leu, Nle, His or Phe, and wherein a carboxy terminal —OH of any of the L-Thr, D-Thr, Ile, Val, Gly, Leu, Nle, His, Phe, Ala, or Asn optionally is replaced by a second blocking moiety B2; and the two Cys residues are joined by a disulfide bond.

In some embodiments, Xaa1, Xaa2, Xaa2*, Xaa3, and Xaa4 are as described above for the various embodiments of SEQ ID NO: 6. For example, in certain embodiments Xaa2* is Trp. In certain embodiments Xaa2 is an analog of Trp having increased hydrophobic character relative to Trp, e.g., 1-methyltryptophan. In certain embodiments Xaa3 is Ala. In certain embodiments Xaa3 is a single methyl unbranched amino acid.

In certain embodiments of the invention Xaa1 is Ile and Xaa4 is L-Thr.

In certain embodiments of the invention Xaa1 is Ile, Xaa2* is Trp, and Xaa4 is L-Thr.

The invention further provides compstatin analogs of SEQ ID NO: 7, as described above, wherein Xaa2 and Xaa2* are independently selected from Trp, analogs of Trp, other amino acids or aromatic amino acid analogs, and Xaa3 is His, Ala or an analog of Ala, Phe, Trp, an analog of Trp, or another aromatic amino acid or aromatic amino acid analog.

In certain embodiments of any of the compstatin analogs described herein, an analog of Phe is used rather than Phe.

Table 2 provides a non-limiting list of compstatin analogs useful in the present invention. The analogs are referred to in abbreviated form in the left column by indicating specific modifications at designated positions (1-13) as compared to the parent peptide, compstatin. Consistent with usage in the art, "compstatin" as used herein, and the activities of compstatin analogs described herein relative to that of compstatin, refer to the compstatin peptide amidated at the C-terminus. Unless otherwise indicated, peptides in Table 2 are amidated at the C-terminus. Bold text is used to indicate certain modifications. Activity relative to compstatin is based on published data and assays described therein (WO2004/026328, WO2007044668, Mallik, 2005; Katragadda, 2006). Where multiple publications reporting an activity were consulted, the more recently published value is used, and it will be recognized that values may be adjusted in the case of differences between assays. It will also be appreciated that in certain embodiments of the invention the peptides listed in Table 2 are cyclized via a disulfide bond between the two Cys residues when used in the therapeutic compositions and methods of the invention. Alternate means for cyclizing the peptides are also within the scope of the invention. As noted above, in various embodiments of the invention one or more amino acid(s) of a compstatin analog (e.g., any of the compstatin analogs disclosed herein) can be an N-alkyl amino acid (e.g., an N-methyl amino acid). For example, and without limitation, at least one amino acid within the cyclic portion of the peptide, at least one amino acid N-terminal to the cyclic portion, and/or at least one amino acid C-terminal to the cyclic portion may be an N-alkyl amino acid, e.g., an N-methyl amino acid. In some embodiments of the invention, for example, a compstatin analog comprises an N-methyl glycine, e.g., at the position corresponding to position 8 of compstatin and/or at the position corresponding to position 13 of compstatin. In some embodiments, one or more of the compstatin analogs in Table 2 contains at least one N-methyl glycine, e.g., at the position corresponding to position 8 of compstatin and/or at the position corresponding to position 13 of compstatin. In some embodiments, one or more of the compstatin analogs in contains at least one N-methyl isoleucine, e.g., at the position corresponding to position 13 of compstatin. For example, a Thr at or near the C-terminal end of a peptide whose sequence is listed in Table 2 may be replaced by N-methyl Ile. As will be appreciated, in some embodiments the N-methylated amino acids comprise N-methyl Gly at position 8 and N-methyl Ile at position 13. In some embodiments the N-methylated amino acids comprise N-methyl Gly in a core sequence such as SEQ ID NO: 3 or SEQ ID NO: 4.

TABLE 2

| Peptide | Sequence | SEQ ID NO: | Activity over compstatin |
|---|---|---|---|
| Compstatin | H-ICVVQDWGHHRCT-CONH2 | 8 | * |
| Ac-compstatin | Ac-ICVVQDWGHHRCT-CONH2 | 9 | 3× more |
| Ac-V4Y/H9A | Ac-ICVYQDWGAHRCT-CONH2 | 10 | 14× more |
| Ac-V4W/H9A —OH | Ac-ICVWQDWGAHRCT-COOH | 11 | 27× more |
| Ac-V4W/H9A | Ac-ICVWQDWGAHRCT-CONH2 | 12 | 45× more |
| Ac-V4W/H9A/T13dT —OH | Ac-ICVWQDWGAHRCdT-COOH | 13 | 55× more |
| Ac-V4(2-Nal)/H9A | Ac-ICV**(2-Nal)QDWGA**HRCT-CONH2 | 14 | 99× more |
| Ac V4(2-Nal)/H9A —OH | Ac-ICV**(2-Nal)QDWGA**HRCT-COOH | 15 | 38× more |
| Ac V4(1-Nal)/H9A —OH | Ac-ICV**(1-Nal)QDWGA**HRCT-COOH | 16 | 30× more |
| Ac-V42Igl/H9A | Ac-ICV(2-Igl)QDWGAHRCT-CONH2 | 17 | 39× more |
| Ac-V42Igl/H9A —OH | Ac-ICV(2-Igl)QDWGAHRCT-COOH | 18 | 37× more |
| Ac-V4Dht/H9A —OH | Ac-ICVDhtQDWGAHRCT-COOH | 19 | 5× more |
| Ac-V4(Bpa)/H9A —OH | Ac-ICV**(Bpa)QDWGA**HRCT-COOH | 20 | 49× more |
| Ac-V4(Bpa)/H9A | Ac-ICV**(Bpa)QDWGA**HRCT-CONH2 | 21 | 86× more |
| Ac-V4(Bta)/H9A —OH | Ac-ICV**(Bta)QDWGA**HRCT-COOH | 22 | 65× more |
| Ac-V4(Bta)/H9A | Ac-ICV**(Bta)QDWGA**HRCT-CONH2 | 23 | 64× more |
| Ac-V4W/H9(2-Abu) | Ac-ICVWQDWG(2-Abu)HRCT-CONH2 | 24 | 64× more |
| +G/V4W/H9A +AN —OH | H-GICVWQDWGAHRCTAN-COOH | 25 | 38× more |
| Ac-V4(5fW)/H9A | Ac-ICV**(5fW)QDWGA**HRCT-CONH$_2$ | 26 | 31× more |
| Ac-V4(5-MeW/H9A | Ac-ICV**(5-methyl-W)QDWGA**HRCT-CONH$_2$ | 27 | 67× more |
| Ac-V4(1-MeW)/H9A | Ac-ICV**(1-methyl-W)QDWGA**HRCT-CONH$_2$ | 28 | 264× more |
| Ac-V4W/W7(5fW)/H9A | Ac-ICVWQD**(5fW)GA**HRCT-CONH$_2$ | 29 | 121× more |
| Ac-V4(5fW)/W7(5fW)/H9A | Ac-ICV**(5fW)QD(5fW)GA**HRCT-CONH$_2$ | 30 | NA |
| Ac-V4(5-MeW)/W7(5fW)H9A | Ac-ICV**(5-methyl-W)QD(5fW)GA**HRCT-CONH$_2$ | 31 | NA |
| Ac-V4(1MeW)/W7(5fW)/H9A | Ac-ICV(1-methyl-W)QD(5fW)GAHRCT-CONH$_2$ | 32 | 264× more |
| +G/V4(6fW)/W7(6fW)H9A +N —OH | H-GICV**(6fW)**QD(6fW)GAHRCTN-COOH | 33 | 126× more |
| Ac-V4(1-formyl-W)/H9A | Ac-ICV(1-formyl-W)QDWGAHRCT-CONH$_2$ | 34 | 264× more |

TABLE 2-continued

| Peptide | Sequence | SEQ ID NO: | Activity over compstatin |
|---|---|---|---|
| Ac-V4(5-methoxy-W)/H9A | Ac-ICV(1-methyoxy-W)QDWGAHRCT-CONH₂ | 35 | 76× more |
| G/V4(5f-W)/W7(5fW)/H9A +N-OH | H-GICV(5fW)QD(5fW)GAHRCTN-COOH | 36 | 112× more |

NA = not available

In certain embodiments of the compositions and methods of the invention the compstatin analog has a sequence selected from sequences 9-36. In certain embodiments of the compositions and methods of the invention the compstatin analog has a sequence selected from SEQ ID NOs: 14, 21, 28, 29, 32, 33, 34, and 36. In certain embodiments of the compositions and/or methods of the invention the compstatin analog has a sequence selected from SEQ ID NOs: 30 and 31. In one embodiment of the compositions and methods of the invention the compstatin analog has a sequence of SEQ ID NO: 28. In one embodiment of the compositions and methods of the invention the compstatin analog has a sequence of SEQ ID NO: 32. In one embodiment of the compositions and methods of the invention the compstatin analog has a sequence of SEQ ID NO: 34. In one embodiment of the compositions and methods of the invention the compstatin analog has a sequence of SEQ ID NO: 36.

In some embodiments a blocking moiety $B^1$ comprises an amino acid, which may be represented as Xaa0. In some embodiments blocking moiety $B^2$ comprises an amino acid, which may be represented as XaaN. In some embodiments blocking moiety $B^1$ and/or $B^2$ comprises a non-standard amino acid, such as a D-amino acid, N-alkyl amino acid (e.g., N-methyl amino acid). In some embodiments a blocking moiety $B^1$ and/or $B^2$ comprises a non-standard amino acid that is an analog of a standard amino acid. In some embodiments an amino acid analog comprises a lower alkyl, lower alkoxy, or halogen substituent, as compared with a standard amino acid of which it is an analog. In some embodiments a substituent is on a side chain. In some embodiments a substituent is on an alpha carbon atom. In some embodiments, a blocking moiety $B^1$ comprising an amino acid, e.g., a non-standard amino acid, further comprises a moiety $B^{1a}$. For example, blocking moiety $B^1$ may be represented as $B^{1a}$-Xaa0. In some embodiments $B^{1a}$ neutralizes or reduces a positive charge that may otherwise be present at the N-terminus at physiological pH. In some embodiments $B^{1a}$ comprises or consists of, e.g., an acyl group that, e.g., comprises between 1 and 12 carbons, e.g., between 1 and 6 carbons. In certain embodiments blocking moiety $B^{1a}$ is selected from the group consisting of: formyl, acetyl, proprionyl, butyryl, isobutyryl, valeryl, isovaleryl, etc. In some embodiments, a blocking moiety $B^2$ comprising an amino acid, e.g., a non-standard amino acid, may further comprise a moiety $B^{2a}$. For example, blocking moiety $B^2$ may be represented as XaaN-$B^{2a}$, where N represents the appropriate number for the amino acid (which will depend on the numbering used in the rest of the peptide). In some embodiments $B^{2a}$ neutralizes or reduces a negative charge that may otherwise be present at the C-terminus at physiological pH. In some embodiments $B^{2a}$ comprises or consists of a primary or secondary amine (e.g., NH₂). It will be understood that a blocking activity of moiety $B^{1a}$-Xaa0 and/or XaaN-$B^{2a}$ may be provided by either or both components of the moiety in various embodiments. In some embodiments a blocking moiety or portion thereof, e.g., an amino acid residue, may contribute to increasing affinity of the compound for C3 or C3b and/or improve the activity of the compound. In some embodiments a contribution to affinity or activity of an amino acid residue may be at least as important as a contribution to blocking activity. For example, in some embodiments Xaa0 and/or XaaN in $B^{1a}$-Xaa0 and/or XaaN-$B^2$a may function mainly to increase affinity or activity of the compound, while $B^{1a}$ and/or $B^2$a may inhibit digestion of and/or neutralize a charge of the peptide. In some embodiments a compstatin analog comprises the amino acid sequence of any of SEQ ID NOs: 5-36, wherein SEQ ID NOs: 5-36 is further extended at the N- and/or C-terminus. In some embodiments, the sequence may be represented as $B^{1a}$-Xaa0-SEQUENCE-XaaN-$B^2$a, where SEQUENCE represents any of SEQ ID NOs: 5-36, wherein $B^{1a}$ and $B^2$a may independently be present or absent. For example, in some embodiments a compstatin analog comprises $B^{1a}$-Xaa0-X'aa1-X'aa2-X'aa3-X'aa4-Gln-Asp-Xaa-Gly-X"aa1-X"aa2-X"aa3-X"aa4-X"aa5-XaaN-$B^2$a (SEQ ID NO: 37), where X'aa1-X'aa2-X'aa3-X'aa4, Xaa, X"aa1, X"aa2, X"aa3, X"aa4, and X"aa5 are as set forth above for SEQ ID NO: 5.

In some embodiments a compstatin analog comprises $B^{1a}$-Xaa0-Xaa1-Cys-Val-Xaa2-Gln-Asp-Xaa2*-Gly-Xaa3-His-Arg-Cys-Xaa4-XaaN-$B^2$a (SEQ ID NO: 38), where Xaa1, Xaa2, Xaa2*, Xaa3, and Xaa4 are as set forth above for SEQ ID NO: 6 or wherein Xaa1, Xaa2, Xaa2*, Xaa3, and Xaa4 are as set forth for SEQ ID NO: 6 or SEQ ID NO: 7.

In some embodiments a compstatin analog comprises $B^{1a}$-Xaa0-Xaa1-Xaa2-Xaa3-Xaa4-Xaa5-Xaa6-Xaa7-Xaa8-Xaa9-Xaa10-Xaa11-Xaa12-Xaa13-XaaN-$B^2$a (SEQ ID NO: 39) wherein Xaa1, Xaa2, Xaa3, Xaa4, Xaa5, Xaa6, Xaa7, Xaa8, Xaa9, Xaa10, Xaa11, Xaa12, and Xaa13 are identical to amino acids at positions 1-13 of any of SEQ ID NOs: 9-36.

In some embodiments Xaa0 and/or XaaN in any compstatin analog sequence comprises an amino acid that comprises an aromatic ring having an alkyl substituent at one or more positions. In some embodiments an alkyl substituent is a lower alkyl substituent. For example, in some embodiments an alkyl substituent is a methyl or ethyl group. In some embodiments a substituent is located at any position that does not destroy the aromatic character of the compound. In some embodiments a substituent is located at any position that does not destroy the aromatic character of a ring to which the substituent is attached. In some embodiments a substituent is located at position 1, 2, 3, 4, or 5. In some embodiments Xaa0 comprises an O-methyl analog of tyrosine, 2-hydroxyphenylalanine or 3-hydroxyphenylalanine. For purposes of the present disclosure, a lower case "m" followed by a three letter amino acid abbreviation may be used to specifically indicate that the amino acid is an N-methyl amino acid. For example, where the abbreviation "mGly" appears herein, it denotes N-methyl glycine (also sometimes referred to as sarcosine or Sar). In some embodiments Xaa0 is or comprises mGly, Tyr, Phe, Arg, Trp, Thr, Tyr(Me), Cha, mPhe, mVal, mIle, mAla, DTyr, DPhe, DArg, DTrp, DThr, DTyr(Me), mPhe, mVal, mIle, DAla, or DCha. For example, in some embodiments a compstatin analog comprises a peptide having a sequence $B^1$-Ile-[Cys-Val-Trp(Me)-Gln-Asp-Trp-mGly-Ala-His-Arg-Cys]-mIle-$B^2$ (SEQ ID NO: 40) or $B^1$-Ile-[Cys-Val-Trp(Me)-Gln-Asp-Trp-mGly-Ala-His-Arg-Cys]-mIle-$B^2$ (SEQ ID NO: 41). The two Cys residues are joined by a disulfide bond in the active compounds. In some embodiments the peptide is acetylated at the N-terminus and/or amidated at the C-terminus. In some embodiments $B^1$ comprises $B^{1a}$-Xaa0 and/or $B^2$ comprises XaaN-$B^2$a, as described above. For example, in some embodiments $B^1$ comprises or consists of Gly, mGly, Tyr, Phe, Arg, Trp, Thr, Tyr(Me), mPhe, mVal, mIle, mAla, DTyr, DPhe, DTrp, DCha, DAla and $B^2$ comprises $NH_2$, e.g., a carboxy terminal —OH of mIle is replaced by $NH_2$. In some embodiments $B^1$ comprises or consists of mGly, Tyr, DTyr, or Tyr(Me) and $B^2$ comprises $NH_2$, e.g., a carboxy terminal —OH of mIle is replaced by $NH_2$. In some embodiments an Ile at position Xaa1 is replaced by Gly. Complement inhibition potency and/or C3b binding parameters of selected compstatin analogs are described in WO/2010/127336 (PCT/US2010/033345) and/or in Qu, et al., Immunobiology (2012), doi:10.1016/j.imbio.2012.06.003.

In some embodiments a blocking moiety or portion thereof, e.g., an amino acid residue, may contribute to increasing affinity of the compound for C3 or C3b and/or improve the activity of the compound. In some embodiments a contribution to affinity or activity of an amino acid or amino acid analog may be more significant than a blocking activity.

In certain embodiments of the compositions and methods of the invention the compstatin analog has a sequence as set forth in Table 2, but where the Ac— group is replaced by an alternate blocking moiety $B^1$, as described herein. In some embodiments the —$NH_2$ group is replaced by an alternate blocking moiety $B^2$, as described herein.

In one embodiment, the compstatin analog binds to substantially the same region of the β chain of human C3 as does compstatin. In one embodiment the compstatin analog is a compound that binds to a fragment of the C-terminal portion of the β chain of human C3 having a molecular weight of about 40 kDa to which compstatin binds (Soulika, A. M., et al., *Mol. Immunol.,* 35:160, 1998; Soulika, A. M., et al., *Mol. Immunol.* 43(12):2023-9, 2006). In certain embodiments the compstatin analog is a compound that binds to the binding site of compstatin as determined in a compstatin-C3 structure, e.g., a crystal structure or NMR-derived 3D structure. In certain embodiments the compstatin analog is a compound that could substitute for compstatin in a compstatin-C3 structure and would form substantially the same intermolecular contacts with C3 as compstatin. In certain embodiments the compstatin analog is a compound that binds to the binding site of a peptide having a sequence set forth in Table 2, e.g., SEQ ID NO: 14, 21, 28, 29, 32, 33, 34, or 36 or another compstatin analog sequence disclosed herein in a peptide-C3 structure, e.g., a crystal structure. In certain embodiments the compstatin analog is a compound that binds to the binding site of a peptide having SEQ ID NO: 30 or 31 in a peptide-C3 structure, e.g., a crystal structure. In certain embodiments the compstatin analog is a compound that could substitute for the peptide of SEQ ID NO: 9-36, e.g., a compound that could substitute for the peptide of SEQ ID NO: 14, 21, 28, 29, 32, 33, 34, or 36 or another compstatin analog sequence disclosed herein in a peptide-C3 structure and would form substantially the same intermolecular contacts with C3 as the peptide. In certain embodiments the compstatin analog is a compound that could substitute for the peptide of SEQ ID NO: 30 or 31 in a peptide-C3 structure and would form substantially the same intermolecular contacts with C3 as the peptide.

One of ordinary skill in the art will readily be able to determine whether a compstatin analog binds to a fragment of the C-terminal portion of the β chain of C3 using routine experimental methods. For example, one of skill in the art could synthesize a photocrosslinkable version of the compstatin analog by including a photo-crosslinking amino acid such as p-benzoyl-L-phenylalanine (Bpa) in the compound, e.g., at the C-terminus of the sequence (Soulika, A. M., et al, supra). Optionally additional amino acids, e.g., an epitope tag such as a FLAG tag or an HA tag could be included to facilitate detection of the compound, e.g., by Western blotting. The compstatin analog is incubated with the fragment and crosslinking is initiated. Colocalization of the compstatin analog and the C3 fragment indicates binding. Surface plasmon resonance may also be used to determine whether a compstatin analog binds to the compstatin binding site on C3 or a fragment thereof. One of skill in the art would be able to use molecular modeling software programs to predict whether a compound would form substantially the same intermolecular contacts with C3 as would compstatin or a peptide having the sequence of any of the peptides in Table 2, e.g., SEQ ID NO: 14, 21, 28, 29, 32, 33, 34, or 36, or in some embodiments SEQ ID NO: 30 or 31 or another compstatin analog sequence disclosed herein.

Compstatin analogs may be prepared by various synthetic methods of peptide synthesis known in the art via condensation of amino acid residues, e.g., in accordance with conventional peptide synthesis methods, may be prepared by expression in vitro or in living cells from appropriate nucleic acid sequences encoding them using methods known in the art. For example, peptides may be synthesized using standard solid-phase methodologies as described in Malik, supra, Katragadda, supra, WO2004026328, and/or WO2007062249. Potentially reactive moieties such as amino and carboxyl groups, reactive functional groups, etc., may be protected and subsequently deprotected using various protecting groups and methodologies known in the art. See, e.g., "Protective Groups in Organic Synthesis", $3^{rd}$ ed. Greene, T. W. and Wuts, P. G., Eds., John Wiley & Sons, New York: 1999. Peptides may be purified using standard approaches such as reversed-phase HPLC. Separation of diasteriomeric peptides, if desired, may be performed using known methods such as reversed-phase HPLC. Preparations may be lyophilized, if desired, and subsequently dissolved in a suitable solvent, e.g., water. The pH of the resulting solution may be adjusted, e.g. to physiological pH, using a base such as NaOH. Peptide preparations may be characterized by mass spectrometry if desired, e.g., to confirm mass and/or disulfide bond formation. See, e.g., Mallik, 2005, and Katragadda, 2006.

A compstatin analog can be modified by addition of a molecule such as polyethylene glycol (PEG) or similar molecules to stabilize the compound, reduce its immunogenicity, increase its lifetime in the body, increase or decrease its solubility, and/or increase its resistance to degradation. Methods for pegylation are well known in the art (Veronese, F. M. & Harris, Adv. Drug Deliv. Rev. 54, 453-456, 2002; Davis, F. F., Adv. Drug Deliv. Rev. 54, 457-458, 2002); Hinds, K. D. & Kim, S. W. *Adv. Drug Deliv. Rev.* 54, 505-530 (2002; Roberts, M. J., Bentley, M. D. & Harris, J. M. *Adv. Drug Deliv. Rev.* 54, 459-476; 2002); Wang, Y. S. et al. *Adv. Drug Deliv. Rev.* 54, 547-570, 2002). A wide variety of polymers such as PEGs and modified PEGs, including derivatized PEGs to which polypeptides can conveniently be attached are described in Nektar Advanced Pegylation 2005-2006 Product Catalog, Nektar Therapeutics, San Carlos, Calif., which also provides details of appropriate conjugation procedures. In another embodiment a compstatin analog is fused to the Fc domain of an immunoglobulin or a portion thereof. In some other embodiments a compstatin analog is conjugated to an albumin moiety or to an albumin binding peptide. Thus in some embodiments a compstatin analog is modified with one or more polypeptide or non-polypeptide components, e.g., the compstatin analog is pegylated or conjugated to another moiety. In some embodiments the component is not the Fc domain of an immunoglobulin or a portion thereof. A compstatin analog can be provided as a multimer or as part of a supramolecular complex, which can include either a single molecular species or multiple different species (e.g., multiple different analogs).

In some embodiments, a compstatin analog of use in methods described herein is a long-acting compstatin analog, that has a terminal half-life of at least 3, 4, 5, 6, or 7 days. In some embodiments a long-acting compstatin analog is a pegylated compstatin analog. Exemplary long-acting compstatin analogs are described below and/or in PCT/US12/37648, entitled "CELL-REACTIVE, LONG-ACTING, OR TARGETED COMPSTATIN ANALOGS AND USES THEREOF", filed May 11, 2012. In some embodiments of any method or composition relating to a compstatin analog, the compstatin analog comprises a compstatin analog whose sequence comprises any of SEQ ID NOs: 3-41, wherein the compstatin analog is a long-acting compstatin analog. In some embodiments a long-acting compstatin analog is administered intravenously. In some embodiments a long-acting compstatin analog is administered subcutaneously.

In some embodiments, a compstatin analog is a multivalent compound comprising a plurality of compstatin analog moieties covalently or noncovalently linked to a polymeric backbone or scaffold. The compstatin analog moieties can be identical or different. In certain embodiments of the invention the multivalent compound comprises multiple instances, or copies, of a single compstatin analog moiety. In other embodiments of the invention the multivalent compound comprises one or more instances of each of two or more non-identical compstatin analog moieties, e.g., 3, 4, 5, or more different compstatin analog moieties. In certain embodiments of the invention the number of compstatin analog moieties ("n") is between 2 and 6. In other embodiments of the invention n is between 7 and 20. In other embodiments of the invention n is between 20 and 100. In other embodiments n is between 100 and 1,000. In other embodiments of the invention n is between 1,000 and 10,000. In other embodiments n is between 10,000 and 50,000. In other embodiments n is between 50,000 and 100,000. In other embodiments n is between 100,000 and 1,000,000.

The compstatin analog moieties may be attached directly to the polymeric scaffold or may be attached via a linking moiety that connects the compstatin analog moiety to the polymeric scaffold. The linking moiety may be attached to a single compstatin analog moiety and to the polymeric scaffold. Alternately, a linking moiety may have multiple compstatin analog moieties joined thereto so that the linking moiety attaches multiple compstatin analog moieties to the polymeric scaffold.

In some embodiments, a compstatin analog comprises an amino acid having a side chain comprising a primary or secondary amine, e.g., a Lys residue. For example, any of the compstatin analog sequences disclosed herein may be extended or modified by addition of a linker comprising one or more amino acids, e.g., one or more amino acids comprising a primary or secondary amine, e.g., in a side chain thereof. For example, a Lys residue, or a sequence comprising a Lys residue, is added at the N-terminus and/or C-terminus of the compstatin analog. In some embodiments, the Lys residue is separated from the cyclic portion of the compstatin analog by a rigid or flexible spacer. A linker or spacer may, for example, comprise a substituted or unsubstituted, saturated or unsaturated alkyl chain, oligo(ethylene glycol) chain, and/or other moieties. The length of the chain may be, e.g., between 2 and 20 carbon atoms. In some embodiments the spacer is or comprises a peptide. The peptide spacer may be, e.g., between 1 and 20 amino acids in length, e.g., between 4 and 20 amino acids in length. Suitable spacers can comprise or consist of multiple Gly residues, Ser residues, or both, for example. Optionally, the amino acid having a side chain comprising a primary or secondary amine and/or at least one amino acid in a spacer is a D-amino acid. A PEG moiety or similar molecule or polymeric scaffold may be linked to the primary or secondary amine, optionally via a linker. In some embodiments, a bifunctional linker is used. A bifunctional linker may comprise two reactive functional groups, which may be the same or different in various embodiments. In various embodiments, one or more linkers, spacers, and/or techniques of conjugation described in Hermanson, supra, is used.

Any of a variety of polymeric backbones or scaffolds could be used. For example, the polymeric backbone or scaffold may be a polyamide, polysaccharide, polyanhydride, polyacrylamide, polymethacrylate, polypeptide, polyethylene oxide, or dendrimer. Suitable methods and polymeric backbones are described, e.g., in WO98/46270 (PCT/US98/07171) or WO98/47002 (PCT/US98/06963). In one embodiment, the polymeric backbone or scaffold comprises multiple reactive functional groups, such as carboxylic acids, anhydride, or succinimide groups. The polymeric backbone or scaffold is reacted with the compstatin analogs. In one embodiment, the compstatin analog comprises any of a number of different reactive functional groups, such as carboxylic acids, anhydride, or succinimide groups, which are reacted with appropriate groups on the polymeric backbone. Alternately, monomeric units that could be joined to one another to form a polymeric backbone or scaffold are first reacted with the compstatin analogs and the resulting monomers are polymerized. In another embodiment, short chains are prepolymerized, functionalized, and then a mixture of short chains of different composition are assembled into longer polymers.

In some aspects a moiety such as a polyethylene glycol (PEG) chain or other polymer(s) that, e.g., stabilize the compound, increase its lifetime in the body, increase its solubility, decrease its immunogenicity, and/or increase its resistance to degradation may be referred to herein as a "clearance reducing moiety" (CRM), and a compstatin analog comprising such a moiety may be referred to as a long-acting compstatin analog.

In some aspects, a long-acting compstatin analog comprises a compound of formula M-L-A, wherein A is a moiety that comprises a CRM, L is an optionally present linking portion, and M comprises a compstatin analog moiety. The compstatin analog moiety can comprise any compstatin analog, e.g., any compstatin analog described above, in various embodiments. Formula M-L-A encompasses embodiments in which L-A is present at the N-terminus of the compstatin analog moiety, embodiments in which L-A is present at the C-terminus of the compstatin analog moiety, embodiments in which L-A is attached to a side chain of an amino acid of the compstatin analog moiety, and embodiments where the same or different L-As are present at both ends of M. It will be appreciated that when certain compstatin analog(s) are present as a compstatin analog moiety in a compound of formula M-L-A, a functional group of the compstatin analog will have reacted with a functional group of L to form a covalent bond to A or L. For example, a long-acting compstatin analog in which the compstatin analog moiety comprises a compstatin analog that contains an amino acid with a side chain containing a primary amine ($NH_2$) group (which compstatin analog can be represented by formula $R^1$—($NH_2$)), can have a formula $R^1$—NH-L-A in which a new covalent bond to L (e.g., N—C) has been formed and a hydrogen lost. Thus the term "compstatin analog moiety" includes molecular structures in which at least one atom of a compstatin analog participates in a covalent bond with a second moiety, which may, e.g., modification of a side chain. Similar considerations apply to compstatin analog moieties present in multivalent compounds. In some embodiments, a blocking moiety at the N-terminus or C-terminus of a compstatin analog is replaced by L-A in the structure of a long-acting compstatin analog.

In some embodiments, L comprises an unsaturated moiety such as —CH═CH— or —$CH_2$—CH═CH—; a moiety comprising a non-aromatic cyclic ring system (e.g., a cyclohexyl moiety), an aromatic moiety (e.g., an aromatic cyclic ring system such as a phenyl moiety); an ether moiety (—C—O—C—); an amide moiety (—C(═O)—N—); an ester moiety (—CO—O—); a carbonyl moiety (—C(═O)—); an imine moiety (—C═N—); a thioether moiety (—C—S—C—); an amino acid residue; and/or any moiety that can be formed by the reaction of two compatible reactive functional groups. In some embodiments, L comprises an oligo(ethylene glycol) moiety and/or a saturated alkyl chain. In some embodiments, L comprises —($CH_2$)$_m$—C(═O)—NH—($CH_2CH_2O$)$_n$($CH_2$)$_p$C(═O)— or —($CH_2$)$_m$—C(═O)—NH—($CH_2$)$_p$($OCH_2CH_2$)$_n$C(═O)—. In some embodiments, m, n, and p are selected so that the number of carbons in the chain is between 1 and 50, e.g., between 4 and 40, e.g., between 6 and 30, e.g., between 8 and 20. In some embodiments, m is between 2 and 10, n is between 1 and 8, and/or p is between 2 and 10. Optionally, at least one —CH2-is replaced by CH—R, wherein R can be any substituent. Optionally, at least one —CH2-is replaced by a heteroatom, cyclic ring system, amide, ester, or ether moiety. In some embodiments, L does not comprise an alkyl group having more than 3 carbon atoms in the longest chain. In some embodiments, L does not comprise an alkyl group having more than 4, 5, 6, 7, 8, 9, 10, or 11 carbon atoms in the longest chain. In certain embodiments, one or more moieties of a linking portion is/are substituted by independent replacement of one or more of the hydrogen (or other) atoms thereon with one or more moieties including, but not limited to aliphatic; aromatic, aryl; alkyl, aralkyl, alkanoyl, aroyl, alkoxy; thio; F; Cl; Br; I; —NO2; —CN; —CF3; —CH2CF3; —CHC12; —CH2OH; —CH2CH2OH; —CH2NH2; —CH2SO2CH3;—or -GRG1 wherein G is —O—, —S—, —NRG2-, —C(═O)—, —S(═O)—, —SO2-, —C(═O)O—, —C(═O)NRG2-, —OC(═O)—, —NRG2C(═O)—, —OC(═O)O—, —OC(═O)NRG2-, —NRG2C(═O)O—, —NRG2C(═O)NRG2-, —C(═S)—, —C(═S)S—, —SC(═S)—, —SC(═S)S—, —C(═NRG2)-, —C(═NRG2)O—, —C(═NRG2)NRG3-, —OC(═NRG2)-, —NRG2C(═NRG3)-, —NRG2SO2-, —NRG2SO2NRG3-, or —SO2NRG2-, wherein each occurrence of RG1, RG2 and RG3 independently includes, but is not limited to, hydrogen, halogen, or an optionally substituted aliphatic, aromatic, or aryl moiety. It will be appreciated that cyclic ring systems when present as substituents may optionally be attached via a linear moiety. Combinations of substituents and variables envisioned by this invention are preferably those that result in the formation of stable compounds useful in any one or more of the compositions or methods described herein. The term "stable", as used herein, preferably refers to compounds which possess stability sufficient to allow manufacture and which maintain the integrity of the compound for a sufficient period of time, e.g., to be useful for one or more purposes described herein.

L can comprise one or more of any of the moieties described in the preceding paragraph, in various embodiments. In some embodiments, L comprises two or more different moieties linked to one another to form a structure typically having a length of between 1 to about 60 atoms, between 1 to about 50 atoms, e.g., between 1 and 40, between 1 and 30, between 1 and 20, between 1 and 10, or between 1 and 6 atoms, where length refers to the number of atoms in the main (longest) chain. In some embodiments, L comprises two or more different moieties linked to one another to form a structure typically having between 1 to about 40, e.g., between 1 and 30, e.g., between 1 and 20, between 1 and 10, or between 1 and 6 carbon atoms in the main (longest) chain.

In some embodiments, a long-acting compstatin analog has an average plasma half-life of at least 1 day, e.g., 1-3 days, 3-7 days, 7-14 days, or 14-28 days, when administered IV at a dose of 10 mg/kg to humans or to non-human primates. In some embodiments, average plasma half-life of a long-acting compstatin analog following administration IV at a dose of 10 mg/kg to humans or to non-human primates is increased by at least a factor of 2, e.g., by a factor of 2-5, 5-10, 10-50, or 50-100-fold as compared with that of a corresponding compstatin analog having the same amino acid sequence (and, if applicable, one or more blocking moiet(ies)) but not comprising the CRM.

In some embodiments, a plasma half-life is a terminal half-life after administration of a single IV dose. In some embodiments, a plasma half-life is a terminal half-life after steady state has been reached following administration of multiple IV doses. In some embodiments, a long-acting compstatin analog achieves a Cmax in plasma at least 5-fold as great as that of a corresponding compstatin analog not comprising the CRM, e.g., between S- and 50-fold as great, following administration of a single IV dose to a primate, or following administration of multiple IV doses. In some embodiments, a long-acting compstatin analog achieves a Cmax in plasma between 10- and 20-fold as great as that of a corresponding compstatin analog not comprising the CRM following administration of a single IV dose to a primate, or following administration of multiple IV doses. In some embodiments a primate is human. In some embodiments a primate is a non-human primate, e.g., a monkey, such as a Cynomolgus monkey or Rhesus monkey. In some embodiments, renal clearance of a long-acting compstatin analog during the first 24 hours following administration IV at a dose of 10 mg/kg to humans or to non-human primates is reduced by at least a factor of 2, e.g., by a factor of 2-5, 5-10, 10-50, or 50-100-fold as compared with renal clearance of a corresponding compstatin analog. The concentration of compstatin analog can be measured in blood and/or urine samples using, e.g., UV, HPLC, mass spectrometry (MS) or antibody to the CRM, or combinations of such methods, such as LC/MS or LC/MS/MS. Pharmacokinetic parameters such as half-life and clearance can be determined using methods known to those of ordinary skill in the art. Pharmacokinetic analysis can be performed, e.g., with WinNonlin software v 5.2 (Pharsight Corporation, St. Louis, Mo.).

In some embodiments, a long-acting compstatin analog has a molar activity of at least about 10%, 20%, 30%, e.g., between 30% and 40%, between 30% and 50%, between 30% and 60%, between 30% and 70%, between 30% and 80%, between 30% and 90%, or more, of the activity of a corresponding compstatin analog having the same amino acid sequence (and, if applicable, one or more blocking moiet(ies)) but not comprising a CRM. In some embodiments wherein a long-acting compstatin analog comprises multiple compstatin analog moieties, the molar activity of the long-acting compstatin analog is at least about 10%, 20%, or 30%, e.g., between 30% and 40%, between 30% and 50%, between 30% and 60%, between 30% and 70%, between 30% and 80%, between 30% and 90%, or more, of the sum of the activities of said compstatin analog moieties. In some embodiments, a polyethylene glycol (PEG) comprises a $(CH_2CH_2O)_n$ moiety having a molecular weight of at least 500 daltons. In some embodiments, a linker comprises an $(CH_2CH_2O)_n$ moiety having an average molecular weight of between about 500; 1,000; 1,500; 2,000; 5,000; 10,000; 20,000; 30,000; 40,000; 50,000; 60,000; 70,000; 80,000; 90,000; and 100,000 daltons. "Average molecular weight" refers to the number average molecular weight. In some embodiments, the polydispersity D of a $(CH_2CH_2O)n$ moiety is between 1.0005 and 1.50, e.g., between 1.005 and 1.10, 1.15, 1.20, 1.25, 1.30, 1.40, or 1.50, or any value between 1.0005 and 1.50.

In some embodiments, a $(CH_2CH_2O)n$ moiety is monodisperse and the polydispersity of a $(CH_2CH_2O)n$ moiety is 1.0. Such monodisperse $(CH_2CH_2O)n$ moieties are known in the art and are commercially available from Quanta BioDesign (Powell, Ohio), and include, by way of nonlimiting example, monodisperse moieties where n is 2, 4, 6, 8, 12, 16, 20, or 24.

In some embodiments, a compound comprises multiple $(CH_2CH_2O)_n$ moieties wherein the total molecular weight of said $(CH_2CH_2O)_n$ moieties is between about 1,000; 5,000; 10,000; 20,000; 30,000; 40,000; 50,000; 60,000; 70,000; 80,000; 90,000; and 100,000 daltons. In some embodiments, the compound comprises multiple $(CH_2CH_2O)_n$ moieties having defined lengths, e.g., n=4, 6, 8, 10, 12, 14, 16, 18, 20, 22, 24, 26, 28, or 30 or more. In some embodiments, the compound comprises a sufficient number of $(CH_2CH_2O)_n$ moieties having defined lengths to result in a total molecular weight of said $(CH_2CH_2O)_n$ moieties of between about 1,000; 5,000; 10,000; 20,000; 30,000; 40,000; 50,000; 60,000; 70,000; 80,000; 90,000; and 100,000 daltons. In some embodiments n is between about 30 and about 3000. In some embodiments a compstatin analog moiety is attached at each end of a linear PEG. A bifunctional PEG having a reactive functional group at each end of the chain may be used, e.g., as described above. In some embodiments the reactive functional groups are identical while in some embodiments different reactive functional groups are present at each end. In some embodiments, multiple $(CH_2CH_2O)_n$ moieties are provided as a branched structure. The branches may be attached to a linear polymer backbone (e.g., as a comb-shaped structure) or may emanate from one or more central core groups, e.g., as a star structure. In some embodiments, a branched molecule has 3 to 10 $(CH_2CH_2O)_n$ chains. In some embodiments, a branched molecule has 4 to 8 $(CH_2CH_2O)_n$ chains. In some embodiments, a branched molecule has 10, 9, 8, 7, 6, 5, 4, or 3 $(CH_2CH_2O)_n$ chains. In some embodiments, a star-shaped molecule has 10-100, 10-50, 10-30, or 10-20 $(CH_2CH_2O)_n$ chains emanating from a central core group. In some embodiments a long-acting compstatin analog thus may comprise, e.g., 3-10 compstatin analog moieties, e.g., 4-8 compstatin analog moieties, each attached to a $(CH_2CH_2O)_n$ chain via a functional group at the end of the chain. In some embodiments a long-acting compstatin analog may comprise, e.g., 10-100 compstatin analog moieties, each attached to a $(CH_2CH_2O)_n$ chain via a functional group at the end of the chain. In some embodiments, branches (sometimes referred to as "arms") of a branched or star-shaped PEG contain about the same number of $(CH_2CH_2O)$ moieties. In some embodiments, at least some of the branch lengths may differ. It will be understood that in some embodiments one or more $(CH_2CH_2O)_n$ chains does not have a comptatin analog moiety attached thereto. In some embodiments at least about 30%, 40%, 50%, 60%, 70%, 80%, 90%, 95%, or 100% of the chains has a compstatin analog moiety attached thereto.

In genera and compounds depicted herein, a polyethylene glycol moiety is drawn with the oxygen atom on the right side of the repeating unit or the left side of the repeating unit. In cases where only one orientation is drawn, the present invention encompasses both orientations (i.e., $(CH_2CH_2O)_n$ and $(OCH_2CH_2)_n$) of polyethylene glycol moieties for a given compound or genus, or in cases where a compound or genus contains multiple polyethylene glycol moieties, all combinations of orientations are encompasses by the present disclosure.

Formulas of some exemplary monofunctional PEGs comprising a reactive functional group are illustrated below. For illustrative purposes, formulas in which the reactive functional group(s) comprise an NHS ester are depicted, but other reactive functional groups could be used, e.g., as described above. In some embodiments, the $(CH_2CH_2O)_n$ are depicted as terminating at the left end with a methoxy group $(OCH_3)$ but it will be understood that the chains depicted below and elsewhere herein may terminate with a different OR moiety (e.g., an aliphatic group, an alkyl group, a lower alkyl group, or any other suitable PEG end group) or an OH group. It will also be appreciated that moieties other than those depicted may connect the $(CH_2CH_2O)_n$ moieties with the NHS group in various embodiments.

In some embodiments, a monofunctional PEG is of formula A:

Formula A

wherein "Reactive functional group" and n are as defined above and described in classes and subclasses herein;
$R^1$ is hydrogen, aliphatic, or any suitable end group; and
T is a covalent bond or a C1-12 straight or branched, hydrocarbon chain wherein one or more carbon units of T are optionally and independently replaced by —O—, —S—, —N(R$^x$)—, —C(O)—, —C(O)O—, —OC(O)—, —N(R$^x$)C(O)—, —C(O)N(R$^x$)—, —S(O)—, —S(O)$_2$—, —N(R$^x$)SO$_2$—, or —SO$_2$N(R$^x$)—; and
each R$^x$ is independently hydrogen or C1-6 aliphatic.
Exemplary monofunctional PEGs of formula A include:

Formula I

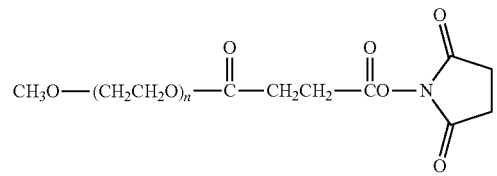

In Formula I, the moiety comprising the reactive functional group has the general structure —CO—(CH$_2$)$_m$—COO—NHS, where m=2. In some embodiments, a monofunctional PEGs has the structure of Formula I, where m is between 1 and 10, e.g., between 1 and 5. For example, in some embodiments m is 3, as shown below:

Formula Ia

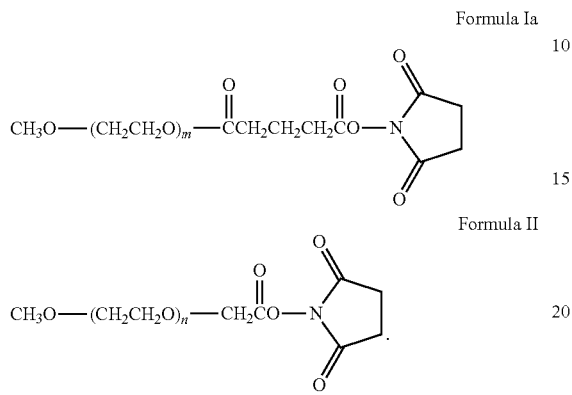

In Formula II, the moiety comprising the reactive functional group has the general structure —(CH$_2$)$_m$—COO—NHS, where m=1. In some embodiments a monofunctional PEG has the structure of Formula II, where m is between 1 and 10 (e.g., wherein m is 5 as shown in Formula III below), or wherein m is 0 (as shown below in Formula IIIa).

Formula III

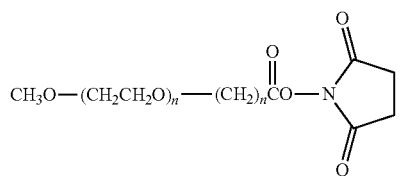

Formula IIIa

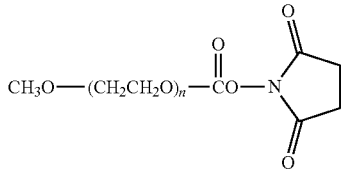

Formula IIIa

In some embodiments a bifunctional linear PEG comprises a moiety comprising a reactive functional group at each of its ends. The reactive functional groups may be the same (homobifunctional) or different (heterobifunctional). In some embodiments the structure of a bifunctional PEG may be symmetric, wherein the same moiety is used to connect the reactive functional group to oxygen atoms at each end of the —(CH$_2$CH$_2$O)$_n$ chain. In some embodiments different moieties are used to connect the two reactive functional groups to the PEG portion of the molecule. The structures of exemplary bifunctional PEGs are depicted below. For illustrative purposes, formulas in which the reactive functional group(s) comprise an NHS ester are depicted, but other reactive functional groups could be used.

In some embodiments, a bifunctional linear PEG is of formula B:

Formula B

wherein each T and "Reactive functional group" is independently as defined above and described in classes and subclasses herein, and n is as defined above and described in classes and subclasses herein.

Exemplary bifunctional PEGs of formula B include:

Formula IV

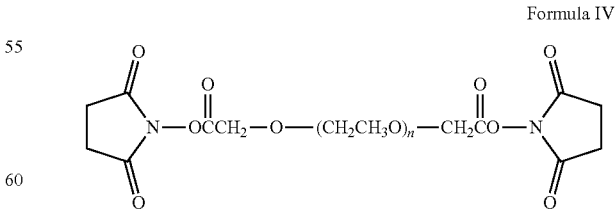

In Formula IV, the moiety comprising the reactive functional group has the general structure —(CH$_2$)$_m$—COO—NHS, where m=1. In some embodiments, a bifunctional PEGs has the structure of Formula IV, where m is between 1 and 10, e.g., between 1 and 5.

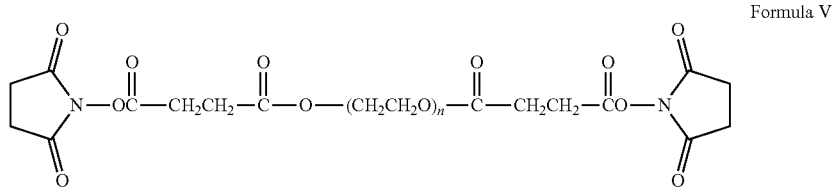

Formula V

In Formula V, the moiety comprising the reactive functional group has the general structure —CO—$(CH_2)_m$—COO—NHS, where m=2. In some embodiments, a bifunctional PEGs has the structure of Formula V, where m is between 1 and 10, e.g., between 1 and 5.

In some embodiments, a branched, comb, or star-shaped PEG comprises a moiety comprising a reactive functional group at the end of each of multiple —$(CH_2CH_2O)_n$ chains. The reactive functional groups may be the same or there may be at least two different groups. In some embodiments, a branched, comb, or star-shaped PEG is of the following formulae:

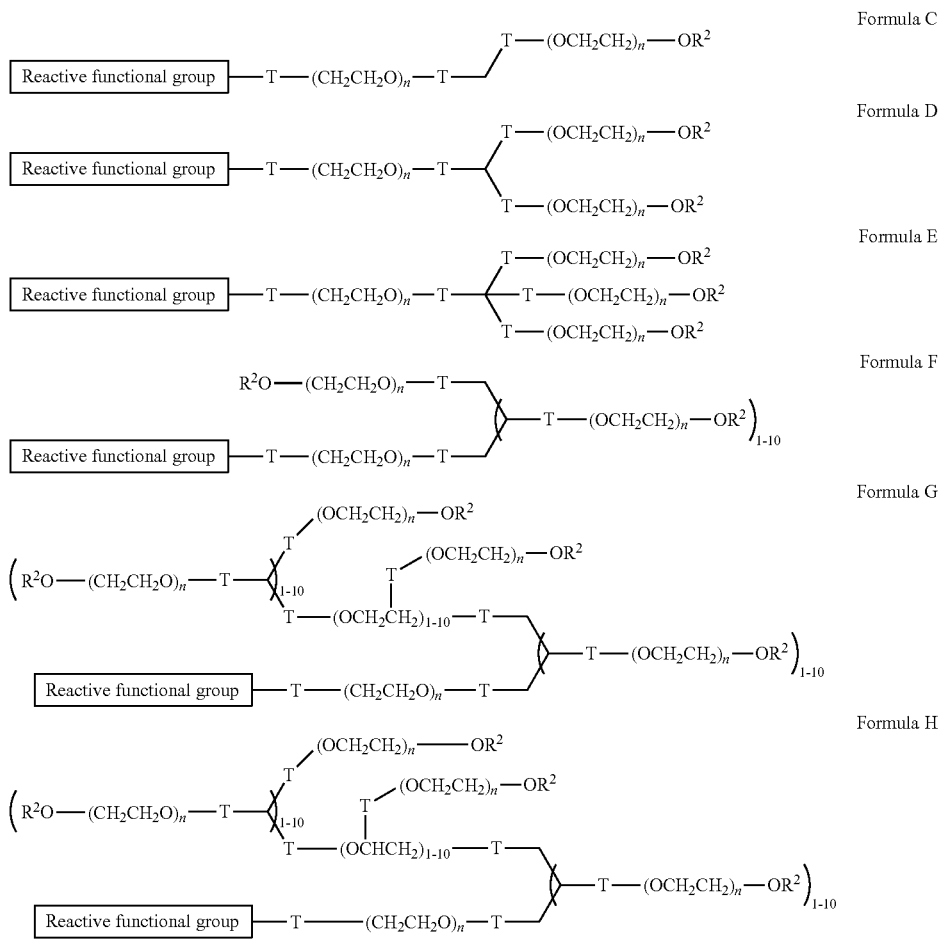

wherein each $R^2$ is independently a "Reactive functional group" or $R^1$, and each T, n, and "Reactive functional group" is independently as defined above and described in classes and subclasses herein. The structure of exemplary branched PEGs (having 8 arms, or branches) comprising NHS moieties as reactive functional groups is depicted below:

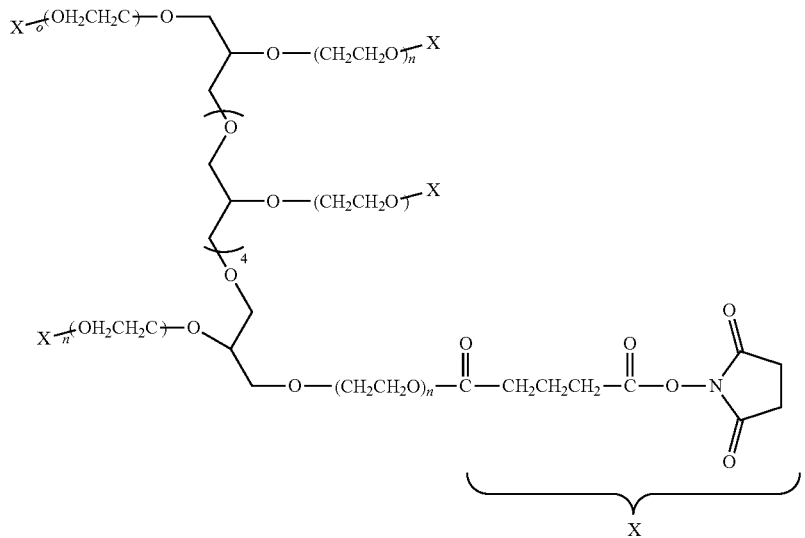
Formula VI
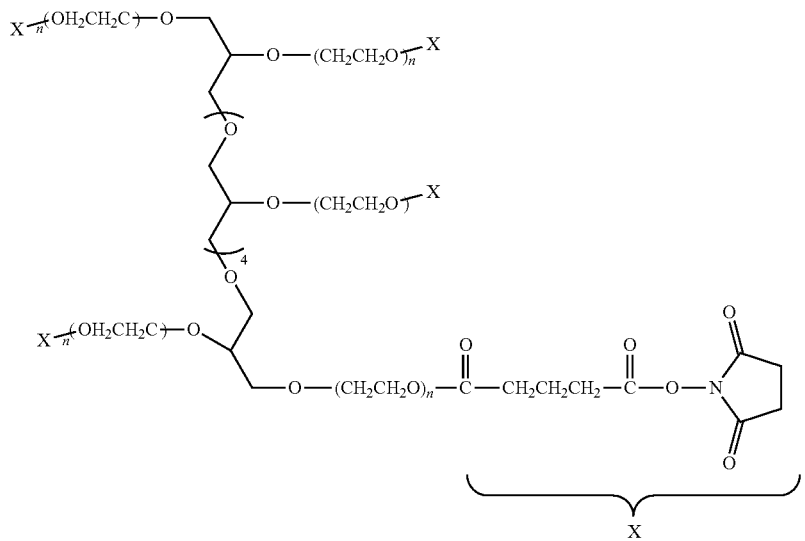
Formula VII
The structure of exemplary branched PEGs (having 4 arms, or branches) comprising NHS moieties as reactive functional groups is depicted below:
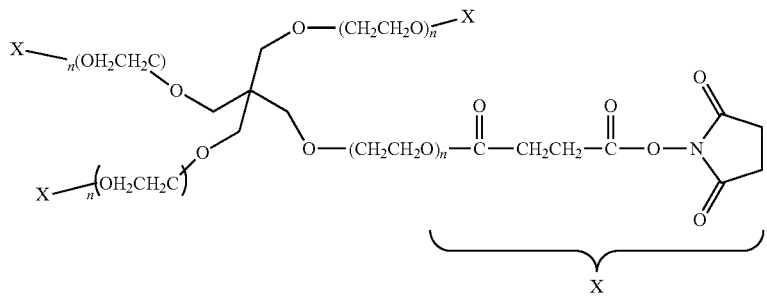
Formula VIII

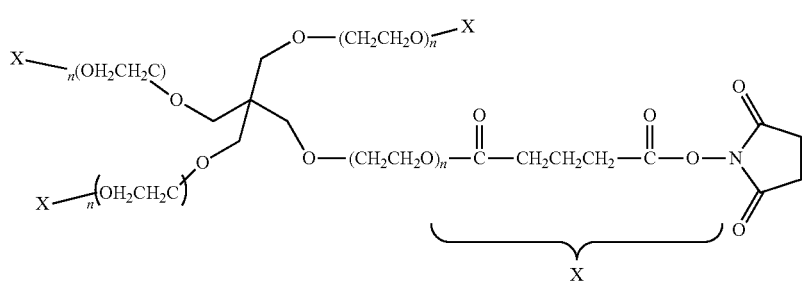

Formula IX

The number of branches emanating from the backbone may be varied. For example, the number 4 in the above formulae VI and VII may be changed to any other integer between 0 and 10 in various embodiments. In certain embodiments, one or more branches does not contain a reactive function group and the branch terminates with a —CH$_2$CH$_2$OH or —CH$_2$CH$_2$OR group, as described above.

In some embodiments a branched PEG has the structure of Formula VII, VIII, or IX (or variants thereof having different numbers of branches) with the proviso that x is

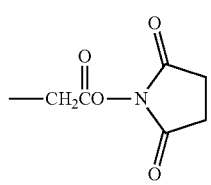

In some embodiments a branched PEG has the structure of Formula VII, VIII, or IX (or variants thereof having different numbers of branches) with the proviso that x is Of course the methylene (CH$_2$) group in the above x moiety may instead comprise a longer alkyl chain (CH$_2$)$_m$, where m is up to 2, 3, 4, 5, 6, 8, 10, 20, or 30, or may comprise one or more other moieties described herein.

In some embodiments, exemplary branched PEGs having NHS or maleimde reactive groups are depicted below:

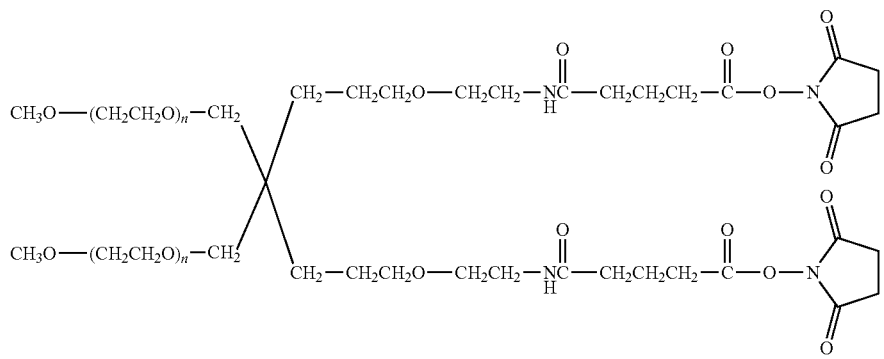

Formula X

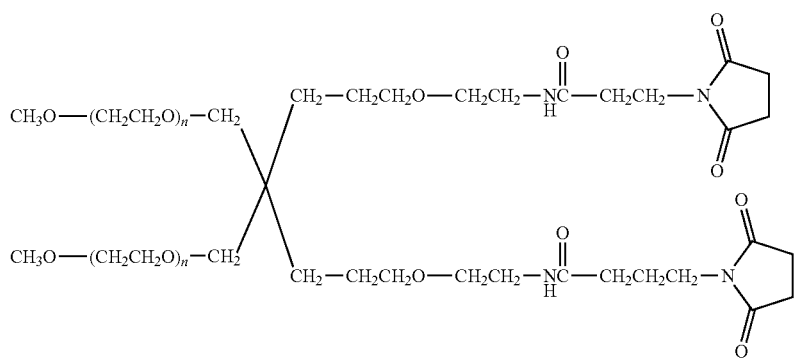

Formula XI

In some embodiments, a variant of Formula X or XI are used, wherein 3 or each of the 4 branches comprise a reactive functional group.

Still other examples of PEGs may be represented as follows:

In some embodiments a branched (multi-arm) PEG or star-shaped PEG comprises a pentaerythritol core, hexaglycerin core, or tripentaerythritol core. It will be understood that the branches may not all emanate from a single point in certain embodiments.

Formula XII

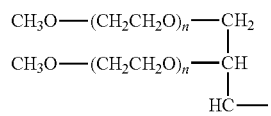
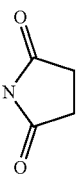

Formula XIII

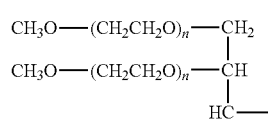
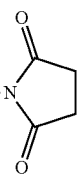

As noted above, it will be appreciated that, as described herein, in various embodiments any of a variety of moieties may be incorporated between the peptide component and $(CH_2CH_2O)_n$—R moiety of a long-acting compstatin analog, such as an linear alkyl, ester, amide, aromatic ring (e.g., a substituted or unsubstituted phenyl), a substituted or unsubstituted cycloalkyl structure, or combinations thereof. In some embodiments such moiet(ies) may render the compound more susceptible to hydrolysis, which may release the peptide portion of the compound from the CRM. In some embodiments, such release may enhance the in vivo tissue penetration and/or activity of the compound. In some embodiments hydrolysis is general (e.g., acid-base) hydrolysis. In some embodiments hydrolysis is enzyme-catalyzed, e.g., esterase-catalyzed. Of course both types of hydrolysis may occur. Examples of PEGs comprising one or more such moieties and an NHS ester as a independently selected. In some embodiments, the reactive functional group (e.g., a primary or secondary amine) is used as a target for addition of a moiety comprising a CRM. Amino acids having a side chain that comprises a primary or secondary amine include lysine (Lys) and diaminocarboxylic acids of general structure $NH_2(CH_2)_nCH(NH_2)COOH$ such as 2,3-diaminopropionic acid (dapa), 2,4-diaminobutyric acid (daba), and ornithine (orn), wherein n=1 (dapa), 2 (daba), and 3 (orn), respectively. In some embodiments at least one amino acid is cysteine, aspartic acid, glutamic acid, arginine, tyrosine, tryptophan, methionine, or histidine. Cysteine has a side chain comprising a sulfhydryl group. Aspartic acid and glutamic acid have a side chain comprising a carboxyl group (ionizable to a carboxylate group). Arginine has a side chain comprising a guanidino group. Tyrosine has a side chain comprising a phenol group (ionizable to a phenolate group). Tryptophan has a side chain comprising an indole ring include include, e.g., tryptophan. Methionine has a side chain comprising a thioether group include, e.g., methionine. Histidine has a side chain comprising an imidazole ring. A wide variety of non-standard amino acids having side chains that comprise one or more such reactive functional group(s) are available, including naturally occurring amino acids and amino acids not found in nature. See, e.g., Hughes, B. (ed.), *Amino Acids, Peptides and Proteins in Organic Chemistry*, Volumes 1-4, Wiley-VCH (2009-2011); Blaskovich, M., Handbook on Syntheses of Amino Acids General Routes to Amino Acids, Oxford University Press, 2010. Embodiments in which one or more non-standard amino acid(s) is/are used to provide a target for addition of a moiety comprising a CRM are encompassed. Any one or more of the amino acid(s) may be protected as appropriate during synthesis of the compound. For example, one or more amino acid(s) may be protected during reaction (s) involving the target amino acid side chain. In some embodiments, wherein a sulfhydryl-containing amino acid is used as a target for addition of a moiety comprising a CRM, the sulthydryl is protected while the compound is being cyclized by formation of an intramolecular disulfide bond between other amino acids such as cysteines.

In certain discussion herein, an amino acid having a side chain containing an amine group is used as an example. Analogous embodiments are encompassed in which an amino acid having a side chain containing a different reactive functional group is used. In some embodiments, an amino acid having a side chain comprising a primary or secondary amine is attached directly to the N-terminus or C-terminus of any of SEQ ID NOs: 3-41 via a peptide bond. In some embodiments, an amino acid having a side chain comprising a primary or secondary amine is attached to the N- or C-terminus of any of SEQ ID NOs: 3-41 via a linking portion, which may contain any one or more of the linking moieties described above. In some embodiments, at least two amino acids are appended to either or both termini. The two or more appended amino acids may be joined to each other by peptide bonds or at least some of the appended amino acids may be joined to each other by a linking portion, which may contain any one or more of the linking moieties described herein.

It will be understood that a corresponding compstatin analog not comprising the CRM may also lack one or more such amino acids which are present in the long-acting compstatin analog to which it corresponds. Thus, a corresponding compstatin analog comprising any of SEQ ID NOs: 3-41 and lacking a CRM will be understood to "have the same amino acid sequence" as SEQ ID NO: 3-41, respectively. For example, a corresponding compstatin analog comprising the amino acid sequence of SEQ ID NO: 14, 21, 28, 29, 32, 33, 34, or 36 and lacking a CRM will be understood to "have the same amino acid sequence" as SEQ ID NO: 14, 21, 28, 29, 32, 33, 34, or 36, respectively.

For descriptive purposes a peptide having the amino acid sequence Ile-Cys*-Val-(1Me)Trp-Gln-Asp-Trp-Gly-Ala-His-Arg-Cys*-Thr (SEQ ID NO: 42) (corresponding to the compstatin analog of SEQ ID NO: 28, wherein asterisks in SEQ ID NO: 42 represent cysteines joined by a disulfide bond in the active compound, and (1Me)Trp represents 1-methyl-tryptophan)), is used as an exemplary compstatin analog moiety; $(CH_2)_n$ and $(O-CH_2-CH_2)_n$ are used as examples of linking portions; lysine is used as an example of an amino acid comprising a reactive functional group (in some compounds), and acetylation and amidation of the N- and C-termini, respectively, are used as optionally present exemplary blocking moieties in some compounds and may be represented in italics, i.e., as Ac and $NH_2$ respectively. In some embodiments, SEQ ID NO: 42 is extended to comprise a Lys residue at the N- or C-terminus of the peptide, e.g., as exemplified below for a C-terminal linkage:

Ac-Ile-Cys*-Val-(1Me)Trp-Gln-Asp-Trp-Gly-Ala-
His-Arg-Cys*-Thr-Lys-NH$_2$ (SEQ ID NO: 43).

In some embodiments, a Lys residue is attached to the N- or C-terminus of SEQ ID NO: 42 via a peptide linker, e.g., as exemplified below for a C-terminal linkage:

Ac-Ile-Cys*-Val-(1Me)Trp-Gln-Asp-Trp-Gly-Ala-
His-Arg-Cys*-Thr-(Gly)$_5$-Lys-NH$_2$ (SEQ ID NO: 44).

In some embodiments, a linker comprising a primary or secondary amine is added to the N- or C-terminus of a compstatin analog. In some embodiments, the linker comprises an alkyl chain and/or an oligo(ethylene glycol) moiety. For example, $NH_2(CH_2CH_2O)_nCH_2C(=O)OH$ (e.g., 8-amino-3,6-dioxaoctanoic acid (AEEAc) or 11-amino-3,6,9-trioxaundecanoic acid) or an NHS ester thereof (e.g., an NHS ester of 8-amino-3,6-dioxaoctanoic acid or 11-amino-3,6,9-trioxaundecanoic acid), can be used. In some embodiments, the resulting compound is as follows (wherein the portion contributed by the linker is shown in bold):

$NH_2(CH_2)_5C(=O)$—Ile-Cys-Val-(1Me)Trp-Gln-Asp-
Trp-Gly-Ala-His-Arg-Cys-Thr-NH$_2$ (SEQ ID NO: 45).

$NH_2(CH_2CH_2O)_2CH_2C(=O)$—Ile-Cys-Val-(1Me)
Trp-Gln-Asp-Trp-Gly-Ala-His-Arg-Cys-Thr-
NH$_2$ (SEQ ID NO: 46)

In some embodiments, a Lys residue is attached to the N- or C-terminus of SEQ ID NO: 42 via a linker comprising a non-peptide portion. For example, the linker can comprise an alkyl chain, oligo(ethylene glycol) chain, and/or cyclic ring system. In some embodiments, 8-AEEAc or an NHS ester thereof is used, resulting (in the case of attachment of Lys at the C-terminus) in the following compound (wherein the portion contributed by 8-AEEAc is shown in bold):

Ac-Ile-Cys*-Val-(1Me)Trp-Gln-Asp-Trp-Gly-Ala-
His-Arg-Cys*-Thr-NH—
$CH_2CH_2OCH_2CH_2OCH_2$—C(=O)-Lys-NH$_2$ (SEQ ID NO: 47)

It will be appreciated that in SEQ ID NOs: 45 and 46, a —C(=O) moiety is attached to the adjacent Ile residue via a C—N bond, wherein the N is part of the amino acid and is not shown. Similarly, in SEQ ID NO: 47, a —C(=O) moiety is attached to the adjacent Lys residue via a C—N bond, wherein the N is part of the amino acid and is not shown. It will also be appreciated that that in SEQ ID NO: 47 the NH moiety is attached to the immediately N-terminal amino acid (Thr), via a C—N bond, wherein the C is the carbonyl carbon of the amino acid and is not shown.

The compounds of SEQ ID NOs: 43-47 can be modified at the primary amine group to produce a long-acting compstatin analog.

Exemplary long-acting compstatin analogs are set forth below, wherein n is sufficient to provide an average molecular weight of between about 500; 1,000; 1,500; 2,000; 5,000; 10,000; 20,000; 30,000; 40,000; 50,000; 60,000; 70,000; 80,000; 90,000; and 100,000 daltons.

(SEQ ID NO: 48)
(CH$_2$CH$_2$O)$_n$C(=O)-Ilc-Cys-Val-(1Me)Trp-Gln-Asp-Trp-
Gly-Ala-His-Arg-Cys-Thr-NH$_2$)

(SEQ ID NO: 49)
Ac-Ile-Cys*-Val-(1Me)Trp-Gln-Asp-Trp-Gly-Ala-His-
Arg-Cys*-Thr-NH—CH$_2$CH$_2$OCH$_2$CH$_2$OCH$_2$—C(=O)-Lys-
C(=O)-(CH$_2$CH$_2$O)n-NH$_2$ (SEQ ID NO: 50)
Ac-Ile-Cys*-Val-(1Me)Trp-Gln-Asp-Trp-Gly-Ala-His-
Arg-Cys*-Thr-Lys-C(=O)-(CH$_2$CH$_2$O)n-NH$_2$.

(SEQ ID NO: 51)
Ac-Ile-Cys*-Val-(1Me)Trp-Gln-Asp-Trp-Gly-Ala-His-
Arg-Cys*-Thr-(Gly)$_5$-Lys-C(=O)-(CH$_2$CH$_2$O)n-NH$_2$ (SEQ ID NO: 52)
Ac-(CH$_2$CH$_2$O)nC(=O)Lys-(Gly)5-Ile-Cys*-Val-(1Me)Trp-
Gln-Asp-Trp-Gly-Ala-His-Arg-Cys*-Thr-NH$_2$)

(SEQ ID NO: 53)
Ac-(CH$_2$CH$_2$O)nC(=O)Lys-Ile-Cys*-Val-(1Me)Trp-Gln-
Asp-Trp-Gly-Ala-His-Arg-Cys*-Thr-NH$_2$)

In SEQ ID NO: 48, the (CH$_2$CH$_2$O)n is coupled via an amide bond to the N-terminal amino acid. In SEQ ID NOs: 49-53, the (CH$_2$CH$_2$O)n moiety is coupled via an amide bond to a Lys side chain; thus it will be understood that the NH$_2$ at the C-terminus in SEQ ID NOs: 49, 50, and 51, represents amidation of the C-terminus of the peptide, and it will be understood that in SEQ ID NOs: 52 and 53, the Ac at the N-terminus represents acetylation of the N-terminus of the peptide, as described above. It will also be appreciated by those of ordinary skill in the art that a free end of a (CH$_2$CH$_2$O)$_n$ moiety typically terminates with an (DR) where the underlined O represents the O atom in the terminal (CH$_2$CH$_2$O) group. (OR) is often a moiety such as a hydroxyl (OH) or methoxy (—OCH$_3$) group though other groups (e.g., other alkoxy groups) could be used. Thus SEQ ID NO: 49, for example, may be represented as Ac-Ile-Cys*-Val-(1Me)Trp-Gln-Asp-Trp-Gly-Ala-His-Arg-Cys*-Thr-NH—CH$_2$CH$_2$OCH$_2$CH$_2$OCH$_2$—C(=O)-Lys-(C(=O)—(CH$_2$CH$_2$O)$_n$—R)—NH$_2$ (SEQ ID NO: 54) wherein R is, e.g., either H or CH$_3$ in the case of a linear PEG. In the case of a bifunctional, branched or star-shaped PEG, R represents the remainder of the molecule. Further, it will be understood that the moiety comprising the reactive functional group may vary, as described herein (e.g., according to any of the formulas described herein). For example, long-acting compstatin analogs comprising the same peptide sequence as SEQ ID NO: 54, in which the moiety comprising the reactive functional group comprises an ester and/or alkyl chain may be represented as follows (SEQ ID NO: 55)
Ac-Ile-Cys*-Val-(1Me)Trp-Gln-Asp-Trp-Gly-Ala-His-
Arg-Cys*-Thr-NH—CH$_2$CH$_2$OCH$_2$CH$_2$OCH$_2$—C(=O)-Lys-
(C(=O)—(CH2)$_m$—(CH$_2$CH$_2$O)$_n$-R)—NH2;

(SEQ ID NO: 56)
Ac-Ile-Cys*-Val-(1Me)Trp-Gln-Asp-Trp-Gly-Ala-His-
Arg-Cys*-Thr-NH—CH$_2$CH$_2$OCH$_2$CH$_2$OCH$_2$—C(=O)-Lys-
(C(=O)—(CH$_2$)$_m$—C(=O)—(CH$_2$CH$_2$O)$_n$-R)—NH2

(SEQ ID NO: 57)
Ac-Ile-Cys*-Val-(1Me)Trp-Gln-Asp-Trp-Gly-Ala-His-
Arg-Cys*-Thr-NH—CH$_2$CH$_2$OCH$_2$CH$_2$OCH$_2$—C(=O)-Lys-
(C(=O)—(CH$_2$)$_m$—C(=O)—(CH$_2$)j(CH$_2$CH$_2$O)$_n$-R)—NH2

In SEQ ID NOs: 55-57 m may range from 1 up to about 2, 3, 4, 5, 6, 7, 8, 10, 15, 20, or 30 in various embodiments, In SEQ ID NOs: 57 j may range from 1 up to about 2, 3, 4, 5, 6, 7, 8, 10, 15, 20, or 30 in various embodiments. It will also be appreciated that, as described herein, in various embodiments other moieties may be incorporated between the Lys-(C(=O)— and (CH$_2$CH$_2$O)$_n$—R, such as an amide, aromatic ring (e.g., a substituted or unsubstituted phenyl), or a substituted or unsubstituted cycloalkyl structure.

In some embodiments a long-acting compstatin analog comprises a variant of SEQ ID NOs: 48-57 in which -Ile-Cys*-Val-(1Me)Trp-Gln-Asp-Trp-Gly-Ala-His-Arg-Cys*-Thr- (SEQ ID NO: 108) is replaced by an amino acid sequence comprising the amino acid sequence of any other compstatin analog, e.g., of any of SEQ ID NOs 3-27 or 29-41, with the proviso that blocking moiet(ies) present at the N- and/or C-termini of a compstatin analog may be absent, replaced by a linker (which may comprise a blocking moiety), or attached to a different N- or C-terminal amino acid present in the corresponding variant(s).

Any compstatin analog, e.g., any compound comprising any of SEQ ID NOs: 3-41 may be attached via its N-terminus or C-terminus directly or indirectly to any moiety comprising a reactive functional group, e.g., any of Formulas I-XVI or Compound I-III, in various embodiments.

In some embodiments a CRM comprises a polypeptide that occurs in human serum, or a fragment thereof or a substantially similar variant of the polypeptide or fragment thereof. In some embodiments the polypeptide, fragment, or variant has a molecular weight of between 5 kD and 150 kD, e.g., at least 5, 10, 20, 30, 40, 50, 60, 70, 80, 90, 100 kd, or more, e.g., between 100 and 120, or 120 and 150 kD. In some embodiments, producing a long-acting compstatin analog comprises reacting a compstatin analog comprising a reactive functional group with one or more amino acid side chains of the polypeptide, wherein the side chain comprises a compatible functional group. In some embodiments, producing a long-acting compstatin analog comprises reacting a compstatin analog comprising a reactive functional group with the N-terminal amine and/or C-terminal carboxyl group of the polypeptide. In some embodiments, producing a long-acting compstatin analog comprises reacting a compstatin analog comprising an amine-reactive functional group with amino acids having a side chain comprising a primary amine (e.g., lysine) and/or with the N-terminal amine of the polypeptide. In some embodiments, producing a long-acting compstatin analog comprises reacting a compstatin analog comprising a carboxyl-reactive functional group with the C-terminal carboxyl group of the polypeptide. In some embodiments a compstatin analog moiety is attached at each terminus of the polypeptide and, optionally, to the side chain of one or more internal amino acids. In some embodiments, producing a long-acting compstatin analog comprises reacting a compstatin analog comprising a sulfhydryl-reactive functional group with one or more sulfhydryl groups of the polypeptide.

In some embodiments, at least one reactive functional group is introduced into the polypeptide. For example, in some embodiments at least one side chain of the polypeptide is modified to convert a first reactive functional group to a different reactive functional group prior to reaction with the compstatin analog. In some embodiments a thiol is introduced. Several methods are available for introducing thiols into biomolecules, including the reduction of intrinsic disulfides, as well as the conversion of amine, aldehyde or carboxylic acid groups to thiol groups. Disulfide crosslinks of cystines in proteins can be reduced to cysteine residues by dithiothreitol (DTT), tris-(2-carboxyethyl)phosphine (TCEP), or or tris-(2-cyanoethyl)phosphine. Amines can be indirectly thiolated by reaction with succinimidyl 3-(2-pyridyldithio)propionate (SPDP) followed by reduction of the 3-(2-pyridyldithio)propionyl conjugate with DTT or TCEP. Amines can be indirectly thiolated by reaction with succinimidyl acetylthioacetate followed by removal of the acetyl group with 50 mM hydroxylamine or hydrazine at near-neutral pH. Amines can be directly thiolated by reaction with 2-iminothiolane, which preserve the overall charge of the molecule and introduces a free thiol. Tryptophan residues in thiol-free proteins can be oxidized to mercaptotryptophan residues, which can then be modified by iodoacetamides or maleimides. A polypeptide comprising one or more thiols may be reacted with a compstatin analog comprising a maleimide group, such as Ac-Ile-Cys*-Val-Trp(1-Me)-Gln-Asp-Trp-Gly-Ala-His-Arg-Cys*-Thr-AEEAc-Lys-(C(=O)—(CH$_2$)$_5$-Mal)-NH$_2$ (SEQ ID NO: 58) to generate a long-acting compstatin analog.

In some embodiments the polypeptide is recombinantly produced. In some embodiments the polypeptide is at least in part recombinantly produced (e.g., in bacteria or in eukaryotic host cells such as fungal, insect, plant, or vertebrate) and/or at least in part produced using chemical synthesis. In some embodiments the polypeptide is purified. In some embodiments the polypeptide is glycosylated. In some embodiments the polypeptide is non-glycosylated. In some embodiments the polypeptide is human serum albumin (HSA). In some embodiments a substantially similar variant of the polypeptide is sufficiently similar to the polypeptide of which it is a variant so as to not be recognized as foreign by a normal immune system of a subject, e.g., a human subject. In some embodiments alterations in the sequence of substantially similar variant as compared with the polypeptide of which it is a variant are selected so as to avoid generating MHC Class I epitopes. Various methods known in the art can be used to predict whether a sequence comprises an MHC Class I epitope.

The structure of compstatin is known in the art, and NMR structures for a number of compstatin analogs having higher activity than compstatin are also known (Malik, supra). Structural information may be used to design compstatin mimetics. In some embodiments, a compstatin mimetic is any compound that competes with compstatin or any compstatin analog (e.g., a compstatin analog whose sequence is set forth in Table 2) for binding to C3 or a fragment thereof (such as a 40 kD fragment of the β chain to which compstatin binds). In some embodiments, the compstatin mimetic has an activity equal to or greater than that of compstatin. In some embodiments, the compstatin mimetic is more stable, orally available, or has a better bioavailability than compstatin. The compstatin mimetic may be a peptide, nucleic acid, or small molecule. In certain embodiments the compstatin mimetic is a compound that binds to the binding site of compstatin as determined in a compstatin-C3 structure, e.g., a crystal structure or a 3-D structure derived from NMR experiments. In certain embodiments the compstatin mimetic is a compound that could substitute for compstatin in a compstatin-C3 structure and would form substantially the same intermolecular contacts with C3 as compstatin. In certain embodiments the compstatin mimetic is a compound that binds to the binding site of a peptide having a sequence set forth in Table 2, e.g., SEQ ID NO: 14, 21, 28, 29, 32, 33, 34, or 36 or other compstatin analog sequence or in certain embodiments SEQ ID NO: 30 or 31, in a peptide-C3 structure. In certain embodiments the compstatin mimetic is a compound that could substitute for a peptide having a sequence set forth in Table 2, e.g., SEQ ID NO: 14, 21, 28, 29, 32, 33, 34, or 36 or other compstatin analog sequence or in certain embodiments SEQ ID NO: 30 or 31, in a peptide-C3 structure and would form substantially the same intermolecular contacts with C3 as the peptide. In certain embodiments the compstatin mimetic has a non-peptide backbone but has side chains arranged in a sequence designed based on the sequence of compstatin.

One of skill in the art will appreciate that once a particular desired conformation of a short peptide has been ascertained, methods for designing a peptide or peptidomimetic to fit that conformation are well known. See, e.g., G. R. Marshall (1993), Tetrahedron, 49: 3547-3558; Hruby and Nikiforovich (1991), in Molecular Conformation and Biological Interactions, P. Balaram & S. Ramasehan, eds., Indian Acad. of Sci., Bangalore, P P. 429-455), Eguchi M, Kahn M., Mini Rev Med Chem., 2(5):447-62, 2002. In some embodiments the design of peptide analogs may be further refined by considering the contribution of various side chains of amino acid residues, e.g., for the effect of functional groups or for steric considerations as described in the art for compstatin and analogs thereof, among others.

It will be appreciated by those of skill in the art that a peptide mimic may serve equally well as a peptide for the purpose of providing the specific backbone conformation and side chain functionalities required for binding to C3 and inhibiting complement activation. Accordingly, it is contemplated as being within the scope of the present invention to produce and utilize C3-binding, complement-inhibiting compounds through the use of either naturally-occurring amino acids, amino acid derivatives, analogs or non-amino acid molecules capable of being joined to form the appropriate backbone conformation. A non-peptide analog, or an analog comprising peptide and non-peptide components, is sometimes referred to herein as a "peptidomimetic" or "isosteric mimetic," to designate substitutions or derivations of a peptide that possesses much the same backbone conformational features and/or other functionalities, so as to be sufficiently similar to the exemplified peptides to inhibit complement activation. More generally, a compstatin mimetic is any compound that would position pharmacophores similarly to their positioning in compstatin, even if the backbone differs.

The use of peptidomimetics for the development of high-affinity peptide analogs is well known in the art. Assuming rotational constraints similar to those of amino acid residues within a peptide, analogs comprising non-amino acid moieties may be analyzed, and their conformational motifs verified, by means of the Ramachandran plot (Hruby & Nikiforovich 1991), among other known techniques.

One of skill in the art will readily be able to establish suitable screening assays to identify additional compstatin mimetics and to select those having desired inhibitory activities. For example, compstatin or an analog thereof could be labeled (e.g., with a radioactive or fluorescent label) and contacted with C3 in the presence of different concentrations of a test compound. The ability of the test compound to diminish binding of the compstatin analog to C3 is evaluated. A test compound that significantly diminishes binding of the compstatin analog to C3 is a candidate compstatin mimetic. For example, a test compound that diminishes steady-state concentration of a compstatin analog-C3 complex, or that diminishes the rate of formation of a compstatin analog-C3 complex by at least 25%, or by at least 50%, is a candidate compstatin mimetic. One of skill in the art will recognize that a number of variations of this screening assay may be employed. Compounds to be screened include natural products, libraries of aptamers, phage display libraries, compound libraries synthesized using combinatorial chemistry, etc. The invention encompasses synthesizing a combinatorial library of compounds based upon the core sequence described above and screening the library to identify compstatin mimetics. Any of these methods could also be used to identify new compstatin analogs having higher inhibitory activity than compstatin analogs tested thus far.

Other Compounds that Inhibit C3 Activation or Activity

Other compounds, e.g., polypeptides, small molecules, monoclonal antibodies, aptamers, etc., that bind to C3 or C3a receptors (C3aR) are of use in certain embodiments of the invention. In certain embodiments the complement inhibitor comprises an Efb protein from *Staphylococcus aureus* or a variant or derivative or mimetic thereof that can bind to C3 and inhibit its activation and/or bind to and inhibit C3b. Exemplary agents are described in PCT Application Pub. WO/2004/094600. In certain embodiments the complement inhibitor comprises a *Staphylococcus* complement inhibitor (SCIN) protein from *Staphylococcus aureus* or a variant or derivative or mimetic of such protein that can bind to C3 convertase and inhibit its activation and/or bind to and inhibit C3b. Aptamers that bind to and inhibit C3 may be identified using methods such as SELEX. U.S. Pat. Pub. No. 20030191084 discloses aptamers that bind to C1q, C3 and C5.

In some embodiments, a protease that degrades C3 may be used as a complement inhibitor. For example, U.S. Pat. No. 6,676,943 discloses human complement C3-degrading protein from *Streptococcus pneumoniae*. Such proteins, or variants thereof, may be used in certain embodiments of the invention.

U.S. Pat. No. 5,942,405, PCT/IB2006/002557 (WO/2007/034277—ARYL SUBSTITUTED IMIDAZO [4,5-C] PYRIDINE COMPOUNDS AS C3A RECEPTOR ANTAGONISTS); PCT/IB2006/002568 (WO/2007/034282-DIARYL-IMIDAZOLE COMPOUNDS CONDENSED WITH A HETEROCYCLE AS C3A RECEPTOR ANTAGONISTS) PCT/IB2006/002561 (WO2007034278—FUSED IMIDAZOLE DERIVATIVES AS C3A RECEPTOR ANTAGONISTS) PCT/US2007/026237 (WO2008079371) MODULATORS OF C3A RECEPTOR AND METHODS OF USE THEREOF disclose exemplary C3aR antagonists. In some embodiments, an RNAi agent that inhibits expression of C3 or C3aR may be used.

Compounds that Inhibit Factor B Activation or Activity

In certain embodiments a complement inhibitor inhibits activation or activity of factor B. For example, the complement inhibitor may bind to factor B and, e.g., inhibit activation of factor B. Exemplary agents that inhibit activation or activity of factor B include, e.g., antibodies, antibody fragments, peptides, small molecules, and aptamers. Exemplary antibodies that inhibit factor B are described in U.S. Pat. Pub. No. 20050260198. In certain embodiments an antibody or antigen-binding fragment selectively binds to factor B within the third short consensus repeat (SCR) domain. In certain embodiments the antibody prevents formation of a C3bBb complex. In certain embodiments the antibody or antigen-binding fragment prevents or inhibits cleavage of factor B by factor D. In some embodiments, an antibody binds to the Bb portion of factor B. PCT/US2008/074489 (WO/2009/029669) discloses exemplary antibodies, e.g., the antibody produced by the hybridoma clone deposited under ATCC Accession Number PTA-8543. In some embodiments, a humanized version of said antibody is used, which may be an antibody fragment. In certain embodiments a complement inhibitor, e.g., antibody, small molecule, aptamer, polypeptide, or peptide, binds to substantially the same binding site on factor B as an antibody described in U.S. Pat. Pub. No. 20050260198 or WO/2009/029669. In some embodiments, the complement inhibitor comprises the monoclonal antibody fragment known as TA106 (formerly under development by Taligen Therapeutics), or antibody, small molecule, aptamer, polypeptide, or peptide, binds to substantially the same binding site on factor B as TA106 is used. In some embodiments, a peptide that binds to and inhibits factor B is identified using, for example, a method such as phage display. In some embodiments, a complement inhibitor comprises an aptamer that binds to and inhibits factor B. In some embodiments, an RNAi agent that inhibits expression of factor B may be used.

Compounds that Inhibit Factor D Activity

In certain embodiments the complement inhibitor inhibits factor D. For example, the complement inhibitor may bind to factor D. Exemplary agents include antibodies, antibody fragments, peptides, small molecules, and aptamers. Exemplary antibodies that inhibit factor D are described in U.S. Pat. No. 7,112,327. In certain embodiments the complement inhibitor is an antibody, small molecule, aptamer, or polypeptide that binds to substantially the same binding site on factor D as an antibody described in U.S. Pat. No. 7,112,327. FCFD4514S (formerly under development by Tanox as TNX-234), is a humanized monoclonal antibody fragment that binds Factor D. In certain embodiments the complement inhibitor comprises FCFD4514S or an antibody, small molecule, aptamer, or polypeptide that binds to substantially the same binding site on factor D as FCFD4514S. Exemplary polypeptides that inhibit alternative pathway activation and are believed to inhibit factor D are disclosed in U.S. Pub. No. 20040038869. Use of peptides that bind to and inhibit factor D, which may be identified using methods such as phage display, is within the scope of the invention. Use of aptamers that bind to and inhibit factor D, which may be identified using methods such as SELEX, is within the scope of the invention. In some embodiments, an RNAi agent that inhibits expression of factor D may be used.

Mammalian Complement Regulatory Proteins and Complement Receptors

In some embodiments the complement inhibitor comprises at least a portion of a mammalian, e.g., human, complement regulatory protein or complement receptor. Examples of complement regulatory proteins include, e.g., CFH, CFH related proteins (such as CFHR1), CFI, CR1, DAF, MCP, CD59, C4 bp, and complement receptor 2 inhibitor trispanning (CRIT; Inal, J., et al, J Immunol., 174(1):356-66, 2005). In some embodiments the complement regulatory polypeptide is one that is normally membrane-bound in its naturally occurring state. In some embodiments of the invention a fragment of such polypeptide that lacks some or all of a transmembrane and/or intracellular domain is used. Soluble forms of complement receptor 1 (sCR1), or soluble portions of other complement receptors, for example, are of use in certain embodiments. For example the compounds known as TP10 or TP20 (Avant Therapeutics) can be used. In some embodiments a soluble complement control protein, e.g., CFH or a CFH related protein, is used. In some embodiments the complement inhibitor is a C3b/C4b Complement Receptor-like molecule such as those described in U.S. Pat. Pub. No. 20020192758. Variants and fragments of mammalian complement regulatory proteins or receptors that retain complement inhibiting activity can be used in certain embodiments.

Chimeric Complement Inhibitors

In certain embodiments of the invention the complement inhibitor comprises a chimeric polypeptide comprising a first polypeptide that inhibits complement activation, linked, e.g., covalently linked, to a second polypeptide that inhibits complement activation and/or that binds to a complement component or complement activation product. In some embodiments, at least one of the polypeptides comprises at least a portion of a mammalian complement regulatory protein. The chimeric polypeptide may contain one or more additional domains located, e.g., between the first and second polypeptides or at a terminus. For example, the first and second polypeptides can be separated by a spacer polypeptide.

In some embodiments, the first and second polypeptides each comprise at least a portion of a mammalian complement regulatory protein. In some embodiments complement inhibitor comprises at least a portion of DAF and at least a portion of MCP. Exemplary chimeric polypeptides are disclosed, e.g., in U.S. Pat. No. 5,679,546, e.g., CAB-2 (also known as MLN-2222). In some embodiments the polypeptide comprises at least 4 SCR domains of at least one mammalian complement regulatory protein or complement receptor. In some embodiments the polypeptide comprises at least 4 SCR domains of each of first and second distinct mammalian complement regulatory proteins.

In some embodiments, a chimeric polypeptide comprises at least a portion of complement receptor 1 (CR1), complement receptor 2 (CR2), complement receptor 3 (CR3), complement receptor 4 (CR4) or a variant or fragment of CR1, CR2, CR3, or CR4 that binds to one or more complement components or complement activation products such as C3b, iC3b, C3d, and/or C3dg. In some embodiments, the polypeptide comprises at least 4 SCRs, e.g., at least 4 SCRs of CR1 or CR2. For example, the polypeptide can comprise the 4 N-terminal SCRs of CR2 (e.g., residues 1-250 of the mature protein). In some embodiments the chimeric polypeptide comprises at least 4 SCR domains of a mammalian complement regulatory protein and at least 4 SCR domains of a mammalian complement receptor.

Compounds that Inhibit Properdin

In some embodiments of the invention antiproperdin antibodies, antibody fragment, or other anti-properdin agents are used. See, e.g., U.S. Pat. Pub. No. 20030198636 or PCT/US2008/068530 (WO/2009/110918—ANTI-PROPERDIN ANTIBODIES) for examples.

Compounds that Inhibit Components of Lectin Pathway

In some embodiments the compounds inhibit one or more components of the lectin pathway. See, e.g., WO/2007/117996) METHODS FOR TREATING CONDITIONS ASSOCIATED WITH MASP-2 DEPENDENT COMPLEMENT ACTIVATION.

Compounds that Inhibit C5 Activation or Activity

In certain embodiments the complement inhibitor inhibits activation of C5. For example, the complement inhibitor may bind to C5 and inhibit its cleavage. In some embodiments, the complement inhibitor inhibits physical interaction of C5 with C5 convertase by, e.g., binding to C5 or C5 convertase or to C5 at a site that would ordinarily participate in such physical interaction. Exemplary agents that inhibit C5 activation include antibodies, antibody fragments, polypeptides, small molecules, and aptamers. Exemplary compounds, e.g., antibodies, that bind to C5 are described, for example, in U.S. Pat. No. 6,534,058; PCT/US95/05688 (WO 1995/029697), PCT/EP2010/007197 (WO2011063980); U.S. Pat. Pub. No. 20050090448; and U.S. Pat. Pub. No. 20060115476. U.S. Pat. Pub. No. 20060105980 discloses aptamers that bind to and inhibit C5. In some embodiments, a humanized anti-C5 monoclonal antibody, e.g., eculizumab (also known as h5G1.1-mAb; Soliris®) (Alexion), or a fragment or derivative thereof that binds to C5. In some embodiments, an antibody comprising at least some of the same complementarity determining regions (CDR1, CDR2 and/or CDR3), e.g., all of CDR1, CDR2, and CDR3, as those of eculizumab's heavy chain and/or light chain is used. In some embodiments, the antibody comprises at least some of the same framework regions as eculizumab. In some embodiments, an antibody that binds to substantially the same binding site on C5 as eculizumab is used. In some embodiments, pexelizumab (also known as h5G1.1-scFv), a humanized, recombinant, single-chain antibody derived from h5G1.1-mAb, is used. In certain embodiments the complement inhibitor comprises a *Staphylococcus* SSL7 protein from *Staphylococcus aureus* or a variant or derivative or mimetic of such protein that can bind to C5 and inhibit its cleavage.

As noted above, bispecific or multispecific antibodies can be used. For example, PCT/US2010/039448 (WO/2010/151526) discloses bispecific antibodies described as binding to two or more different proteins, wherein at least two of the proteins are selected from C5a, C5b, a cellular receptor for C5a (e.g., C5aR1 or C5L2), the C5b-9 complex, and a component or intermediate of terminal complement such as C5b-6, C5b-7, or C5b-8. In some embodiments an RNAi agent that inhibits expression of C5 or C5aR may be used.

In some embodiments, a complement inhibitor known as OmCI, or a variant, derivative, or mimetic thereof, is used. OmCI binds to C5 and inhibits its activation most likely by inhibiting interaction with convertase. OmCI is naturally produced by the tick *Ornithodoros moubata*. See, e.g., PCT/GB2004/002341 (WO/2004/106369) and PCT/GB2010/000213 (WO/2010/100396), for description of OmCI and certain variants thereof. It has been shown that OmCI binds to eicosanoids, in particular leukotriene (LKs), e.g., LTB4. In some embodiments, an OmCI polypeptide (or a variant, derivative, or fragment thereof) that retains the capacity to binds to a LK, e.g., LTB4, is used. In some embodiments, an OmCI polypeptide (or a variant, derivative, or fragment thereof) that has reduced capacity or substantially lacks capacity to bind to a LK, e.g., LTB4, is used.

In some embodiments the agent is an antagonist of a C5a receptor (C5aR). In some embodiments, the C5aR antagonist comprises a peptide. Exemplary C5a receptor antagonists include a variety of small cyclic or acyclic peptides such as those described in March, D R, et al., Mol. Pharmacol., 65(4), 2004, and in Woodruff, T M, et al., J Pharmacol Exp Ther., 314(2):811-7, 2005, U.S. Pat. No. 6,821, 950; U.S. Ser. No. 11/375,587; and/or PCT/US06/08960 (WO2006/099330), or a mimetic thereof. In certain embodiments the complement inhibitor binds to C5aR and inhibits binding of C5a thereto. In certain embodiments a cyclic peptide comprising the sequence [OPdChaWR] (SEQ ID NO: 59) is used. In certain embodiments a cyclic peptide comprising the sequence [KPdChaWR] (SEQ ID NO: 60) is used. In certain embodiments a peptide comprising the sequence $(Xaa)_n$[OPdChaWR] (SEQ ID NO: 61) is used, wherein Xaa is an amino acid residue and n is between 1 and 5. In certain embodiments a peptide comprising the sequence $(Xaa)_n$[KPdChaWR] (SEQ ID NO: 62) is used, wherein Xaa is an amino acid residue and n is between 1 and 5. In certain embodiments n is 1. In certain embodiments n is 1 and Xaa is a standard or nonstandard aromatic amino acid. For example, the peptides F—[OPdChaWR] (SEQ ID NO: 63), F—[KPdChaWR] (SEQ ID NO: 64); Cin-[OPdChaWR] (SEQ ID NO: 65), and HCin-[OPdChaWR] (SEQ ID NO: 66) are of use in certain embodiments. Optionally the free terminus comprises a blocking moiety, e.g., the terminal amino acid is acetylated. For example, in some embodiments the C5aR antagonist is AcF—[OPdChaWR] (SEQ ID NO: 67) (also known as PMX-53). (Abbreviations: 0: ornithine; Cha: cyclohexylalanine; Cin: cinnamoyl; Hcin: hydrocinnamoyl; square brackets denote internal peptide bond). In some embodiments, a C5aR antagonist comprises a compound, e.g., a peptide, disclosed in U.S. Pat. Pub. No. 20060183883 (Ser. No. 10/564,788), e.g., a compound as represented therein by formula I, formula II, formula IV, formula V, or formula VI. An exemplary C5aR antagonist is the peptide known as JPE-1375 (Jerini AG, Germany).

In some embodiments, a C5aR antagonist is a small molecule. Various small molecule C5aR antagonists are disclosed in the following references: PCT/US2005/015897 (WO/2005/110416; 4,5-DISUBSTITUTED-2-ARYL PYRIMIDINES); PCT/EP2006/005141 (WO2006128670); PCT/US2008/072902 (WO/2009/023669; SUBSTITUTED 5,6,7,8-TETRAHYDROQUINOLINE DERIVATIVES); PCT/US2009/068941 (WO/2010/075257; C5AR ANTAGONISTS). An exemplary small molecule C5aR antagonist is CCX168 (ChemoCentryx, Mountain View, Calif.).

In certain embodiments the complement inhibitor is an agent, e.g., an antibody, small molecule, aptamer, or polypeptide, that binds to substantially the same binding site on C5 or C5aR as a compound described in any of the aforementioned references disclosing agents that bind to C5 or C5aR. In some embodiments the complement inhibitor is not an antagonist of a C5a receptor.

Multimodal Complement Inhibitors

In certain embodiments of the invention the complement inhibitor binds to more than one complement protein and/or inhibits more than one step in a complement activation pathway. Such complement inhibitors are referred to herein as "multimodal". In certain embodiments of the invention the complement inhibitor comprises a virus complement control protein (VCCP). The invention contemplates use of any of the agents described in U.S. Ser. No. 11/247,886 and PCT/US2005/36547. Poxviruses and herpesviruses are families of large, complex viruses with a linear double-stranded DNA genome. Certain of these viruses encode immunomodulatory proteins that are believed to play a role in pathogenesis by subverting one or more aspects of the normal immune response and/or fostering development of a more favorable environment in the host organism (Kotwal, G J, *Immunology Today*, 21(5), 242-248, 2000). Among these are VCCPs. Poxvirus complement control proteins are members of the complement control protein (CCP) superfamily and typically contain 4 SCR modules. In certain embodiments the VCCP is a poxvirus complement control protein (PVCCP). The PVCCP can comprise a sequence encoded by, e.g., vaccinia virus, variola major virus, variola minor virus, cowpox virus, monkeypox virus, ectromelia virus, rabbitpox virus, myxoma virus, Yaba-like disease virus, or swinepox virus. In other embodiments the VCCP is a herpesvirus complement control protein (HVCCP). The HVCCP can comprise a sequence encoded by a *Macaca fuscata* rhadinovirus, cercopithecine herpesvirus 17, or human herpes virus 8. In other embodiments the HVCCP comprises a sequence encoded by herpes simplex virus *Saimiri* ORF 4 or ORF 15 (Albrecht, J C. & Fleckenstein, B., *J. Virol.*, 66, 3937-3940, 1992; Albrecht, J., et al., *Virology*, 190, 527-530, 1992).

The VCCP may inhibit the classical complement pathway, the alternate complement pathway, the lectin pathway, or any two or more of these. In certain embodiments of the invention the VCCP, e.g., a PVCCP, binds to C3b, C4b, or both. In certain embodiments of the invention the PVCCP comprises one or more putative heparin binding sites (K/R—X—K/R) and/or possesses an overall positive charge. In some embodiments the PVCCP comprises at least 3 SCR modules (e.g., modules 1-3), e.g., 4 SCR modules. The PVCCP protein can be a precursor of a mature PVCCP (i.e., can include a signal sequence that is normally cleaved off when the protein is expressed in virus-infected cells) or can be a mature form (i.e., lacking the signal sequence).

Vaccinia complement control protein (VCP) is a virus-encoded protein secreted from vaccinia infected cells. VCP is 244 amino acids in length, contains 4 SCRs, and is naturally produced by intracellular cleavage of a 263 amino acid precursor. VCP runs as an ~35 kD protein in a 12% SDS/polyacrylamide gel under reducing conditions and has a predicted molecular mass of about 28.6 kD. VCP is described in U.S. Pat. Nos. 5,157,110 and 6,140,472, and in Kotwal, G K, et al., *Nature*, 355, 176-178, 1988. FIGS. 3A and 3B of U.S. Ser. No. 11/247,886 and PCT/US2005/36547 (WO2006042252) show the sequence of the precursor and mature VCP proteins, respectively. VCP has been shown to inhibit the classical pathway of complement activation via its ability to bind to C3 and C4 and act as a cofactor for factor I mediated cleavage of these components as well as promoting decay of existing convertase (Kotwal, G K, et al., *Science*, 250, 827-830, 1990; McKenzie et al., *J. Infect. Dis.*, 1566, 1245-1250, 1992). It has also been shown to inhibit the alternative pathway by causing cleavage of C3b into iC3b and thereby preventing the formation of the alternative pathway C3 convertase (Sahu, A, et al., *J. Immunol.*, 160, 5596-5604, 1998). VCP thus blocks complement activation at multiple steps and reduces levels of the proinflammatory chemotactic factors C3a, C4a, and C5a.

VCP also possesses the ability to strongly bind heparin in addition to heparan sulfate proteoglycans. VCP contains two putative heparin binding sites located in modules 1 and 4 (Jha, P and Kotwal, G J, and references therein). VCP is able to bind to the surface of endothelial cells, possibly via interaction with heparin and/or heparan sulfate at the cell surface, resulting in decreased antibody binding (Smith, S A, et al., *J. Virol.*, 74(12), 5659-5666, 2000). VCP can be taken up by mast cells and possibly persist in tissue for lengthy periods of time, thereby potentially prolonging its activity (Kotwal, G J, et al., In GP. Talwat, et al. (eds), 10$^{th}$ International Congress of Immunology., Monduzzi Editore, Bologna, Italy, 1998). In addition, VCP can reduce chemotactic migration of leukocytes by blocking chemokine binding (Reynolds, D, et al., in S. Jameel and L. Villareal (ed., Advances in animal virology. Oxford and IBN Publishing, New Delhi, India, 1999). VCP and other PVCCPs have a relatively small size relative to mammalian CCPs, which is advantageous for delivery in the present invention.

Variola virus major and minor encode proteins that are highly homologous to VCP and are referred to as smallpox inhibitor of complement enzymes (SPICE) (Rosengard, A M, et al., Proc. Natl. Acad. Sci., 99(13), 8803-8813. U.S. Pat. No. 6,551,595). SPICE from various variola strains sequenced to date differs from VCP by about 5% (e.g., about 11 amino acid differences). Similarly to VCP, SPICE binds to C3b and C4b and causes their degradation, acting as a cofactor for factor I. However, SPICE degrades C3b approximately 100 times as fast as VCP and degrades C4b approximately 6 times as fast as VCP. The amino acid sequence of SPICE is presented in FIG. 6 (SEQ ID NO: 12) and sequenced (Miller, C G, et al., Virology, 229, 126-133, 1997 and Uvarova, E A and Shchelkunov, S N, Virus Res., 81(1-2), 39-45, 2001). MCP differs from the other PVCCPs described herein in that it contains a truncation of the C-terminal portion of the fourth SCR.

It will be appreciated that the exact sequence of complement control proteins identified in different virus isolates may differ slightly. Such proteins fall within the scope of the present invention. Complement control proteins from any such isolate may be used, provided that the protein has not undergone a mutation that substantially abolishes its activity. Thus the sequence of a VCCP such as SPICE or VCP may differ from the exact sequences presented herein or under the accession numbers listed in Table 3. It will also be appreciated that a number of amino acid alterations, e.g., additions, deletions, or substitutions such as conservative amino acid substitutions, may be made in a typical polypeptide such as a VCCP without significantly affecting its activity, such that the resulting protein is considered equivalent to the original polypeptide. The viral polypeptides identified by accession number in Table 3 below are of use in various embodiments of the invention.

TABLE 3

Representative Viral Complement Control Proteins

| Virus | Protein | Accession | Virus Type |
|---|---|---|---|
| Variola | D12L | NP_042056 | Orthopoxvirus |
| | D15L (SPICE) | AAA69423 | Orthopoxvirus |
| Vaccinia | VCP | AAO89304 | Orthopoxvirus |
| Cowpox | CPXV034 | AAM13481 | Orthopoxvirus |
| | C17L | CAA64102 | Orthopoxvirus |
| Monkeypox | D14L | AAV84857 | Orthopoxvirus |
| Ectromelia virus | Complement control protein | CAE00484 | Orthopoxvirus |
| Rabbitpox | RPXV017 | AAS49730 | Orthopoxvirus |
| Macaca fuscata rhadinovirus | JM4 | AAS99981 | Rhadinavirus (Herpesvirus) |
| Cercopithecine herpesvirus 17 | Complement binding protein (ORF4) | NP_570746 | Herpesvirus |
| Human herpes virus 8 | Complement binding protein (ORF4) | AAB62602 | Herpesvirus | of U.S. Ser. No. 11/247,886 and PCT/US2005/36547 (WO2006042252) and can be described as follows. Referring to FIG. 6 of U.S. Ser. No. 11/247,886 and PCT/US2005/36547 (WO2006042252), a signal sequence extends from amino acid 1 to about amino acid 19. Four SCRs extend from about amino acid 20 to amino acid 263. Each SCR is characterized by four cysteine residues. The four cysteine residues form two disulfide bonds in the expressed protein. The boundaries of each SCR are best defined by the first and fourth cysteine residues in the sequence that forms the disulfide bonds of the SCR. An invariant tryptophan residue is present between cysteine 3 and cysteine 4 of each SCR. SCR1 extends from amino acid 20 or 21 to amino acid 81. Both residues are cysteines that may be involved in disulfide bonding. SCR2 extends from amino acid 86 to amino acid 143. SCR3 extends from amino acid 148 to amino acid 201. SCR4 extends from amino acid 206 to amino acid 261. The SCRs include the complement binding locations of SPICE. SPICE or any of the portions thereof that inhibit complement activation, e.g., SPICE and SPICE-related polypeptides containing four SCRs, such as those described in U.S. Pat. No. 6,551,595, are of use in the present invention.

Complement control proteins from cowpox virus (referred to as inflammation modulatory protein, IMP) and monkeypox virus (referred to herein as monkeypox virus complement control protein, MCP) have also been identified In addition to the VCCPs described above, a number of other viral proteins exist that interfere with one or more steps in a complement pathway. These proteins are also of use in certain embodiments of the present invention. Certain of these proteins do not necessarily display clear homology to cellular complement regulators known to date. For example, HSV-1, HSV-2, VZV, PRV, BHV-1, EHV-1, and EHV-4 all encode versions of a conserved glycoprotein known as gC (Schreurs, et al., J Virol., 62, 2251-2257, 1988; Mettenleiter, et al, J Virol., 64, 278-286; 1990; Herold, et al., J Virol., 65, 1090-1098; 1991). With the exception of VZV, the gC protein encoded by these viruses binds to C3b (Friedman, et al., Nature, 309, 633-634,1984; Huemer, et al., Virus Res., 23, 271-280, 1993) gC1 (from HSV-1) accelerates decay of the classical pathway C3 convertase and inhibits binding of properdin and C5 to C3. Purified EBV virions possess an activity that accelerates decay of the alternative pathway C3 convertase and serves as a cofactor for the complement regulatory protein factor 1 (Mold et al., J Exp Med, 168, 949-969, 1988). The foregoing proteins are referred to collectively as virus complement interfering proteins (VCIPs). By any of a variety of means, such as interfering with one or more steps of complement activation, accelerating decay of a complement component, and/or enhancing activity of a complement regulatory protein, these VCIPs are said to inhibit complement. Any of these proteins, or derivatives thereof, e.g., fragments or variants thereof, can be used as a therapeutic agent in the invention. As in the case of VCCPs, will be appreciated that the exact sequence of VCIPs identified in different virus isolates may differ slightly. Such proteins fall within the scope of the present invention.

In certain embodiments of the invention a fragment or variant of a VCCP or VCIP is locally administered to a subject. Preferred fragments and variants of a PVCCP possess at least one of the following activities: (i) ability to bind to C3, C3b, or both; (ii) ability to act as a cofactor for factor I cleavage of C3; (iii) ability to bind to C4, C4b, or both; (iv) ability to act as a cofactor for factor I cleavage of C4; (v) ability to accelerate decay of existing C3 convertase of the classical pathway, alternate pathway, or both; (vi) ability to bind heparin; (vii) ability to bind to heparan sulfate proteoglycans; (viii) ability to reduce chemotactic migration of leukocytes; (ix) ability to block chemokine (e.g, MIP-1α) binding, e.g., to the surface of a cell (e.g., a leukocyte or endothelial cell surface); (x) ability to inhibit antibody binding to class I MHC molecules; (xi) ability to inhibit the classical complement pathway; (xii) ability to inhibit the alternative complement pathway; and (xiii) ability to inhibit complement-mediated cell lysis. Preferred PVCCP fragments and variants display complement binding activity, by which is meant ability to detectably bind to one or more complement components, preferably (in the case of VCCPs) selected from the group consisting of: C3, C3b, C4, and C4b. Preferred fragments or variants of HVCCPs may also display ability to detectably bind to one or more complement components. Preferably the binding of the VCCP to the complement component is specific. It will be understood that a VCCP may be able to bind to only a single complement component or may be able to bind to more than one different complement component.

In certain embodiments of the invention the PVCCP fragment or variant comprises at least 3 SCR modules (e.g., modules 1-3), preferably 4 SCR modules. Preferably each of the SCR modules displays significant sequence identity to an SCR module found in a naturally occurring PVCCP, e.g., VCP or SPICE. Preferably the multiple SCR modules are arranged in an N to C manner so as to maximize overall identity to a naturally occurring PVCCP. If the sequence of a PVCCP fragment or variant contains an SCR domain that differs from the SCR consensus sequence at one or more positions, in certain embodiments of the invention the amino acid(s) at the one or more differing positions is identical to that found at a corresponding position in the most closely related SCR found in a naturally occurring PVCCP. In certain embodiments the PVCCP variant comprises at least one SCR module from a first PVCPP and at least one SCR module from a second PVCPP. In certain embodiments the PVCCP variant comprises at least one SCR module from a PVCCP and at least one SCR from a mammalian complement control protein (RCA protein). Any number of SCR modules, e.g., 1, 2, 3, 4, or more can come from any particular PVCCP or RCA protein in various embodiments of the invention. All such combinations and permutations are contemplated, even if not explicitly set forth herein.

Generally a fragment or variant of a naturally occurring VCCP or VCIP possesses sufficient structural similarity to its naturally occurring counterpart that it is recognized by a polyclonal antibody that recognizes the naturally occurring counterpart. In certain embodiments of the invention a fragment or variant of a VCCP possesses sufficient structural similarity to VCP or SPICE so that when its 3-dimensional structure (either actual or predicted structure) is superimposed on the structure of VCP or SPICE, the volume of overlap is at least 70%, preferably at least 80%, more preferably at least 90% of the total volume of the VCP structure. A partial or complete 3-dimensional structure of the fragment or variant may be determined by crystallizing the protein as described for VCP (Murthy, 2001). Alternately, an NMR solution structure can be generated, as performed for various VCP fragments (Wiles, A P, et al., *J. Mol. Biol.* 272, 253-265, 1997). A modeling program such as MODELER (Sali, A. and Blundell, T L, *J. Mol. Biol.,* 234, 779-815, 1993), or any other modeling program, can be used to generate a predicted structure. The model can be based on the VCP structure and/or any known SCR structure. The PROSPECT-PSPP suite of programs can be used (Guo, J T, et al., *Nucleic Acids Res.* 32 (Web Server issue):W522-5, Jul. 1, 2004). Similar methods may be used to generate a structure for SPICE.

Fragments or variants of a VCCP or VCIP may be generated by any available means, a large number of which are known in the art. For example, VCCPs, VCIPs, and fragments or variants thereof can be produced using recombinant DNA technology as described below. A VCCP or VCIP fragment may be chemically synthesized, produced using PCR amplification from a cloned VCCP or VCIP sequence, generated by a restriction digest, etc. Sequences for a VCCP variant may be generated by random mutagenesis of a VCCP sequence (e.g., using X-rays, chemical agents, or PCR-based mutagenesis), site-directed mutagenesis (e.g., using PCR or oligonucleotide-directed mutagenesis, etc. Selected amino acids can be changed or added.

While not wishing to be bound by any theory, it is likely that amino acid differences between naturally occurring PVCCPs occur at positions that are relevant in conferring differences in particular properties such as ability to bind heparin, activity level, etc. For example, VCP and SPICE differ at only 11 amino acids, but SPICE has a much higher activity as a cofactor for cleavage of C3b (e.g., cleavage occurs at a much faster rate with SPICE than with VCP). The amino acid differences are likely to be responsible for the differential activities of the two proteins. The amino acids at these positions are attractive candidates for alteration to identify variants that have yet greater activity.

Additional Complement Inhibitors

In some embodiments a complement inhibitor is a naturally occurring mammalian complement regulatory protein or a fragment or derivative thereof. For example, the complement regulatory protein may be CR1, DAF, MCP, CFH, or CFI. In some embodiments of the invention the complement regulatory polypeptide is one that is normally membrane-bound in its naturally occurring state. In some embodiments of the invention a fragment of such polypeptide that lacks some or all of a transmembrane and/or intracellular domain is used. Soluble forms of complement receptor 1 (sCR1), for example, are of use in the invention. For example the compounds known as TP10 or TP20 (Avant Therapeutics) can be used. C1 inhibitor (C1-INH) is also of use. In some embodiments a soluble complement control protein, e.g., CFH, is used. In some embodiments of the invention the polypeptide is modified to increase its solubility.

In some embodiments, a complement inhibitor is a C1s inhibitor. For example, U.S. Pat. No. 6,515,002 describes compounds (furanyl and thienyl amidines, heterocyclic amidines, and guanidines) that inhibit C1s. U.S. Pat. Nos. 6,515,002 and 7,138,530 describe heterocyclic amidines that inhibit C1s. U.S. Pat. No. 7,049,282 describes peptides that inhibit classical pathway activation. Certain of the peptides comprise or consist of WESNGQPENN (SEQ ID NO: 68) or KTISKAKGQPREPQVYT (SEQ ID NO: 69) or a peptide having significant sequence identity and/or three-dimensional structural similarity thereto. In some embodiments these peptides are identical or substantially identical to a portion of an IgG or IgM molecule. U.S. Pat. No. 7,041,796 discloses C3b/C4b Complement Receptor-like molecules and uses thereof to inhibit complement activation. U.S. Pat. No. 6,998,468 discloses anti-C2/C2a inhibitors of complement activation. U.S. Pat. No. 6,676,943 discloses human complement C3-degrading protein from *Streptococcus pneumoniae*.

In some embodiments, a complement inhibitor that binds to substantially the same binding site (e.g., a binding site on a complement component such as C3, C5, factor B, factor D, or an active complement split product) as a complement inhibitor described above is used. In general, the ability of first and second agents to bind to substantially the same site on a target molecule, such as a complement component or receptor, can be assessed using methods known in the art, such as competition assays, molecular modeling, etc. (See, e.g., discussion of compstatin analog mimetics.) In some embodiments the first and/or second agent can be labeled with a detectable label, e.g., a radiolabel, fluorescent label, etc. In some embodiments the target molecule, first agent, or second agent is immobilized on a support, e.g., a slide, filter, chip, beads, etc. In some embodiments, a second antibody that binds to substantially the same binding site as a first antibody comprises one or more CDR(s) that are at least 90%, 91%, 92%, 93%, 94%, 95%, 96%, 97%, 98%, 99%, or 100% identical to CDR(s) of the first antibody.

In some embodiments any of the methods of treatment may in certain embodiments comprise administering one or more doses of an angiogenesis inhibitor to a subject, e.g., a subject at increased risk of development or progression of AMD. In some embodiments the angiogenesis inhibitor is administered by intravitreal injection. In some embodiments the angiogenesis inhibitor is approved by a government agency responsible for regulating pharmaceutical agents, e.g., the US FDA, for use in treating AMD or has demonstrated approximately equivalent efficacy to an approved agent in at least one clinical trial. In some embodiments the angiogenesis inhibitor is Lucentis, Avastin, or Eyelea. A variety of different agents that inhibit the activity and/or expression of VEGF, e.g., VEGF-A, or one or more VEGF receptors are of use in certain embodiments. Such agents are referred to herein as "anti-VEGF agents". Useful agents include antibodies, antibody fragments, and nucleic acids that bind to one or more VEGF isoforms or VEGF receptors. The binding may inhibit interaction of one or more VEGF isoforms with its receptor(s). Macugen (Pfizer, Eyetech) is a VEGF nucleic acid ligand (also referred to as an aptamer) that binds to and inhibits VEGF.sub.165 (U.S. Pat. No. 6,051,698). Lucentis (Genentech) is a humanized antibody fragment that binds and inhibits Vascular Endothelial Growth Factor A (VEGF-A) (Gaudreault, J., et al., Invest Opthalmol. Vis. Sci. 46, 726-733 (2005) and references therein. Avastin (Genentech) is a full length humanized antibody that also binds to VEGF (reviewed in Ferrara, N. Endocr Rev., 25(4):581-611, 2004). Other angiogenesis inhibitors of use in certain embodiments are combretastatin or a derivative or prodrug thereof such as Combretastatin A4 Prodrug (CA4P); VEGF-Trap (aflibercept; Eyelea, Regeneron Pharmaceuticals), a fusion protein containing extracellular domains of two VEGF receptors connected to the Fc region of an antibody (U.S. Pat. No. 5,844,099); EVIZON (squalamine lactate); AG-013958 (Pfizer, Inc.); JSM6427 (Jerini A G), rapamycin (sirolimus) and analogs thereof, anecortave acetate and other anti-angiogenic steroids, etc. In certain embodiments an angiogenesis inhibitor is an agent that inhibits expression of one or more pro-angiogenic molecules through RNAi. Such agents are referred to herein as RNAi agents and include siRNA and shRNA. In certain embodiments an angiogenesis inhibitor is an RNAi agent, e.g., an siRNA, that inhibits expression of one or more VEGF isoforms (e.g., VEGF165); or inhibits expression of a VEGF receptor (e.g., VEGFR1). One of ordinary skill in the art will be able to design appropriate RNAi agents based on the known sequences of these molecules (or any other target pro-angiogenic molecule including, but not limited to, angiogenin, angiopoietin, fibroblast growth factors, PEDF, etc.), which are available in public databases, e.g., GenBank. Other antiangiogenic molecules include thalidomide and its antiangiogenic derivatives such as iMiDs (Bamias A, Dimopoulos M A. Eur J Intern Med. 14(8):459-469, 2003; Bartlett J B, et al. Nat Rev Cancer. 4(4):314-22, 2004), and various peptides such as angiostatin, endostatin, canstatin, etc.

In some embodiments an angiogenesis inhibitor is administered to a subject identified as at risk of developing advanced AMD. In some embodiments an angiogenesis inhibitor is administered to a subject in whom increased VEGF or increased macrophage activity marker has been detected, e.g., in eye-derived EVs or in combination with increased levels of an eye-derived cellular marker. In some embodiments an angiogenesis inhibitor is administered in combination with a complement inhibitor and/or anti-Th17 agent. In various embodiments a complement inhibitor, anti-Th17 agent, or angiogenesis inhibitor may be any of the various complement inhibitor, anti-Th17 agent, or angiogenesis inhibitors disclosed herein. In some embodiments, for example, a complement inhibitor is a compstatin analog, and the angiogenesis inhibitor is Lucentis, Avastin, or Eyelea. In some embodiments an angiogenesis inhibitor is administered for a limited duration or limited number of doses, e.g., 1, 2, 3, doses, or up to 3-6 months of treatment. In some embodiments an angiogenesis inhibitor is not administered.

X. Compositions and Administration

In some aspects, compositions comprising a substrate of a CAPP or IAP are provided, the substrates being useful to detect complement activation or inflamed endothelium in vivo. In various embodiments, a composition can have any feature or combination of features discussed herein so long as they are not mutually exclusive. In some aspects, the composition is sufficiently free of endotoxin, heavy metals, and unidentified and/or uncharacterized substances so as to be acceptable, without further purification, for administration to a human subject or for the manufacture of a composition to be administered to a human subject. In some embodiments, the composition is sterile.

Suitable preparations, e.g., substantially pure preparations of a CAPP substrate or IAP substrate or other diagnostic agent, or a therapeutic agent, may be combined with pharmaceutically acceptable carriers or vehicles, etc., to produce a composition appropriate for administration to a subject. The term "pharmaceutically acceptable carrier or vehicle" refers to a non-toxic carrier or vehicle that does not destroy the activity of the compound with which it is formulated. It will be understood that "activity" in this context may refer to activity as a diagnostic agent, e.g., as a substrate for a CAPP or IAP or for binding to inflamed endothelium, or pharmacological activity, e.g., complement inhibiting activity, e.g., therapeutic activity, as appropriate. One of skill in the art will understand that a carrier or vehicle is "non-toxic" if it is compatible with administration to a subject in an amount appropriate to deliver the compound without causing undue toxicity. Pharmaceutically acceptable carriers or vehicles that may be used in the compositions include, but are not limited to, water, physiological saline, Ringer's solution, sodium acetate or potassium acetate solution, 5% dextrose, and the like. A composition may include other components as appropriate for the formulation desired, e.g., as discussed herein. Supplementary active compounds, e.g., compounds independently useful for treating a subject suffering from a complement-mediated disorder, can also be incorporated into the compositions.

In some embodiments, the invention provides a pharmaceutically acceptable composition suitable for administration to humans, packaged together with a label approved by a government agency responsible for regulating pharmaceutical agents, e.g., the U.S. Food & Drug Administration, the composition comprising a substrate for a CAPP or IAP, wherein the substrate produces a detectable signal upon cleavage. The substrate may be any of the substrates described herein.

In some embodiments, the invention provides a kit or comprising: (a) a pharmaceutically acceptable substrate for a CAPP or IAP; (b) a pharmaceutically acceptable carrier or vehicle. In some embodiments the substrate is in solid form, e.g., a powder. In some embodiments the kit or pack contains instructions for (a) dissolving or diluting the substrate in the carrier; (b) administering the substrate or a composition comprising the substrate to a subject; (c) detecting cleavage of the substrate in the subject; and/or (d) interpreteting or using a result of detecting cleavage of the substrate in the subject.

A pharmaceutically acceptable composition can be administered to a subject by any suitable route of administration including, but not limited to, intravenous, intramuscular, subcutaneously, by inhalation, by nasal delivery, intrathecally, intracranially, intraarterially, orally, rectally, transdermally, intraocularly (e.g., intravitreally), etc. In some embodiments, a composition is administered intravenously. In some embodiments, a composition is administered intra-arterially. In some embodiments a composition is administered locally, either into the vascular system supplying an organ or tissue, or extra-vascularly in the vicinity of an organ or tissue. It will be understood that "pharmaceutical composition" or "pharmaceutically acceptable composition" encompasses, in addition to compositions useful for and/or intended for therapeutic use, to compositions useful for and/or intended for use in diagnosis, e.g., compositions acceptable for administration to a subject, e.g., a human or veterinary subject, that comprise one or more diagnostic agents useful for detecting high risk drusen, detecting complement activation in vivo, and/or detecting inflamed endothelium, such as the imaging agents described herein.

Pharmaceutical compositions suitable for injectable use (e.g., intravenous administration or subcutaneous administration) or by pump or catheter typically include sterile aqueous solutions (where water soluble) or dispersions and sterile powders for the extemporaneous preparation of sterile injectable solutions or dispersion. Sterile solutions can be prepared by incorporating the compound in the required amount in an appropriate solvent, optionally with one or a combination of ingredients such as buffers such as acetates, citrates, lactates or phosphates; agents for the adjustment of tonicity such as sodium chloride or dextrose; antibacterial agents such as benzyl alcohol or methyl parabens; antioxidants such as ascorbic acid, glutathione, or sodium bisulfate; chelating agents such as ethylenediaminetetraacetic acid; and other suitable ingredients etc., as desired, followed by filter-based sterilization. One of ordinary skill in the art will be aware of numerous physiologically acceptable compounds that may be included in a pharmaceutical composition. Other useful compounds include, for example, carbohydrates, such as glucose, sucrose, lactose; dextrans; amino acids such as glycine; polyols such as mannitol. These compounds may, for example, serve as bulking agents and/or stabilizers, e.g., in a powder and/or when part of the manufacture or storage process involves lyophilization. Surfactant(s) such as Tween-80, Pluronic-F108/F68, deoxycholic acid, phosphatidylcholine, etc., may be included in a composition, e.g., to increase solubility or to provide microemulsion to deliver hydrophobic drugs. pH can be adjusted with acids or bases, such as hydrochloric acid or sodium hydroxide, if desired. The parenteral preparation can be enclosed in ampoules, disposable syringes or infusion bags or multiple dose vials made of glass or plastic. Preferably solutions for injection are sterile and acceptably free of endotoxin.

Generally, dispersions are prepared by incorporating the active compound into a sterile vehicle which contains a basic dispersion medium and appropriate other ingredients from those enumerated above. In the case of sterile powders for the preparation of sterile injectable solutions, methods of preparation can include vacuum drying and freeze-drying which yields a powder of the active ingredient plus any additional desired ingredient, e.g., from a previously sterile-filtered solution thereof.

In some embodiments an agent or composition is administered within the orbit, which is the cavity within the skull in which the eye and its appendages are situated. Methods of local administration to the eye include, e.g., choroidal injection, transscleral injection or placing a scleral patch, selective arterial catheterization, eyedrops or eye ointments, intraocular administration including transretinal, subconjunctival bulbar, intravitreal injection, suprachoroidal injection, subtenon injection, scleral pocket and scleral cutdown injection, by osmotic pump, etc. Intraocular administration of drugs intended for treatment of macular degeneration and other intraocular conditions is well known in the art. In some embodiments an agent is administered within several millimeters of the portion of the sclera that overlies the posterior segment of the eye, or immediately adjacent to the exterior surface of the sclera.

In some embodiments an agent or composition is administered to the eye using iontophoresis, e.g., transcleral iontophoresis. Iontophoresis is an active method of delivery in which an electrical field created by a low-level of electrical current is used to enhance the penetration of molecules, typically charged molecules, across tissue barriers. The electrical field may ionize an agent to be delivered and/or modify the permeability of the cells so that the agent is more effectively delivered. Typically agents delivered via iontophoresis are ionized. However, neutral molecules can potentially be delivered using iontophoresis, e.g., on the basis of electro-osmosis or solute-associated fluid transport. In some embodiments a transscleral iontophoresis delivery device such as the EyeGate® II Delivery System (EyeGate Pharma, Inc., Waltham, Mass.) is used. The EyeGate® II system features an ocular applicator, syringe, adaptor for transferring the drug product from reservoirs to the applicator and generator to provide consistent current to the electrode. Ocuphor (Iomed Inc., USA) and Visulex (Aciont Inc., USA) are other ocular iontophoresis systems. Exemplary ocular iontophoresis systems are described in, e.g., U.S. Pat. Nos. 6,154,671; 6,539,251; U.S. Ser. No. 11/297,942; International (PCT) Application Publications WO/2011/041377 (OCULAR IONTOPHORESIS OF CHARGED MICELLES CONTAINING BIOACTIVE AGENTS); WO2010009087 (IONTOPHORETIC DELIVERY OF A CONTROLLED-RELEASE FORMULATION IN THE EYE), and various references cited in or citing any of the foregoing, among others. In some embodiments a diagnostic agent, e.g., a substrate for a CAPP or IAP, or a therapeutic agent, to be administered via iontophoresis comprises one or more charged groups. In some embodiments one, two, or more amino acids are included, e.g., added at either or both ends, to improve iontophoretic mobility of the agent. One of ordinary skill in the art will be aware of amino acids bearing charged side chains at various different pH ranges.

In some embodiments a formulation for ocular administration comprises a substrate for a CAPP and a penetration enhancer. Examples of penetration enhancers of use in formulations for ocular administration, e.g., via eyedrops, include, e.g., benzalkonium chloride (BAK) and EDTA. In some embodiments a formulation for ocular administration comprises a diagnostic agent, e.g., a substrate for a CAPP or IAP, and a cyclodextrin. In some embodiments a cyclodextrin may be alpha, beta, or gamma-cyclodextrin, or mixtures thereof. In some embodiments a cyclodextrin derivative may be used. In some embodiments the agent and cyclodextrin for a complex. In some embodiments a formulation for ocular administration comprises a diagnostic agent, e.g., a substrate for a CAPP or IAP, wherein the substrate is esterified or comprises a fatty acid or other lipophilic moiety. In some embodiments a diagnostic agent is provided as an emulsion. In some embodiments a formulation for ocular administration comprises a diagnostic agent, e.g., a substrate for a CAPP or IAP, and one or more mucoadhesive or viscous polymer vehicles. Such vehicles may increase precorneal drug retention by enhancing viscosity and/or allowing mucoadhesion. Examples of such excipients of use in ophthalmic formulations include gellan gum, polycarbophil, carbopol and poly(styrene-divinyl benzene) sulfonic acid. Punctal plug delivery systems are also contemplated as means to administer a diagnostic agent in certain embodiments. Punctal plugs can be made from various polymers in a variety of shapes and sizes, with the final dimensions being limited by the punctum. Punctal plugs are often composed of a cylindrical body containing the compound to be administered. They may have an outer shell comprising material impermeable to the compound and the tear fluid, an optional cap material containing pores and an optional unit to retain the punctal plug over prolonged periods of time. Any of these delivery methods may be used to administer a therapeutic agent to the eye in certain embodiments, e.g., any of the various therapeutic agents discussed herein.

In certain embodiments a composition may be administered by a periocular approach, which term is used to refer to any route of administration that locally delivers a composition into the region outside the eye, i.e., exterior to the sclera. The composition is thus delivered to an area outside of and close to the posterior segment of the eye. In certain embodiments a composition administered close to the posterior segment of the eye is administered such that the composition is delivered within 10 mm of at least one point on the exterior surface of the portion of the sclera that covers the outside of the posterior segment of the eye. In some embodiments the composition is delivered within 5 mm of at least one point on the exterior surface of the portion of the sclera that covers the outside of the posterior segment of the eye. In certain embodiments the composition is delivered within 1-2 mm of at least one point on the exterior surface of the portion of the sclera that covers the outside of the posterior segment of the eye, or within 1 mm or less of at least one point on the exterior surface of the portion of the sclera that covers the outside of the posterior segment of the eye. Periocular administration may be accomplished using, e.g., retrobulbar, peribulbar, sub-Tenon, or subconjunctival injection, by subretinal injection, by suprachoroidal injection, or by use of a catheter or cannula directed to any of the regions accessed by the afore-mentioned techniques. Most commonly a syringe is used, but a pump or any other source of pressure could also be used. In certain embodiments a composition is administered adjacent to the sclera, outside the eye, e.g., by retrobulbar, sub-Tenon, or subconjunctival injection. In certain embodiments a composition is administered into the sclera itself, e.g., by injection or using a catheter or cannula (see, e.g., U.S. Pat. No. 6,378,526). The agent (e.g., diagnostic agent, therapeutic agent) diffuses across the sclera and into the eye.

In some embodiments an agent or composition is provided in unit dosage form. Unit dosage form as used herein refers to physically discrete units suited as unitary dosages for the subject to whom an agent or composition is to be administered; each unit containing a predetermined quantity of agent calculated to produce the desired effect in association, in some embodiments, with an appropriate pharmaceutical carrier. In certain embodiments a unit dosage form is an amount appropriate for administration to the eye, e.g., by intravitreal injection. In some embodiments a unit dosage form is provided in a prefilled syringe.

Administration to the eye using implants is contemplated in certain embodiments. A macroscopic implantable device suitable for introduction into the posterior or anterior segment of the eye may be referred to herein as an ocular implant. Such devices are also sometimes referred to as ocular inserts. Such devices may be macroscopic implants comprising the agent or may be comprised of a plurality of nanoparticles or microparticles impregnated with or encapsulating or at least in part coated with the agent in various embodiments. Implants may be biodegradable or nondegradable solid dosage forms, typically comprising one or more polymers, that slowly release the agent of interest over prolonged periods, e.g., weeks or months, up to, e.g., 6-12 months, or 1-2 years in various embodiments. In certain embodiments an ocular implant comprises between 100 μg and 10 mg of an agent, e.g., between 100 μg and 1 mg of an agent. In some embodiments a plurality of microparticles or nanoparticles are administered. The plurality of microparticles or nanoparticles may collectively comprise, e.g., between 100 μg and 10 mg of an agent, e.g., between 100 μg and 1 mg of an agent. The particles may be administered in a suitable liquid vehicle or gel-forming composition. Exemplary ocular implants, particles, and gel-forming compositions and methods for manufacture thereof are described, e.g., in U.S. Ser. No. 11/544,389; U.S. Ser. No. 12/681,392; and/or U.S. Ser. No. 12/525,799. In certain embodiments the ocular implant is introduced into the space occupied by the vitreous humor. In certain embodiments the implant is administered by intravitreal injection or sutured in the pars plana area. In certain embodiments periocular implants, which are macroscopic implantable device suitable for introduction in the vicinity of the eye, e.g., are used. In certain embodiments the periocular implant is made of similar materials to those used for ocular implants. Information regarding various ocular drug delivery technologies of use in various embodiments may be found in Kompella, U B, et al., Ther Deliv. 2010; 1(3): 435-456 and/or in references cited therein, such as Choonara Y E, et al., J Pharm Sci 2009; 99(5):2219-2239.

Oral administration may be used in certain embodiments. Oral compositions generally include an inert diluent or an edible carrier. For the purpose of oral therapeutic administration, the active compound can be incorporated with excipients and used in the form of tablets, troches, or capsules, e.g., gelatin capsules. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. A liquid composition can also be administered orally. Formulations for oral delivery may incorporate agents to improve stability within the gastrointestinal tract and/or to enhance absorption.

For administration by inhalation, a compound may be delivered in the form of an aerosol spray from a pressured container or dispenser which contains a suitable propellant, e.g., a gas such as carbon dioxide. A metered dose inhaler or nebulizer may be used. The aerosol may comprise liquid particles or dry aerosol (e.g., dry powders, large porous particles, etc.).

For topical application, a compound may be formulated in a suitable ointment containing the active component suspended or dissolved in one or more carriers. Carriers for topical administration include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated as a suitable lotion or cream containing a compound suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol, and water.

Systemic administration can also be by transmucosal or transdermal means. For transmucosal or transdermal administration, penetrants appropriate to the barrier to be permeated may be used in the formulation. Such penetrants are generally known in the art, and include, for example, for transmucosal administration, detergents, bile salts, and fusidic acid derivatives. Transmucosal administration can be accomplished, e.g., through the use of nasal sprays or suppositories. For transdermal administration, the active compounds are typically formulated into ointments, salves, gels, or creams as generally known in the art.

The compounds can also be prepared in the form of suppositories (e.g., with conventional suppository bases such as cocoa butter and other glycerides) or retention enemas for rectal delivery.

In certain embodiments a compound is prepared with carriers that will protect the compound against rapid elimination from the body, such as a controlled release formulation, including implants and microencapsulated delivery systems. For example, a compound may be incorporated into or encapsulated in a microparticle or nanoparticle formulation. Biodegradable, biocompatible polymers can be used, such as ethylene vinyl acetate, polyanhydrides, polyglycolic acid, collagen, polyorthoesters, polyethers, polylactic acid, PLGA, etc. Liposomes or other lipid-based particles can be used as pharmaceutically acceptable carriers. These can be prepared according to methods known to those skilled in the art, for example, as described in U.S. Pat. No. 4,522,811 and/or other references listed herein. Depot formulations may be used. In some embodiments a compound is released from the depot over time, e.g., so as to provide a therapeutic concentration for longer than if the compound was administered intravenously. One of ordinary skill in the art will appreciate that the materials and methods selected for preparation of a controlled release formulation, implant, etc., should be such as to retain activity of the compound.

It will be appreciated that an agent can be provided as a pharmaceutically acceptable salt. Pharmaceutically acceptable salts include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Also, pharmaceutically-acceptable salts can be prepared as alkaline metal or alkaline earth salts, such as sodium, potassium or calcium salts, if appropriate depending on the identity of the active agent.

It will be understood that the pharmaceutically acceptable carriers, compounds, and preparation methods mentioned herein are exemplary and non-limiting. See, e.g., Remington: The Science and Practice of Pharmacy. 21st Edition. Philadelphia, Pa. Lippincott Williams & Wilkins, 2005, for additional discussion of pharmaceutically acceptable compounds and methods of preparing pharmaceutical compositions of various types.

A pharmaceutical composition can be administered in an amount effective to achieve a desired effect. Appropriate doses and dosing regimen depend at least in part upon the potency and half-life of a therapeutic agent and may optionally be tailored to the particular recipient, for example, through administration of increasing doses until a preselected desired response is achieved, such as a desired degree of complement inhibition and/or reduction of complement activation in the case of a complement inhibitor. If desired, the specific dose level for any particular subject may be selected based at least in part upon a variety of factors including the activity of the specific compound employed, the particular condition being treated, the age, body weight, general health, route of administration, the rate of excretion, any drug combination, and/or the degree of complement activation or inflamed endothelium detected.

EXAMPLES

Example 1: Design and Synthesis of Fluorogenic NIR C3 Convertase Substrate

The following sequence from human C3, encompassing the cleavage site for C3 convertase, is obtained from the MEROPS database: Leu-Ala-Arg-Ser-Asn-Leu-Asp-Glu-Asp-Ile-Ile (SEQ ID NO: 98). The sequence is modified to include Glycine at the N terminus and Lysine at the C terminus to form: Gly-Leu-Ala-Arg-Ser-Asn-Leu-Asp-Glu-Asp-Ile-Ile-Lys (SEQ ID NO: 99). (It will be appreciated that Gly is already present in the corresponding position in human C3). The modified peptide is synthesized on a peptide synthesizer using standard Fmoc chemistry. The amino terminus is deprotected and conjugated to a Cy5.5 dye using a Cy5.5-NHS ester reagent (GE Healthcare-Life Sciences). Cy7Q is used as the "quenching" fluorophore and is attached to the Cy5.5-conjugated peptide to prepare a fluorogenic C3 convertase substrate. The Cy5.5-labeled peptide is further modified by attaching a Cy7Q-NHS ester (GE Healthcare-Life Sciences) to the amine group of the lysine residue to yield the fluorogenic composition Cy5.5-Gly-Leu-Ala-Arg-Ser-Asp-Val-Asp-Glu-Asp-Ile-Ile-Lys(Cy7Q) (SEQ ID NO: 109), which may be represented as Cy5.5-SEQ ID NO: 99-Cy7Q. A portion of the peptide material is amidated at the C-terminus. The resulting amidated peptide may be represented as Cy5.5-Gly-Leu-Ala-Arg-Ser-Asp-Val-Asp-Glu-Asp-Ile-Ile-Lys(Cy7Q)-$NH_2$ (SEQ ID NO: 110) which may be abbreviated as Cy5.5-SEQ ID NO: 99-Cy7Q-$NH_2$ where it will be understood that the —$NH_2$ at the C-terminus represents replacement of the OH group of the carboxy group of lysine by $NH_2$. The products are analyzed by LCMS. The measured molecular mass is compared with calculated to confirm identity. The material is used as such or further purified prior to use.

Example 2: Design and Synthesis of Fluorogenic NIR C3 Convertase Substrate

Example 1 is repeated, except that HiLyte Fluor™ 750 (AnaSpec) is used instead of Cy5.5 as the fluorophore, and QXL™680 (AnaSpec) is used as the dark quencher instead of Cy7Q. The resulting substrates may be represented as HiLyte Fluor™ 750-SEQ ID NO: 99-QXL™680 and HiLyte Fluor™ 750-SEQ ID NO: 99-QXL™680-$NH_2$.

Example 3: Design and Synthesis of Fluorogenic NIR C3 Convertase Substrate

Example 1 is repeated, except that IRDye 800CW (LI-COR Biosciences) is used instead of Cy5.5 as the fluorophore, and IRDye QC-1 (LI-COR Biosciences) is used as the dark quencher instead of Cy7Q. The resulting substrates may be represented as IRDye 800CW-SEQ ID NO: 99-IRDye QC-1 and IRDye 800CW-SEQ ID NO: 99-IRDye QC-1-$NH_2$.

Example 4: Design and Synthesis of Fluorogenic C3 Convertase Substrate

Example 1 is repeated except that FITC is used as the fluorophore instead of Cy5.5, and DABCYL is used as the dark quencher instead of Cy7Q. The resulting substrates may be represented as FITC-SEQ ID NO: 99-DABCYL and FITC-SEQ ID NO: 99-DABCYL-$NH_2$.

Example 5: Design and Synthesis of Fluorogenic C3 Convertase Substrates Based on Rat C3 Sequence Examples 1~4 are repeated except that a sequence from rat C3, namely LARSDVDEDII (SEQ ID NO: 104), is used instead of SEQ ID NO: 98.

Example 6: Design and Synthesis of Fluorogenic C3 Convertase Substrates Based on Mouse C3 Sequence Examples 1~4 are repeated, except that a sequence from mouse C3, namely LARSELEEDII (SEQ ID NO: 105) is used instead of SEQ ID NO: 99.

Example 7: Design and Synthesis of Additional Fluorogenic C3 Convertase Substrates Examples 1-6 are repeated, except that a beta-Alanine residue (β-Ala) is used at the N-terminus instead of Glycine.

Example 8: Design and Synthesis of Additional Fluorogenic C3 Convertase Substrates Examples 1-6 are repeated, except that sequences without Glycine at the N-terminus, i.e., SEQ ID NO: 98, 104, and 105 are used and the fluorophore is attached to the N-terminal amino group of Leucine in SEQ ID NO: 98, 104, or 105.

Example 9: In Vitro Testing of Fluorogenic C3 Convertase Substrates

The fluorogenic C3 convertase substrates described in Examples 1-8 are each individually incubated with 200 µL human or monkey plasma for 2 h at room temperature in wells coated with a complement activating substance such as latex or wells containing activated complement prepared as described in the following Example. The resulting mixture is analyzed using a reverse phase HPLC system at 670 nm. A new peak is observed in addition to the original peak. The new peak represents the cleavage product. The assay is repeated using rat or mouse plasma instead of human or monkey plasma.

Specificity is confirmed by incubating the human or monkey plasma with a compstatin analog (SEQ ID NO: 28) prior to adding the plasma to the wells. Lack of cleavage product in such cases confirms that the cleavage product results from activity of the C3 convertase.

Example 10: In Vitro Testing of Fluorogenic C3 Convertase Substrates

The fluorogenic C3 convertase substrates described in Examples 1-8 are each individually by measuring the signal generated in the presence of complement activation, which is activated via the classical pathway using a standard complement activation protocol (suitable for use as a complement inhibition assay). Human or monkeyplasma, chicken ovalbumin (OVA), polyclonal anti-OVA antibodies are added to wells and incubated, followed by addition of substrate being tested. After an additional incubation, the sample is exposed to light of an appropriate excitation wavelength, and signal from cleavage product detected. The cleavage product is detected using a fluorescence plate reader such as the Synergy MxF Monochromator-Based Fluorescence Microplate Reader (BioTek).

Details of the protocol are as follows:
Protocol for Classical Complement Inhibition Assay
Materials:
  Ninety-six well plate (polystyrene plate, Thermo Scientific, 9205)
  Chicken OVA (Sigma A5503-5G)
  Rabbit anti-chicken OVA (Abcam ab1221)

Veronal Buffer (5× concentration, Lonza 12-624E)
Human plasma (collected with Lepirudin at 50 ug/ml final concentration)
Tween-20 Wash Buffer (0.05% Tween 20-PBS buffer)
Fluorogenic substrate Protocol:
1. Add 100 ul/well of 1% chicken OVA (in PBS)
2. Incubate overnight @ 4° C. or room temperature for 1-2 hr.
3. Remove by shaking and tapping the plate.
4. Block by adding 200 ul of blocking buffer
5. Incubate for 1 h at room temp
6. Remove by shaking and tapping the plate
7. Add 100 ul of 1:1000 dilution of Polyclonal anti-chicken OVA in blocking buffer
8. Incubate for 1 h at room temp
9. Wash twice with wash buffer
10. Add 50 ul $VB^{++}$ to wells #2 to 12
11. Add 100 ul of starting substrate dilution (2× in $VB^{++}$) to well 1.
12. Serially dilute (1:2) the substrate from wells 1 to 10 as follow
    a. Take 50 ul of solution from the originating well
    b. Add this to the next well
    c. Mix by pipetting several times
    d. Repeat up to well #10
Note: from well #10 remove 50 ul and discard.
13. Add 50 ul of 2× plasma (1:37.5 dilution of original plasma) dilution to wells 1 to 11
14. Incubate for 2 h
15. Read the plate at the appropriate wavelength to detect flourophore.

$VB^{++}$
Formula:

| | |
|---|---|
| Barbital | 5 mM |
| NaCl | 72.5 mM |
| $MgCl_2$ | 0.5 mM |
| $CaCl_2$ | 0.15 mM |
| PH | 7.4 |

Stock Solutions:

| Veronal Buffer (5X) | | | |
|---|---|---|---|
| | Prod # | MW | For 500 ml |
| 9 mM Sodium Barbitone | Sigma B0500 | 206.17 | 927 mg |
| 15.5 mM diethylbarbituric acid | Sigma B0375 | 184.19 | 1.42 grams |

| Mg—Cl2 (200X) | | | |
|---|---|---|---|
| | Prod # | MW | For 50 ml |
| 100 mM $MgCl_2$—$6H_2O$ | Sigma M0250 | 203.30 | 1.00 gram |

| $CaCl_2$ (500x) | | | |
|---|---|---|---|
| | Prod # | MW | For 50 ml |
| 75 mM $CaCl_2$ | Sigma C7902 | 147.01 | 551.28 mg |

To prepare 50 ml of working buffer:
Weight 210 mg NaCl
Add 10 ml of 5×VB
Add 100 ul of $CaCl_2$) (500×)
Add 250 ul MgCl (200×)
Adjust volume to 50 ml with $H_2O$
Adjust pH to 7.4

Data is analyzed using GraphPad Prism5 software. The assay is repeated using rat or mouse plasma instead of human or monkey plasma.

Example 11: Testing Fluorogenic C3 Convertase Substrates to Detect Complement Activation in the Eye Complement is activated in the eye of non-human subjects using a blue light laser or by directly injecting lipopolysaccharide (LPS). Fluorogenic C3 convertase substrates described in Example 1-8 are each administered intravenously or by intravitreal injection to the subjects at varying doses ranging from 0.1 mg/kg to 100 mg/kg. Each subject receives a single dose of a single substrate. Eyes are monitored using a scanning laser ophthalmoscope following administration of the substrate to detect complement activation by detecting fluorescence arising as a result of dequenching resulting from cleavage of the substrate.

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims. It will be appreciated that the invention is in no way dependent upon particular results achieved in any specific example or with any specific embodiment. Articles such as "a", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. For example, and without limitation, it is understood that where claims or description indicate that a residue at a particular position may be selected from a particular group of amino acids or amino acid analogs, the invention includes individual embodiments in which the residue at that position is any of the listed amino acids or amino acid analogs. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims or from the description above is introduced into another claim. For example, any claim that is dependent on another claim can be modified to include one or more elements, limitations, clauses, or descriptive terms, found in any other claim that is dependent on the same base claim. Furthermore, where the claims recite a composition, it is to be understood that methods of administering the composition according to any of the methods disclosed herein, and methods of using the composition for any of the purposes disclosed herein are included within the scope of the invention, and methods of making the composition according to any of the methods of making disclosed herein are included within the scope of the invention, unless otherwise indicated or unless it would be evident to one of ordinary skill in the art that a contradiction or inconsistency would arise. It is contemplated that all embodiments described herein are applicable to all different aspects of the invention where appropriate. It is also contemplated that any of the embodiments or aspects can be freely combined with one or more other such embodiments or aspects whenever appropriate. Methods of diagnosing a subject, e.g., diagnosing a subject as having one or more high risk drusen, can include a step of (i) providing a subject who has, or is at increased risk of having, AMD or has at least one symptom of AMD, wherein it is of use to determine whether the subject has the disease or evaluate risk of development or progression of AMD; (ii) administering a diagnostic agent to the subject, wherein the agent is useful for diagnosis, e.g., for detecting complement activation in vivo or inflamed endothelium or high risk drusen; (iii) obtaining, transmitting, or analyzing an image or dataset from an eye of a subject to whom a diagnostic agent has been administered; (iv) generating or providing a diagnosis or prediction based at least in part on an image or dataset acquired from an eye of a subject to whom a diagnostic agent has been administered; (v) providing or obtaining a sample from a subject, e.g., a body fluid sample; (vi) processing and/or analyzing a sample obtained from a subject, so as to detect or facilitate detection of eye-derived EVs or a Th17 biomarker in the sample; (vii) preparing a composition suitable for detection of eye-derived EVs or a Th17 biomarker; (viii) generating or providing a diagnosis or prediction based at least in part on an measurement made on a sample obtained from a subject; and/or (ix) administering a treatment to the subject, e.g., based at least in part on the diagnosis or prediction. Methods of treating a subject can include a step of providing a subject in need of such treatment (e.g., a subject who has had, or is at increased risk of having, a disease), a step of diagnosing a subject as having a disease and/or a step of selecting a subject for treatment with a complement inhibitor, e.g., a compstatin analog, or anti-Th17 agent.

Where elements are presented as lists, it is to be understood that each subgroup of the elements is also disclosed, and any element(s) can be removed from the group. For purposes of conciseness only some of these embodiments have been specifically recited herein, but the invention includes all such embodiments. It should also be understood that, in general, where the invention, or aspects of the invention, is/are referred to as comprising particular elements, features, etc., certain embodiments of the invention or aspects of the invention consist, or consist essentially of, such elements, features, etc. It should also be understood that, unless clearly indicated to the contrary, in any methods claimed herein that include more than one step or act, the order of the steps or acts of the method is not necessarily limited to the order in which the steps or acts of the method are recited. Applicants reserve the right to specify that any process, act, or step of a process may be performed by an apparatus, which may be an apparatus mentioned herein or known in the art. The apparatus may be specifically adapted or modified to perform the process, act, or step or may perform the process, act, or step on a sample or subject specifically adapted or treated for purposes of performing the process, act, or step thereon. Applicants also reserve the right to specify that any process, act, or step of a process that may be amenable to being performed at least in part mentally is not entirely performed mentally or is only partially performed mentally or is performed substantially or entirely by an apparatus (which term should be understood to include any "machine") and/or by effecting a physical transformation. Applicants also reserve the right to specify that any process, act, or step of a process that may be amenable to being performed at least in part using a writing implement such as a pen or pencil, and a surface suitable for writing on, such as paper, is not entirely performed using a writing implement and surface suitable for writing or is only partially performed in such manner or is performed substantially or entirely by an apparatus and/or by effecting a physical transformation.

Where a phrase such as "at least", "up to", "no more than", or similar phrases, precedes a series of numbers herein, it is to be understood that the phrase applies to each number in the list in various embodiments (it being understood that, depending on the context, 100% of a value, e.g., a value expressed as a percentage, may be an upper limit), unless the context clearly dictates otherwise. For example, "at least 1, 2, or 3" should be understood to mean "at least 1, at least 2, or at least 3" in various embodiments. It will also be understood that any and all reasonable lower limits and upper limits are expressly contemplated. A reasonable lower or upper limit may be selected by one of ordinary skill in the art based, e.g., on factors such as convenience, cost, time, effort, availability (e.g., of samples, agents, or reagents), statistical considerations, etc. Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It should also be understood that unless otherwise indicated or evident from the context, any product or composition described herein may be considered "isolated".

Any particular embodiment, aspect, element, feature, etc., or combination thereof, may be explicitly excluded from any one or more claims.

We claim:

1. A method of treating a subject at risk of development or progression of age-related macular degeneration (AMD), the method comprising:
   (a) providing a body fluid sample obtained from the subject;
   (b) detecting an increased level of eye-derived extracellular vesicles (EVs) in the body fluid sample of the subject relative to a level of eye-derived EVs in a body fluid sample from a healthy individual not suffering from AMD; and
   (c) administering a complement inhibitor to the subject based at least in part on detecting an increased level of eye-derived EVs in step (b).

2. The method of claim 1, wherein at least some of the eye-derived EVs originate from retinal cells or retinal pigment epithelial (RPE) cells.

3. The method of claim 1, wherein the EVs comprise at least one cell-type specific marker for RPE cells or retinal cells.

4. The method of claim 1, wherein the EVs comprise at least one cell-type specific marker for RPE cells or retinal cells, wherein the marker is an eye-specific opsin.

5. The method of claim 1, wherein the body fluid is blood.

6. The method of claim 1, wherein the method comprises detecting one or more eye-specific cellular markers in or on the EVs.

7. The method of claim 1, wherein the EVs comprise exosomes.

* * * * *

SEQUENCE LISTING

<160> NUMBER OF SEQ ID NOS: 110

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: misc_feature
<222> LOCATION: (2)..(12)
<223> OTHER INFORMATION: Disulfide bond

<400> SEQUENCE: 1

Ile Cys Val Val Gln Asp Trp Gly His His Arg Cys Thr
1               5                   10

<210> SEQ ID NO 2
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(19)
<223> OTHER INFORMATION: Any independently selected amino acid or amino
      acid analog
<220> FEATURE:
<221> NAME/KEY: misc_feature
<222> LOCATION: (1)..(19)
<223> OTHER INFORMATION: This region may encompass 2 to 19 residues,
      wherein some residues may be absent
<220> FEATURE:
<221> NAME/KEY: MOD_RES
<222> LOCATION: (22)..(22)
<223> OTHER INFORMATION: Trp or an analog of Trp
<220> FEATURE:
<221> NAME/KEY: MOD_RES
<222> LOCATION: (24)..(42)
<223> OTHER INFORMATION: Any independently selected amino acid or amino
      acid analog
<220> FEATURE:
<221> NAME/KEY: misc_feature
<222> LOCATION: (24)..(42)
<223> OTHER INFORMATION: This region may encompass 2 to 19 residues,
      wherein some residues may be absent

<400> SEQUENCE: 2

Xaa Xaa Xaa Xaa Xaa Xaa Xaa Xaa Xaa Xaa Xaa Xaa Xaa Xaa Xaa Xaa
1               5                   10                  15

Xaa Xaa Xaa Gln Asp Xaa Gly Xaa Xaa Xaa Xaa Xaa Xaa Xaa Xaa Xaa
            20                  25                  30

Xaa Xaa Xaa Xaa Xaa Xaa Xaa Xaa Xaa Xaa
        35                  40

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Trp or an analog of Trp
<220> FEATURE:
<221> NAME/KEY: MOD_RES
<222> LOCATION: (4)..(4)
<223> OTHER INFORMATION: Trp or an analog of Trp
<220> FEATURE:
<223> OTHER INFORMATION: see specification as filed for detailed
      description of substitutions and preferred embodiments

<400> SEQUENCE: 3

Xaa Gln Asp Xaa Gly
1               5
```

```
<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Trp or an analog of Trp
<220> FEATURE:
<221> NAME/KEY: MOD_RES
<222> LOCATION: (4)..(4)
<223> OTHER INFORMATION: Trp or an analog of Trp
<220> FEATURE:
<221> NAME/KEY: MOD_RES
<222> LOCATION: (6)..(6)
<223> OTHER INFORMATION: His, Ala, analogs of Ala, Phe or Trp
<220> FEATURE:
<223> OTHER INFORMATION: see specification as filed for detailed
      description of substitutions and preferred embodiments

<400> SEQUENCE: 4

Xaa Gln Asp Xaa Gly Xaa
1               5

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Any independently selected amino acid or amino
      acid analog
<220> FEATURE:
<221> NAME/KEY: MOD_RES
<222> LOCATION: (4)..(4)
<223> OTHER INFORMATION: Trp or analog of Trp
<220> FEATURE:
<221> NAME/KEY: MOD_RES
<222> LOCATION: (7)..(7)
<223> OTHER INFORMATION: Trp or analog of Trp
<220> FEATURE:
<221> NAME/KEY: MOD_RES
<222> LOCATION: (9)..(13)
<223> OTHER INFORMATION: Any independently selected amino acid or amino
      acid analog
<220> FEATURE:
<223> OTHER INFORMATION: see specification as filed for detailed
      description of substitutions and preferred embodiments

<400> SEQUENCE: 5

Xaa Xaa Xaa Xaa Gln Asp Xaa Gly Xaa Xaa Xaa Xaa Xaa
1               5                   10

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Ile, Val, Leu, B1-Ile, B1-Val, B1-Leu or a
      dipeptide comprising Gly-Ile or B1-Gly-Ile, wherein B1 represents
      a first blocking moiety
<220> FEATURE:
```

```
<221> NAME/KEY: misc_feature
<222> LOCATION: (1)..(2)
<223> OTHER INFORMATION: This region may encompass 1 to 2 residues,
      wherein some positions may be absent
<220> FEATURE:
<221> NAME/KEY: misc_feature
<222> LOCATION: (3)..(13)
<223> OTHER INFORMATION: Disulfide bond
<220> FEATURE:
<221> NAME/KEY: MOD_RES
<222> LOCATION: (5)..(5)
<223> OTHER INFORMATION: Independently selected from Trp or analogs of
      Trp
<220> FEATURE:
<221> NAME/KEY: MOD_RES
<222> LOCATION: (8)..(8)
<223> OTHER INFORMATION: Independently selected from Trp or analogs of
      Trp
<220> FEATURE:
<221> NAME/KEY: MOD_RES
<222> LOCATION: (10)..(10)
<223> OTHER INFORMATION: His, Ala or an analog of Ala, Phe, Trp or an
      analog of Trp
<220> FEATURE:
<221> NAME/KEY: MOD_RES
<222> LOCATION: (14)..(16)
<223> OTHER INFORMATION: L-Thr, D-Thr, Ile, Val, Gly, a dipeptide
      selected from Thr-Ala or Thr-Asn, or a tripeptide comprising
      Thr-Ala-Asn, wherein a c-term -OH of any of the L-Thr, D-Thr, Ile,
      Val, Gly, Ala or Asn is optionally replaced by a second blocking
      moiety
<220> FEATURE:
<221> NAME/KEY: misc_feature
<222> LOCATION: (14)..(16)
<223> OTHER INFORMATION: This region may encompass 1 to 3 residues,
      wherein some positions may be absent
<220> FEATURE:
<223> OTHER INFORMATION: see specification as filed for detailed
      description of substitutions and preferred embodiments

<400> SEQUENCE: 6

Xaa Xaa Cys Val Xaa Gln Asp Xaa Gly Xaa His Arg Cys Xaa Xaa Xaa
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Ile, Val, Leu, Ac-Ile, Ac-Val, Ac-Leu or a
      dipeptide comprising Gly-Ile or Ac-Gly-Ile
<220> FEATURE:
<221> NAME/KEY: misc_feature
<222> LOCATION: (1)..(2)
<223> OTHER INFORMATION: This region may encompass 1 to 2 residues,
      wherein some positions may be absent
<220> FEATURE:
<221> NAME/KEY: misc_feature
<222> LOCATION: (3)..(13)
<223> OTHER INFORMATION: Disulfide bond
<220> FEATURE:
<221> NAME/KEY: MOD_RES
<222> LOCATION: (5)..(5)
<223> OTHER INFORMATION: Independently selected from Trp or analogs of
      Trp
<220> FEATURE:
<221> NAME/KEY: MOD_RES
<222> LOCATION: (8)..(8)
<223> OTHER INFORMATION: Independently selected from Trp or analogs of
      Trp
<220> FEATURE:
<221> NAME/KEY: MOD_RES
```

```
<222> LOCATION: (10)..(10)
<223> OTHER INFORMATION: His, Ala or an analog of Ala, Phe, Trp or an
      analog of Trp
<220> FEATURE:
<221> NAME/KEY: MOD_RES
<222> LOCATION: (14)..(16)
<223> OTHER INFORMATION: L-Thr, D-Thr, Ile, Val, Gly, a dipeptide
      selected from Thr-Ala or Thr-Asn, or a tripeptide comprising
      Thr-Ala-Asn, wherein a c-term -OH of any of L-Thr, D-Thr, Ile,
      Val, Gly, Ala, or Asn is optionally replaced by -NH2
<220> FEATURE:
<221> NAME/KEY: misc_feature
<222> LOCATION: (14)..(16)
<223> OTHER INFORMATION: This region may encompass 1 to 3 residues,
      wherein some positions may be absent
<220> FEATURE:
<223> OTHER INFORMATION: see specification as filed for detailed
      description of substitutions and preferred embodiments

<400> SEQUENCE: 7

Xaa Xaa Cys Val Xaa Gln Asp Xaa Gly Xaa His Arg Cys Xaa Xaa Xaa
1               5                   10                  15

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term CONH2

<400> SEQUENCE: 8

Ile Cys Val Val Gln Asp Trp Gly His His Arg Cys Thr
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term CONH2

<400> SEQUENCE: 9

Ile Cys Val Val Gln Asp Trp Gly His His Arg Cys Thr
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term CONH2

<400> SEQUENCE: 10

Ile Cys Val Tyr Gln Asp Trp Gly Ala His Arg Cys Thr
1               5                   10
```

```
<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term COOH

<400> SEQUENCE: 11

Ile Cys Val Trp Gln Asp Trp Gly Ala His Arg Cys Thr
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term CONH2

<400> SEQUENCE: 12

Ile Cys Val Trp Gln Asp Trp Gly Ala His Arg Cys Thr
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (13)..(13)
<223> OTHER INFORMATION: d-Thr
<220> FEATURE:
<223> OTHER INFORMATION: C-term COOH

<400> SEQUENCE: 13

Ile Cys Val Trp Gln Asp Trp Gly Ala His Arg Cys Thr
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 2-Nal
<220> FEATURE:
<223> OTHER INFORMATION: C-term CONH2

<400> SEQUENCE: 14

Ile Cys Val Ala Gln Asp Trp Gly Ala His Arg Cys Thr
1               5                   10
```

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 2-Nal
<220> FEATURE:
<223> OTHER INFORMATION: C-term COOH

<400> SEQUENCE: 15

Ile Cys Val Ala Gln Asp Trp Gly Ala His Arg Cys Thr
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 1-Nal
<220> FEATURE:
<223> OTHER INFORMATION: C-term COOH

<400> SEQUENCE: 16

Ile Cys Val Ala Gln Asp Trp Gly Ala His Arg Cys Thr
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 2-Igl
<220> FEATURE:
<223> OTHER INFORMATION: C-term CONH2

<400> SEQUENCE: 17

Ile Cys Val Gly Gln Asp Trp Gly Ala His Arg Cys Thr
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)

<223> OTHER INFORMATION: 2-Igl
<220> FEATURE:
<223> OTHER INFORMATION: C-term COOH

<400> SEQUENCE: 18

Ile Cys Val Gly Gln Asp Trp Gly Ala His Arg Cys Thr
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Dht
<220> FEATURE:
<223> OTHER INFORMATION: C-term COOH

<400> SEQUENCE: 19

Ile Cys Val Trp Gln Asp Trp Gly Ala His Arg Cys Thr
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Bpa
<220> FEATURE:
<223> OTHER INFORMATION: C-term COOH

<400> SEQUENCE: 20

Ile Cys Val Phe Gln Asp Trp Gly Ala His Arg Cys Thr
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Bpa
<220> FEATURE:
<223> OTHER INFORMATION: C-term CONH2

<400> SEQUENCE: 21

Ile Cys Val Phe Gln Asp Trp Gly Ala His Arg Cys Thr
1               5                   10

<210> SEQ ID NO 22
<211> LENGTH: 13
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Bta
<220> FEATURE:
<223> OTHER INFORMATION: C-term COOH

<400> SEQUENCE: 22

Ile Cys Val Xaa Gln Asp Trp Gly Ala His Arg Cys Thr
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Bta
<220> FEATURE:
<223> OTHER INFORMATION: C-term CONH2

<400> SEQUENCE: 23

Ile Cys Val Xaa Gln Asp Trp Gly Ala His Arg Cys Thr
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: 2-Abu
<220> FEATURE:
<223> OTHER INFORMATION: C-term CONH2

<400> SEQUENCE: 24

Ile Cys Val Trp Gln Asp Trp Gly Xaa His Arg Cys Thr
1               5                   10

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term COOH

<400> SEQUENCE: 25

Gly Ile Cys Val Trp Gln Asp Trp Gly Ala His Arg Cys Thr Ala Asn
1               5                   10                  15
```

```
<210> SEQ ID NO 26
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 5f-Trp
<220> FEATURE:
<223> OTHER INFORMATION: C-term CONH2

<400> SEQUENCE: 26

Ile Cys Val Trp Gln Asp Trp Gly Ala His Arg Cys Thr
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 5-methyl-Trp
<220> FEATURE:
<223> OTHER INFORMATION: C-term CONH2

<400> SEQUENCE: 27

Ile Cys Val Trp Gln Asp Trp Gly Ala His Arg Cys Thr
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 1-methyl-Trp
<220> FEATURE:
<223> OTHER INFORMATION: C-term CONH2

<400> SEQUENCE: 28

Ile Cys Val Trp Gln Asp Trp Gly Ala His Arg Cys Thr
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
```

```
<222> LOCATION: (7)..(7)
<223> OTHER INFORMATION: 5f-Trp
<220> FEATURE:
<223> OTHER INFORMATION: C-term CONH2

<400> SEQUENCE: 29

Ile Cys Val Trp Gln Asp Trp Gly Ala His Arg Cys Thr
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 5f-Trp
<220> FEATURE:
<221> NAME/KEY: MOD_RES
<222> LOCATION: (7)..(7)
<223> OTHER INFORMATION: 5f-Trp
<220> FEATURE:
<223> OTHER INFORMATION: C-term CONH2

<400> SEQUENCE: 30

Ile Cys Val Trp Gln Asp Trp Gly Ala His Arg Cys Thr
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 5-methyl-Trp
<220> FEATURE:
<221> NAME/KEY: MOD_RES
<222> LOCATION: (7)..(7)
<223> OTHER INFORMATION: 5f-Trp
<220> FEATURE:
<223> OTHER INFORMATION: C-term CONH2

<400> SEQUENCE: 31

Ile Cys Val Trp Gln Asp Trp Gly Ala His Arg Cys Thr
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 1-methyl-Trp
<220> FEATURE:
<221> NAME/KEY: MOD_RES
<222> LOCATION: (7)..(7)
```

<223> OTHER INFORMATION: 5f-Trp
<220> FEATURE:
<223> OTHER INFORMATION: C-term CONH2

<400> SEQUENCE: 32

Ile Cys Val Trp Gln Asp Trp Gly Ala His Arg Cys Thr
1               5                   10

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (5)..(5)
<223> OTHER INFORMATION: 6f-Trp
<220> FEATURE:
<221> NAME/KEY: MOD_RES
<222> LOCATION: (8)..(8)
<223> OTHER INFORMATION: 6f-Trp
<220> FEATURE:
<223> OTHER INFORMATION: C-term COOH

<400> SEQUENCE: 33

Gly Ile Cys Val Trp Gln Asp Trp Gly Ala His Arg Cys Thr Asn
1               5                   10                  15

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 1-formyl-Trp
<220> FEATURE:
<223> OTHER INFORMATION: C-term CONH2

<400> SEQUENCE: 34

Ile Cys Val Trp Gln Asp Trp Gly Ala His Arg Cys Thr
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 1-methoxy-Trp
<220> FEATURE:
<223> OTHER INFORMATION: C-term CONH2

<400> SEQUENCE: 35

Ile Cys Val Trp Gln Asp Trp Gly Ala His Arg Cys Thr
1               5                   10

```
<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (5)..(5)
<223> OTHER INFORMATION: 5f-Trp
<220> FEATURE:
<221> NAME/KEY: MOD_RES
<222> LOCATION: (8)..(8)
<223> OTHER INFORMATION: 5f-Trp
<220> FEATURE:
<223> OTHER INFORMATION: C-term COOH

<400> SEQUENCE: 36

Gly Ile Cys Val Trp Gln Asp Trp Gly Ala His Arg Cys Thr Asn
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(4)
<223> OTHER INFORMATION: Any independently selected amino acid or amino
      acid analog
<220> FEATURE:
<221> NAME/KEY: MOD_RES
<222> LOCATION: (5)..(5)
<223> OTHER INFORMATION: Trp or analog of Trp
<220> FEATURE:
<221> NAME/KEY: MOD_RES
<222> LOCATION: (8)..(8)
<223> OTHER INFORMATION: Trp or analog of Trp
<220> FEATURE:
<221> NAME/KEY: MOD_RES
<222> LOCATION: (10)..(14)
<223> OTHER INFORMATION: Any independently selected amino acid or amino
      acid analog
<220> FEATURE:
<221> NAME/KEY: MOD_RES
<222> LOCATION: (15)..(15)
<223> OTHER INFORMATION: Any amino acid
<220> FEATURE:
<223> OTHER INFORMATION: see specification as filed for detailed
      description of substitutions and preferred embodiments

<400> SEQUENCE: 37

Xaa Xaa Xaa Xaa Xaa Gln Asp Xaa Gly Xaa Xaa Xaa Xaa Xaa Xaa
1               5                   10                  15

<210> SEQ ID NO 38
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: Any amino acid
<220> FEATURE:
<221> NAME/KEY: MOD_RES
<222> LOCATION: (2)..(3)
<223> OTHER INFORMATION: Ile, Val, Leu, B1-Ile, B1-Val, B1-Leu or a
      dipeptide comprising Gly-Ile or B1-Gly-Ile, wherein B1 represents
      a first blocking moiety
<220> FEATURE:
<221> NAME/KEY: misc_feature
<222> LOCATION: (2)..(3)
<223> OTHER INFORMATION: This region may encompass 1 to 2 residues,
      wherein some positions may be absent
<220> FEATURE:
<221> NAME/KEY: misc_feature
<222> LOCATION: (4)..(14)
<223> OTHER INFORMATION: Disulfide bond
<220> FEATURE:
<221> NAME/KEY: MOD_RES
<222> LOCATION: (6)..(6)
<223> OTHER INFORMATION: Independently selected from Trp or analogs of
      Trp
<220> FEATURE:
<221> NAME/KEY: MOD_RES
<222> LOCATION: (9)..(9)
<223> OTHER INFORMATION: Independently selected from Trp or analogs of
      Trp
<220> FEATURE:
<221> NAME/KEY: MOD_RES
<222> LOCATION: (11)..(11)
<223> OTHER INFORMATION: His, Ala or an analog of Ala, Phe, Trp or an
      analog of Trp
<220> FEATURE:
<221> NAME/KEY: MOD_RES
<222> LOCATION: (15)..(17)
<223> OTHER INFORMATION: L-Thr, D-Thr, Ile, Val, Gly, a dipeptide
      selected from Thr-Ala or Thr-Asn, or a tripeptide comprising
      Thr-Ala-Asn, wherein a c-term -OH of any of the L-Thr, D-Thr, Ile,
      Val, Gly, Ala or Asn is optionally replaced by a second blocking
      moiety
<220> FEATURE:
<221> NAME/KEY: misc_feature
<222> LOCATION: (15)..(17)
<223> OTHER INFORMATION: This region may encompass 1 to 3 residues,
      wherein some positions may be absent
<220> FEATURE:
<221> NAME/KEY: MOD_RES
<222> LOCATION: (18)..(18)
<223> OTHER INFORMATION: Any amino acid
<220> FEATURE:
<223> OTHER INFORMATION: see specification as filed for detailed
      description of substitutions and preferred embodiments

<400> SEQUENCE: 38

Xaa Xaa Xaa Cys Val Xaa Gln Asp Xaa Gly Xaa His Arg Cys Xaa Xaa
1               5                   10                  15

Xaa Xaa

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Ile or Gly
<220> FEATURE:
<221> NAME/KEY: MOD_RES
<222> LOCATION: (3)..(3)
```

<223> OTHER INFORMATION: Ile or Cys
<220> FEATURE:
<221> NAME/KEY: MOD_RES
<222> LOCATION: (4)..(4)
<223> OTHER INFORMATION: Val or Cys
<220> FEATURE:
<221> NAME/KEY: MOD_RES
<222> LOCATION: (5)..(5)
<223> OTHER INFORMATION: Val, Tyr, Trp, 2-Nal, 1-Nal, 2-Igl, Dht, Bpa,
      Bta, 5f-Trp, 5-methyl-Trp, 1-methyl-Trp, 1-formyl-Trp or
      1-methyoxy-Trp
<220> FEATURE:
<221> NAME/KEY: MOD_RES
<222> LOCATION: (6)..(6)
<223> OTHER INFORMATION: Gln, Trp, 6f-Trp or 5f-Trp
<220> FEATURE:
<221> NAME/KEY: MOD_RES
<222> LOCATION: (7)..(7)
<223> OTHER INFORMATION: Asp or Gln
<220> FEATURE:
<221> NAME/KEY: MOD_RES
<222> LOCATION: (8)..(8)
<223> OTHER INFORMATION: Trp, Asp or 5f-Trp
<220> FEATURE:
<221> NAME/KEY: MOD_RES
<222> LOCATION: (9)..(9)
<223> OTHER INFORMATION: Gly, Trp, 6f-Trp or 5f-Trp
<220> FEATURE:
<221> NAME/KEY: MOD_RES
<222> LOCATION: (10)..(10)
<223> OTHER INFORMATION: His, Ala, 2-Abu or Gly
<220> FEATURE:
<221> NAME/KEY: MOD_RES
<222> LOCATION: (11)..(11)
<223> OTHER INFORMATION: His or Ala
<220> FEATURE:
<221> NAME/KEY: MOD_RES
<222> LOCATION: (12)..(12)
<223> OTHER INFORMATION: Arg or His
<220> FEATURE:
<221> NAME/KEY: MOD_RES
<222> LOCATION: (13)..(13)
<223> OTHER INFORMATION: Cys or Arg
<220> FEATURE:
<221> NAME/KEY: MOD_RES
<222> LOCATION: (14)..(14)
<223> OTHER INFORMATION: Thr, d-Thr or Cys
<220> FEATURE:
<221> NAME/KEY: MOD_RES
<222> LOCATION: (15)..(15)
<223> OTHER INFORMATION: Any amino acid
<220> FEATURE:
<223> OTHER INFORMATION: see specification as filed for detailed
      description of substitutions and preferred embodiments

<400> SEQUENCE: 39

Xaa Xaa Xaa Xaa Xaa Xaa Xaa Xaa Xaa Xaa Xaa Xaa Xaa Xaa Xaa
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: misc_feature
<222> LOCATION: (3)..(13)
<223> OTHER INFORMATION: Disulfide bond
<220> FEATURE:
<221> NAME/KEY: MOD_RES
<222> LOCATION: (5)..(5)

```
-continued

<223> OTHER INFORMATION: Trp(Me)
<220> FEATURE:
<221> NAME/KEY: MOD_RES
<222> LOCATION: (9)..(9)
<223> OTHER INFORMATION: mGly
<220> FEATURE:
<221> NAME/KEY: MOD_RES
<222> LOCATION: (14)..(14)
<223> OTHER INFORMATION: mIle
<220> FEATURE:
<221> NAME/KEY: MOD_RES
<222> LOCATION: (15)..(15)
<223> OTHER INFORMATION: Any amino acid
<220> FEATURE:
<223> OTHER INFORMATION: see specification as filed for detailed
      description of substitutions and preferred embodiments

<400> SEQUENCE: 40

Xaa Ile Cys Val Trp Gln Asp Trp Gly Ala His Arg Cys Ile Xaa
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: misc_feature
<222> LOCATION: (3)..(13)
<223> OTHER INFORMATION: Disulfide bond
<220> FEATURE:
<221> NAME/KEY: MOD_RES
<222> LOCATION: (5)..(5)
<223> OTHER INFORMATION: Trp(Me)
<220> FEATURE:
<221> NAME/KEY: MOD_RES
<222> LOCATION: (9)..(9)
<223> OTHER INFORMATION: mGly
<220> FEATURE:
<221> NAME/KEY: MOD_RES
<222> LOCATION: (14)..(14)
<223> OTHER INFORMATION: mIle
<220> FEATURE:
<221> NAME/KEY: MOD_RES
<222> LOCATION: (15)..(15)
<223> OTHER INFORMATION: Any amino acid
<220> FEATURE:
<223> OTHER INFORMATION: see specification as filed for detailed
      description of substitutions and preferred embodiments

<400> SEQUENCE: 41

Xaa Ile Cys Val Trp Gln Asp Trp Gly Ala His Arg Cys Ile Xaa
1               5                   10                  15

<210> SEQ ID NO 42
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
```

-continued

<400> SEQUENCE: 42

Ile Cys Val Trp Gln Asp Trp Gly Ala His Arg Cys Thr
1               5                   10

<210> SEQ ID NO 43
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 43

Ile Cys Val Trp Gln Asp Trp Gly Ala His Arg Cys Thr Lys
1               5                   10

<210> SEQ ID NO 44
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 44

Ile Cys Val Trp Gln Asp Trp Gly Ala His Arg Cys Thr Gly Gly
1               5                   10                  15

Gly Gly Lys

<210> SEQ ID NO 45
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2(CH2)5C(=O)
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2
<220> FEATURE:
<223> OTHER INFORMATION: see specification as filed for detailed
      description of substitutions and preferred embodiments

```
<400> SEQUENCE: 45

Ile Cys Val Trp Gln Asp Trp Gly Ala His Arg Cys Thr
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2(CH2CH2O)2CH2C(=O)
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2
<220> FEATURE:
<223> OTHER INFORMATION: see specification as filed for detailed
      description of substitutions and preferred embodiments

<400> SEQUENCE: 46

Ile Cys Val Trp Gln Asp Trp Gly Ala His Arg Cys Thr
1               5                   10

<210> SEQ ID NO 47
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: NH-CH2CH2OCH2CH2OCH2-C(=O)-Lys
<220> FEATURE:
<223> OTHER INFORMATION: C-term NH2
<220> FEATURE:
<223> OTHER INFORMATION: see specification as filed for detailed
      description of substitutions and preferred embodiments

<400> SEQUENCE: 47

Ile Cys Val Trp Gln Asp Trp Gly Ala His Arg Cys Thr Lys
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term (CH2CH2O)nC(=O)
<220> FEATURE:
<221> NAME/KEY: MOD_RES
<222> LOCATION: (4)..(4)
<223> OTHER INFORMATION: (1Me)Trp
<220> FEATURE:
```

```
<223> OTHER INFORMATION: C-term NH2
<220> FEATURE:
<223> OTHER INFORMATION: see specification as filed for detailed
      description of substitutions and preferred embodiments

<400> SEQUENCE: 48

Ile Cys Val Trp Gln Asp Trp Gly Ala His Arg Cys Thr
1               5                   10

<210> SEQ ID NO 49
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: NH-CH2CH2OCH2CH2OCH2-C(=O)-Lys-C(=O)-(CH2CH2O)n
<220> FEATURE:
<223> OTHER INFORMATION: C-term NH2
<220> FEATURE:
<223> OTHER INFORMATION: see specification as filed for detailed
      description of substitutions and preferred embodiments

<400> SEQUENCE: 49

Ile Cys Val Trp Gln Asp Trp Gly Ala His Arg Cys Thr Lys
1               5                   10

<210> SEQ ID NO 50
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: Lys-C(=O)-(CH2CH2O)n
<220> FEATURE:
<223> OTHER INFORMATION: C-term NH2
<220> FEATURE:
<223> OTHER INFORMATION: see specification as filed for detailed
      description of substitutions and preferred embodiments

<400> SEQUENCE: 50

Ile Cys Val Trp Gln Asp Trp Gly Ala His Arg Cys Thr Lys
1               5                   10

<210> SEQ ID NO 51
<211> LENGTH: 19
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (19)..(19)
<223> OTHER INFORMATION: Lys-C(=O)-(CH2CH2O)n
<220> FEATURE:
<223> OTHER INFORMATION: C-term NH2
<220> FEATURE:
<223> OTHER INFORMATION: see specification as filed for detailed
      description of substitutions and preferred embodiments

<400> SEQUENCE: 51

Ile Cys Val Trp Gln Asp Trp Gly Ala His Arg Cys Thr Gly Gly
1               5                   10                  15

Gly Gly Lys

<210> SEQ ID NO 52
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: (CH2CH2O)nC(=O)Lys
<220> FEATURE:
<221> NAME/KEY: misc_feature
<222> LOCATION: (8)..(18)
<223> OTHER INFORMATION: Disulfide bond
<220> FEATURE:
<221> NAME/KEY: MOD_RES
<222> LOCATION: (10)..(10)
<223> OTHER INFORMATION: (1Me)Trp
<220> FEATURE:
<223> OTHER INFORMATION: C-term NH2
<220> FEATURE:
<223> OTHER INFORMATION: see specification as filed for detailed
      description of substitutions and preferred embodiments

<400> SEQUENCE: 52

Lys Gly Gly Gly Gly Gly Ile Cys Val Trp Gln Asp Trp Gly Ala His
1               5                   10                  15

Arg Cys Thr

<210> SEQ ID NO 53
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
```

```
<222> LOCATION: (1)..(1)
<223> OTHER INFORMATION: (CH2CH2O)nC(=O)Lys
<220> FEATURE:
<221> NAME/KEY: misc_feature
<222> LOCATION: (3)..(13)
<223> OTHER INFORMATION: Disulfide bond
<220> FEATURE:
<221> NAME/KEY: MOD_RES
<222> LOCATION: (5)..(5)
<223> OTHER INFORMATION: (1Me)Trp
<220> FEATURE:
<223> OTHER INFORMATION: C-term NH2
<220> FEATURE:
<223> OTHER INFORMATION: see specification as filed for detailed
      description of substitutions and preferred embodiments

<400> SEQUENCE: 53

Lys Ile Cys Val Trp Gln Asp Trp Gly Ala His Arg Cys Thr
1               5                   10

<210> SEQ ID NO 54
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: NH-CH2CH2OCH2CH2OCH2-C(=O)-Lys-(C(=O)-
      (CH2CH2O)n-R)
<220> FEATURE:
<223> OTHER INFORMATION: C-term NH2
<220> FEATURE:
<223> OTHER INFORMATION: see specification as filed for detailed
      description of substitutions and preferred embodiments

<400> SEQUENCE: 54

Ile Cys Val Trp Gln Asp Trp Gly Ala His Arg Cys Thr Lys
1               5                   10

<210> SEQ ID NO 55
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: NH-CH2CH2OCH2CH2OCH2-C(=O)-Lys-(C(=O)-(CH2)m-
      (CH2CH2O)n-R)
<220> FEATURE:
```

<223> OTHER INFORMATION: C-term NH2
<220> FEATURE:
<223> OTHER INFORMATION: see specification as filed for detailed
      description of substitutions and preferred embodiments

<400> SEQUENCE: 55

Ile Cys Val Trp Gln Asp Trp Gly Ala His Arg Cys Thr Lys
1               5                   10

<210> SEQ ID NO 56
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: NH-CH2CH2OCH2CH2OCH2-C(=O)-Lys-(C(=O)-(CH2)m-
      C(=O)- (CH2CH2O)n-R)
<220> FEATURE:
<223> OTHER INFORMATION: C-term NH2
<220> FEATURE:
<223> OTHER INFORMATION: see specification as filed for detailed
      description of substitutions and preferred embodiments

<400> SEQUENCE: 56

Ile Cys Val Trp Gln Asp Trp Gly Ala His Arg Cys Thr Lys
1               5                   10

<210> SEQ ID NO 57
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: NH-CH2CH2OCH2CH2OCH2-C(=O)-Lys-(C(=O)-(CH2)m-
      C(=O)- (CH2)j (CH2CH2O)n-R)
<220> FEATURE:
<223> OTHER INFORMATION: C-term NH2
<220> FEATURE:
<223> OTHER INFORMATION: see specification as filed for detailed
      description of substitutions and preferred embodiments

<400> SEQUENCE: 57

Ile Cys Val Trp Gln Asp Trp Gly Ala His Arg Cys Thr Lys
1               5                   10

```
<210> SEQ ID NO 58
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: AEEAc-Lys-(C(=O)-(CH2)5-Mal)
<220> FEATURE:
<223> OTHER INFORMATION: C-term NH2
<220> FEATURE:
<223> OTHER INFORMATION: see specification as filed for detailed
      description of substitutions and preferred embodiments

<400> SEQUENCE: 58

Ile Cys Val Trp Gln Asp Trp Gly Ala His Arg Cys Thr Lys
1               5                   10

<210> SEQ ID NO 59
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(5)
<223> OTHER INFORMATION: Cyclic
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (3)..(3)
<223> OTHER INFORMATION: dCha

<400> SEQUENCE: 59

Xaa Pro Ala Trp Arg
1               5

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(5)
<223> OTHER INFORMATION: Cyclic
<220> FEATURE:
<221> NAME/KEY: MOD_RES
<222> LOCATION: (3)..(3)
<223> OTHER INFORMATION: dCha

<400> SEQUENCE: 60

Lys Pro Ala Trp Arg
1               5
```

```
<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid and this region may encompass
      1 to 5 residues, wherein some position may be
      absent
<220> FEATURE:
<221> NAME/KEY: MOD_RES
<222> LOCATION: (6)..(6)
<223> OTHER INFORMATION: Ornithine
<220> FEATURE:
<221> NAME/KEY: misc_feature
<222> LOCATION: (6)..(10)
<223> OTHER INFORMATION: Cyclic
<220> FEATURE:
<221> NAME/KEY: MOD_RES
<222> LOCATION: (8)..(8)
<223> OTHER INFORMATION: dCha

<400> SEQUENCE: 61

Xaa Xaa Xaa Xaa Xaa Xaa Pro Ala Trp Arg
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid and this region may encompass
      1 to 5 residues, wherein some position may be
      absent
<220> FEATURE:
<221> NAME/KEY: misc_feature
<222> LOCATION: (6)..(10)
<223> OTHER INFORMATION: Cyclic
<220> FEATURE:
<221> NAME/KEY: MOD_RES
<222> LOCATION: (8)..(8)
<223> OTHER INFORMATION: dCha

<400> SEQUENCE: 62

Xaa Xaa Xaa Xaa Xaa Lys Pro Ala Trp Arg
1               5                   10

<210> SEQ ID NO 63
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ornithine
<220> FEATURE:
<221> NAME/KEY: misc_feature
<222> LOCATION: (2)..(6)
<223> OTHER INFORMATION: Cyclic
<220> FEATURE:
<221> NAME/KEY: MOD_RES
```

```
<222> LOCATION: (4)..(4)
<223> OTHER INFORMATION: dCha

<400> SEQUENCE: 63

Phe Xaa Pro Ala Trp Arg
1               5

<210> SEQ ID NO 64
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(6)
<223> OTHER INFORMATION: Cyclic
<220> FEATURE:
<221> NAME/KEY: MOD_RES
<222> LOCATION: (4)..(4)
<223> OTHER INFORMATION: dCha

<400> SEQUENCE: 64

Phe Lys Pro Ala Trp Arg
1               5

<210> SEQ ID NO 65
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term cinnamoyl
<220> FEATURE:
<221> NAME/KEY: MOD_RES
<222> LOCATION: (1)..(1)
<223> OTHER INFORMATION: Ornithine
<220> FEATURE:
<221> NAME/KEY: misc_feature
<222> LOCATION: (1)..(5)
<223> OTHER INFORMATION: Cyclic
<220> FEATURE:
<221> NAME/KEY: MOD_RES
<222> LOCATION: (3)..(3)
<223> OTHER INFORMATION: dCha

<400> SEQUENCE: 65

Xaa Pro Ala Trp Arg
1               5

<210> SEQ ID NO 66
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H-cinnamoyl
<220> FEATURE:
<221> NAME/KEY: MOD_RES
<222> LOCATION: (1)..(1)
<223> OTHER INFORMATION: Ornithine
<220> FEATURE:
<221> NAME/KEY: misc_feature
<222> LOCATION: (1)..(5)
<223> OTHER INFORMATION: Cyclic
<220> FEATURE:
<221> NAME/KEY: MOD_RES
<222> LOCATION: (3)..(3)
```

```
<223> OTHER INFORMATION: dCha

<400> SEQUENCE: 66

Xaa Pro Ala Trp Arg
1               5

<210> SEQ ID NO 67
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(2)
<223> OTHER INFORMATION: Ornithine
<220> FEATURE:
<221> NAME/KEY: misc_feature
<222> LOCATION: (2)..(6)
<223> OTHER INFORMATION: Cyclic
<220> FEATURE:
<221> NAME/KEY: MOD_RES
<222> LOCATION: (4)..(4)
<223> OTHER INFORMATION: dCha

<400> SEQUENCE: 67

Phe Xaa Pro Ala Trp Arg
1               5

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Trp Glu Ser Asn Gly Gln Pro Glu Asn Asn
1               5                   10

<210> SEQ ID NO 69
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Lys Thr Ile Ser Lys Ala Lys Gly Gln Pro Arg Glu Pro Gln Val Tyr
1               5                   10                  15

Thr

<210> SEQ ID NO 70
<211> LENGTH: 30
<212> TYPE: PRT
<213> ORGANISM: Homo sapiens

<400> SEQUENCE: 70

Gly Ala Thr Asn Pro Thr Gln Lys Thr Lys Glu Ser Leu Gly Arg Lys
1               5                   10                  15

Ile Gln Ile Gln Arg Ser Gly His Leu Asn Leu Tyr Leu Leu
                20                  25                  30
```

<210> SEQ ID NO 71
<211> LENGTH: 30
<212> TYPE: PRT
<213> ORGANISM: Homo sapiens

<400> SEQUENCE: 71

Leu Arg Lys Lys Ser Arg Asp Lys Gly Gln Ala Gly Leu Gln Arg Ala
1               5                   10                  15

Leu Glu Ile Leu Gln Glu Glu Asp Leu Ile Asp Glu Asp Asp
            20                  25                  30

<210> SEQ ID NO 72
<211> LENGTH: 30
<212> TYPE: PRT
<213> ORGANISM: Homo sapiens

<400> SEQUENCE: 72

Cys Glu Pro Val Cys Gly Leu Ser Ala Arg Thr Thr Gly Gly Arg Ile
1               5                   10                  15

Tyr Gly Gly Gln Lys Ala Lys Pro Gly Asp Phe Pro Trp Gln
            20                  25                  30

<210> SEQ ID NO 73
<211> LENGTH: 34
<212> TYPE: PRT
<213> ORGANISM: Homo sapiens

<400> SEQUENCE: 73

Thr Gly Val Glu Ala Ala Ala Ser Ala Ile Ser Val Ala Arg Thr
1               5                   10                  15

Leu Leu Val Phe Glu Val Gln Gln Pro Phe Leu Phe Val Leu Trp Asp
            20                  25                  30

Gln Gln

<210> SEQ ID NO 74
<211> LENGTH: 30
<212> TYPE: PRT
<213> ORGANISM: Homo sapiens

<400> SEQUENCE: 74

Gly Arg Thr Ala Thr Ser Glu Tyr Gln Thr Phe Phe Asn Pro Arg Thr
1               5                   10                  15

Phe Gly Ser Gly Glu Ala Asp Cys Gly Leu Arg Pro Leu Phe
            20                  25                  30

<210> SEQ ID NO 75
<211> LENGTH: 30
<212> TYPE: PRT
<213> ORGANISM: Homo sapiens

<400> SEQUENCE: 75

Val Asp Ala Glu Asp Gly His Gly Pro Gly Gln Gln Lys Arg Lys
1               5                   10                  15

Ile Val Leu Asp Pro Ser Gly Ser Met Asn Ile Tyr Leu Val
            20                  25                  30

<210> SEQ ID NO 76
<211> LENGTH: 30
<212> TYPE: PRT
<213> ORGANISM: Homo sapiens

<400> SEQUENCE: 76

```
Leu Arg Arg Gln His Ala Arg Ala Ser His Leu Gly Leu Ala Arg Ser
1               5                   10                  15

Asn Leu Asp Glu Asp Ile Ile Ala Glu Glu Asn Ile Val Ser
            20                  25                  30
```

<210> SEQ ID NO 77
<211> LENGTH: 30
<212> TYPE: PRT
<213> ORGANISM: Homo sapiens

<400> SEQUENCE: 77

```
Gln Leu Arg Ala Asn Ile Ser His Lys Asp Met Gln Leu Gly Arg Leu
1               5                   10                  15

His Met Lys Thr Leu Leu Pro Val Ser Lys Pro Glu Ile Arg
            20                  25                  30
```

<210> SEQ ID NO 78
<211> LENGTH: 6
<212> TYPE: PRT
<213> ORGANISM: Homo sapiens

<400> SEQUENCE: 78

```
Leu Ala Arg Ser Asn Leu
1               5
```

<210> SEQ ID NO 79
<211> LENGTH: 7
<212> TYPE: PRT
<213> ORGANISM: Homo sapiens

<400> SEQUENCE: 79

```
Leu Ala Arg Ser Asn Leu Asp
1               5
```

<210> SEQ ID NO 80
<211> LENGTH: 8
<212> TYPE: PRT
<213> ORGANISM: Homo sapiens

<400> SEQUENCE: 80

```
Leu Ala Arg Ser Asn Leu Asp Glu
1               5
```

<210> SEQ ID NO 81
<211> LENGTH: 9
<212> TYPE: PRT
<213> ORGANISM: Homo sapiens

<400> SEQUENCE: 81

```
Leu Ala Arg Ser Asn Leu Asp Glu Asp
1               5
```

<210> SEQ ID NO 82
<211> LENGTH: 10
<212> TYPE: PRT
<213> ORGANISM: Homo sapiens

<400> SEQUENCE: 82

```
Leu Ala Arg Ser Asn Leu Asp Glu Asp Ile
1               5                   10
```

<210> SEQ ID NO 83
<211> LENGTH: 11

```
<212> TYPE: PRT
<213> ORGANISM: Homo sapiens

<400> SEQUENCE: 83

Leu Ala Arg Ser Asn Leu Asp Glu Asp Ile Ile
1               5                   10

<210> SEQ ID NO 84
<211> LENGTH: 8
<212> TYPE: PRT
<213> ORGANISM: Homo sapiens

<400> SEQUENCE: 84

Gly Leu Ala Arg Ser Asn Leu Asp
1               5

<210> SEQ ID NO 85
<211> LENGTH: 9
<212> TYPE: PRT
<213> ORGANISM: Homo sapiens

<400> SEQUENCE: 85

Gly Leu Ala Arg Ser Asn Leu Asp Glu
1               5

<210> SEQ ID NO 86
<211> LENGTH: 10
<212> TYPE: PRT
<213> ORGANISM: Homo sapiens

<400> SEQUENCE: 86

Gly Leu Ala Arg Ser Asn Leu Asp Glu Asp
1               5                   10

<210> SEQ ID NO 87
<211> LENGTH: 11
<212> TYPE: PRT
<213> ORGANISM: Homo sapiens

<400> SEQUENCE: 87

Gly Leu Ala Arg Ser Asn Leu Asp Glu Asp Ile
1               5                   10

<210> SEQ ID NO 88
<211> LENGTH: 12
<212> TYPE: PRT
<213> ORGANISM: Homo sapiens

<400> SEQUENCE: 88

Gly Leu Ala Arg Ser Asn Leu Asp Glu Asp Ile Ile
1               5                   10

<210> SEQ ID NO 89
<211> LENGTH: 6
<212> TYPE: PRT
<213> ORGANISM: Homo sapiens

<400> SEQUENCE: 89

Leu Gly Arg Leu His Met
1               5

<210> SEQ ID NO 90
<211> LENGTH: 7
<212> TYPE: PRT
<213> ORGANISM: Homo sapiens
```

<400> SEQUENCE: 90

Leu Gly Arg Leu His Met Lys
1               5

<210> SEQ ID NO 91
<211> LENGTH: 7
<212> TYPE: PRT
<213> ORGANISM: Homo sapiens

<400> SEQUENCE: 91

Gln Leu Gly Arg Leu His Met
1               5

<210> SEQ ID NO 92
<211> LENGTH: 8
<212> TYPE: PRT
<213> ORGANISM: Homo sapiens

<400> SEQUENCE: 92

Gln Leu Gly Arg Leu His Met Lys
1               5

<210> SEQ ID NO 93
<211> LENGTH: 8
<212> TYPE: PRT
<213> ORGANISM: Homo sapiens

<400> SEQUENCE: 93

Leu Gly Arg Leu His Met Lys Thr
1               5

<210> SEQ ID NO 94
<211> LENGTH: 8
<212> TYPE: PRT
<213> ORGANISM: Homo sapiens

<400> SEQUENCE: 94

Met Gln Leu Gly Arg Leu His Met
1               5

<210> SEQ ID NO 95
<211> LENGTH: 9
<212> TYPE: PRT
<213> ORGANISM: Homo sapiens

<400> SEQUENCE: 95

Met Gln Leu Gly Arg Leu His Met Lys
1               5

<210> SEQ ID NO 96
<211> LENGTH: 9
<212> TYPE: PRT
<213> ORGANISM: Homo sapiens

<400> SEQUENCE: 96

Asp Met Gln Leu Gly Arg Leu His Met
1               5

<210> SEQ ID NO 97
<211> LENGTH: 10
<212> TYPE: PRT
<213> ORGANISM: Homo sapiens

<400> SEQUENCE: 97

Asp Met Gln Leu Gly Arg Leu His Met Lys
1               5                   10

<210> SEQ ID NO 98
<211> LENGTH: 11
<212> TYPE: PRT
<213> ORGANISM: Homo sapiens

<400> SEQUENCE: 98

Leu Ala Arg Ser Asn Leu Asp Glu Asp Ile Ile
1               5                   10

<210> SEQ ID NO 99
<211> LENGTH: 13
<212> TYPE: PRT
<213> ORGANISM: Homo sapiens

<400> SEQUENCE: 99

Gly Leu Ala Arg Ser Asn Leu Asp Glu Asp Ile Ile Lys
1               5                   10

<210> SEQ ID NO 100
<211> LENGTH: 60
<212> TYPE: PRT
<213> ORGANISM: Homo sapiens

<400> SEQUENCE: 100

Lys Lys Val Phe Leu Asp Cys Cys Asn Tyr Ile Thr Glu Leu Arg Arg
1               5                   10                  15

Gln His Ala Arg Ala Ser His Leu Gly Leu Ala Arg Ser Asn Leu Asp
            20                  25                  30

Glu Asp Ile Ile Ala Glu Glu Asn Ile Val Ser Arg Ser Glu Phe Pro
        35                  40                  45

Glu Ser Trp Leu Trp Asn Val Glu Asp Leu Lys Glu
    50                  55                  60

<210> SEQ ID NO 101
<211> LENGTH: 60
<212> TYPE: PRT
<213> ORGANISM: Rattus norvegicus

<400> SEQUENCE: 101

Leu Lys Ala Phe Met Asp Cys Cys Asn Tyr Ile Thr Lys Leu Arg Glu
1               5                   10                  15

Gln His Arg Arg Asp His Val Leu Gly Leu Ala Arg Ser Asp Val Asp
            20                  25                  30

Glu Asp Ile Ile Pro Glu Glu Asp Ile Ile Ser Arg Ser His Phe Pro
        35                  40                  45

Glu Ser Trp Leu Trp Thr Ile Glu Glu Leu Lys Glu
    50                  55                  60

<210> SEQ ID NO 102
<211> LENGTH: 60
<212> TYPE: PRT
<213> ORGANISM: Mus musculus

<400> SEQUENCE: 102

Ile Lys Ala Phe Ile Asp Cys Cys Asn His Ile Thr Lys Leu Arg Glu
1               5                   10                  15

Gln His Arg Arg Asp His Val Leu Gly Leu Ala Arg Ser Glu Leu Glu
            20                  25                  30

Glu Asp Ile Ile Pro Glu Asp Ile Ile Ser Arg Ser His Phe Pro
        35                  40                  45

Gln Ser Trp Leu Trp Thr Ile Glu Glu Leu Lys Glu
    50                  55                  60

<210> SEQ ID NO 103
<211> LENGTH: 60
<212> TYPE: PRT
<213> ORGANISM: Macaca fascicularis

<400> SEQUENCE: 103

Lys Lys Ala Phe Leu Asp Cys Cys Asn Tyr Ile Thr Glu Leu Arg Arg
1               5                   10                  15

Gln His Ala Arg Ala Ser His Leu Gly Leu Ala Arg Ser Asn Leu Asp
            20                  25                  30

Glu Asp Ile Ile Ala Glu Glu Asn Ile Val Ser Arg Ser Glu Phe Pro
        35                  40                  45

Glu Ser Trp Leu Trp Lys Ile Glu Glu Leu Lys Glu
    50                  55                  60

<210> SEQ ID NO 104
<211> LENGTH: 11
<212> TYPE: PRT
<213> ORGANISM: Rattus norvegicus

<400> SEQUENCE: 104

Leu Ala Arg Ser Asp Val Asp Glu Asp Ile Ile
1               5                   10

<210> SEQ ID NO 105
<211> LENGTH: 11
<212> TYPE: PRT
<213> ORGANISM: Mus musculus

<400> SEQUENCE: 105

Leu Ala Arg Ser Glu Leu Glu Glu Asp Ile Ile
1               5                   10

<210> SEQ ID NO 106
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Lys Gly Arg Gly Asp Ser
1               5

<210> SEQ ID NO 107
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Trp or an analog of Trp
<220> FEATURE:
<223> OTHER INFORMATION: see specification as filed for detailed
      description of substitutions and preferred embodiments

```
<400> SEQUENCE: 107

Gln Asp Xaa Gly
1

<210> SEQ ID NO 108
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp

<400> SEQUENCE: 108

Ile Cys Val Trp Gln Asp Trp Gly Ala His Arg Cys Thr
1               5                   10

<210> SEQ ID NO 109
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Cy5.5
<220> FEATURE:
<221> NAME/KEY: MOD_RES
<222> LOCATION: (13)..(13)
<223> OTHER INFORMATION: Lys(Cy7Q)

<400> SEQUENCE: 109

Gly Leu Ala Arg Ser Asp Val Asp Glu Asp Ile Ile Lys
1               5                   10

<210> SEQ ID NO 110
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Cy5.5
<220> FEATURE:
<221> NAME/KEY: MOD_RES
<222> LOCATION: (13)..(13)
<223> OTHER INFORMATION: Lys(Cy7Q)
<220> FEATURE:
<223> OTHER INFORMATION: C-term NH2

<400> SEQUENCE: 110

Gly Leu Ala Arg Ser Asp Val Asp Glu Asp Ile Ile Lys
1               5                   10
```